excluded

FIG. 1A
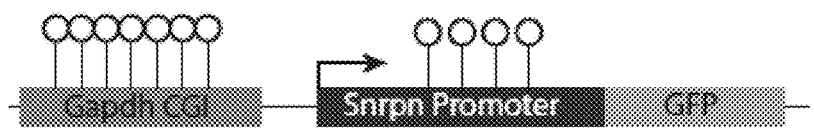
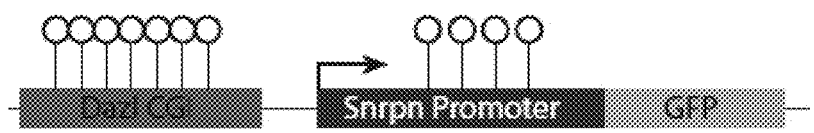
FIG. 1B
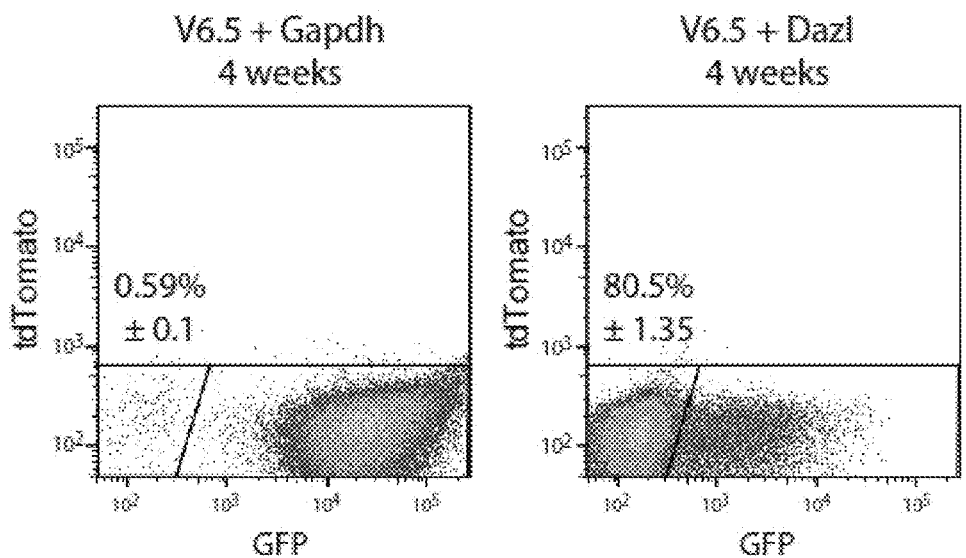

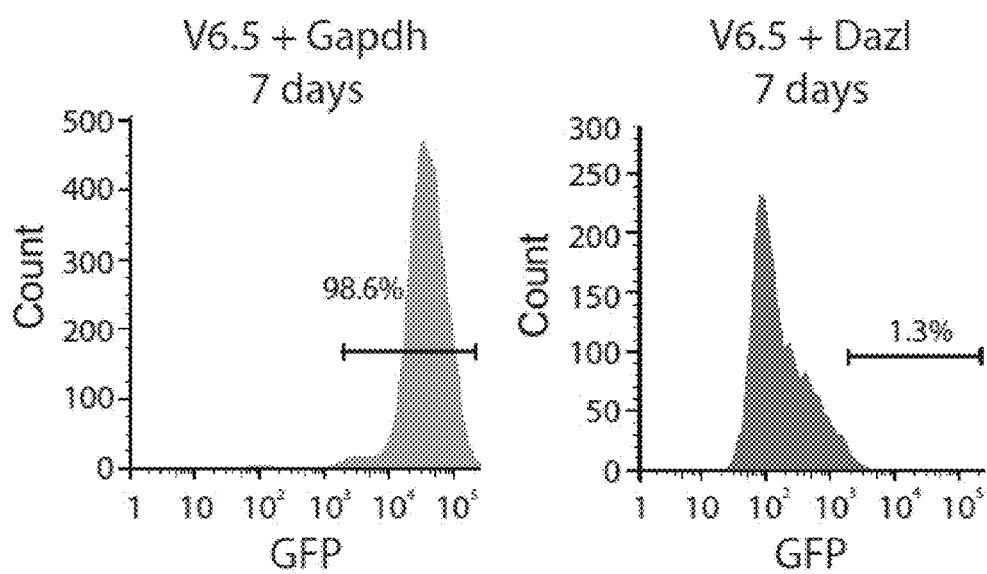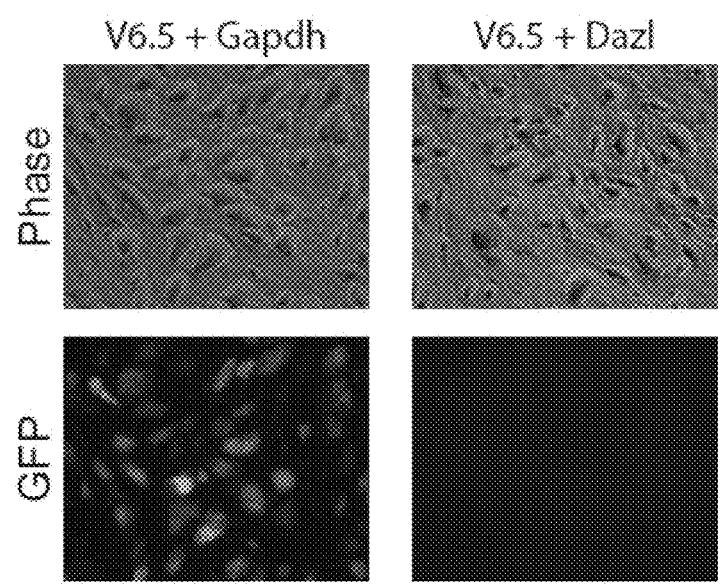

FIG. 2A
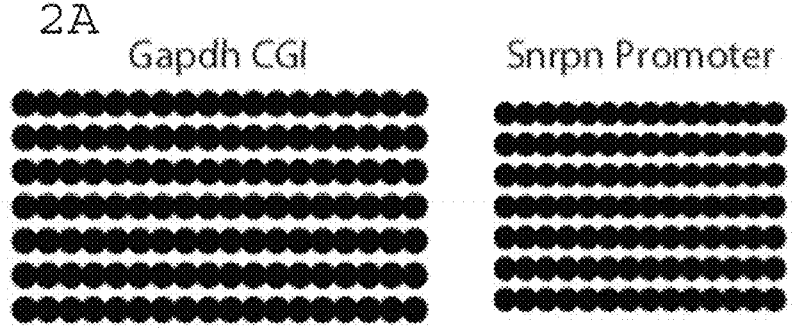
FIG. 2B
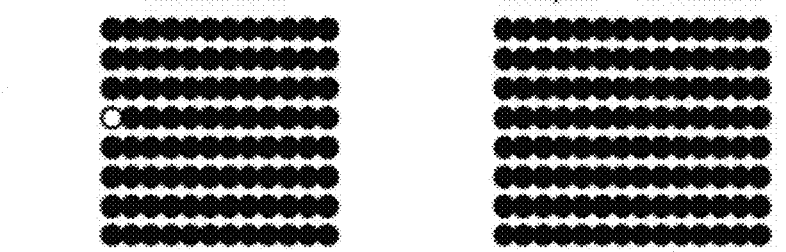
FIG. 2C
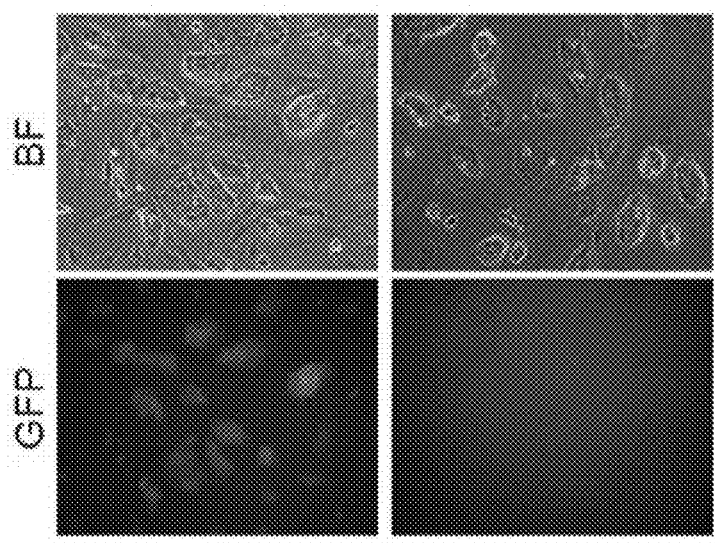

FIG. 2G
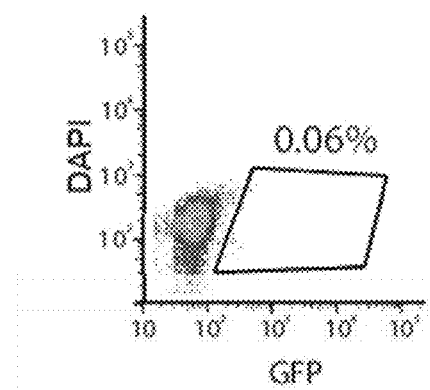
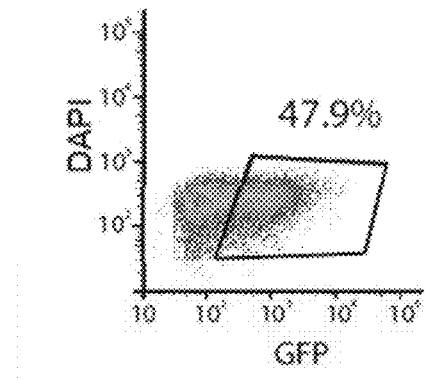
FIG. 2H
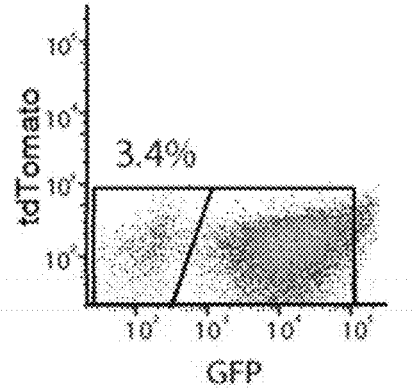
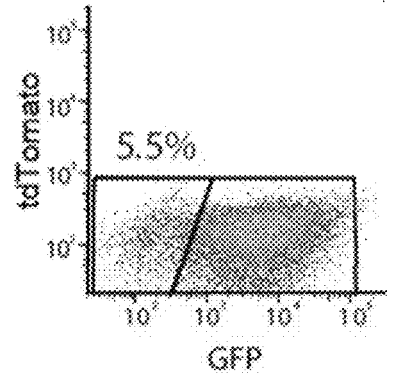
FIG. 2I
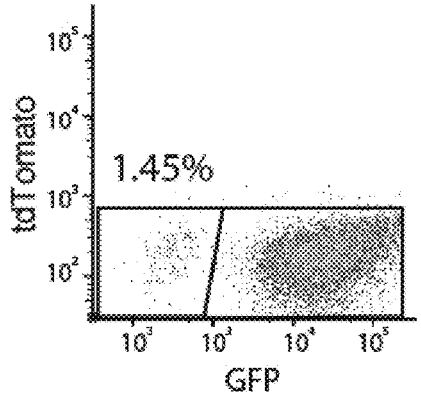
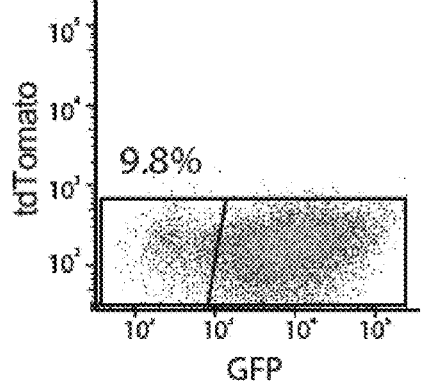

FIG. 3C
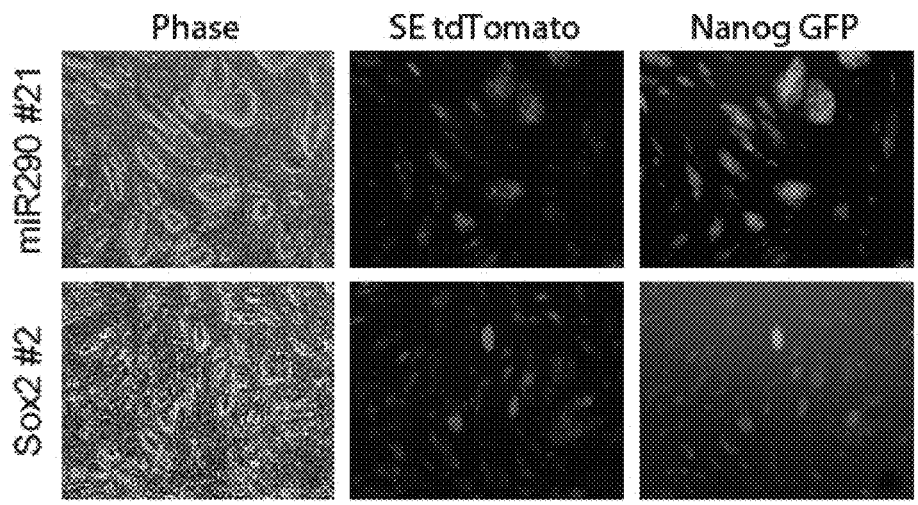
FIG. 3D
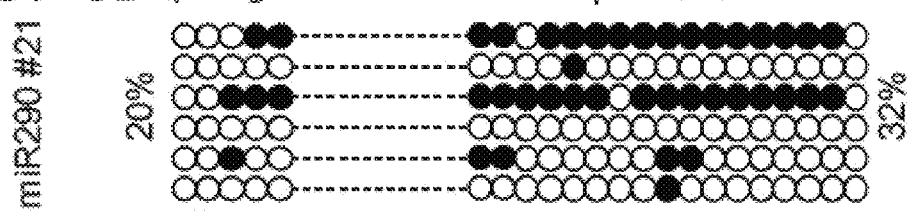
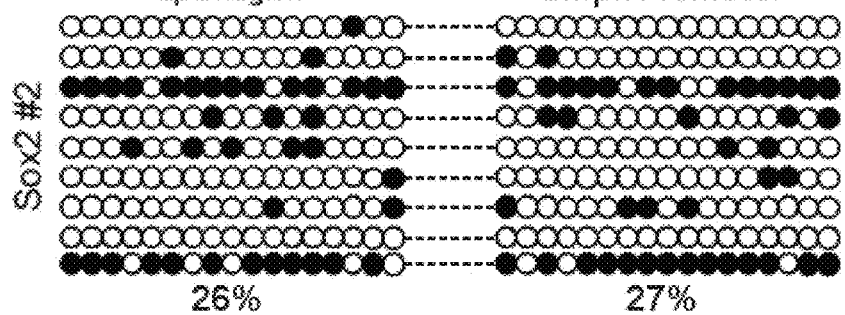

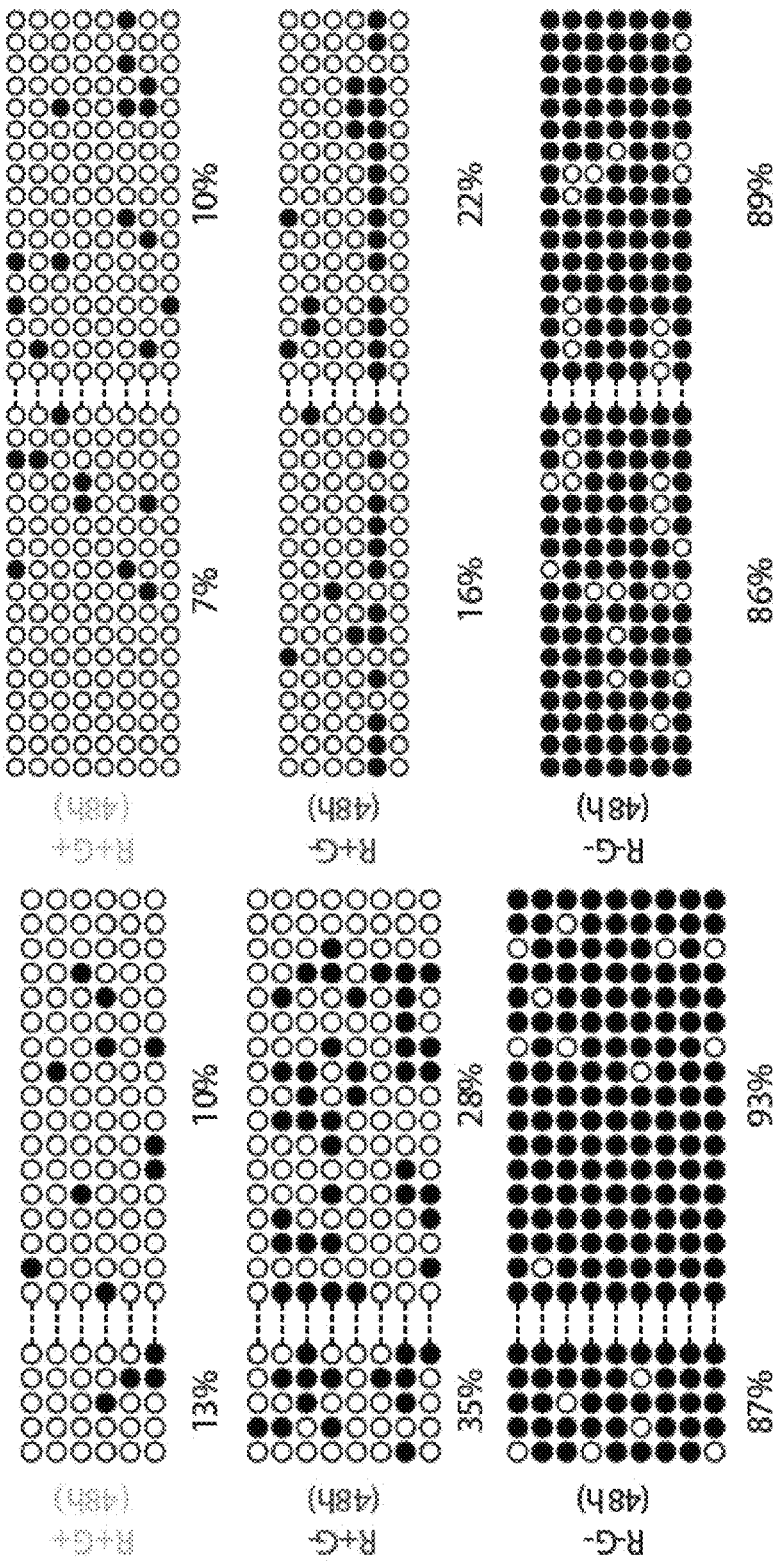

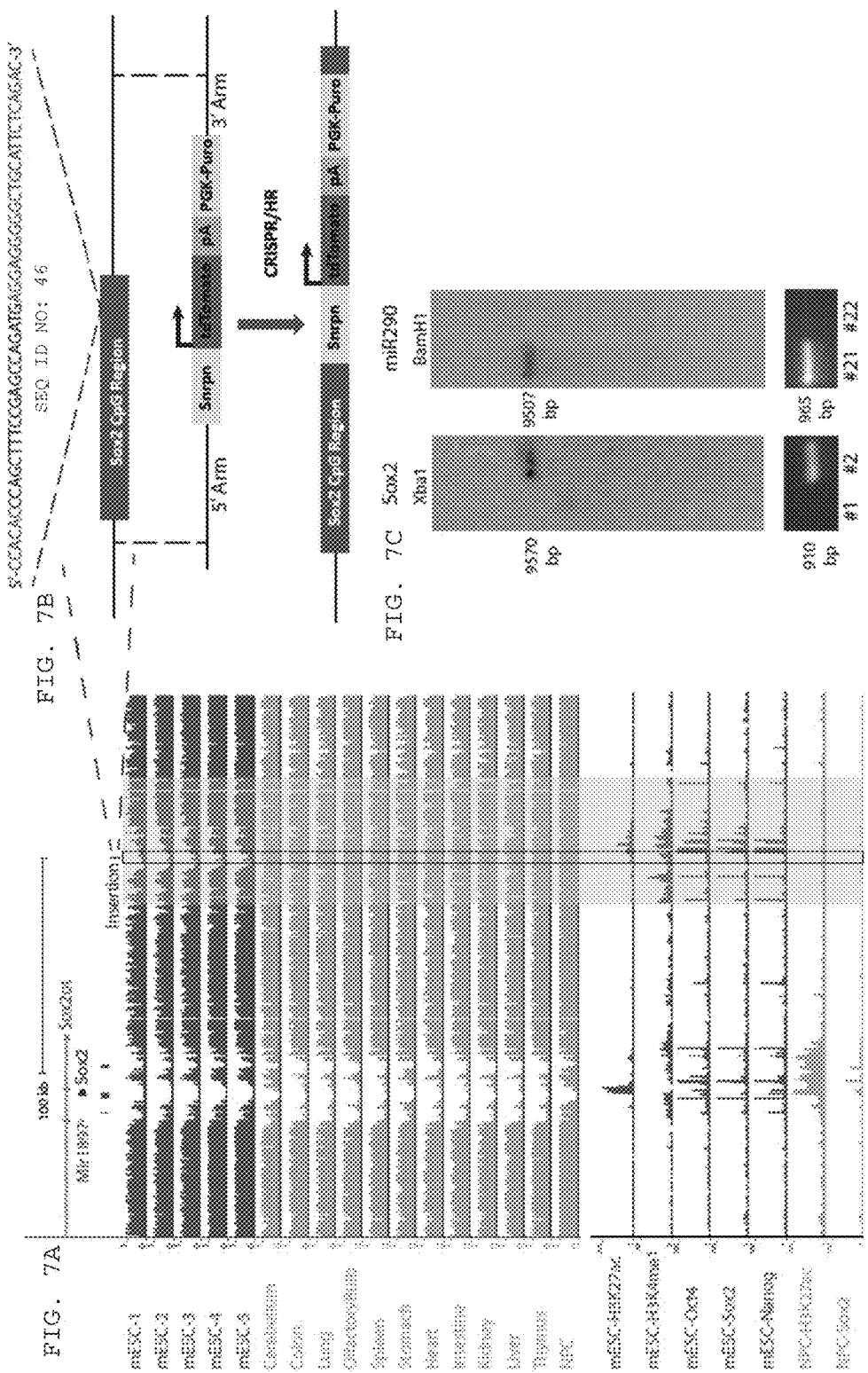

Sequence from Snrpn promoter region

GTAGATTAAGAACCAGCCTCAGAAAAGCAACAACAAAATACACACCCTGCAGCGCTGAG
CTACACTCCACCATTCCTAGCCCTAGTCTATTGTCTTTTCATTTTTCCATAAGTAGTCTG
TCCTTGTGATTTTCATTTGCATTTCCATGGTGACTGACAATAGTATCTAATTGTTTAGTT
CTATGTAAATAGATTTCTTCAGCTGTTTTCGAAAGTTCAGGTTTTGGTTACATTTAGAA
CTGAATGTATCTTCATTGAAGTTGAATTTAGGATGTTTGCGAACTGGATGCTAGCTCAG
TGCGGGGGGAAGGGAAGTAGAGAACTTCCAACTTTGTTAGAATACCTCATTAACAGTTC
TTGCAGGCCCTCATTAAGCTATGCTAAACCCATGTAAATTTAGCTTCCTTAGTTTTCTCC
TTGCCATTTTGTTTTCCTAATCTTCAAATAATTGCATATTGAAGTTACTACCACAATAAT
ACTTTTACTAGGCAGACAGGAAATTAATAGGTCAAAAGTAACTGAAATAAATTCTTATA
TATGTATCCACAATCTACAAAATGTTTTTGTTTTTGTTTTAGATATTGTTACAAATTG
AACCTGGCCTTGAGTATGCAAAAATACTGCTTTCTTAGAATAAGTTTCCTAAGAGCTGG
AATTACTGGATGGCATTTCTATGAGGTCATATATTTGTTAGTAAATAGTGTCACTTTT
CACCCCCAGGCATAACAACATTTAGGAAGCCCTGTCTCTAAAACCAACAACAACAAAAG
AAGCAGATACATAAGTTTCATAACTGAATGTTCTTCCTATTAAAATTTAATCACACCAT
GATCTGGAGGAAATAGTTTTCTCCCAGTCATATGTTCTAACACAGAGAAAGAAAATACA
AGTAATACTACATTAATGTAGAATGTAGAATTAGGAATCAGGATAACTTTTTTTTCTGT
ACAGAATTTTAAGTATCTGACAATTTGGCTGGGCTTCATGTTTGATTGTGTGTGTGTGT
GTGTGTGTGTGTGTGTGATACACTATGTAACATGATATAGCCTAGAAACCAGTCT
TCCTCATATTGGAGATCAAACCTTTTTCCTCTCCCACATAATAAAAATCTGTGTGATGC
TTGCAATCACTTGGGAGCAATTTTTTAAAAAATTAAATGTATTTAGTAATAGGCAATT
ATATCCATTATTCCAGATTGACAGTGATTTTTTTTTTTTAATACACGCTCAAATTTCCG
CAGTAGGAATGCTCAAGCATTCCTTTTGGTAGCTGCCTTTTGGCAGGACATTCCGGTCAG
AGGGACAGAGACCCCTGCATTGCGGCAAAAATGTGCGCATGTGCAGCCATTGCCTGGGAC
GCATGCGTAGGGAGCCGCGCGACAAACCTGAGCCATTGCGGCAAGACTAGCGCAGAGAGG
AGAGGGAGCCGGAGATGCCAGACGCTTGGTTCTGAGGAGTGATTTGCAACGCAATGGAG
CGAGGAAGGTCAGCTGGGCTTGTGGATTCT (SEQ ID NO: 3)

Cloned Snrpn minimal promoter

ACGCTCAAATTTCCGCAGTAGGAATGCTCAAGCATTCCTTTTGGTAGCTGCCTTTTGGCA
GGACATTCCGGTCAGAGGGACAGAGACCCCTGCATTGCGGCAAAAATGTGCGCATGTGCA
GCCATTGCCTGGGACGCATGCGTAGGGAGCCGCGCGACAAACCTGAGCCATTGCGGCAAG
ACTAGCGCAGAGAGGAGAGGGAGCCGGAGATGCCAGACGCTTGGTTCTGAGGAGTGATT
TGCAACGCAATGGAGCGAGGAAGGTCAGCTGGGCTTGTGGATTCT (SEQ ID NO: 1)

Red = Forward and reverse primers

Blue = less conserved

Green = conserved region

Purple = start of transcription

Dark purple = start of translation

FIG. 9

IGF2R

Bold/Underline - 5'UTR + First exon

Yellow - start of transcription (position 594)

Entire region - imprinted differentially methylated region (DMR)

Green - CpG Islands

```
GCAGAAGACTCCACTAGAATAATCTACTCTGGAGACAATGACATCATGTGAGCAACCACA
CAGGAAGCTAACTGAGAGACGTGAAGGGTAAAGTCTTGAAAGCCTACAGAGATGACCACC
TCTCAACCCTTGTCAAAAGAAGAAAAAGCTTCAACCACTGACAAATGGCTACTTTAAATA
AGGAAAACTGAGAGTTGCCACAGAAGGGGTCAATCTGCAGTTGAAACCACCACTACCCAA
CTCCAAGAGCAT
```

```
AGATGGAGTTAGGTGGAAAAGCCCAGGTTGATGTTTAGTGTTGCAAGTGGATGCAGG
GTTAAGAGGTCAGTCTTTCTAGAATCCCGCGTGGGAGTTTCCGACTCATGCCCCGGAGAG
CCTCACAGCAGCTCTGTGGAAATGTGACTTCCCAAGCAGGGCTTTCTACAGCAAGTTAGG
TGACTGGTGGACTAATATGCAGTGTGCAGAGAAACCAAAATGTAACAAGCAAATGACAAA
CA (SEQ ID NO: 4)
```

FIG. 10

GNAS

Bold/Underline - 5'UTR + First exon

Yellow - start of transcription (position 3421)

Entire region - imprinted differentially methylated region (DMR)

Green - CpG Islands

```
GCCCTTCCTTTGTTCCCTTTATCGGAACCACCCTCCATGTTGGTTCTGTCCTTTCTAAAA
GCTTGATTCAAATCCTGATCTGAGAAGGAGGGAGAAACACACACCTTTCACCATCTACCC
CATTTCCTCCTCTCCACTTCCTGCCCAAAGAGCCCGGATGCTGCATGGACGCCTCAGAAA
GCACATCCATTTTCTCCCTTCTTTCCCACTGCTCCTACAGGAGCAAAGGTGTCCGTCCGA
TCATTTATGTAACCAGACCCCACACTTCCTTACATTGGACCCTTTGTTCCAGATAGGTGA
AGGTGTGCCCGCTCTGCCCCGCCCCTTCTATTCAGTCAAGACATCTTGCTATGGAGACCC
ATTCCAGGCGCCATTTTCTCCATCTGGTCTTTGCAACCCTCCTATTGGAGGCCTTCTCT
TTCCATTTTCATGCCGTTCTGCTCTTTCACAAGGAGACTGGCATGCTCTGGAGGTTTCTC
CCTGTCAGAGAAGCACGATATAAGAAAGAATGTGGAACAAAGGATTCTCACAGATCATAA
GAATGTCTGAACAAAGAGAACCTGAAACCATTTTTTTTTCCTTTTGGATGAATGGTGCTT
TAGGGATGGGTGTGAGAGGCCTGGAGAGCCCACAAGACCCGCGTGGCGGTCTCCTTGGGT
CGCCAACCTCAGCGTCTACTGACCTTTCACCTTGTGCAGGGTTCAGCATCTCTGGGAAAT
GAAATCTGTCCATCTTGTACTGCTCGTCTGCATCGGAGCAGTAAGCTCTCTTTCTCCATA
GGCCTGGCCCACCACCTCCAGGCCCTGGAAAAGCCTCTCTCCGCGGTGCCTCGGCGATAG
CCCTCTCTGTGTAGTGAGTTAGCCTACCGCCATCATGAGCCCAAGGGATGGTCCATGGGG
GTCCCTGACCTTCCCACCTTGCCTTGGCGATTTAGGGCATCAAAAAGCTTGGCCCCCAAG
GCACTCACGGCGACCGTGGCCTTCTAGGCCTGGCCGCCATACGCCCGCCCGCCAACCGCT
TCCAACCAACCCAGCAAGCACAACCTCTTTGGGCGTTCCAACGCGGCGCCCCTATTGGA
CCTCCCACCCATATCCGGTTTCCGGTCCGAAGCCCCCTGCTCATTCGCCAGGCATCCTTG
ATTGGCGTGACCCCAGCCCAATAGCTGACCTGTCGCTGGGGTCGGAGGGGAGTGGGCTAG
TGGTTGAGACCCAGTTGGCCTATTCGGTGTATGTTCAAACCGTTTCGCCATTTTGAGTGT
GTGTGTGTGTATATGTGGGGGAGGGTAGTTGGCCAAACTTTGGACCAAAGTTCAAAGTGT
CCGGCATGCAGTGTGTTCAGCCGTAGAGTTGAGGTGACACGCCTTCGGCAGGTCGCAGGC
ATTCTCTGGGGGTTCACTTTGTCTGCTTTCTTCTACTCAGGGTGACCACGTGGACGCTGT
AGGCAAGGGGCTGTAGTGTGCCGAGCCTGTAGTGAGAAGAGGGACATGTTAGACTTCAGA
GAATTAAATCTGCCGCGGCACACAGCATGCATCTTGCAATATACCCATCTGCATGGTGCA
TAATTGCCGCAGCCTGCTTTATGTACCACTTCATACTCTCTTTTCTCAGGGTCCTGCAGG
CCAGACCTGCCCACTGCCTAGCTGTATTGCAACAAAAGACAATGCCTCGCGCCATCGCCA
TTACCTACTGGCAAAATGTCCGCGGTGTGCGCGTGCCGCGGGCGCGCGGCAAAACAAAAA
AAAACAGAACCCCAAAGGCAAACAATTAACAAAAAAACCCTGCCCAGGAATAATCTGCAG
ATCCCAGACCTAAAGCATTTTATGATTATTCGCTGAGCCCACCGGGCAATGTGACTGTAT
AAACTCCTGCAGCTCTGAGCCCACCCCGGCACCGCAAGGGGCGCGCAGCCGCAGGCTTTG
TGACCGCGCTTAATTTCGCCTGGGTGGACTGTTGCAGTTCAACGTATAGCAAATGCTCTA
TGGTGCTCACAACAGAAGGAGGAGGGGATAAAAGGGGGCTGGAGAAGGGCTTGAGAGAGG
AAATGAACACGGAATCCGCAGCTGGCGCTGGTGGCTGGAAGATGCGAGTCTCGGCAGCTG
TTGCCACCATGGCACGGTTGGTCGGTGGGTTAAGTGCATTTCAGGTTTTCTAGTCTGCGA
GACCACCCTAAATGGGCCATCAACTACACCCCAAATCTCCTTTTGCCTTTACCCAGAAGA
CAGAAGTACAAGACCTGAGCTAGGTGGGGGGTCTTCCGGTAAGCCTTAAGCCCCCTCCCC
TATTTGCACGAAAGCGGCAAACATGAATAACTCCTAAGGGGGCTTTGCTTGATTTTCTGC
AGTGCACTGCTGAGACCTTTATTTCTACTGCATCACCGTCCATATAAACAGAGCAAGCCC
TGACTACAACACACTATACCACTGTTGAGAGCTCCGAGGTGTAATGGGGATGGGGGACAT
TGAAGGGATTTGCTGGAGCCATCCCCAACAAACAGCAAACATAAACATTAAAAAAAGAAA
AAAAAGGAAAAAAAGAAATAAAGAAAAGTACCCTAGAGCATTTACGAAACAAATTGCG
TGTTTACATTCGGCACTTCCTCACCCTGTCTCTACCCTTCCGGTGGGCTCACGACCACCT
GTCGCATTTGTGTGTGTGTGCCTCTACCCCTTTCCTTGTATCCTAAAGCCTCCATTTC
```

FIG. 11A

CTGACTTGGAGATGAGTATGGGTAATTGCCTGAGTGTGGGGTCCTTAGATAAGGAATTTA
CCGCATACTGGGGTAATCTGGGGTGATAAAGCCCTCCTGCAGTCCCTCCTCCCCTCGAGA
CTCTTAAATGCCAAGAAGGCGGAGCTAAAGTACA
GCAAAGTACGAAGAGAGAACAGAAAAGTTCCTAAAGTTGTTGGCCGACCACAGCCCGAAG
GGGTAAGTGTAACTAGGAAGGTGACAGACTTCACCAGCAAGAGATGACTCACTTCAGCCA
TGGTCCTGGGTTCTAGCCCCTGATTATCTATCCTTACAAAGTTTGGAAACTGAGGCTGGA
GAACTTTCCAACAAAAATTTGAATTTTTAAAAAAAAATTTTTTTTCACCCTAGTTTGGC
TGGGTGCTCCGTCTTACGGGGCCCCAAATTTATTTTGAAAAGTCGCCACCGTGTTATGGG
CATGTTCAACTGCCTCCACGGCAATAATATGTCAGGACAACACGATATCCCCCCTGAAGT
CGGGGAGCAGCCCGAGCAAGAACCTTTGGAAGCCCCAGGGGCAGCTGCCCCCGGTGCTGG
GGCTGGCCCAGCCGAAGAAATGGCGACCGAACCGGACTCCGAACCGTCTAACAATGAGCC
CGTCCCCGACGAGACTGGCAGTGAGATCAGTGGACCCCAGAAGACTCCAAATCTGACAT
CCAAAGCCCCTGCCAGGCCTTCGAGGAAGTCCGAGTGGGTGGAGACTACAGCCCACCTCC
GGAGGAAGCCATGCCATTCGAGACACAACAGCCCAGCCTGGGAGATTTCTGGCCCACCCT
GGAGCAGCCAGGACCATCTGGGACCCCATCAGGCCTCCAAGCCTTCAACCCAGCGATTTT
GGAGCCCGGGACCCCCACTGGCGCGAGCCCAGGCCTGGGAGCCTATACCCCCCCACCAGA
AGAAGCTATGCCATTTGAGTTCAACGAGCCTGCCCAGGGAGACCATAGCCAGCCTCCCTT

FIG. 11B

MEG3

Bold/Underline - 5' UTR

Yellow - start of transcription (position 1532)

Entire region - imprinted differentially methylated region (DMR)

```
CTTGTCAGGGGCCTTCTTTTGGGGGCTCTTTGCAAAAATGGGGTGTTTTCTTTCTCTCC
CAGTATCTGACACATTCAGAAAGCTCTTTTTGATGCCCCAAAGCCCTAAACCTTCATTT
TCACCCTCCGAAGTGCATCGGTTCCTACCTTAACAACGCCCCACCCCTGAAAAGGCCTG
AGTCACCTCGCCGGCAAGCTGCTGATCGGTAACCCTGGGCTCAGCGGTGGCTTTCTCAG
TGCCTCTCAGCCCCAGGACCCGAGTCACAGTGGCATCCTAGGCTTGCTGGCCATAGGGG
CTTACGCGAAAGCAGCTGCAGAGGCGTAAATAAGGCGGCGGCGGGGGGTGGGGTGGGG
GGCTCTTCCAGCTTCATGTCCTCCACAGGGCCTCTGACTTTCCTTTTAGGGTCTCAATCA
TTCTCGCTCCTTTTCTGTCACCAGACGCTTCTTCTTTGGACTCACAGTTGCCACCCACCT
GTCACCCCAAGATAGATCCTTCGTCCCTTTCAACAGCATTCTGACCTTTTCGAGAGGACA
TTTGATGGACATGTTGCCCCCTTTGCCACTTAGGGTAGGCAGAGCAGCCGGAGGTACCAC
CTGTTAAGGATTAGCTCTCCTGTGCCAAGTCTCAGAGCGTCCGCAGCCAGCAGCTACGCA
CCATAGCAACATGTGTCTGCTTGGGCTGCGGAGAGGGGGGGCGCCCTTCAAAGTGTGGG
GAATCAGCCCGATTTGGGGGTGTACTCTAAGCATTACCACAGGGACCCCATTTTCACTAA
TTAAGTACTTTTCTTAGGGGGCACAGTTGCGCCTATATTCACAGTACACTCCGGGTTGCT
GGGTACCCTGTAACGGGCAGAAATGGGTCCTTGGGAAAGGGCGGAATAGCGCAAGGTTT
TTGGTGCACAGGTTGTATCTTCTGTAAAGCCTGGGACTCAAAATCAAGGTCCTTTTGCCT
CAACAATGCCAAATTCCCCGTATCAAGATAGTCCGTCAGAATCGGGGTACCCTATGTGGG
GGTGACAGCCTCCAGGCTAACATTTGGGAATCAATTATTTTATCTGGGATTTTTATTAAA
AATTTCCAGTGCAATTAGGAAAAAACAACGCTCTCCTTTCCTAAGCCGGAGCCCCTGACT
GATGTTCTGAGAAACCCAGGCAAGCCATCTGCCGATCCCCGGTACCCCACCTTTATCCTT
GGTCGCCTGAGAACAATCACCAGTTGGGGTTATTTCCCCCCAGTTTCTGTCTACAAATCG
CCCTTCCATCCACAACTAGGGCTCATGTAGGGAAAAATCACCAGCGACCACAGGGTGTTG
GTCATGGCGGCCAGGGGCACTGCGGCAGATTTTTTTTTCCTTCGTTCTTTGCTGCAGTCT
GGGTGCGGCTACAGCAATTTGTCATAGAATCTGGGGGGCTCATTTTCCGGCCAATCACT
TTTAGAGAAATGAGCGCATTGCAGCAGAATGCGCTGACGTCAAAGACCACCCCTTCTGCG
CCTTTATATAAACCCCACCCAGCCAGCCCCTAGCACAGAAGACGAAGAGCTGGAATAGAG
CTCGCCTCGGCTCTGCTGGCCTTGGCTGCAGCTCTTCCAGAAACCCGGGGCGCCCACAGA
AGAATCTCTTACCTGGTGAGTGGTTAGCCATCCTTTGCCTGAAAGGATGTGCAAAAATGA
AGACGACATCACTATCTGGCTTCGGCTCCGTCCTCCTGGACATGCCGAAAGGCCAGTGCT
GGGGACCTTCTCCCAAAGCCAGCCCCTTAGCCTGGTCCCCAGCATCCAACACGAAATTCT
GCAAGGAAAAGAATCCTCAGGCACATTTTTCTCGCGGGTGTGGGGGGTCCGGTCCACTA
GGGCTTTTTTTCTCACTAGTGTGGGCAGCGCGGTAGAGACCCTGATTAAGAAAAGCAGCA
ATAATGAGATATTCCGCCCCCAAATCCAGTGTATTTTTGTTTCTGGGGTCTAAAAACCTG
GTTTTGGTGGCTGAAAGCCCCCCTTAGAATCGCATTAATGGTGAGAGACATGGCGGCGAT
GCATCATCCCGCAAGCCCCATAAAATGGGGGGGGGGTACCTGAAAAGGGGGTCTCGAGC
CATCTTTTCTCCTAGCCAGGTTCTCGGCGGAACGTGGGCGTAAGATTTAGAGGTTCATG
TTGACCAGCAATTCTGAATCCAGATACTCGGGTTTAGTATAGACCTAACCTCGGGCAAAA
TATAGTGGGAAAAAAATGTAACCATTACTAGCCGTTTCCTGACGCAGCTACTTTAACAG
CGGAAAGAGAGGGCGTCAAAGGCAAATCTAGCCGGAGACCCCAGATCACAGAGAAGGCT
GCGGAACCGGGGGGCAAAGGCAGAATAGATGTGGGGGGTGGGCTAGGGTAGAAAAACCC
CACGTCCTTGCGTCTCATAGGAAGGAAAAGATAAAATGCAGAAAAGGGGGTGTGTGGAGG
TGTGGGGGTGATCTGAGTGCTGGAAATTTGGAGGCAGGGTTCTTTTTGGCATTGCGCAT
GATGGCTGCGGCTAGATTCTGACGTGTTGAAGGCTTTTGACTTTTGGTAAATCACCTTTT
GCCGTTTCCTTTGTCCCCGTGAAGCCCCCCTGGCCGCCCCTCCTCATTCTGGGCTGGC
TGGCTGAGGGGGGGCAGCCTGAGGGCTGCAGCGTGGCAGGTTTCTAGAATGTTCTATT
GATGGCCGCAAGAGGGCGCTGGTGGCACTGCGGAATTTTGGGGGCGGGGTGGGAGGGA
AGAGGAGGTGGCCTTTGTTCTCCT    (SEQ ID NO: 6)
```

FIG. 12

REPORTER OF GENOMIC METHYLATION AND USES THEREOF

RELATED APPLICATIONS

This application claims the benefit of U.S. Provisional Application No. 62/137,110, filed Mar. 23, 2015, U.S. Provisional Application No. 62/138,888, filed Mar. 26, 2015, and U.S. Provisional Application No. 62/139,611, filed Mar. 27, 2015. The entire teachings of the above applications are incorporated herein by reference.

GOVERNMENT SUPPORT

This invention was made with government support under grant number HD 045022 awarded by the National Institutes of Health. The Government has certain rights in the invention.

BACKGROUND

DNA methylation is recognized as a principal contributor to the stability of gene expression in development and to the maintenance of cellular identity (Bird, 2002; Cedar and Bergman, 2012; Jaenisch and Bird, 2003; Reik et al., 2001). A variety of methods for measuring DNA methylation are available. These include digestion of DNA with methylation-sensitive restriction enzymes, affinity-based enrichment and sequencing of DNA fragments containing methylated cytosine, and chemical conversion methods. A widely used chemical conversion method relies on the fact that treatment of DNA with bisulfite converts cytosine to uracil but leaves 5-methylcytosine intact. Thus, 5-methylcytosine patterns can be mapped by treating DNA with bisulfite, followed by sequencing. Microarray analysis (e.g., using the Illumina 450K Human Methylation array) of bisulfite-treated DNA has also been extensively used in studying methylation.

Recent advances in sequencing technologies have allowed the establishment of methylation maps from multiple cell types in both human (Ziller et al., 2013) and mouse (Hon et al., 2013). However, changes in DNA methylation are dynamic, and it is still largely unknown how epigenomic information dictates spatial and temporal gene expression programs (Smith and Meissner, 2013).

SUMMARY

In some aspects, described herein are methods that allow tracing of real-time changes in DNA methylation in living cells. Methods described herein couple DNA methylation to a detectable readout, allowing detection of the methylation state of a region of genomic DNA. Also described herein are products, e.g., nucleic acid constructs, vectors, cells, and non-human animals of use in the methods. Also described herein are methods of making the nucleic acid constructs, vectors, cells, and non-human animals. Also described herein are methods of identifying an agent that affects the methylation state of a region of DNA in the genome of a cell.

In some embodiments, the methylation state of a region of DNA in the genome of a cell is monitored over time, allowing for detection of changes in DNA methylation pattern. In some embodiments, methylation state of a region of DNA in the genome of a cell is detected at least once before a cell begins to undergo a change in cell state or a change in cell identity and at least once during the change in cell state or cell identity. In some embodiments, methylation state of a region of genomic DNA is detected at least once before a cell begins to undergo a change in cell state and at least once after the cell has undergone a change in cell state or cell identity. In some embodiments, a change in methylation of a region of genomic DNA that occurs in association with a change in cell state or a change in cell identity is detected. In some embodiments, a cell is exposed to an agent or condition and a change in methylation of a region of genomic DNA that occurs as a result of agent or condition is detected.

In some aspects, described herein is a nucleic acid comprising: (i) a mammalian imprinted gene promoter; and (ii) a sequence that encodes a reporter molecule that is detectable in individual mammalian cells, wherein the promoter is operably linked to the sequence that encodes the reporter molecule.

In some aspects, described herein is a nucleic acid comprising: (i) a mammalian imprinted gene promoter; and (ii) a sequence that encodes a reporter molecule, wherein the promoter is operably linked to the sequence that encodes the reporter molecule, and (iii) a first homology arm located 5' from the promoter and a second homology arm located 3' from the sequence that encodes a reporter molecule, wherein the homology arms comprise sequences that are homologous to sequences that flank a target location in a mammalian genome. In some embodiments the reporter molecule is one that is detectable in individual mammalian cells.

In some embodiments, the mammalian imprinted gene promoter in a nucleic acid described herein comprises at least a portion of a parent-of-origin differentially methylated region (DMR). In some embodiments, the nucleic acid further comprises a first homology arm located 5' from the promoter and a second homology arm located 3' from the sequence that encodes a reporter molecule, wherein the homology arms comprise sequences that are homologous to sequences that flank a target location in a mammalian genome. In some embodiments the target location is in proximity to a CpG island, CpG island shore, superenhancer, enhancer, promoter, or gene body. In some embodiments the CGI is a low density CGI. In some embodiments the CGI is a high density CGI. In some embodiments the target location is within a CpG island, CpG island shore, superenhancer, enhancer, promoter, or gene body. In some embodiments the target location is within 10 kb of a transcription start site (TSS). In some embodiments the target location is in proximity to a genetic locus that is aberrantly methylated in subjects suffering from a disorder associated with aberrant DNA methylation. For example, in some embodiments the target location is aberrantly hypermethylated or aberrantly hypomethylated in subject suffering from such a disorder.

In some embodiments the imprinted gene promoter is from a gene that is imprinted both in mice and humans. In some embodiments the imprinted gene promoter is from a gene that is imprinted in a species-specific manner. In some embodiments the imprinted gene promoter is from a gene selected from the group consisting of: Snrpn, Igf2r, Gnas, Igf2, Meg3 (Gtl2), Airn, Kcnq1ot1, Mest, Grb10, and Peg10. In some embodiments imprinted gene promoter is from the Snrpn gene. In some embodiments the sequence of the promoter comprises SEQ ID NO: 1 or SEQ ID NO: 2.

In some embodiments, the reporter molecule in a nucleic acid described herein comprises a fluorescent protein or a luciferase. In some embodiments the fluorescent protein is a green fluorescent protein, red fluorescent protein, or infrared fluorescent protein. In some embodiments the reporter molecule comprises a site-specific recombinase. In some embodiments the site-specific recombinase is Cre. In some embodiments, the nucleic acid further comprises a drug resistance marker or nutritional marker operably linked to a constitutive promoter.

In some embodiments, a nucleic acid comprising (i) a mammalian imprinted gene promoter and (ii) a sequence that encodes a reporter molecule further comprises a CpG-rich region, CpG shore, or low CpG region that is naturally found in a mammalian genome.

In some embodiments, a nucleic acid comprising (i) a mammalian imprinted gene promoter and (ii) a sequence that encodes a reporter molecule further comprises a sequence homologous to a regulatory region of a mammalian gene. In some embodiments the gene is a cell type specific gene. In some embodiments, the regulatory region comprises a CpG-rich region, CpG shore, or low CpG region.

In some embodiments, a nucleic acid comprising (i) a mammalian imprinted gene promoter and (ii) a sequence that encodes a reporter molecule further comprises a STOP cassette that inhibits synthesis of the reporter molecule and is flanked by recombination sites for a site-specific recombinase.

In some aspects, described herein is a vector comprising a nucleic acid comprising: (i) a mammalian imprinted gene promoter and (ii) a sequence that encodes a reporter molecule, wherein the promoter is operably linked to the sequence that encodes the reporter molecule. In some embodiments, the mammalian imprinted gene promoter may be any of the mammalian imprinted gene promoters described herein. In some embodiments, the reporter molecule may be any of the reporter molecules described herein. In some embodiments the vector is a transposon vector, plasmid, retroviral vector, lentiviral vector, or adeno-associated viral vector.

In some aspects, described herein is a kit comprising: (a) one or more nucleic acids comprising (i) a mammalian imprinted gene promoter; and (ii) a sequence that encodes a reporter molecule, wherein the promoter is operably linked to the sequence that encodes the reporter molecule and, optionally, one or more of the following: (b) a DNA methyltransferase; (c) a transfection reagent; (d) a buffer solution; and (e) instructions for use of the kit.

In some aspects, described herein is a cell comprising a nucleic acid comprising (i) a mammalian imprinted gene promoter and (ii) a sequence that encodes a reporter molecule, wherein the promoter is operably linked to the sequence that encodes the reporter molecule, and wherein the nucleic acid is integrated into the genome of the cell. In some embodiments the mammalian imprinted gene promoter comprises at least a portion of a parent-of-origin differentially methylated region (DMR). In some embodiments the imprinted gene is imprinted both in mice and humans. In some embodiments the imprinted gene is imprinted in a species-specific manner, e.g., in mice but not in humans, or in humans but not in mice. In some embodiments the imprinted gene promoter is a promoter of a gene selected from the group consisting of: Snrpn, Igf2r, Gnas, Igf2, Meg3 (Gtl2), Airn, Kcnq1ot1, Mest, Grb10, and Peg10. In some embodiments the imprinted gene promoter is from the Snrpn gene. In some embodiments the sequence of the promoter comprises SEQ ID NO: 1 or SEQ ID NO: 2.

In some embodiments the reporter molecule may be any of the reporter molecules described herein. In some embodiments the reporter molecule is detectable in individual cells. In some embodiments the reporter molecule comprises a fluorescent protein or a luciferase. In some embodiments the reporter molecule comprises a site-specific recombinase, e.g., Cre.

In some embodiments the nucleic acid is integrated into the genome of the cell in proximity to an enhancer, super-enhancer, promoter, gene body, CpG island, CpG island shore, or low CpG density region. In some embodiments the region is a distal regulatory region. In some embodiments the nucleic acid is integrated into the genome at a location no more than 10 kB away from a transcriptional start site. In some embodiments the nucleic acid is integrated into the genome at a location more than 10 kB away from a transcriptional start site.

In some embodiments the cell is a mammalian cell, e.g., a human or mouse cell. In some embodiments the cell is a somatic cell. In some embodiments the cell is a pluripotent stem cell. In some embodiments the cell is a germ cell, stem cell, or zygote. In some embodiments the cell is a primary cell. In some embodiments the cell is a diseased cell. In some embodiments the cell is a cancer cell. In some embodiments the cell is a white blood cell or fibroblast. In some embodiments the cell is a cell that has been isolated from an embryo. In some embodiments the cell is a cell that has been isolated from a subject suffering from a disorder associated with aberrant DNA methylation. In some embodiments, the genomic DNA of the cell comprises at least one region that has aberrant DNA methylation.

In some embodiments, the reporter molecule comprises a site-specific recombinase, and the genome of the cell further comprises recombination sites for the recombinase flanking a DNA segment whose excision or inversion results in a detectable change in the cell. In some embodiments the genome of the cell comprises a sequence encoding a second reporter molecule, wherein excision or inversion of the DNA segment results in turning expression of the second reporter molecule on or off. In some embodiments the second reporter molecule comprises a fluorescent protein or a luciferase. In some embodiments the genome of the cell further comprises a nucleic acid comprising a cell state or cell type specific promoter operably linked to a sequence that encodes an additional reporter molecule. In some embodiments the additional reporter molecule comprises a fluorescent protein or a luciferase. In some embodiments the cell state or cell type specific promoter is an endogenous promoter. In some embodiments the sequence that encodes the additional reporter molecule is integrated into the genome of the cell such that its transcription is under control of the endogenous promoter.

In some aspects, described herein is non-human mammal comprising at least one cell that comprises a nucleic acid comprising (i) a mammalian imprinted gene promoter and (ii) a sequence that encodes a reporter molecule, wherein the promoter is operably linked to the sequence that encodes the reporter molecule, and wherein the nucleic acid is integrated into the genome of the cell. In some embodiments the mammalian imprinted gene promoter comprises at least a portion of a parent-of-origin differentially methylated region (DMR). In some embodiments the imprinted gene is a gene that is imprinted both in mice and humans. In some embodiments the imprinted gene promoter is from a gene selected from the group consisting of: Snrpn, Igf2r, Gnas, Igf2, Meg3 (Gtl2), Airn, Kcnq1ot1, Mest, Grb10, and Peg10. In some embodiments the promoter is from the Snrpn gene. In some embodiments the sequence of the promoter comprises SEQ ID NO: 1 or SEQ ID NO: 2.

In some embodiments the reporter molecule may be any reporter molecule described herein. In some embodiments the reporter molecule comprises a fluorescent protein or a luciferase. In some embodiments the reporter molecule is detectable in vivo. In some embodiments the reporter molecule comprises a site-specific recombinase, e.g., Cre. In some embodiments the nucleic acid is integrated into the genome of the cell in proximity to an enhancer, superenhancer, promoter, gene body, CpG island, CpG shore, or low density CpG region. In some embodiments the nucleic acid is integrated into the genome at a location no more than 10 kB away from a transcriptional start site. In some embodiments the non-human mammal is a non-human primate or rodent. In some embodiments the non-human mammal is a mouse.

In some embodiments all or substantially all somatic cells of the non-human mammal have the nucleic acid or polypeptide integrated into their genome. In some embodiments the reporter molecule comprises a site-specific recombinase and the genome of the at least one cell further comprises recombination sites for the recombinase flanking a region that encodes a second reporter molecule. In some embodiments the second reporter molecule comprises a fluorescent protein or a luciferase. In some embodiments the genome of the at least one cell further comprises a cell state or cell type specific promoter operably linked to a region that encodes an additional reporter molecule. In some embodiments the additional reporter molecule comprises a fluorescent protein or a luciferase. In some embodiments the nucleic acid is integrated into a superenhancer, enhancer, promoter, gene body, CpG island, CpG shore, or low density CpG region. In some embodiments the nucleic acid is integrated into the genome at a location no more than 10 kB away from a transcriptional start site of a gene.

In some embodiments the nucleic acid is integrated into the genome of the at least one cell in proximity to a region that has aberrant DNA methylation in subjects suffering from a disorder associated with aberrant DNA methylation. In some embodiments the animal has a mutation associated with a disorder associated with aberrant DNA methylation. In some embodiments the animal has a mutation in at least one gene that encodes a DNA modifying enzyme. In some embodiments the mammal serves as a model for a human disorder associated with aberrant DNA methylation.

In some aspects, described herein is a method of generating an engineered mammalian cell comprising: (a) providing a mammalian cell; (b) introducing a nucleic acid or vector that comprises (i) a mammalian imprinted gene promoter; and (ii) a sequence that encodes a reporter molecule operably linked to the promoter into the cell; and (c) maintaining the cell for a time sufficient for the nucleic acid or vector to be integrated into the genome of the cell or a descendant of the cell, thereby generating an engineered mammalian cell. In some embodiments the method comprises contacting the cell with a targetable nuclease that cuts DNA in the genome of the cell at a location in proximity to a region of interest. In some embodiments contacting the cell with a targetable nuclease comprises expressing the targetable nuclease in the cell. In some embodiments the targetable nuclease comprises a Cas9 protein, and the method comprises contacting the cell with a guide RNA that targets the nuclease to a location in proximity to the region of interest (e.g., within the region of interest). The region of interest may be any region of interest described herein. The reporter molecule may be any reporter molecule described herein. The imprinted gene promoter may be any imprinted gene promoter described herein.

In some aspects, described herein is a method of detecting the methylation state of a DNA region of interest in the genome of a cell comprising: (a) providing one or more cells comprising (i) a mammalian imprinted gene promoter and (ii) a sequence that encodes a reporter molecule, wherein the sequence that encodes a reporter molecule is operably linked to the promoter and the nucleic acid is integrated in proximity to a region of interest in the genome of the cell; and (b) measuring expression of the reporter molecule by the one or more cells, wherein the level of expression of the reporter molecule is indicative of the level of methylation of the region of interest, thereby detecting the methylation state of the region of interest. In some embodiments expression of the reporter molecule is indicative of hypomethylation of the DNA region of interest and lack of expression of the reporter molecule is indicative of hypermethylation of the DNA region of interest. In some embodiments, measuring expression of the reporter molecule comprises measuring fluorescence or bioluminescence. In some embodiments measuring expression of the reporter molecule comprises performing fluorescence or bioluminescence imaging. In some embodiments measuring expression of the reporter molecule comprises performing fluorescence activated cell sorting (FACS).

In some embodiments the reporter molecule comprises a site-specific recombinase, and the genome of the cell further comprises recombination sites for the recombinase flanking a DNA segment whose excision or inversion results in turning expression of the second reporter molecule on or off, and measuring expression of the reporter molecule comprises measuring the second reporter molecule. In some embodiments the second reporter molecule comprises a fluorescent protein or a luciferase. In some embodiments the genome of the cell further comprises a cell type or cell state specific promoter operably linked to a nucleic acid sequence that encodes an additional reporter molecule. In some embodiments the promoter is an endogenous promoter of a cell type or cell state specific gene. In some embodiments the method further comprises measuring expression of the additional reporter molecule.

In some embodiments the method of detecting the methylation state of a DNA region of interest comprises exposing the cell to an agent or condition of interest; measuring expression of the reporter molecule encoded by a sequence that is operably linked to a mammalian imprinted gene promoter; and comparing the level of expression of the reporter molecule with a control value, wherein a difference between the measurement and the control value indicates that the agent or condition affects methylation of the region of interest. In some embodiments the agent is a small molecule. In some embodiments the method comprises placing the cell under conditions in which it undergoes a change in cell state; and measuring expression of the reporter molecule at one or more time points during the change in cell state, one or more time points after the change in cell state, or both. In some embodiments the change in cell state comprises a change to a more differentiated state or to a less differentiated state. In some embodiments the change in cell state comprises a change from a somatic cell to an induced pluripotent stem cell. In some embodiments the method further comprises measuring expression of one or more markers of cell identity or cell state by the one or more cells. In some embodiments expression of the reporter molecule is measured in an individual cell and its descendants. In some embodiments the cell is in a subject.

In some aspects, described herein is a method of monitoring the methylation state of a DNA region of interest in a cell over a period of time comprising steps of: (a) providing one or more cells comprising (i) a mammalian imprinted gene promoter and (ii) a sequence that encodes a reporter molecule, wherein the sequence that encodes the reporter molecule is operably linked to the promoter and the nucleic acid is integrated in proximity to a region of interest in the genome of the cell; and (b) measuring expression of the reporter molecule by the one or more cells at two or more time points, wherein the level of expression of the reporter molecule is indicative of the level of methylation of the region of interest, thereby monitoring the methylation state of the region of interest over a period of time. In some embodiments, a decrease in expression of the reporter molecule between first and second time points is indicative of an increase in the level of methylation of the region of interest, and a decrease in expression of the reporter molecule between first and second time points is indicative of an increase in the level of methylation of the region of interest. In some embodiments at least two of the time points are at least 12 hours apart. In some embodiments at least two of the time points are at least 7 days apart. In some embodiments the method comprises comparing the methylation state of the region of interest at a first time point with the methylation state of the region of interest at a second time point, thereby determining whether methylation of the region of interest increased or decreased between the first and second time points. In some embodiments measuring expression of the reporter molecule comprises measuring fluorescence or bioluminescence. In some embodiments measuring expression of the reporter molecule comprises performing fluorescence or bioluminescence imaging. In some embodiments measuring expression of the reporter molecule comprises performing fluorescence activated cell sorting (FACS). In some embodiments the reporter molecule comprises a site-specific recombinase, and the genome of the cell further comprises recombination sites for the recombinase flanking a DNA segment whose excision or inversion results in turning expression of the second reporter molecule on or off, and measuring expression of the reporter molecule comprises measuring the second reporter molecule. In some embodiments the second reporter molecule comprises a fluorescent protein or a luciferase. In some embodiments the genome of the cell further comprises a cell type or cell state specific promoter operably linked to a nucleic acid sequence that encodes an additional reporter molecule. In some embodiments the cell type or cell state specific promoter is an endogenous promoter of a cell type or cell state specific gene.

In some embodiments the method of monitoring the methylation state of a DNA region of interest comprises: exposing the cell to an agent or condition of interest; measuring expression of the reporter molecule at two or more time points; comparing the level of expression of the reporter molecule between two or more of the time points, wherein a difference between at least two of the time points indicates that the agent or condition affects methylation of the region of interest. In some embodiments the agent is a small molecule. In some embodiments the method comprises placing the cell under conditions in which it undergoes a change in cell state; and measuring expression of the reporter molecule at one or more time points during the change in cell state, one or more time points after the change in cell state, or both. In some embodiments the change in cell state comprises a change to a more differentiated state or to a less differentiated state. In some embodiments the change in cell state comprises a change from a somatic cell to an induced pluripotent stem cell. In some embodiments the method further comprises measuring expression of one or more endogenous genes or one or more additional reporter molecules by the one or more cells. In some embodiments the one or more endogenous genes or reporter molecules is a marker of cell identity or cell state. In some embodiments expression of the reporter molecule is measured in an individual cell and in one or more descendants of the cell.

In some aspects, described herein is a method of evaluating the effect of an agent on the methylation state of a DNA region of interest in a cell comprising steps of: contacting one or more cells comprising (i) a mammalian imprinted gene promoter; and (ii) a sequence that encodes a reporter molecule, wherein the sequence that encodes the reporter molecule is operably linked to the promoter and the nucleic acid is integrated in proximity to a region of interest in the genome of the cell, with a test agent; measuring expression of the reporter molecule; and comparing the level of expression of the reporter molecule with a control value, wherein a difference between the measured value and the control value indicates that the test agent modulates the methylation state of the region of interest. In some embodiments the test agent is a small molecule. In some embodiments the test agent is a protein or a nucleic acid. In some embodiments the method comprises detecting an increase in the level of expression of the reporter molecule as compared to the control value, thereby determining that the agent decreases methylation of the region of interest. In some embodiments the method comprises detecting a decrease in the level of expression of the reporter molecule as compared to the control value, thereby determining that the agent increases DNA methylation of the region of interest. In some embodiments the region of interest has aberrant DNA methylation in cells affected by a disorder. In some embodiments the region of interest is aberrantly hypermethylated in a disorder of interest, and the method comprises detecting an increase in the level of expression of the reporter molecule as compared to the control value, thereby determining that the agent decreases DNA methylation of the region of interest. In some embodiments the region of interest is aberrantly hypomethylated in a disorder of interest, and the method comprises detecting a decrease in the level of expression of the reporter molecule as compared to the control value, thereby determining that the agent increases DNA methylation of the region of interest.

In some aspects, described herein is a method of identifying an agent that modulates the methylation state of a DNA region of interest in a cell comprising steps of: contacting one or more cells of any of claims 24-54 with a test agent; measuring expression of the reporter molecule; comparing the level of expression of the reporter molecule with a control value; and detecting a difference between the measurement and the control value, thereby identifying the test agent as an agent that modulates the methylation state of a DNA region of interest in a cell. In some embodiments the test agent is a small molecule, a protein, or a nucleic acid. In some embodiments the method comprises detecting an increase in the level of expression of the reporter molecule as compared to the control value, thereby identifying the test agent as an agent that decreases the level of methylation of the region of interest. In some embodiments the method comprises detecting a decrease in the level of expression of the reporter molecule as compared to the control value, thereby identifying the test agent as an agent that increases the level of methylation of the region of interest. In some embodiments the region of interest has aberrant DNA methylation in cells affected by a disorder. For example in some embodiments the region of interest has aberrantly high DNA methylation in cells affected by a disorder. In some embodiments the region of interest has aberrantly low DNA methylation (e.g., aberrant loss of DNA methylation) in cells affected by a disorder. In some embodiments the method further comprises administering a test agent that modulates methylation of the region of interest to a mammalian subject. In some embodiments the mammalian subject serves as an animal model for a disorder associated with aberrant DNA methylation.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A-1G illustrate that an active minimal Snrpn promoter can be repressed in cis by means of spreading of DNA methylation into the promoter region. (FIG. 1A) Schematic representation of the sleeping-beauty based vectors. Endogenous CpG Islands (CGI) of Dazl and Gapdh genes were cloned upstream of a minimal Snrpn promoter region–driving GFP. Lollipops schematically represent individual CpG. (FIG. 1B) Flow cytometric analysis of V6.5 mESCs grown for 4 weeks in serum+LIF, following stable integration of unmethylated Gapdh and Dazl reporter vectors, demonstrating robust repression of GFP signal in the Dazl reporter cells. Shown are the mean percentages of GFP negative cells ±STD of two biological replicates. (FIG. 1C) Flow cytometric analysis of the proportion of GFP positive cells of Gapdh-GFP-positive sorted cells (left panel) and Dazl-GFP-negative sorted cells (right panel), following 7 days in culture. (FIG. 1D and FIG. 1E) Phase and fluorescence images of the sorted V6.5 mESCs, comprising stable integration of the Gapdh (left) and Dazl (right) vectors (FIG. 1D), and following prolonged culturing for 7 weeks (FIG. 1E). (FIG. 1F and FIG. 1G) Bisulfite sequencing analysis of the stably transfected Gapdh (FIG. 1F) and Dazl (FIG. 1G) reporter cell lines was performed on the gene promoter-associated CGI (left) and the downstream Snrpn promoter region (right). Open circles represents unmethylated CpGs; Filled circles—methylated CpGs.

FIGS. 2A-2I demonstrate that an in vitro repressed Snrpn promoter can be reactivated in cis by means of spreading of DNA demethylation into the promoter region. (FIG. 2A and FIG. 2B) Bisulfite sequencing analysis of the in vitro methylated Gapdh (FIG. 2A) and Dazl (FIG. 2B) vectors was performed on the gene promoter-associated CGI (left panels) and the downstream Snrpn promoter region (right panels). (FIG. 2C) Phase and fluorescence images of the stably integrated V6.5 mESCs, harboring Gapdh (left) and Dazl (right) in vitro methylated vectors, following one week of antibiotics selection. (FIG. 2D) Flow cytometric analysis of the proportion of GFP positive cells in V6.5 mESCs, stably integrated with either Gapdh (left panel) or Dazl (right panel) in vitro methylated vectors, following 2 weeks in culture. (FIG. 2E and FIG. 2F) Bisulfite sequencing analysis of the stably transfected Gapdh (FIG. 2E) and Dazl (FIG. 2F) reporter cell lines, was performed on the gene promoter-associated CGI left panels) and the downstream Snrpn promoter region (right panels). (FIG. 2G) Flow cytometric analysis of the proportion of GFP positive cells in V6.5 mESCs (upper panel), and Dnmt1 KO mESCs (lower panel), stably integrated with in vitro methylated Dazl reporter vector. (FIG. 2H) Flow cytometric analysis of the proportion of GFP negative cells in mESCs deficient for both Dnmt3a and Dnmt3b (Dnmt3ab KO), which were stably integrated with unmethylated Gapdh (upper panel) and Dazl (lower panel) reporter vectors. (FIG. 2I) Flow cytometric analysis of the proportion of GFP negative V6.5 mESCs grown in 2i+LIF, following stable integration of Gapdh (upper panel) and Dazl (lower panel) unmethylated reporter vectors.

FIGS. 3A-3D illustrate that generation of DNA methylation reporter cell lines for the pluripotent-specific miR290 and Sox2 SE regions. (FIG. 3A) Regional view depicting the DNA methylation (upper panel) and chromatin (lower panel) landscape of miR290 upstream pluripotent-specific SE. Shown are average methylation levels and enrichment of chromatin marks in mouse undifferentiated cells (green) and in adult tissues (gold), in respect to the genomic organization of the genes. DNA methylation varies from 1—hypermethylated to 0—hypomethylated; Characteristic clusters of typical enhancer marks and binding of tissue-specific TF determine the SE region (light blue). (FIG. 3B) CRISPR/Cas-based strategy used to integrate the DNA methylation reporter into the endogenous SE region. Green sequence—endogenous miR290 CpG region; Black sequence—targeting vector; Red sequence PAM recognition site. (FIG. 3C) Phase and fluorescence images of correctly integrated DNA methylation reporter cell lines for miR290 (upper panel) and Sox2 (lower panel) endogenous SE regions. GFP marks endogenous expression levels of Nanog, whereas tdTomato reflects the endogenous DNA methylation levels at both miR290 and Sox2 SE regions. (FIG. 3D) Bisulfite sequencing analysis was performed on undifferentiated mESCs harboring the DNA methylation reporter in either miR290 SE region (upper panel) or Sox2 SE region (lower panel). For each cell line, the PCR amplicon (marked with dashed line) includes both the endogenous CGI (left) and the downstream integrated Snrpn promoter region (right).

FIGS. 4A-4E show the dynamics of de novo DNA methylation of miR290 and Sox2 SE regions upon in vitro differentiation. (FIG. 4A) Schematic representation of the RA-based differentiation protocol used on miR290 and Sox2 reporter cell lines. GFP marks endogenous expression levels of Nanog, whereas tdTomato reflects the endogenous DNA methylation levels at both miR290 and Sox2 SE regions. (FIG. 4B) Flow cytometric analysis of the proportion of GFP positive cells (X axis) and tdTomato positive cells (Y axis) during 7 days of differentiation of miR290 #21 (upper panel) and Sox2 #2 (lower panel) reporter cell lines. (FIG. 4C) Bar graph summarizing the proportion of the different cell populations during the course of 7 days RA differentiation for both miR290 #21 (upper panel) and Sox2 #2 (lower panel) reporter cell lines. Data represents two biological replicates. R—tdTomato; G—GFP. (FIG. 4D and FIG. 4E) Bisulfite sequencing analysis on the three main cell populations—sorted at 48 hours following initial treatment with RA. For both miR290 #21 (FIG. 4D) and Sox2 #2 (FIG. 4E) cell lines, the PCR amplicon (marked with dashed line) includes the endogenous CGI (left) and the downstream integrated Snrpn promoter region (right). R—tdTomato; G—GFP.

(FIG. 5A) miR290 (upper panel) and Sox2 (lower panel) reporter chimeric embryos (Experiment embryos). For controls, Gapdh CGI reporter mESCs driving GFP and constitutively expressing tdTomato (Control Gapdh-GFP and tdTomato, respectively), were injected into a host blastocyst. Both miR290 and Sox2 embryos were compared to the same control embryo (left embryo in each panel). (FIG. 5B) Schematic representation of the experimental procedure to monitor the dynamics of demethylation during reprogramming of miR290 and Sox2 reporter cell lines. GFP marks endogenous expression levels of Nanog, whereas tdTomato reflects the endogenous DNA methylation levels at both miR290 and Sox2 SE regions. (FIG. 5C) Flow cytometric analysis of the proportion of GFP positive cells (X axis) and tdTomato positive cells (Y axis) in PO MEFs derived from miR290 #21 (left) and Sox2 #2 (right) chimeric embryos. (FIG. 5D) Bisulfite sequencing analysis was performed on PO MEFs derived from miR290 #21 (upper panel) and Sox2 #2 (lower panel) chimeras. For each cell line, the PCR amplicon (marked with dashed line) includes both the endogenous CGI (left) and the downstream integrated Snrpn promoter region (right). (FIG. 5E) Analysis of the proportion of GFP positive cells (X axis) and tdTomato positive cells (Y axis) during the course of reprogramming of MEFs derived from miR290 #21 (upper panel) and Sox2 #2 (lower panel) chimeras. Shown are flow cytometric data from different time points following addition of dox supplemented with 3C culture condition. (FIG. 5F) Representative images of established miR290 and Sox2 iPSC lines, derived from sorted double positive (tdTomato$^+$/GFP$^+$) colonies. (FIG. 5G) Bisulfite sequencing analysis was performed on P2 iPSCs derived from miR290 #21 (upper panel) and Sox2 #2 (lower panel) MEFs. For each cell line, the PCR amplicon (marked with dashed line) includes both the endogenous CGI (left) and the downstream integrated Snrpn promoter region (right).

(FIG. 6B) Flow cytometric analysis of V6.5 mESCs, following stable integration of unmethylated Gapdh and Dazl reporter vectors. Shown are the mean percentages of GFP negative cells ±STD of three biological replicates.

FIGS. 7A-7C illustrate the integration of DNA methylation reporter into pluripotent-specific SE regions. (FIG. 7A) Regional view depicting the DNA methylation (upper panel) and chromatin (lower panel) landscape of Sox2 upstream pluripotent-specific SE. Shown are average methylation levels and enrichment of chromatin marks in mouse undifferentiated cells (green) and in adult tissues (gold), in respect to the genomic organization of the genes. DNA methylation varies from 1—hypermethylated to 0—hypomethylated; Characteristic clusters of typical enhancer marks and binding of tissue-specific TF determine the SE region (light blue). (FIG. 7B) CRISPR/Cas-based strategy used to integrate the DNA methylation reporter into the SE region. Green sequence—endogenous Sox2 CpG region; Black sequence—targeting vector; Red sequence PAM recognition site. (FIG. 7C) Southern blot analysis (upper panels) and PCR (lower panels), were used to identify single and correct integration of GLINER into the endogenous miR290 (left) and Sox2 (right) SE region. Restriction enzymes used to detect the tdTomato-based probe, are designated above.

(FIG. 8A) Representative phase and fluorescence images of established MEFs derived from miR290 #21 (left) and Sox2 #2 (right) mESC lines, demonstrating complete repression of both tdTomato and GFP signals. (FIG. 8B) Analysis of the proportion of GFP positive cells (X axis) and tdTomato positive cells (Y axis) of Sox2 iPSCs following a split at day 28 of reprogramming. Shown are two consecutive passages, demonstrating a shift in the single GFP positive population towards a double positive cell population.

FIG. 9 depicts the sequence from Snrpn promoter region and minimal Srnpn promoter.

FIG. 10 depicts the sequence of Igftr promoter-associated differentially methylated region.

FIGS. 11A-11C depict the sequence of Gnas promoter-associated differentially methylated region.

FIG. 12 depicts the sequence of Meg3 promoter-associated differentially methylated region

DETAILED DESCRIPTION OF CERTAIN EMBODIMENTS

Glossary

Figure 1E:
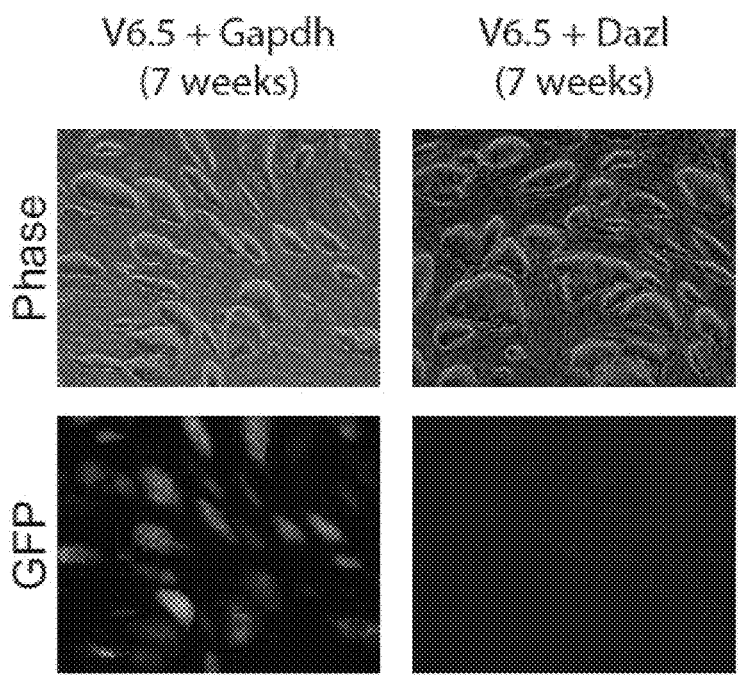

Certain terms used in the present application, and related information, are collected here for convenience. General or specific features of the description of terms in this glossary may be applied in or to any aspect, embodiment, context, description, or claim in which such term is used.

The term "aberrant DNA methylation" is used to indicate that the overall level of DNA methylation in the genome of one or more cells of interest and/or the DNA methylation level of one or more regions of DNA in the genome of one or more cells of interest is detectably different from a control level that is typical of that found in normal cells. If the level of methylation differs detectably from the control level (is higher than the control level or lower than the normal level) in either or both strands of a region of genomic DNA, the region is considered to be aberrantly methylated. The control level used for particular cell(s) of interest may be obtained from control cells maintained under the same or comparable conditions as the cells of interest (so long as those conditions are not known to significantly affect DNA methylation) or under standard conditions, which refers to typical culture conditions for cells of a given type or conditions in a normal, healthy subject or in a typical biological sample obtained from a normal, healthy subject. The control level of methylation for a particular DNA region is typically the level of methylation that such region normally exhibits when present in normal cells in its natural location. Normal cells from which a control level is obtained are typically of the same species as cells of interest for which they serve as a control. Control cells may be of the same cell type, developmental stage, and/or differentiation state as cells for which they serve as a control. For example, if a DNA region is known or suspected to be methylated in a cell or tissue specific manner, cells of the same type may be used as control cells; if methylation of a DNA region is known or suspected to be developmentally regulated, cells of the same developmental stage may be used as control cell. In some embodiments, the cell(s) of interest are obtained from a subject suffering from a disorder. Normal cells could be cells obtained from a subject not suffering from a disorder, e.g., a healthy subject. In some embodiments, normal cells are cells in the same tissue or organ as cells affected by a disorder, but located outside the area affected by the disorder. A control level may be measured using the same or a comparable assay as that used to obtain a value with which the control value is compared. Historical controls (e.g., values reported in the scientific literature or in databases or online resources such as the UCSC Genome Browser or GENCODE (available on the worldwide web at subdomain gencodegenes.org; ENCODE Project Consortium. Nature. 2012; 489(7414):57-74) may be used.

The term "biological sample" or "sample" refers to any biological specimen. In general, a biological sample of interest herein comprises one or more cells, tissue, or cellular material (e.g., material derived from cells, such as a cell lysate or fraction thereof). A biological sample may be obtained from (i.e., originates from, was initially removed from) a subject. In some embodiments a biological sample contains at least some intact cells. In some embodiments a biological sample retains at least some of the microarchitecture of a tissue from which it was removed. A biological sample may be subjected to one or more processing steps after having been obtained from a subject and/or may be split into one or more portions. The term "biological sample" encompasses processed samples, portions of samples, etc., and such samples are considered to have been obtained from the subject from whom the initial sample was removed. In some embodiments a sample may be obtained from an individual who has been diagnosed with or is suspected of having a mitochondrial disorder. A sample, e.g., a sample used in a method or composition disclosed herein, may have been procured directly from a subject, or indirectly, e.g., by receiving the sample from one or more persons who procured the sample directly from the subject, e.g., by a procedure on the subject.

The term "DNA region of interest" (also referred to as a "region of interest") refers to any DNA region selected by the artisan, e.g., for use in a product described herein or for use in or analysis according to methods described herein. A DNA region may be part of a larger piece of DNA or may be a separate piece of DNA with free 5' and 3' termini. In some embodiments a DNA region of interest is a stretch of DNA within a chromosome. In some embodiments a DNA region of interest is a segment of genomic DNA that is naturally present in the genome of a cell in its normal location. In some embodiments a DNA region of interest is a DNA segment that has been inserted into the genome of a cell by the hand of man. The DNA region of interest may be one that occurs naturally in the genome but at a different location from the location at which it is inserted. The DNA region of interest may be one for which the nucleotide sequence is contained in a publically available database or other publically available resource. The DNA region of interest may also be a naturally occurring variation of a reference nucleotide sequence (e.g., a sequence contained in a publically available database), including, for example, polymorphic variations of the sequence. A DNA region of interest may comprise a DNA element such as a promoter, enhancer, CpG island, gene body, or a portion thereof. For example, the DNA region of interest may comprise a promoter in an RGM construct (e.g., polymorphic variants of a mammalian imprinted gene promoter such as might possibly exist in different individuals or, where relevant, different strains or substrains). One of ordinary skill in the art appreciates, for example, that genome sequences from a variety of different mouse strains and substrains are available and that sequences from any such strain or substrain (or individual) could be used in various embodiments, and that one could obtain nucleic acids comprising a mammalian imprinted gene promoter or portion thereof, or other sequences such as those of a DNA region of interest by, for example, amplification using appropriate primers, regardless of whether the genome of such individual, strain, or substrain has been sequenced. It is notable that there are a large number of publicly available sequenced mouse genomes (see, for example, worldwide web at subdomain sanger-.ac.uk/resources/mouse/genomes/). In addition, one of ordinary skill in the art appreciates that many identified polymorphisms and other genetic variants can be found in the NCBI's Single Nucleotide Polymorphism database (db-SNP), for humans and various other species.

In certain embodiments the length of a region of DNA is between about 100 base pairs (bp) and about 500 bp, between about 500 bp and about 1000 bp (1 kb), between about 1 kb and about 2 kb, between about 2 kb and about 3 kb, between about 3 kb and about 4 kb, between about 4 kb and about 5 kb, between about 5 kb and about 10 kb, between about 10 kb and about 20 kb, or between about 20 kb and about 50 kb. In some embodiments a DNA region of interest comprises between about 10 and about 25 CpGs, between about 25 and about 50 CpGs, between about 50 and about 100 CpGs, between about 100 and about 250 CpGs, between about 250 and about 500 CpGs, between about 500 and about 1000 CpGs, or more.

The term "hypermethylation" refers to a higher level of methylation than the average level of methylation in the mammalian genome. A DNA region is considered hypermethylated if at least 80% of the CpG dinucleotides in the region are methylated. In some embodiments, at least 85%, at least 90%, at least 95%, at least 98%, at least 99%, or more (e.g., 100%) of the CpGs in the region are methylated. Where indicated or evident from the context, the term "hypermethylation" refers to an aberrantly high level of methylation as compared with a control level or an increased level of methylation as compared with a particular level with which it is compared. For example, if a particular region of genomic DNA has a level of methylation of 70% in cancer cells and normally has a level of methylation of 10% in normal cells, the DNA region is considered to be hypermethylated in cancer cells.

The term "hypomethylation" refers to a lower level of methylation than the average level of methylation in the mammalian genome. A DNA region is considered hypomethylated if no more than 50% of the CpG dinucleotides in the region are methylated. In some embodiments, no more than 40%, no more than 30%, no more than 20%, no more than 10%, no more than 5%, no more than 2%, or no more than 1% of the CpGs in the region are methylated. Where indicated or evident from the context, the term "hypomethylation" refers to an aberrantly low level of methylation as compared with a control level. For example, if a particular region of genomic DNA has a level of methylation of 10% in cancer cells and normally has a level of methylation of 70% in normal cells, the DNA region is considered to be hypomethylated in cancer cells.

"Imprinting" refers to the differential expression of alleles of the same gene in a parent-of-origin-specific manner, or to the biological process by which such a pattern is established. An "imprinted gene" is a gene that is subject to imprinting. Mammalian somatic cells are normally diploid, i.e., they contain two homologous sets of autosomes (chromosomes that are not sex chromosomes)—one set inherited from each parent, and a pair of sex chromosomes. Thus, mammalian somatic cells normally contain two copies of each autosomal gene—a maternal copy and a paternal copy. The two copies (often referred to as "alleles") may be identical or may differ at one or more nucleotide positions. For most genes, the alleles inherited from the mother and father exhibit similar expression levels. In contrast, imprinted genes are normally expressed in a parent-of-origin specific manner—either the maternal allele (the allele on the chromosome inherited from the mother) is expressed and the paternal allele (the allele present on the chromosome inherited from the father) is not, or the paternal allele is expressed and the maternal allele is not. The allele that is not expressed may be referred to as the "imprinted allele" or "imprinted copy". Imprinted genes can occur in large, coordinately regulated clusters or small domains composed of only one or two genes. Imprinting has generally been found to be conserved between mice and humans, i.e., if a gene is imprinted in mice, the orthologous gene is typically imprinted in humans as well, and vice versa. Parental allele-specific expression of imprinted genes is generally due to an imprinting control region.

As used herein, an "imprinting control region" (ICR), also referred to as an "imprinting control center" is a DNA region that controls the imprinting of at least one gene (typically a cluster of genes). In other words, ICRs control the monoallelic expression of the at least one gene in a manner that depends on the parental origin of the alleles. An ICR must be on the same chromosome as the imprinted gene(s) whose expression it affects but can be located a considerable distance away (e.g., up to several megabases away). ICRs are differentially methylated and are examples of differentially methylated regions (DMRs).

The term "isolated" means 1) separated from at least some of the components with which it is usually associated in nature; 2) prepared or purified by a process that involves the hand of man; and/or 3) not occurring in nature, e.g., present in an artificial environment. In some embodiments an isolated nucleic acid is a nucleic acid that is not found in nature and/or is outside a cell. In some embodiments an isolated cell is a cell that has been removed from a subject, generated in vitro, separated from at least some other cells in a cell population or sample, or that remains after at least some other cells in a cell population or sample have been removed or eliminated.

The term "level of methylation" refers to the proportion of cytosine nucleotide residues that are methylated within a given region of DNA, i.e., the total number of methylated cytosine residues in the region by the total number of nucleotides in the region. DNA methylation in mammals occurs most frequently on cytosines in CpG dinucleotides, and the level of methylation is often the same or about the same as the level of CpG methylation. Where the present disclosure refers to a level of methylation, certain embodiments relate specifically to the level of CpG methylation, i.e., the number of CpGs in the region that are methylated on the cytosine residue divided by the total number of CpGs in the region.

"Modulate" as used herein means to decrease (e.g., inhibit, reduce, suppress) or increase (e.g., stimulate, activate, enhance) a level, response, property, activity, pathway, or process. A "modulator" is an agent capable of modulating a level, response, property, activity, pathway, or process. In some embodiments modulation may refer to inhibition by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments modulation may refer to an increase by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%. 100%, 200% (2-fold), 5-fold, 10-fold, or more.

The terms "approximately" or "about" as used herein generally include numbers that fall within a range of 20% or in some embodiments within a range of 10% of a number or in some embodiments within a range of 5% of a number in either direction (greater than or less than the number) unless otherwise stated or otherwise evident from the context (except where such number would impermissibly exceed 100% of a possible value). Where the number is a nucleotide or amino acid position, "about" encompasses positions up to 5, 10, or 20 residues away. If the nucleotide or amino acid position defines an end of a nucleic acid or amino acid segment, "about" includes positions that fall within a range of 20% or in some embodiments within a range of 10% or in some embodiments within a range of 5% of the length of the nucleic acid or amino acid segment. For any embodiment in which a numerical value is prefaced by "about" or "approximately", an embodiment is disclosed in which the exact value is recited. For any embodiment in which a numerical value is not prefaced by "about" or "approximately", an embodiment in which the value is prefaced by "about" or "approximately" is disclosed.

The term "cell type specific gene" refers to a gene that is typically expressed selectively in one or a small number of cells types relative to its expression in many or most other cell types. A cell type specific gene is typically transcribed under direction of a cell type specific promoter in those cells in which it is transcribed. One of skill in the art will be aware of numerous genes that are considered cell type specific. "Cell type" is used interchangeably herein with "cell identity". A cell type specific gene need not be expressed only in a single cell type but may be expressed in one or several, e.g., up to about 5, or about 10 different cell types out of the approximately 200 commonly recognized (e.g., in standard histology textbooks) and/or most abundant cell types in an adult vertebrate, e.g., mammal, e.g., human. In some embodiments, a cell type specific gene is one whose expression level can be used to distinguish a cell, e.g., a cell as disclosed herein, such as a cell of one of the following types from cells of the other cell types: adipocyte (e.g., white fat cell or brown fat cell), cardiac myocyte, chondrocyte, endothelial cell, epidermal cells, epithelial cells, exocrine gland cell, fibroblast, glial cell, hematopoietic cells, hepatocyte, hair follicle cells, keratinocyte, macrophage, melanocyte, monocyte, mononuclear cell, myeloid cell, neuron, neutrophil, osteoblast, osteoclast, pancreatic islet cell (e.g., a beta cell), Sertoli cell, skeletal myocyte, smooth muscle cell, B cell, plasma cell, T cell (e.g., regulatory, cytotoxic, helper), or dendritic cell. In some embodiments a cell type specific gene is lineage specific, e.g., it is specific to a particular lineage (e.g., hematopoietic, neural, muscle, etc.). In some embodiments a cell type specific gene may be used to distinguish cells of a particular subtype within a more general type. For example, a cell type specific gene may be specifically expressed in a particular subtype of neuron as compared with other subtypes of neuron. In some embodiments, a cell type specific gene is a gene that is more highly expressed in a given cell type than in most (e.g., at least 80%, at least 90%) or all other cell types. Thus specificity may relate to level of expression, e.g., a gene that is widely expressed at low levels but is highly expressed in certain cell types could be considered cell type specific to those cell types in which it is highly expressed. It will be understood that expression can be normalized based on total mRNA expression (optionally including miRNA transcripts, long non-coding RNA transcripts, and/or other RNA transcripts) and/or based on expression of a housekeeping gene in a cell. In some embodiments, a gene is considered cell type specific for a particular cell type if it is expressed at levels at least 2, 5, or at least 10-fold greater in that cell than it is, on average, in at least 25%, at least 50%, at least 75%, at least 90% or more of the cell types of an adult of that species, or in a representative set of cell types. One of skill in the art will be aware of databases containing expression data for various cell types, which may be used to select cell type specific genes. In some embodiments a cell type specific gene is a transcription factor. The transcription factor may be one that is involved in establishing or maintaining the particular identity (cell type) of the cell ("master transcription factors"). In some embodiments a cell type specific gene is one that encodes a protein or RNA that plays a role in a biological process or function for which cells of a given type are particularly adapted (i.e., it is the only cell type or one of only a few cell types that carry out that biological process or function). Cell type specific genes include, e.g., genes that encode certain intermediate filament proteins (e.g., keratins), tubulins, integrins, enzymes involved in synthesis of specialized cell products such as neurotransmitters or hormones or growth factors, receptors for specialized cell products, CD molecules. Cell type specific genes and/or their encoded gene products may be referred to as "markers" of cell identity. One of ordinary skill in the art would appreciate that cells of a given type may be identified by their level of expression (e.g., "positive" or "negative") of one or a combination of cell identity markers. Other characteristics such as morphology, light scatter, and/or location of the cell in the body, may be used alternately or in combination with marker expression levels.

The term "cell state specific gene" refers to a gene that is typically expressed selectively in cells in a particular state relative to its expression in many or most cells that are not in that state. In some embodiments a cell state specific gene is one that encodes a protein or RNA that plays a role in establishing or maintaining the particular cell state. For example, the gene may be characterized in that inhibiting its expression causes the cell to cease being in a particular state, e.g., causes the cell to enter a different state or may be characterized in that ectopically expressing the gene (sometimes in combination with one or more other genes) causes a cell that is not in a particular state to assume that state. Cell state specific genes and/or their encoded gene products may be referred to as "markers" of cell state. One of ordinary skill in the art would appreciate that cells of a given type may be identified by their level of expression (e.g., "positive" or "negative") of one or a combination of cell state markers. Other characteristics such as morphology, light scatter, and/or location of the cell in the body, may be used alternately or in combination with marker expression levels.

The term "DNA methylation" refers to the covalent attachment of a methyl group to DNA at the C5 position of a cytosine ring. In mammals, DNA methylation typically occurs at a cytosine (C) that is followed, in the 5' to 3'direction, by a guanine (G). This dinucleotide is often referred to as a CpG. There are approximately 28 million CpGs in the diploid mammalian genome, of which roughly 60%-80% are methylated in somatic cells (Smith, Z. D., and Meissner, A. (2013)). Three enzymes, DNA methyltransferase 1 (DNMT1), DNMT3A, and DNMT3B, are responsible for DNA methylation and maintenance in mammals. DNA methylation is heritable through somatic cell divisions. DNMT1 has a preference for hemimethylated DNA (i.e., double-stranded DNA that is methylated on only one cytosine within CpGs located opposite one another in the two strands) and is mainly responsible for maintaining genomic DNA methylation patterns during DNA replication by methylating cytosines in the newly synthesized strand, thereby converting hemimethylated CpG dinucleotides generated after replication to fully methylated CpG. DNMT3A and DNMT3B are mainly responsible for de novo DNA methylation, i.e., methylation at sites that are not hemimethyl-ated. However, all three enzymes may contribute to both maintenance and de novo DNA methylation. DNMT3L is a catalytically inactive protein that interacts with these enzymes to stimulate DNA methylation. DNA can be demethylated by active and passive processes. So-called passive demethylation occurs through failure to methylate cytosines on the newly synthesized strand during DNA replication, which can result from downregulation of DNMT1. Active demethylation refers to processes in which the methyl group is enzymatically processed and removed. Members of a family often-eleven translocation (TET) proteins (e.g., Tet1, Tet2, Tet3) can catalyze stepwise oxidation of 5hmC to 5-formylcytosine (5fC) and 5-carboxylcytosine (5caC). 5fC and 5caC can be recognized and excised by thymine DNA glycosylase (TDG) to generate an abasic site, which can be repaired to unmodified cytosine through the base excision repair pathway.

The term "disorder associated with aberrant DNA methylation" refers to any disorder in which aberrant DNA methylation is found more frequently in at least some cells in subjects who have the disorder than in cells of healthy subjects. The term "disorder" encompasses any disorder, disease, syndrome, or other clinical condition. Examples of disorders associated with aberrant DNA methylation include Alzheimer's disease, autism spectrum disorders, autoimmune disorders (e.g., rheumatoid arthritis, lupus), cancer, male infertility, psychiatric disorders (e.g., bipolar disorder, depression, schizophrenia), Rett syndrome, and Fragile X syndrome. Those of ordinary skill in the art are familiar with the clinical characteristics and methods for diagnosis of disorders of interest herein. Imprinting disorders are considered to be disorders associated with aberrant DNA methylation.

The term "identity" or "percent identity" refers to a measure of the extent to which the sequence of two or more nucleic acids or polypeptides is the same. The percent identity between a sequence of interest A and a second sequence B may be computed by aligning the sequences, allowing the introduction of gaps to maximize identity, determining the number of residues (nucleotides or amino acids) that are opposite an identical residue, dividing by the minimum of $TG_A$ and $TG_B$ (here $TG_A$ and $TG_B$ are the sum of the number of residues and internal gap positions in sequences A and B in the alignment), and multiplying by 100. When computing the number of identical residues needed to achieve a particular percent identity, fractions are to be rounded to the nearest whole number. Sequences can be aligned with the use of a variety of computer programs known in the art. For example, computer programs such as BLAST2, BLASTN, BLASTP, Gapped BLAST, etc., may be used to generate alignments and/or to obtain a percent identity. The algorithm of Karlin and Altschul (Karlin and Altschul, Proc. Natl. Acad. Sci. USA 87:22264-2268, 1990) modified as in Karlin and Altschul, Proc. Natl. Acad Sci. USA 90:5873-5877, 1993 is incorporated into the NBLAST and XBLAST programs of Altschul et al. (Altschul, et al., J. Mol. Biol. 215:403-410, 1990). In some embodiments, to obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. See worldwide web at subdomain ncbi.nlm.nih.gov and/or McGinnis, S. and Madden, T L, W20-W25 Nucleic Acids Research, 2004, Vol. 32, Web server issue. Other suitable programs include CLUSTALW (Thompson J D, Higgins D G, Gibson T J, Nuc Ac Res, 22:4673-4680, 1994) and GAP (GCG Version 9.1; which implements the Needleman & Wunsch, 1970 algorithm (Needleman S B, Wunsch C D, J Mol Biol, 48:443-453, 1970.) Percent identity may be evaluated over a window of evaluation. In some embodiments a window of evaluation may have a length of at least 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more, e.g., 100%, of the length of the shortest of the sequences being compared. In some embodiments a window of evaluation is at least 100; 200; 300; 400; 500; 600; 700; 800; 900; 1,000; 1,200; 1,500; 2,000; 2,500; 3,000; 3,500; 4,000; 4,500; or 5,000 amino acids. In some embodiments no more than 20%, 10%, 5%, or 1% of positions in either sequence or in both sequences over a window of evaluation are occupied by a gap. In some embodiments no more than 20%, 10%, 5%, or 1% of positions in either sequence or in both sequences are occupied by a gap.

The term "imprinting disorder" refers to any disorder caused by alterations in the normal imprinting pattern, any disorder caused by changes in expression or gene dosage of an imprinted gene, and/or any disorder caused by the mutation or deletion of an imprinted gene. Non-limiting examples of imprinting disorders include Angelman syndrome, Prader-Willi syndrome, Beckwith-Wiedemann syndrome, Silver-Russell syndrome, and certain forms of pseudohypoparathyroidism.

The term "integrated" when used to refer to refer to a nucleic acid (e.g., a DNA methylation reporter) being integrated into the genome of a cell means that the nucleic acid is incorporated into the genome of the cell. It should be understood that use of the term "integrated" is not intended to imply any particular mechanism by which such incorporation occurs. "Integration" encompasses processes by which exogenous DNA is directly incorporated into the genome as well as processes in which exogenous nucleic acid is used as a template for homology-directed repair of a break in genomic DNA resulting in some sequences from the exogenous DNA being introduced into the genome. The incorporated DNA is joined to the genomic DNA by phosphodiester bonds, and, if the cell undergoes cell division, it will typically be replicated and inherited by the cell's descendants, and is considered to be integrated into the genome of the cell's descendants. The terms "integrated", "inserted", "introduced", and "incorporated" into the genome of a cell may be used interchangeably herein.

An "effective amount" or "effective dose" of an agent (or composition containing such agent) generally refers to the amount sufficient to achieve a desired biological and/or pharmacological effect, e.g., when contacted with a cell in vitro or administered to a subject according to a selected administration form, route, and/or schedule. As will be appreciated by those of ordinary skill in the art, the absolute amount of a particular agent or composition that is effective may vary depending on such factors as the desired biological or pharmacological endpoint, the agent to be delivered, the target tissue, etc. Those of ordinary skill in the art will further understand that an "effective amount" may be contacted with cells or administered in a single dose, or through use of multiple doses, in various embodiments. It will be understood that any agents, nucleic acid constructs, compounds, and compositions herein may be employed in an amount effective to achieve a desired biological and/or therapeutic effect.

The term "matched cells" typically refers to cells of the same species and cell type as particular cells of interest, or to comparable cells known to have similar properties with respect to DNA methylation of the DNA region(s) under consideration. Matched cells may be of the same developmental stage and/or differentiation state as cells of interest. Any method or experiment that includes manipulating a cell (e.g., exposing a cell to an agent) may include a comparison with matched cells as controls that are not so manipulated.

The term "promoter" refers to a regulatory region of DNA that directs transcription of a nucleic acid (the process by which RNA is synthesized using DNA as a template). A promoter for a particular gene is typically located within the region extending from up to about 2 kilobases (kb) upstream from the transcription start site (TSS) for that gene up to about 500 bp downstream from the TSS. A promoter contains DNA sequences with which general transcription factors and RNA polymerase associate to form a transcription pre-initiation complex near the transcription start site and typically also contains one or more binding sites for additional transcription factor(s). A promoter that comprises a variant or fragment of a naturally occurring promoter region may be said to be "derived from" the naturally occurring promoter. Mammalian promoters can be generally classified into those that contain a TATA box, those that are CpG enriched (e.g., contain a CpG island), and those that contain both a TATA box and are CpG enriched. A "constitutive" or "ubiquitous" promoter is one that is active ("on") in most cells (in the case of a multicellular organism), cell states, and under most environmental conditions. Promoters that are not constitutive may be cell type specific or tissue-specific (active in particular cell types or tissues but inactive ("off") in others) or cell state specific (active in cells in particular states but inactive in other cells), may be subject to developmental regulation (active during one or more stages of development but not in others), may be active only during particular stages of a biological process such as cell division, and/or may be subject to environmental regulation. An "inducible" promoter is one whose activity can be regulated by an environmental condition such as the presence or absence of a particular substance, temperature, etc.

The term "minimal promoter" refers to the smallest portion of a promoter that has the ability to drive transcription at a detectable level. For purposes of the present disclosure, a "minimal promoter" may contain up to an additional 50, 100, or 200 bp of sequence flanking either or both sides of this smallest portion. For example, if the smallest portion of a naturally occurring promoter that has the ability to drive transcription at a detectable level extends from −100 to +50 (with +1 representing the TSS), then a minimal promoter may comprise a sequence that extends from −300 to +250. In some embodiments a minimal promoter is able to drive transcription at a level at least 50%, 60%, 70%, 80%, or 90% of the level of a naturally occurring promoter region from which it is derived, e.g., between about 50% and about 75% or between about 75% and about 100% of the level of the promoter from which it is derived, when measured under the same or comparable conditions using the same or a comparable assay. In some embodiments, a minimal promoter is characterized in that removal of at least 50 nt, or in some embodiments removal of at least 100 nt, or in some embodiments removal of at least 200 nt, from either or both ends, would markedly reduce the level of transcription, e.g., by at least 50%, or at least 75%.

The term "promoter region" refers to a region of genomic DNA that extends from 2.5 kb upstream of the transcriptional start site (TSS) of a gene to 500 bp downstream of the TSS, i.e., from position −2500 to position +500 relative to the TSS (defined as position +1).

The term "enhancer" refers to a region of genomic DNA to which proteins (e.g., transcription factors) bind to enhance (increase) transcription of a gene. Enhancers may be located some distance away from the promoters and transcription start site (TSS) of genes whose transcription they regulate and may be located upstream or downstream of the TSS. Enhancers can be identified using methods known to those of ordinary skill in the art based on one or more characteristic properties. For example, H3K27Ac is a histone modification associated with active enhancers (Creyghton et al., 2010b; Rada-Iglesias et al., 2010). In some embodiments enhancers are identified as regions of genomic DNA that when present in a cell show enrichment for acetylated H3K27 (H3K27Ac), enrichment for methylated H3K4 (H3K4me1), or both. Enhancers can additionally or alternately be identified as regions of genomic DNA that when present in a cell are enriched for occupancy by transcription factors. Histone modifications can be detected using chromatin immunoprecipitation (ChIP) followed by microarray hybridization (ChIP-Chip) or followed by sequencing (ChIP-Seq) or other methods known in the art. These methods may also or alternately be used to detect occupancy of genomic DNA by transcription factors (or other proteins). A peak-finding algorithm such as that implemented in MACS version 1.4.2 (model-based analysis of ChIP-seq) or subsequent versions thereof may be used to identify regions of ChIP-seq enrichment over background (Zhang, Y., et al. (2008). Genome Biol. 9, R137). In some embodiments a p-value threshold of enrichment of $10^{-9}$ may be used.

The term "superenhancer" refers to a region of genomic DNA that contains at least two enhancers, e.g., a cluster of enhancers, wherein the genomic region is occupied when present within a cell by more transcriptional coactivator (e.g., Mediator) than the average single enhancer within the cell. Super-enhancers are typically also enriched for occupancy by cell type specific transcription factors, including master transcription factors and other genes that play key roles in cell identity and can enhance the expression of such genes. Super-enhancers can be identified and/or assigned to genes whose transcription is regulated by the superenhancer using methods known in the art. Occupancy of genomic DNA by Mediator, transcription factors, or other proteins can be detected using ChIP-Chip, ChIP-Seq, or other methods known in the art. Numerous super-enhancers and their target genes have been identified. See, e.g., U.S. Patent Application Pub. Nos. 20140296218 and 20140287932; Whyte et al., 2013; Hnisz et al., 2013; Lovén et al. (2013) Cell 153, 320-334) and/or PCT/US2013/066957 (WO/2014/066848). A catalog of super-enhancers, typical enhancers, and associated genes in 86 human samples from a broad range of cell and tissue types, and description of methods used to identify them, is found in Hnisz et al. and in PCT/US2013/066957 (WO/2014/066848).

The term "transcription start site" (TSS) refers to the DNA nucleotide at which transcription of a RNA begins, i.e., the nucleotide that is transcribed to yield the first ribonucleotide in an RNA transcript. TSSs may be defined based on RefSeq gene annotations.

The term "gene body" refers to the portion of a gene that is transcribed, from the transcription start site to the end of the transcribed region.

The terms "enriched" or "enrichment" refer to the presence of something at a higher level in a first region or under a first condition than in a second region or under a second condition with which it is compared. If a second location or condition is not specified, it should be assumed that enrichment refers to the level in the first region or under the condition relative to the background level of that thing in the setting in which it occurs. For example, a DNA region is considered "enriched" for a particular nucleotide or sequence motif or for a particular nucleic acid modification or histone modification if that nucleotide or modification is present at a higher level within the region than in the genome as a whole. Preferably the difference between the two levels is statistically significant. In some embodiments, enrichment refers to an increase by at least a factor of 2, 5, 10, 20, or 50-fold. In some embodiments enrichment is evident as a peak when the level of a particular nucleic acid modification or other genomic feature is measured across the genome or a portion thereof.

The term "nucleic acid" refers to polynucleotides such as deoxyribonucleic acid (DNA) and ribonucleic acid (RNA). The terms "nucleic acid" and "polynucleotide" are used interchangeably herein and should be understood to include double-stranded polynucleotides, single-stranded (such as sense or antisense) polynucleotides, and partially double-stranded polynucleotides. A nucleic acid often comprises standard nucleotides typically found in naturally occurring DNA or RNA (which can include modifications such as methylated nucleobases), joined by phosphodiester bonds. In some embodiments a nucleic acid may comprise one or more non-standard nucleotides, which may be naturally occurring or non-naturally occurring (i.e., artificial; not found in nature) in various embodiments and/or may contain a modified sugar or modified backbone linkage. Nucleic acid modifications (e.g., base, sugar, and/or backbone modifications), non-standard nucleotides or nucleosides, etc., such as those known in the art as being useful in the context of RNA interference (RNAi), aptamer, CRISPR technology, polypeptide production, reprogramming, or antisense-based molecules for research or therapeutic purposes may be incorporated in various embodiments. Such modifications may, for example, increase stability (e.g., by reducing sensitivity to cleavage by nucleases), decrease clearance in vivo, increase cell uptake, or confer other properties that improve the translation, potency, efficacy, specificity, or otherwise render the nucleic acid more suitable for an intended use. Various non-limiting examples of nucleic acid modifications are described in, e.g., Deleavey G F, et al., Chemical modification of siRNA. Curr. Protoc. Nucleic Acid Chem. 2009; 39:16.3.1-16.3.22; Crooke, S T (ed.) Antisense drug technology: principles, strategies, and applications, Boca Raton: CRC Press, 2008; Kurreck, J. (ed.) Therapeutic oligonucleotides, RSC biomolecular sciences. Cambridge: Royal Society of Chemistry, 2008; U.S. Pat. Nos. 4,469,863; 5,536,821; 5,541,306; 5,637,683; 5,637,684; 5,700,922; 5,717,083; 5,719,262; 5,739,308; 5,773,601; 5,886,165; 5,929, 226; 5,977,296; 6,140,482; 6,455,308 and/or in PCT application publications WO 00/56746 and WO 01/14398. Different modifications may be used in the two strands of a double-stranded nucleic acid. A nucleic acid may be modified uniformly or on only a portion thereof and/or may contain multiple different modifications. Where the length of a nucleic acid or nucleic acid region is given in terms of a number of nucleotides (nt) it should be understood that the number refers to the number of nucleotides in a single-stranded nucleic acid or in each strand of a double-stranded nucleic acid unless otherwise indicated. An "oligonucleotide" is a relatively short nucleic acid, typically between about 5 and about 100 nt long.

The term "operably linked" refers to a nucleic acid regulatory element and a nucleic acid sequence being appropriately positioned relative to each other so as to place expression of the nucleic acid under the influence or control of the regulatory element(s). For example, a promoter and a nucleic acid are considered "operably linked" if they are positioned in such a way in a DNA molecule that the promoter region is capable of directing transcription of the nucleic acid under appropriate conditions. As used herein, "operably linked" refers to the positional relationship between the regulatory element(s) and the nucleic acid sequence as distinct from the activity level of the promoter. It will be understood that whether a particular promoter does in fact direct transcription of an operably linked nucleic acid molecule, and the level of transcription, may depend on a variety of factors, such as the presence or absence of appropriate transcription factors and/or the presence or absence of inhibitory substances or other factors that may affect the activity of the promoter.

The term "pluripotent" refers to a cell that has the ability to self-renew and to differentiate into cells of all three embryonic germ layers (endoderm, mesoderm and ectoderm) and, typically, has the potential to divide in vitro for a long period of time, e.g., at least 20, at least 25, or at least 30 passages, or more (e.g., up to 80 passages, or up to 1 year, or more), without losing its self-renewal and differentiation properties. A pluripotent cell is said to exhibit or be in a "pluripotent state". A pluripotent cell line or cell culture is often characterized in that the cells can differentiate into a wide variety of cell types in vitro and in vivo. Cells that are able to form teratomas containing cells having characteristics of endoderm, mesoderm, and ectoderm when injected into SCID mice are considered pluripotent. Cells that possess ability to participate in formation of chimeras (upon injection into a blastocyst of the same species that is transferred to a suitable foster mother of the same species) that survive to term are pluripotent. If the germ line of the chimeric animal contains cells derived from the introduced cell, the cell is considered germline-competent in addition to being pluripotent. Pluripotent cells (also referred to as pluripotent stem cells) include embryonic stem (ES) cells and induced pluripotent stem (iPS) cells. Embryonic stem cells are pluripotent stem cells that are derived directly from an embryo, e.g., from a single blastomere, morula or from the inner cell mass of blastocyst, or by somatic cell nuclear transfer (SCNT). Those of ordinary skill in the art are aware of suitable methods for deriving mammalian ES cells from mice, rats, humans, non-human primates, and other mammalian species. See Behringer, R, et al., Manipulating the Mouse Embryo, A Laboratory Manual, 4$^{th}$ ed., Cold Spring Harbor Laboratory Press, Cold Spring Harbor, N.Y., 2013 for exemplary techniques for deriving murine ES cells. Exemplary techniques for deriving primate ES cells are found in U.S. Pat. No. 6,200,806; Turksen, K. (ed.), Methods in Molecular Biology, Vo. 331 Humana Press, Inc. Totowa, N H, 2006, PCT/US2011/000850 (WO/2011/142832); and Zaninovic N, et al., Methods Mol Biol. 2014; 1154:121-44.

The term "polypeptide" refers to a polymer of amino acids linked by peptide bonds. A protein is a molecule comprising one or more polypeptides. A peptide is a relatively short polypeptide, typically between about 2 and 100 amino acids (aa) in length, e.g., between 4 and 60 aa; between 8 and 40 aa; between 10 and 30 an. The terms "protein", "polypeptide", and "peptide" may be used interchangeably. In general, a polypeptide may contain only standard amino acids or may comprise one or more non-standard amino acids (which may be naturally occurring or non-naturally occurring amino acids) and/or amino acid analogs in various embodiments. A "standard amino acid" is any of the 20 L-amino acids that are commonly utilized in the synthesis of proteins by mammals and are encoded by the genetic code. A "non-standard amino acid" is an amino acid that is not commonly utilized in the synthesis of proteins by mammals. Non-standard amino acids include naturally occurring amino acids (other than the 20 standard amino acids) and non-naturally occurring amino acids. An amino acid, e.g., one or more of the amino acids in a polypeptide, may be modified, for example, by addition, e.g., covalent linkage, of a moiety such as an alkyl group, an alkanoyl group, a carbohydrate group, a phosphate group, a lipid, a polysaccharide, a halogen, a linker for conjugation, a protecting group, a small molecule (such as a fluorophore), etc.

The terms "purified" may be used herein to refer to an isolated nucleic acid or polypeptide that is present in the substantial absence of other biological macromolecules, e.g., other nucleic acids and/or polypeptides. In some embodiments a purified nucleic acid (or nucleic acids) is substantially separated from cellular polypeptides. In some embodiments, the ratio of nucleic acid to polypeptide is at least 5:1 or at least 10:1 by dry weight. In some embodiments a purified polypeptide is separated from cellular nucleic acids. In some embodiments, the ratio of nucleic acid to polypeptide is at least 5:1 or at least 10:1 by dry weight. In some embodiments, a nucleic acid or polypeptide is purified such that it constitutes at least 75%, 80%, 85%, or 90% by weight, e.g., at least 95% by weight, e.g., at least 99% by weight, or more, of the total nucleic acid or polypeptide material present. In some embodiments, water, buffers, ions, and/or small molecules (e.g., precursors such as nucleotides or amino acids), can optionally be present in a purified preparation. A purified molecule may be prepared by separating it from other substances (e.g., other cellular materials), or by producing it in such a manner to achieve purity. In some embodiments, a purified molecule or composition refers to a molecule or composition comprising one or more molecules that is prepared using any art-accepted method of purification.

As used herein, two regions or positions (or a region and a position) within a DNA molecule (e.g., a chromosome) are said to be "in proximity to" each other if the distance between them in terms of nucleotides (i.e., the length of any intervening DNA between them) is no more than 20 kb. In some embodiments the distance is no more than 10 kb, no more than 5 kb, no more than 2 kb, no more than 1 kb, no more than 500 nt, no more than 250 nt, no more than 100 nt, no more than 50 nt, no more than 25 nt, no more than 10 nt, no more than 5 nt, or 0 nt (i.e., the regions, positions, or region and position are directly adjacent to each other). If a first nucleic acid is integrated into a particular region of DNA in the genome, the nucleic acid is said to be in proximity to the region of DNA, and vice versa.

The term "reporter molecule" refers to a molecule that can be used as an indicator of the occurrence or level of a particular biological process, activity, event, or state in a cell or organism. Reporter molecules typically have one or more properties or enzymatic activities that allow them to be readily measured or that allow selection of a cell that expresses the reporter molecule. In general, a cell can be assayed for the presence of a reporter molecule by measuring the reporter molecule itself or an enzymatic activity of the reporter protein. Detectable characteristics or activities that a reporter molecule may have include, e.g., fluorescence, bioluminescence, ability to catalyze a reaction that produces a fluorescent or colored substance in the presence of a suitable substrate, or other readouts based on emission and/or absorption of photons (light). Typically, a reporter molecule is a molecule that is not endogenously expressed by a cell or organism in which the reporter molecule is used.

The term "reporter gene" refers to a nucleic acid that encodes a reporter molecule. A reporter gene can be operably linked to a promoter sequence to produce a reporter construct that can be used to assay for the transcriptional activity of the promoter in a cell. The reporter construct may be assembled in or inserted into a vector. The reporter construct or vector may be transferred into one or more cells. After transfer, cells are assayed for the presence of the reporter molecule by measuring the reporter molecule or the activity (e.g., enzymatic activity) of the reporter molecule. In some embodiments, a reporter gene is codon-optimized for expression in mammalian cells.

The term "reprogramming" refers to a process that alters the differentiation state of a somatic cell to a less differentiated state or that converts a somatic cell from one cell type to a different cell type, Reprogramming that converts a cell of a first differentiated cell type to a cell of a second differentiated cell type without undergoing an intermediate pluripotent state is sometimes referred to as "transdifferentiation" or "direct reprogramming". In some embodiments, reprogramming comprises altering the differentiation state of a somatic cell to a pluripotent state. The resulting pluripotent cell is sometimes referred to as an "induced pluripotent stem cell" (iPS cell). Those of ordinary skill in the art are aware of suitable in vitro methods for reprogramming, e.g., for deriving iPS cells from mammalian somatic cells of diverse species, e.g., mice, rats, humans, non-human primates, and other mammalian species. In general, embryonic, fetal, or adult somatic cells may be used. In general, any type of somatic cell may be used, such as fibroblasts, keratinocytes, peripheral mononuclear cells, to name a few. See Behringer, R, et al., Manipulating the Mouse Embryo, A Laboratory Manual, 4$^{th}$ ed., Cold Spring Harbor Laboratory Press, Cold Spring Harbor, N.Y., 2013; US Pat. Pub. Nos. 20110076678 and 20120028821 for exemplary techniques for generating iPS cells. In general, suitable methods can include causing a somatic cell to express appropriate pluripotency-associated genes, e.g., genes that encode pluripotency-associated transcription factors (TFs). Examples of TFs that can be used to generate iPS cells include Oct4, Klf4 (or other Klf family members such as Klf2 or Klf5), Sox2 (or other Sox family members such as Sox1 or Sox3), Nanog, Lin28, and Myc (c-Myc, L-Myc, N-Myc). A single factor may be expressed or two, three, four, or more of these factors may be expressed in various combinations (e.g., Oct4, Klf4, and Sox2; Oct4, Klf4, Sox2, and Myc; or Oct4, Sox2, Nanog, and Lin28) as known in the art. In some embodiments microRNAs may be used in generating iPS cells. For example, miR-302, miR-367, miR-200c, or miR-369s may be used. In some embodiments inhibition of p53 by RNAi (e.g., using a shRNA cassette that encodes a shRNA that inhibits p53 expression) may be combined with expression of one or more reprogramming factors Expression may be achieved by a variety of methods. One or more vectors comprising expression cassettes encoding the factors (which may become integrated into the genome or may be extrachromosomal elements such as episomes derived from Epstein-Barr virus (e.g., as described in Yu, J., et al., Science. (2009) 324(5928):797-801) or translatable mRNA (e.g., synthetic modified stabilized mRNA (e.g., as described in Warren et al. (Cell Stem Cell 7(5):618-30, 2010, Mandal P K, Rossi D J. Nat Protoc. 2013 8(3):568-82, US Pat. Pub. No. 20120046346 and/or PCT/US2011/032679 (WO/2011/130624) encoding the factors may be introduced into cells, e.g., by transfection. Transdifferentiation of a cell from a first cell type to a second cell type can be performed by ectopically expressing one or more lineage-specific transcription factors, e.g., master transcription factors, of the second cell type in the cell of the first cell type. For example, expressing the bHLH transcription factor MyoD in fibroblasts can transform them into myoblasts by activating muscle-specific genes. Direct reprogramming of fibroblasts and other cell types to neurons, cardiomyocytes, hepatocytes, skeletal muscle cells, and other cell types has been achieved. See Morriss, S A and Daley, G Q, Cell Research (2013) 23:33-48 for review. For example, cells have been directly reprogrammed into β-islet cells, cardiomyocytes, and neurons by using NPM (Ngn3, Pdx1, and Mafa), GMT (GATA4, MEF2C, and TBX5), and ABM (Ascl1, Brn2, and Myt11), respectively. As known in the art various small molecules such as histone deacetylase inhibitors (HDACs) or molecules that act on various signaling pathways can enhance reprogramming (e.g., increase reprogramming efficiency) and/or replace one or more of the transcription factors. It will be understood that many different reprogramming factors, small molecules, and combinations thereof have been successfully used for reprogramming. In some embodiments cells to be reprogrammed harbor genes encoding one or more reprogramming factors under control of an inducible promoter. Reprogramming may be performed by placing the cells under inducing conditions, e.g., contacting the cells with a suitable inducing agent. In some embodiments a reprogramming method that avoids integration of exogenous DNA into the genome may be used. In some embodiments cells to be reprogrammed are obtained from a non-human animal that harbors one or more transgenes comprising a reprogramming factor operably linked to an inducible promoter.

The term "selectable marker" or "selectable marker gene" refers to a nucleic acid that encodes an RNA or protein that confers on a cell an increased ability to survive and/or proliferate under particular conditions ("selective conditions") relative to cells that lack or do not express the selectable marker. In some embodiments the selectable marker allows the cell to survive or proliferate under selective conditions that, absent the selectable marker, would ordinarily cause the cell to die or cease proliferating. The particular selective conditions may be the presence of an ordinarily toxic substance in the culture medium or an insufficient amount of particular nutrient(s) that are required by the cell for survival or proliferation. Those of ordinary skill in the art are aware of suitable selectable markers of use in cells of interest, e.g., bacterial or mammalian cells. Antibiotic resistance markers are a non-limiting example of a class of selectable marker. A selectable marker of this type that is commonly used in mammalian cells is the neomycin resistance gene (an aminoglycoside 3'-phosphotransferase, 3' APH II). Expression of this selectable marker renders cells resistant to various antibiotics such as G418. Additional antibiotic resistance markers encode enzymes conferring resistance to Zeocin™, hygromycin, puromycin, blasticidin, gentamicin, kanamycin, etc. A second non-limiting class of selectable markers is nutritional markers. Such selectable markers generally encode enzymes that function in a biosynthetic pathway to produce a compound that is needed for cell proliferation or survival. In general, under nonselective conditions the compound is present in the environment or is produced by an alternative pathway in the cell. Under selective conditions, functioning of the biosynthetic pathway in which the selectable marker is involved is needed to produce the compound.

The term "site-specific recombinase" (also referred to simply as a "recombinase" herein) refers to a protein that can recognize and catalyze the recombination of DNA between specific sequences in a DNA molecule. Such sequences may be referred to as "recombination sequences" or "recombination sites" for that particular recombinase. Tyrosine recombinases and serine recombinases are the two main families of site-specific recombinase. Examples of site-specific recombinase systems include the Cre/Lox system (Cre recombinase mediates recombination between loxP), the Flp/Frt system (Flp recombinase mediates recombination between FRT sites), and the PhiC31 system (PhiC31 recombinase mediates DNA recombination at sequences known as attB and attP sites). Recombinase systems similar to Cre include the Dre-rox, VCre/VloxP, and SCre/SloxP systems (Anastassiadis K, et al. (2009) Dis Model Mech 2(9-10):508-515; Suzuki E, Nakayama M (2011) Nucl. Acids Res. (2011) 39 (8): e49. It should be understood that reference to a particular recombinase system is intended to encompass the various engineered and mutant forms of the recombinases and recombination sites and codon-optimized forms of the coding sequences known in the art. Site-specific recombinases can be used to delete or invert DNA located between the recombination sites or mediate integration. For example, inverted Lox sites on the same chromosome will cause an inversion of the intervening DNA, while a direct repeat of Lox sites (Lox sites in the same orientation) will cause deletion of the intervening DNA. DNA placed between two loxP sites is said to be "floxed". A gene may be modified by the insertion of two loxP sites that allow the excision of the floxed gene segment through Cre-mediated recombination. In some embodiments, expression of Cre may be under control of a cell type specific, cell state specific, or inducible expression control element (e.g., cell type specific, cell state specific, or inducible promoter) or Cre activity may be regulated by a small molecule. For example, Cre may be fused to a ligand binding domain of a receptor (e.g., a steroid hormone receptor) so that its activity is regulated by receptor ligands. Cre-ER(T) or Cre-ER(T2) recombinases may be used, which comprise a fusion protein between a mutated ligand binding domain of the human estrogen receptor (ER) and Cre, the activity of which can be induced by, e.g., 4-hydroxy-tamoxifen. Placing Lox sequences appropriately allows a variety of genomic manipulations. For example, genes can be activated or repressed.

The term "safe harbor" locus refers to an intragenic or extragenic region of the mammalian genome that is able to accommodate the predictable expression of newly integrated DNA without adverse effects on the host cell (or on an animal whose cells harbour the integrated DNA). In some embodiments the safe harbour locus is the AAVSV1 (the natural integration site for the wild-type AAV on chromosome 19), ROSA26, or CCR5 locus. The locations of these loci are well known in the art.

The term "small molecule" as used herein, refers to an organic molecule that is less than about 2 kilodaltons (kDa) in mass. In some embodiments, the small molecule is less than about 1.5 kDa, or less than about 1 kDa. In some embodiments, the small molecule is less than about 800 daltons (Da), 600 Da, 500 Da, 400 Da, 300 Da, 200 Da, or 100 Da. Often, a small molecule has a mass of at least 50 Da. In some embodiments, a small molecule is non-polymeric. In some embodiments, a small molecule is not an amino acid. In some embodiments, a small molecule is not a nucleotide. In some embodiments, a small molecule is not a saccharide. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups.

A "subject" may be any vertebrate organism in various embodiments. In some embodiments a subject is a mammal, e.g., a human, non-human primate, rodent (e.g., mouse, rat, hamster), rabbit, ungulate (e.g., ovine, bovine, equine, caprine species), canine, or feline. A subject may be individual to whom an agent is administered, e.g., for experimental, diagnostic, and/or therapeutic purposes or from whom a biological sample (e.g., a sample containing one or more cells) is obtained.

The term "targetable nuclease" refers to a nuclease that can be programmed to produce site-specific DNA breaks, e.g., double-stranded breaks (DSBs), at a selected site in DNA. Such a site may be referred to as a "target site". The target site can be selected by appropriate design of the targetable nuclease or by providing a guide molecule (e.g., a guide RNA) directs the nuclease to the target site. Examples of targetable nucleases include zinc finger nucleases (ZFNs), transcription activator-like effector nucleases (TALENs), and RNA-guided nucleases (RGNs) such as the Cas proteins of the CRISPR/Cas Type II system, and engineered meganucleases.

A "variant" of a particular polypeptide or polynucleotide has one or more alterations (e.g., additions, substitutions, and/or deletions) with respect to the polypeptide or polynucleotide, which may be referred to as the "original polypeptide" or "original polynucleotide", respectively. An addition may be an insertion or may be at either terminus. A variant may be shorter or longer than the original polypeptide or polynucleotide. The term "variant" encompasses "fragments". A "fragment" is a continuous portion of a polypeptide or polynucleotide that is shorter than the original polypeptide. In some embodiments a variant comprises or consists of a fragment. In some embodiments a fragment or variant is at least 20%, 30%, 40%, 50%, 60%, 70%, 80%, 90%, 95%, 96%, 97%, 98%, 99%, or more as long as the original polypeptide or polynucleotide. A fragment may be an N-terminal, C-terminal, or internal fragment. In some embodiments a variant polypeptide comprises or consists of at least one domain of an original polypeptide. In some embodiments a variant polynucleotide hybridizes to an original polynucleotide under stringent conditions, e.g., high stringency conditions, for sequences of the length of the original polypeptide. In some embodiments a variant polypeptide or polynucleotide comprises or consists of a polypeptide or polynucleotide that is at least 50%, 60%, 70%, 80%, 90%, 95%, 96%, 97%, 98%, 99%, or more identical in sequence to the original polypeptide or polynucleotide over at least 20%, 30%, 40%, 50%, 60%, 70%, 80%, 90%, 95%, 96%, 97%, 98%, 99%, or 100% of the original polypeptide or polynucleotide. In some embodiments a variant polypeptide comprises or consists of a polypeptide that is at least 50%, 60%, 70%, 80%, 90%, 95%, 96%, 97%, 98%, 99%, or more identical in sequence to the original polypeptide over at least 20%, 30%, 40%, 50%, 60%, 70%, 80%, 90%, 95%, 96%, 97%, 98%, 99%, or 100% of the original polypeptide, with the proviso that, for purposes of computing percent identity, a conservative amino acid substitution is considered identical to the amino acid it replaces. In some embodiments a variant polypeptide comprises or consists of a polypeptide that is at least 50%, 60%, 70%, 80%, 90%, 95%, 96%, 97%, 98%, 99%, or more identical to the original polypeptide over at least 20%, 30%, 40%, 50%, 60%, 70%, 80%, 90%, 95%, 96%, 97%, 98%, 99%, or 100% of the original polypeptide, with the proviso that any one or more amino acid substitutions (up to the total number of such substitutions) may be restricted to conservative substitutions. In some embodiments a percent identity is measured over at least 100; 200; 300; 400; 500; 600; 700; 800; 900; 1,000; 1,200; 1,500; 2,000; 2,500; 3,000; 3,500; 4,000; 4,500; or 5,000 amino acids. In some embodiments the sequence of a variant polypeptide comprises or consists of a sequence that has N amino acid differences with respect to an original sequence, wherein N is any integer between 1 and 10 or between 1 and 20 or any integer up to 1%, 2%, 5%, or 10% of the number of amino acids in the original polypeptide, where an "amino acid difference" refers to a substitution, insertion, or deletion of an amino acid. In some embodiments a difference is a conservative substitution. Conservative substitutions may be made, e.g., on the basis of similarity in side chain size, polarity, charge, solubility, hydrophobicity, hydrophilicity and/or the amphipathic nature of the residues involved. For example, non-polar (hydrophobic) amino acids include alanine, leucine, isoleucine, valine, proline, tryptophan, and methionine; polar/neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. It should be understood that the use of functional variants of any of the nucleic acids and/or polypeptides described herein is within the scope of the present disclosure. In some embodiments a variant is a functional variant, i.e., the variant at least in part retains at least one activity of interest of the original polypeptide or polynucleotide. An activity of interest may be any activity that is useful in a composition or a method described herein. An activity may be, e.g., fluorescence, catalytic activity (e.g., luciferase activity, cleavage activity), binding activity, ability to perform or participate in a biological function or process, etc. In some embodiments a variant may have an activity of at least 10%, 20%, 30%, 40%, 50%, 60%, 70%, 80%, 90%, 95%, or more, of the activity of the original polypeptide or polynucleotide, up to approximately 100%, 125%, 150%, 200%, 500%, 1000%, or more of the activity of the original polypeptide or polynucleotide, in various embodiments. In some embodiments a variant may have a qualitatively different activity to the polynucleotide or polypeptide from which it is derived. In some embodiments a variant, e.g., a functional variant, comprises or consists of a polypeptide at least 90%, 91%, 92%, 93%, 94%, 95%, 96%, 97%, 98%, 99%. 99.5% or 100% identical to an original polypeptide or polynucleotide over at least 70%, 75%, 80%, 85%, 90%, 95%, 96%, 97%, 98%, or 99% or 100% of the original polypeptide or polynucleotide. In some embodiments a variant may have reduced activity with respect to one or more activities that may be detrimental or undesirable in the context of a composition or method described herein, while retaining one or more activities that is useful or desirable in a composition or method described herein. In some embodiments an alteration, e.g., a substitution or deletion, e.g., in a functional variant, does not alter or delete an amino acid or nucleotide that is known or predicted to be important for an activity, e.g., a known or predicted catalytic residue or residue involved in binding a substrate or cofactor. In some embodiments nucleotide(s), amino acid(s), or region(s) exhibiting lower degrees of conservation across species as compared with other amino acids or regions may be selected for alteration. Variants may be tested in one or more suitable assays to assess activity.

The term "vector" as used herein refers to a nucleic acid or a virus or portion thereof (e.g., a viral capsid or genome) capable of mediating entry of, e.g., transferring, transporting, etc., a nucleic acid into a cell. Where the vector is a nucleic acid, the nucleic acid to be transferred is generally linked to, e.g., present in, the vector. A nucleic acid vector may include sequences that direct autonomous replication (e.g., an origin of replication) and/or may include sequences sufficient to allow integration of part or all of the nucleic acid into host cell genomic DNA. Useful nucleic acid vectors include, for example, naturally occurring or modified viral genomes or portions thereof or nucleic acids (DNA or RNA) that can be packaged into viral capsids, DNA or RNA plasmids, and transposons. Plasmid vectors typically include an origin of replication and may include one or more selectable marker genes. Plasmids may comprise part or all of a viral genome (e.g., a viral promoter, enhancer, processing or packaging signals, etc.). Viruses or portions thereof that can be used to introduce nucleic acid molecules into cells are referred to as viral vectors. Useful viral vectors include adenoviruses, adeno-associated viruses, retroviruses, lentiviruses, vaccinia virus and other poxviruses, herpesviruses (e.g., herpes simplex virus), and others. In some embodiments a virus having tropism for a particular cell type (e.g., neurons or a particular type of neuron) may be used. Examples of expression vectors that may be used in mammalian cells include, e.g., the pcDNA vector series, pSV2 vector series, pCMV vector series, pRSV vector series, pEF1 vector series, Gateway® vectors, etc. Useful transposons include, e.g., Tol2, Minos, Sleeping Beauty (SB) and PiggyBac (PB). One of ordinary skill in the art appreciates how to use a viral vector, plasmid, transposon system, or other vector to introduce a DNA sequence of interest into the genome of a cell. For example, it would be understood that a transposase would be supplied to the cell if a transposon vector is used.

The term "CpG island" (CGI) refers to a region of genomic DNA that has an elevated G+C content (proportion of nucleotides that are either G or C) as compared with the mammalian genome as a whole, in which CpG dinucleotides are underrepresented. In vertebrates, CpG islands are enriched in certain regions of the genome involved in initiation of gene transcription, such as promoters. CGIs colocalize with the majority of annotated gene promoters in both the human and mouse genomes, including most housekeeping genes and a number of tissue-specific genes and developmental regulator genes. A promoter that contains, is contained in, or overlaps with a CGI may be referred to as "CGI promoter". Such a CGI is said to be associated with or colocalized with the promoter, and vice versa. CGIs frequently exist in an unmethylated state that is transcriptionally permissive and marked by histone modifications that are characteristic of transcriptionally active chromatin such as histone acetylation (H3/H4Ac) and H3K4me3. While often unmethylated in normal cells, CGIs can become methylated under certain conditions and in certain tissues. DNA methylation of CGIs is associated with stable long-term silencing of CGI promoters.

In some aspects, CGIs are identified as regions of genomic DNA at least 200 bp in length that have a G+C content of at least 50% and a CpG frequency (observed/expected) of at least 0.6 (Gardiner-Garden, M. and Frommer, M. (1987) CpG islands in vertebrate genomes. J. Mol. Biol. 196, 261-282). The observed to expected (O/E) ratio in a given DNA segment can be calculated by dividing the proportion of CpG dinucleotides in the segment by what is expected by chance, which can be calculated using the formula $$O/E = \frac{\#CpG/N}{\#C/N \times \#G/N}$$

where N is the number of base pairs (bp) in the segment. In some aspects, the CGI definition of Gardiner-Garden and Frommer (GF definition) is refined by excluding sequences that meet the above criteria but lie within or substantially overlap a repetitive sequence in the genome. Repetitive sequences includes those sequence elements known as LINEs, SINEs, and Alu sequences, which are well known in the art. In some embodiments a CGI does not comprise or consist of or overlap with an Alu sequence or other repetitive sequence found in a genome of interest. In some embodiments a CGI is at least 300 bp, at least 400 bp, or at least 500 bp long, e.g., between about 500 bp and about 1 kb, between about 1 kb and about 2 kb, between about 2 kb and about 5 kb, or between about 5 kb and about 10 kb long. Exclusion of repetitive sequences can be achieved by applying the criteria of the GF definition to a modified version of a genome in which repeats have been masked and are not considered for purposes of identifying sequences that meet the criteria. RepeatMasker is a computer program that screens DNA sequences for interspersed repeats and low complexity DNA sequences. The output includes a modified version of the query sequence in which all the annotated repeats have been masked (Smit, A F A, Hubley, R & Green, P. RepeatMasker Open-3.0.1996-2010; available on the worldwide web at subdomain repeatmasker.org). Window-Masker (Morgulis A., et al., *Bioinformatics* 2006; 22:134-141) and Tandem Repeats Finder (Benson G. *Nucleic Acids Res.* 1999; 27:573-580.) CGIs identified based on the GF definition applied to various vertebrate genomes (e.g., human, mouse) are available in the UCSC Genome Browser in the "CpG Islands" tracks. The UCSC Genome Browser provides the option to use either a masked or unmasked genome. "CpG island shores" are the regions extending 2 kb on either side of a CpG island. These regions have a lower CpG density than do CGIs and are harbor numerous cancer-specific and tissue-specific differentially methylated regions. A "low CpG region" is a region that has a lower CpG density than that found in CpG islands.

The term "differentially methylated region" (DMR) refers to a region of genomic DNA that is differentially marked by DNA methylation (has a different methylation pattern) in two or more settings. Unless otherwise specified, the term "differentially methylated region" as used herein refers to a region of genomic DNA that is differentially methylated in two homologous parental chromosomes present in a cell, i.e., the region is differentially methylated in a parent-of-origin specific manner. In other words, the methylation level within the region differs depending on whether it is in the paternal or maternal chromosome. Such a DMR may be referred to as a parent-of-origin DMR. The term "differentially methylated region" may sometimes be used to refer to a region of genomic DNA that is differentially marked by methylation in two or more settings on either or both chromosomes in a way that is not determined by the parental origin of the chromosomes. Where this use is intended herein, the term "differentially methylated region" will be immediately preceded by a word or phrase that contains the term "specific" and refers to the settings in which the region is differentially methylated. The two or more settings may, for example, be two or more cell types or cell states. For example, a "tissue-specific DMR" refers to a region of genomic DNA that is differentially marked by methylation in two or more different tissues or cell types. A "disease-specific DMR" refers to a region of genomic DNA that is differentially marked by methylation in tissues or cells affected by a disease as compared with tissues or cells that are otherwise matched but are not affected by a disease (normal tissues or cells). A "reprogramming-specific DMR" refers to a region of genomic DNA that is differentially marked by methylation in reprogrammed cells (i.e., cells that are undergoing or result from reprogramming) as compared with the original cells.

A "germline differentially methylated region" (gDMR) is a DMR that becomes differentially methylated in the germline. Thus, gDMRs are already differentially methylated in the gametes at the time of fertilization. Some gDMRs are methylated during oogenesis while the others are methylated during spermatogenesis. Therefore, in a given diploid cell or organism, certain gDMRs (those methylated during oogenesis) are methylated on the maternally inherited chromosome, and certain gDMRs (those methylated during spermatogenesis) are methylated on the paternally inherited chromosome.

A "secondary differentially methylated region", also referred to as a "somatic differentially methylated region" is a differentially methylated region that becomes differentially methylated after fertilization. Secondary DMRs are subsequently maintained throughout normal development, and are therefore not regulated by the DNA methylation machinery in a tissue-specific manner.

The present disclosure encompasses the recognition that studies of epigenetic changes such as DNA methylation have heretofore been hampered by two experimental constraints that limit mechanistic studies of methylation and gene regulation. Changes in DNA methylation during processes such as development, lineage commitment, and disease are dynamic. One limitation of standard methods for methylation analysis (i.e., methods used in the art for methylation analysis prior to the present disclosure) is that it provides only a static "snapshot" view of the methylation state during cell state transitions. Prior to the present disclosure, following the dynamics of DNA methylation has been hindered by the inability to translate epigenetic changes into a traceable readout. Another limitation of standard methods for methylation analysis is that they are based on examining bulk populations of cells, precluding assessment of methylation changes in individual cells.

Described herein is a DNA methylation reporter (also referred to as a Reporter of Genomic Methylation (RGM) or "RGM construct") that permits detection of genomic methylation states in individual cells. In some aspects, a DNA methylation reporter described herein allows the tracing of real-time changes in DNA methylation in live cells. The DNA methylation reporter comprises a promoter that, when introduced into DNA in proximity to a region of interest (e.g., a region comprising CpG dinucleotides), may be utilized to report on methylation changes of the adjacent sequences.

The design of the DNA methylation reporter is based at least in part on the insight that a promoter useful for reporting on methylation of a DNA region of interest should preferably be one whose activity (i.e., activity with regard to directing (driving) transcription of an operably linked DNA sequence) is sensitive to exogenous methylation changes (i.e., methylation changes outside of the promoter itself) without being independently regulated by the DNA methylation machinery. In other words, the activity of the promoter can be affected by exogenous methylation changes but should not ordinarily be subject to regulation by methylation during the processes of development or cellular differentiation. The DNA methylation reporter described herein comprises a promoter whose activity can be affected by exogenous methylation changes without being independently regulated by the DNA methylation machinery. Such a promoter may be referred to herein as an "RGM promoter". An RGM construct comprises an RGM promoter operably linked to a nucleic acid sequence that encodes a reporter molecule. In general, the RGM promoter is located upstream of (i.e., in the 5' direction from) the sequence that encodes the reporter molecule. In some aspects, described herein is the identification of suitable promoters and their use as sensors for DNA methylation of a DNA region of interest.

In order to use an RGM construct to measure methylation of a DNA region of interest, the RGM construct is positioned in proximity to the DNA region of interest in a cell. For example, the RGM construct may be integrated into a region of interest in the genome of the cell. The cell is subsequently assayed for the reporter molecule. Transcription of the reporter gene (the DNA sequence that encodes the reporter molecule) is dependent on activity of the RGM promoter, which is sensitive to the level of methylation of the region of interest. Activity of the RGM promoter allows transcription of the reporter gene, producing RNA that encodes the reporter molecule. The level of the reporter molecule serves as an indicator of the level of methylation of the region of interest.

Thus, in some aspects, described herein is a method of detecting the methylation state of a DNA region of interest in the genome of a cell comprising: a) providing a cell comprising a nucleic acid comprising an RGM promoter operably linked to a nucleic acid sequence that encodes a reporter molecule, wherein the nucleic acid is integrated in proximity to a region of interest in the genome of the cell; and b) measuring expression of the reporter molecule by the one or more cells, wherein the level of expression of the reporter molecule is indicative of the level of methylation of the region of interest, thereby detecting the methylation state of the region of interest. For example, in some embodiments, lack of expression of the reporter molecule is indicative of methylation, e.g., hypermethylation, of the region of interest, while expression of the reporter molecule is indicative of low or absent methylation of the region of interest.

In some embodiments, the RGM promoter is active if the region of interest is hypomethylated, thus allowing transcription of the reporter gene. In some embodiments, methylation of the region of interest inhibits activity of the RGM promoter, thereby inhibiting transcription of the reporter gene. In some embodiments, if the cell is positive for the reporter molecule, this indicates that the region of interest is hypomethylated. In some embodiments, if a cell is negative for the reporter molecule, this indicates that the region of interest is hypermethylated.

In some embodiments, the RGM promoter is inactive if the region of interest is hypomethylated, thus allowing transcription of the reporter gene. In some embodiments, methylation of the region of interest increases activity of the RGM promoter, thereby increasing transcription of the reporter gene. In some embodiments, if the cell is positive for the reporter molecule, this indicates that the region of interest is hypermethylated. In some embodiments, if a cell is negative for the reporter molecule, this indicates that the region of interest is hypomethylated.

In some embodiments, a change in the level of the reporter molecule indicates a change in the level of methylation of the region of interest. For example, in some embodiments, an increase in the level of the reporter molecule over a period of time indicates that the RGM promoter has become more active and, therefore, that the region of interest has undergone a change in methylation (e.g., has become less densely methylated) during that period. In some embodiments a decrease in the level of the reporter molecule over a period of time indicates that the RGM promoter has become less active and, therefore, that the region of interest has undergone a change in methylation (e.g., has become more densely methylated) during that period. Without wishing to be bound by any theory, it is believed that methylation may be propagated from the DNA region of interest into the RGM promoter, resulting in modulation of its transcriptional activity.

Depending on the particular RGM promoter, methylation may increase or decrease its transcription activity. As discussed further below, the Snrpn promoter is exemplified herein in detail as an RGM promoter. In the case of an RGM construct comprising a Snrpn promoter, methylation of the DNA region of interest reduces transcriptional activity, thus reducing production of the reporter molecule, and demethylation of the DNA region of interest increases transcriptional activity, thus increasing production of the reporter molecule.

In some embodiments, an RGM construct is integrated into the genome of a mammalian cell in proximity to a DNA region of interest (ROI) in the genome of the cell. The RGM construct may be used to report on methylation of the region of interest (i.e., to provide a measurable indication of the methylation state of the region of interest). The RGM construct may be integrated within the DNA region of interest or the 5' or 3' end of the RGM construct may be directly adjacent to the DNA region of interest or may be located up to about 5 nt, 10 nt, 50 nt, 100 nt, 250 nt, 500 nt, 1 kb, 2 kb, 3 kb, 4 kb, 5 kb, 10 kb, or 20 kb from the nearest nucleotide of the DNA region of interest. In some embodiments the RGM construct is located 5' with respect to the ROI. In some embodiments the RGM construct is located 3' with respect to the ROI. In some embodiments an RGM construct is integrated at a predetermined location in the genome in proximity to a region of interest using any of a variety of methods for genome modification (see discussion below). In some embodiments an RGM construct is integrated into the genome at a random location, where "random" in this context means that the location is not predetermined by the artisan. The RGM construct may then be used to report on methylation in a region of the genome in proximity to the location at which it is inserted. If desired, the region of the genome or the location at which the RGM construct is integrated may be identified, e.g., by sequencing.

In some embodiments, after integration of a nucleic acid comprising an RGM construct into the genome of a cell, DNA comprising the RGM promoter and, optionally, at least a portion of a DNA region of interest, may be isolated and its methylation state determined using standard methodology for methylation analysis. For example, the DNA may be subjected to bisulfite treatment, amplified (e.g., by PCR), and sequenced. Determining the methylation state of the RGM promoter and, optionally, the methylation state of at least a portion of a DNA region of interest, using standard methodology may be performed in order to confirm that the RGM is faithfully reporting on the methylation state of sequences in its proximity.

While it is contemplated that a DNA region of interest whose methylation state is measured using an RGM reporter will often be located in the genome of a cell, in some embodiments a RGM construct may be used to report on methylation of a region of interest in extrachromosomal DNA, such as a region of DNA in an episomal vector (e.g., an oriP/EBNA-1 episome), minicircle DNA, or other type of extrachromosomal DNA. In some embodiments, an RGM construct is introduced into an extrachromosomal DNA element prior to introduction of the DNA element into a cell. It should also be understood that in embodiments in which a cell comprises two or more reporter constructs or expression cassettes, any one or more of such constructs may be integrated into the genome or may be in an episome in various embodiments.

In some aspects, the disclosure is based in part on the discovery that promoters of imprinted genes (also referred to as "imprinted gene promoters") can serve as methylation sensors and are suitable promoters for use in a DNA methylation reporter. Imprinted gene promoters exhibit inherent sensitivity to DNA methylation of adjacent or nearby genomic regions, resulting in transcriptional activation or silencing of the imprinted gene. Methylation of a genomic region in proximity to an imprinted gene promoter can lead to methylation of the imprinted gene promoter. Depending on the particular imprinted gene promoter, methylation can inhibit transcriptional activity of the promoter or increase transcriptional activity of the promoter. This mechanism has been established for a subgroup of germline-derived differentially methylated regions (DMRs) that act as imprinting control regions and affect in cis the methylation state of secondary regulatory promoter elements, which in turn control imprinted gene promoter activity. The methylation state of such promoter elements is subsequently maintained throughout normal development, and therefore not regulated by the DNA methylation machinery in a tissue-specific manner. The present disclosure provides the insight that these characteristics of imprinted gene promoters make them well suited to serve as DNA methylation sensors.

Accordingly, in some embodiments, the promoter in a RGM construct of the present disclosure is an imprinted gene promoter. An example of imprinting occurs in the so-called Prader-Willi Angelman (PWA) region on human chromosome 15 (in 15q11-13) or the orthologous region on mouse chromosome 7, in which a DMR associated with the small nuclear ribonucleoprotein polypeptide N (Snrpn) gene promoter region controls its parent-of-origin monoallelic expression. In both humans and mice, the upstream region of the Snrpn gene comprises a region that is densely methylated only on the maternal allele, which is silenced.

In some embodiments, the imprinted gene promoter in a RGM construct is derived from the Snrpn gene. As described in the Examples, a RGM construct comprising a minimal Snprn promoter operably linked to a reporter gene can faithfully report on changes in DNA methylation associated with a nearby DNA region of interest. For example, a RGM construct comprising a minimal Snprn promoter, when positioned in proximity to a CpG island, can be used to accurately report on gain and loss of DNA methylation of the CpG island. A RGM construct inserted into the genome of a cell can be used to accurately detect DNA methylation changes in non-coding regulatory regions such as enhancers and super-enhancers.

In some embodiments the sequence of the promoter in an RGM construct is from the Snrpn promoter region that drives transcription of a bicistronic transcript that encodes Snrpn protein and a protein identified as the Snrpn upstream reading frame (Snurf). This promoter region is also known as the Snurf-Snrpn promoter region. Where the present disclosure refers to the Snrpn promoter region, it should be understood that the term refers to the Snurf-Snrpn promoter region, and the promoter of the Snrpn gene refers to the promoter that drives transcription of the bicistronic transcript that encodes the Snrpn and Snurf proteins (Snurf-Snrpn transcript). Those of ordinary skill in the art will appreciate that transcription of certain other transcripts that also encode Snrpn but lack the complete open reading frame for Snurf is driven by different promoter(s) located upstream. The bicistronic transcript corresponds to RefSeq accession number NM_013670.3 (mouse) or NM_003097.3 (human). In some embodiments the sequence of the promoter in an RGM construct comprises or consists of the following sequence from the Snrpn promoter region (where underlining indicates a portion of the sequence that is highly conserved between the mouse and human Snrpn promoter regions):

(SEQ ID NO: 1)
ACGCTCAAATTTCCGCAGTAGGAATGCTCAAGCATTCCTTTTGGTAGC

TGCCTTTTGG<u>CAGGACATTCCGGTCAGAGGGACAGAGACCCCTGCATT</u>

<u>GCGGCAAAAATGTGCGCATGTGCAGCCATTGCCTGGGACGCATGCGTA</u>

<u>GGGAGCCGCGCGACAAACCTGAGCCATTGCGGCAAGACTAGCGCAGAG</u>

<u>AGGAGAGGGAGCCGGAGATGCCAGACGCTTGGTTCTGAGGAGTGATTT</u>

<u>GCAACGCAATGGAGCGAGGAAGGT</u>CAGCTGGGCTTGTGGATTCT.

In some embodiments the sequence of the promoter in an RGM construct comprises or consists of a sequence at least 70%, 75%, 80%, 85%, 90%, 95%, 96%, 97%, 98%, 99%, 100% identical to SEQ ID NO: 1 across a portion of SEQ ID NO: 1 that comprises at least 150, 175, 200, 210, 220, 230, 240, 250, 260, 270, 280 or all 284 nucleotides of SEQ ID NO: 1. In some embodiments the portion of SEQ ID NO: 1 is highly conserved between the mouse and human Snrpn promoter regions. For example, in some embodiments the promoter comprises or consists of a sequence at least 70%, 75%, 80%, 85%, 90%, 95%, 96%, 97%, 98%, 99%, 100% identical to nucleotides 59-264 of SEQ ID NO: 1, i.e., at least 70%, 75%, 80%, 85%, 90%, 95%, 96%, 97%, 98%, 99%, 100% identical to the following sequence:

(SEQ ID NO: 2)
CAGGACATTCCGGTCAGAGGGACAGAGACCCCTGCATTGCGGCAAAAA

TGTGCGCATGTGCAGCCATTGCCTGGGACGCATGCGTAGGGAGCCGCG

CGACAAACCTGAGCCATTGCGGCAAGACTAGCGCAGAGAGGAGAGGGA

GCCGGAGATGCCAGACGCTTGGTTCTGAGGAGTGATTTGCAACGCAAT

GGAGCGAGGAAGGT.

In some embodiments the promoter in an RGM construct comprises or consists of a sequence at least 70%, 75%, 80%, 85%, 90%, 95%, 96%, 97%, 98%, 99%, or 100% identical to a portion of SEQ ID NO: 1 at least 150 nucleotides long, starting at any position of SEQ ID NO: 1 between positions 1 and position 100 (e.g., position 1, 10, 20, 30, 40, 50, 60, 70, 80, 90, or 100) and extending up to any position of SEQ ID NO: 1 at or above position 200, e.g., at or above position 210, 220, 230, 240, 250, 260, 270, 280, or 284. All combinations of starting and ending positions are disclosed. For example, in some embodiments the promoter comprises or consists of a sequence at least 70%, 75%, 80%, 85%, 90%, 95%, 96%, 97%, 98%, 99%, 100% identical to the sequence extending from position X to position Y of SEQ ID NO: 1, where X can be any integer between 1 and 100, and Y can be any integer between 200 and 284. In some embodiments the promoter in an RGM construct comprises or consists of a sequence at least 70%, 75%, 80%, 85%, 90%, 95%, 96%, 97%, 98%, 99%, or 100% identical to nucleotides 60-264, 65-264, 70-264, 75-264, 80-264, 85-264, 90-265, 95-264, 100-264, 105-264, 110-264, 115-264, 120-264, 125-264, 130-264, 135-264, or 140-264 of SEQ ID NO: 1.

The Snrpn promoter set forth in SEQ ID NO: 1 contains 16 CG dinucleotides. For purposes of description, the CG dinucleotides can be numbered consecutively from 1 to 16, starting with the CG at positions 2-3 (CG #1) and ending with the CG at positions 255-256 (CG #16). In some embodiments, a variant of SEQ ID NO: 1 comprises a sequence that includes at least 8, 9, 10, 11, 12, 13, 14, 15, or all 16 of the CG dinucleotides of SEQ ID NO: 1 (i.e., these CG dinucleotides are not mutated or absent from the sequence).

In some embodiments a Snrpn promoter used in an RGM construct may comprise additional sequence from the Snrpn promoter region. FIG. 9 shows sequences from the Snrpn promoter region, including the minimal Snrpn promoter as well as upstream sequences (SEQ ID NO: 3). In some embodiments an RGM promoter comprises an additional approximately 100, 200, 300, 400, 500 nt, or more of the sequence located upstream of the minimal Snrpn promoter. Any of the RGM constructs described herein may comprise a Snrpn promoter, e.g., a minimal Snrpn promoter, operably linked to a reporter gene.

Although the Snprn promoter is exemplified in most detail herein, it should be understood other imprinted gene promoters may be used in certain embodiments. In some embodiments the sequence of an RGM construct comprises at least a portion of the sequence extending from nucleotide position −5000 to nucleotide position +5000 in the genome of a mammal (e.g., a mouse, rat, or human), where +1 represents the TSS of an imprinted gene, negative numbers represent nucleotide positions located 5' to the TSS, and positive numbers (whether or not shown with a plus sign) represent nucleotide positions located 3' to the TSS. In some embodiments the length of the sequence that is included in the RGM construct is between about 200 nt and about 500 nt, between about 500 nt and about 1000 nt, between about 1000 nt and about 2000 nt, between about 2000 nt and about 3000 nt, between about 3000 and about 4000 nt, or between about 4000 nt and about 5000 nt. In some embodiments the sequence in an RGM construct comprises or consists of a sequence that extends from about nucleotide position −5000, −4500, −4000, −3500, −3000, −2500, −2000, −1900, −1800, −1700, −1600, −1500, −1400, −1300, −1200, −1100, −1000, −900, −800, −700, −600, −500, −400, −300, −250, −200, −150, −100, or −50 with respect to the TSS (position +1) of an imprinted gene, up to and including position +1 (the TSS) 10, 25, 50, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2500, 3000, 3500, 4000, 4500, or 5000 of an imprinted gene, or a variant of such a sequence that is at least 70%, 75%, 80%, 85%, 90%, 95%, 96%, 97%, 98%, 99%, or 99.5% identical to the sequence. All combinations of starting and ending positions are disclosed. In some embodiments the sequence comprises the 5' untranslated region of the imprinted gene. In some embodiments the sequence comprises at least the first exon of the imprinted gene. In some embodiments the sequence comprises one, two, or more CpG islands (CGIs). In some embodiments the imprinted gene promoter is associated with a parent-of-origin DMR. In some embodiments the DMR is a germline-derived DMR. In some embodiments the DMR is a secondary DMR. In some embodiments the imprinted gene promoter is associated with a CGI. An imprinted gene promoter is considered to be associated with a DMR or CGI is the imprinted gene promoter comprises, overlaps with, or is located in proximity to (e.g., within) a DMR or CGI, respectively. In some embodiments the sequence of the promoter in an RGM construct is derived from an imprinted gene promoter that is associated with a DMR, and the RGM construct comprises an at least 150, 200, 250, 300, 400, 500, 600, 700, 800, 900, or 1000 nt portion of the sequence of the DMR, or a variant of such a sequence that is at least 70%, 75%, 80%, 85%, 90%, 95%, 96%, 97%, 98%, 99%, or 99.5% identical to such portion.

In some embodiments the sequence of the promoter in an RGM construct comprises an at least 150, 200, 250, 300, 400, or 500 nt portion of an imprinted gene promoter region wherein the sequence of the portion is highly conserved between the human and mouse orthologs of the gene. For example, the sequence may be at least 95%, 96%, 97%, 98%, 99%, 99.5%, or 100% identical in the human and mouse orthologs of the imprinted gene. In some embodiments the sequence of the promoter in an RGM construct consists of an at least 150, 200, 250, 300, 400, or 500 nt portion of an imprinted gene promoter region, wherein the sequence of the portion is highly conserved between the human and mouse orthologs of the gene, and, in some embodiments, further comprising up to 25, 50, 100, 150, or 200 nt of the sequence that is located upstream and/or up to 25, 50, 100, 150, or 200 nt of the sequence that is located downstream from the highly conserved portion. In some embodiments the imprinted gene is a gene that is widely expressed in mammalian tissues, such as Snrpn, e.g., the gene is expressed in the predominant cell types found in at least 10 or more organs or tissues. In some embodiments the imprinted gene may be less widely expressed, e.g., its expression may be tissue or cell type specific. In some embodiments an RGM construct comprising an imprinted gene promoter that is selectively expressed in one or more tissue or cell types may be integrated into the genome of a cell of such cell type. In some embodiments an RGM construct comprising an imprinted gene promoter that is selectively expressed in one or more tissues or cell types may be used to detect or monitor methylation of a ROI in one or more of those tissues or cell types. In some embodiments the imprinted gene is a gene that is imprinted in at least mice and humans. In some embodiments the imprinted gene is imprinted in a species-specific manner, e.g., it is imprinted in mice and not in humans, or vice versa. In some embodiments the imprinted gene is imprinted in at least mice, rats, humans, cattle, sheep, or horses. In some embodiments an RGM construct comprising an imprinted gene promoter that is imprinted in a species-specific manner may be integrated into the genome of a cell of a species in which the gene is imprinted. In some embodiments an RGM construct comprising an imprinted gene promoter that is imprinted in a species-specific manner may be used to detect or monitor methylation state of a ROI in cells of a species in which the gene is imprinted.

In some embodiments the mammalian imprinted gene promoter is from the Igf2r, Gnas, Igf2, Meg3 (Gtl2), Airn, Kcnq1ot1, Mest, Grb10, and Peg10 genes (see Table 1 for Gene IDs of the human and mouse orthologs of these genes). In some embodiments the imprinted gene promoter is associated with a parent-of-origin DMR. For example, in some embodiments the imprinted gene promoter is from the Igf2r, Gnas, or Meg3 gene. In some embodiments the imprinted gene promoter comprises or overlaps a CpG island.

TABLE 1

Selected Mammalian Imprinted Genes

| Gene Name | Gene ID (mouse) | Gene ID (human) |
|---|---|---|
| Igf2r | 16004 | 3482 |
| Gnas | 14683 | 2778 |
| Meg3 | 17263 | 55384 |
| Igf2 | 16002 | 3481 |
| Airn | 104103 | 100271873 |
| Kcnq1ot1 | 63830 | 10984 |
| Mest | 17294 | 4232 |
| Grb10 | 14783 | 2887 |
| Peg10 | 170676 | 23089 |

In some embodiments the imprinted gene is the Igf2r gene. The Igf2r promoter is associated with a DMR, which includes the Igf2r TSS. The DMR associated with the murine Igf2r promoter is depicted in FIG. 10 (SEQ ID NO: 4). In some embodiments the promoter in an RGM construct comprises or consists of a minimal Igf2r promoter. In some embodiments the RGM construct comprises a sequence extending from about position −350, −300, −250, −200, or −150 to about position +1, +100, +200, +300, +400, +500, or +600, where +1 is the TSS of the Igfr2 gene. All combinations of starting and ending positions are disclosed. In some embodiments the RGM promoter comprises the CpG island in the Igfr2 promoter region, or a variant thereof that is at least 70%, 75%, 80%, 85%, 90%, 95%, 96%, 97%, 98%, 99%, or 99.5% identical thereto.

Figure 11C:

In some embodiments the imprinted gene is the Gnas gene. The Gnas promoter is associated with a DMR, which includes the Gnas TSS. The DMR associated with the murine Gnas promoter is depicted in FIG. 11 (SEQ ID NO: 5). In some embodiments the promoter in an RGM construct is a minimal Gnas promoter. In some embodiments the RGM construct comprises a sequence extending from about position −600, −550, −500, −450, −400, −350, −300, −250, −200, or −150 to about position +1, +100, +200, +300, +400, +500, or +600, where +1 is the TSS of GNAS. In some embodiments the RGM construct comprises a sequence extending from about position −2820, 2500, −2000, −1500, or −1000 to about position −10, −1, +1, +100, +200, +300, +400, +500, or +600, where +1 is the TSS of Gnas. In some embodiments the sequence further comprises a sequence extending from about position +600 to about position +1000, +1500, +2000, +2500, or +3000, where +1 is the TSS of GNAS. All combinations of starting and ending positions are disclosed.

In some embodiments the imprinted gene is the Meg3 (Gtl2) gene. The Meg3 promoter is associated with a DMR, which includes the Meg3 TSS. The DMR associated with the murine Meg3 promoter is depicted in FIG. 12 (SEQ ID NO: 6). In some embodiments the promoter in an RGM construct comprises or consists of a minimal Meg3 promoter. In some embodiments the RGM construct comprises a sequence extending from about position −350, −300, −250, −200, or −150 to about position +1, +100, +200, +300, +400, +500, or +600, where +1 is the TSS of Meg3. All combinations of starting and ending positions are disclosed.

In some aspects, disclosed herein is a nucleic acid comprising an RGM construct and one or more additional DNA sequences. For example, in some embodiments, a nucleic acid comprising an RGM construct further comprises a second reporter construct. The second reporter construct typically encodes a reporter molecule that is distinguishable from the reporter molecule encoded by the RGM construct. In some embodiments, the second reporter construct may be used to identify or select for cells that have taken up the nucleic acid and that have the second reporter construct and the RGM construct stably integrated into their genome. In some embodiments the reporter gene in the second reporter construct is a selectable marker gene. The second reporter construct may be positioned either 5' or 3' with respect to the RGM construct in the nucleic acid. Typically, the promoter of the second reporter construct is one that is not subject to regulation by DNA methylation and is not affected by methylation of exogenous DNA (i.e., DNA outside the promoter in the second reporter construct). In some embodiments the promoter is a constitutive promoter. For example, in some embodiments the phosphoglycerate kinase (PGK) promoter, cytomegalovirus enhancer/chicken β-actin hybrid promoter (CAG promoter), cytomegalovirus (CMV) promoter, ubiquitin promoter, beta-actin promoter or elongation factor-1 alpha promoter is used. In some embodiments the nucleic acid may comprise an additional reporter construct that comprises a cell type or cell state specific promoter operably linked to a reporter gene. Expression of the reporter gene indicates that the cell type or cell state specific promoter is active and may be used to identify a cell as being of a particular cell type or as being in a particular cell state. Thus, in some embodiments the nucleic acid may comprise a plurality of elements arranged as follows: RGM-SMC, RGM-SRC, RGM-SRC-SMC or RGM-SMC-SRC, where SMC represents a selectable marker cassette and SRC represents a second (or third) reporter construct. In some embodiments, a nucleic acid comprising an RGM construct does not comprise a selectable marker gene. In some embodiments, a nucleic acid comprising an RGM construct does not comprise a selectable marker cassette.

In some embodiments, a nucleic acid comprising an RGM construct serves as a donor nucleic acid for homologous recombination in order to introduce at least the RGM construct into the genome of a cell. To that end, in some embodiments, a nucleic acid comprising an RGM construct further comprises one or more nucleic acid sequences that are homologous to sequences in the mammalian genome that are located on one or both sides of a selected location in the genome that comprises a site at which the RGM construct is to be integrated. In some embodiments, homology arms may be positioned on each side of a segment of the nucleic acid that is to be integrated into the genome of a cell (see FIG. 3 for an example). For example, the nucleic acid may comprise a plurality of elements arranged as follows: HA1-RGM-[SMC]-[SRC]-HA2, where HA1 and HA2 represent first and second homology arms, SMC and SRC represent a selectable marker cassette and a second reporter cassette, respectively, and the brackets are used to indicate that the element within the brackets may or may not be present in various embodiments. The homologous sequences facilitate integration of the segment into the cell in a region of the genome comprising sequences that are homologous to the homology arms. Thus HA and HA2 may be homologous to adjacent sequences in a region of interest in the genome. In some embodiments, one of the homology arms is homologous to a region of the genome that is 5' to a target location in the genome, and the other homology arm is homologous to a region of the genome that is 3' to a target location in the genome. In some embodiments, a targetable nuclease that is programmed to cleave DNA at or within the target location is used to cut the genomic DNA. Repair by homologous recombination (homology-directed repair) using the nucleic acid as a donor results in incorporation of at least the region located between the homology arms into the genome. Thus in some aspects, a nucleic acid comprising an RGM construct serves as a donor nucleic acid for homologous recombination to integrate the RGM construct into the genome in proximity to a region of interest.

In some embodiments the one or more additional nucleic acid sequences comprises a DNA region of interest. In some embodiments, the DNA region of interest comprises a sequence that is normally hypermethylated when present in the genome of at least some mammalian cell types in its natural location. In some embodiments, the DNA region of interest comprises a sequence that is normally hypomethylated when present in the genome of at least some mammalian cell types in its natural location. In some embodiments, the DNA region of interest comprises at least a portion of a mammalian CpG island (CGI). In some embodiments the CGI is one that, when present in the genome of a mammalian cell in its natural location, is associated with a promoter that is normally widely expressed in a constitutive manner in vivo. In some embodiments the CGI is one that, when present in the genome of a cell in its natural location in vivo, is normally hypomethylated in its native state in vivo. For example, in some embodiments the CGI is associated with the Gapdh promoter. In mammalian cells the Gapdh promoter typically comprises a hypomethylated CGI, which is consistent with its constitutive expression in all tissues. In some embodiments the CGI is one that, when present in the genome of a cell in its natural location in vivo, is associated with a promoter that is normally expressed in a cell type specific manner. In some embodiments the CGI is one that is associated with a promoter that is normally expressed exclusively in germ cells. In some embodiments the CGI is one that is normally hypermethylated when present in the genome of a cell in its natural location in vivo. For example, in some embodiments the CpG island is associated with the Dazl promoter, which is expressed specifically in germ cells and is normally hypermethylated in all tissues except germ cells.

In some embodiments a nucleic acid may be contacted with one or more DNA modifying enzymes before being introduced into a cell. In some embodiments the DNA modifying enzyme comprises a methyltransferase. In some embodiments the DNA modifying enzyme comprises a CpG methyltransferase. In some embodiments the DNA modifying enzyme comprises a bacterial DNA methyltransferase. In some embodiments the DNA modifying enzyme comprises a eukaryotic DNA methyltransferase, e.g., a mammalian DNA methyltransferase. In some embodiments the nucleic acid construct is contacted with a CpG methyltransferase under appropriate conditions and for a sufficient time so that at least 50%, 60%, 70%, 75%, 80%, 85%, 90%, 95%, 96%, 97%, 98%, 99%, 100% of the CpGs in the RGM promoter are methylated. The nucleic acid may further comprise a ROI. The nucleic acid may be integrated into the genome of a cell and the methylation state of the ROI may subsequently be determined by measuring expression of the reporter molecule and/or by standard methodology for methylation analysis.

In some aspects, described herein is a nucleic acid comprising a mammalian imprinted gene promoter and a restriction site located 3' with respect to the promoter. The restriction site is appropriately positioned to allow the insertion of a reporter gene of choice in order to create an RGM construct. The ordinary skilled artisan may select a reporter gene of choice from, e.g., those described herein.

A nucleic acid comprising an RGM construct and a DNA region of interest can be introduced into a cell and integrated into the genome of the cell at a random location or at a predetermined location. The RGM construct may be used to report on methylation of the DNA region of interest. If desired, the region of the genome or the location at which the nucleic acid is integrated may be identified, e.g., by sequencing. In some embodiments, the nucleic acid is subjected to methylation in vitro before the nucleic acid is introduced into a cell. For example, the nucleic acid may be contacted with a DNA methylating enzyme in vitro.

In some embodiments, a nucleic acid comprising an RGM construct (and, optionally, one or more additional DNA sequences such as an additional reporter construct, homology arms, and/or a DNA region of interest) is incorporated into a vector that can be used to transfer the nucleic acid into a cell. Any of a wide variety of vectors may be used in various embodiments. Those of ordinary skill in the art are aware of suitable vectors for introducing nucleic acids into cells of interest, e.g., mammalian cells. For example, DNA or RNA plasmids, viral vectors (e.g., based on adenoviruses, adeno-associated viruses, retroviruses, lentiviruses, vaccinia virus and other poxviruses, herpesviruses) or transposons may be used.

In general, any method known in the art for introducing nucleic acid constructs or vectors into cells may be used to introduce a nucleic acid or vector comprising an RGM construct into cells. One of ordinary skill in the art will select a suitable method depending on, e.g., the particular vector, cell type, or experimental conditions (e.g., in vitro or in vivo). In some embodiments, transfection, viral infection, electroporation, or microinjection may be used. Those of ordinary skill in the art are aware of suitable transfection reagents. In some embodiments an RGM construct or vector comprising an RGM construct may be injected into a living nonhuman animal, which may be an embryo, fetus, postnatal, juvenile, or adult animal. In some embodiments the animal may subsequently be subjected to imaging. In some embodiments cells that have an RGM construct integrated into their genome are introduced into a nonhuman animal. If the cells are not immunologically compatible (e.g., are of a different species or noncompatible strain), the animal may be immunocompromised if appropriate to reduce the likelihood that the cells would be rejected. In some embodiments the introduced cells may contribute to one or more organs or tissues of the non-human mammal, e.g., the nervous system.

In general, a reporter molecule may be measured at any time after introduction of the RGM construct into a cell or subject. In some embodiments the reporter molecule may be first measured between about 12 hours and about 7 days, between 1 and 2 weeks, between 2 and 6 weeks, between 8 and 12 weeks, or more after introducing the RGM construct into a cell or subject. In some embodiments, a stable cell line comprising a nucleic acid comprising an RGM construct integrated into its genome is derived.

In some embodiments, a control reporter construct may be introduced into cells in addition to an RGM reporter construct. In some embodiments, a control reporter construct comprises a constitutive promoter operably linked sequence encoding a reporter molecule that is distinguishable from the reporter molecule encoded by the RGM construct, operably linked to a constitutive promoter whose activity is not affected either by methylation of the promoter itself or by methylation of sequences exogenous to the promoter. In some embodiments the control reporter construct may be used to normalize the signal from the reporter molecule encoded by the RGM construct.

In some embodiments a nucleic acid sequence encoding a reporter molecule (or other gene product to be expressed in a cell) comprises a transcription terminator, which term refers to a section of nucleic acid sequence that mediates transcriptional termination by providing signals in the newly synthesized RNA that trigger processes which release the RNA from the transcriptional complex. In the case of a eukaryotic mRNA transcribed by RNA polymerase II, a transcription terminator may comprise a sequence that is transcribed to produce a sequence that triggers cleavage of and addition of a polyA tail to the newly synthesized mRNA. For example, the nucleic acid may comprise a plurality of elements arranged as follows: RGMP-RG-polyA, where RGMP represents an RGM Promoter, RG, represents a reporter gene, and polyA represents a transcription terminator that when present in mRNA triggers cleavage and addition of polyA. Those of ordinary skill in the art are aware of suitable transcription terminators for use in cells of interest, e.g., mammalian cells. For example, the simian virus 40 (sv40) late polyadenylation signal (SVLPA) or the human or bovine growth hormone polyadenylation signal may be used.

In some embodiments a nucleic acid comprising a DNA methylation reporter is integrated into the genome of a cell in proximity to a DNA region of interest (ROI). In general, the ROI may be anywhere in the genome. In some embodiments the ROI is in a non-transcribed region of the genome. In some embodiments the ROI is no more than 1 kilobase (kb), 2 kb, 3 kb, 4 kb, 5 kb, 6 kb, 7 kb, 8 kb, 9 kb, 10 kb, 20 kb, or 50 kb away from a start site for transcription of an RNA (a transcription start site (TSS)). In some embodiments the RNA transcript is included in the NCBI RNA reference sequence collection (RefSeq), which is available on the worldwide web at subdomain ncbi.nlm.nih.gov/refseq (Pruitt K D, Tatusova T, Maglott D R. NCBI Reference Sequence (RefSeq): a curated non-redundant sequence database of genomes, transcripts and proteins. *Nucleic Acids Res.* 2005 Jan. 1; 33 (Database issue):D501-4; Pruitt, K D, et al., Nucleic Acids Res. 2012 January; 40 (Database issue): D130-5. doi: 10.1093/nar/gkr1079; Pruitt, K D, et al., Nucleic Acids Res. 2014 January; 42 (Database issue): D756-63. doi: 10.1093/nar/gkt1114). RefSeq provides genomic, transcript, and coding sequences as well as gene annotations that include, among other things, TSSs for mammalian genes. Wherever relevant, a RefSeq sequence may be used for any genomic sequence, transcript, or protein sequence of interest herein.

In some embodiments the region of interest is a regulatory region of a gene of interest. In some embodiments the RGM construct is integrated at a location a distance of no more than 1 kb, 2 kb, 3 kb, 4 kb, 5 kb, 10 kb, 15 kb, 20 kb, or 50 kb from a regulatory region of a gene. In some embodiments the location is a distance of no more than 1 kilobases (kb), 2 kb, 3 kb, 4 kb, 5 kb, 10 kb, 20 kb, or 50 kb from the 5' end of an open reading frame. In some embodiments the location is a distance of no more than 1 kilobases (kb), 2 kb, 3 kb, 4 kb, 5 kb, 10 kb, 20 kb, or 50 kb from a CpG island. For purposes of the present disclosure, the "distance" between two locations in terms of nucleotides (i.e., the number of intervening nucleotides between the two locations) is calculated as follows: If one location is a single nucleotide and the other location is a region two or more nucleotides long, the number of intervening nucleotides is the number of nucleotides between the single nucleotide and the closer of the two terminal nucleotides of the other region. If both locations are regions two or more nucleotides long, the number of intervening nucleotides is the number of nucleotides between the closest terminal nucleotides of the two regions, i.e., the number of nucleotides that would need to be removed to make the two regions contiguous. A regulatory region may be any region that affects the level of transcription from the gene. Examples of regulatory regions include superenhancers, enhancers, and promoters. In some embodiments the ROI comprises a superenhancer, enhancer, or promoter. In some embodiments an RGM construct is integrated into a superenhancer, enhancer, or promoter. In some embodiments the ROI is a distal regulatory region, which term refers to a regulatory region outside the promoter region of a gene. In some embodiments the ROI is not an imprinting control region. In some embodiments the ROI is an imprinting control region. In some embodiments the ICR is IG-DMR or H19-DMD.

In general, a gene of interest may be any gene. In some embodiments the gene of interest encodes a protein. In some embodiments the gene of interest encodes a transcription factor, a transcriptional co-activator or co-repressor, an enzyme, a receptor, a secreted protein, a transmembrane protein, a histone, a peripheral membrane protein, a soluble protein, a nuclear protein, a mitochondrial protein, a lysosomal protein, a growth factor, a cytokine, an interferon, a chemokine, a hormone, an extracellular matrix protein, a motor protein, a cell adhesion molecule, a major or minor histocompatibility (MHC) protein, a transporter, a channel an immunoglobulin (Ig) superfamily (IgSF) gene, a tumor necrosis factor, an NF-kappaB protein, an integrin, a cadherin superfamily member, a selectin, a clotting factor, a complement factor, a plasminogen, plasminogen activating factor, a proto-oncogene, an oncogene, a tumor suppressor gene, a chaperone, a heat shock factor, a heat shock protein. In some embodiments the gene encodes a DNA modifying enzyme or a histone modifying enzyme. In some embodiments the gene encodes a kinase, a phosphatase, a GTPase, or an ATPase. In some embodiments the gene encodes a long non-coding RNA, which term refers to an RNA at least 200 nt long that is not a microRNA precursor. In some embodiments the gene encodes a microRNA precursor. In some embodiments the gene is an imprinted gene. In most embodiments the gene is not an imprinted gene.

It will be appreciated that, in general, an RGM construct comprising a promoter derived from a mammalian imprinted gene is used as a reporter for methylation of a region of the genome that is not the promoter region or gene body of the imprinted gene from which the promoter in such construct is derived. Thus, in general, the region of interest is not the promoter region or gene body of an imprinted gene from which the promoter in the RGM construct was derived. For example, if the RGM construct comprises a Snrpn promoter, the construct is typically not integrated into the Snrpn promoter or gene body nor used to report on methylation state of the endogenous Snrpn promoter region or gene body. In some embodiments an RGM construct comprising an imprinted gene promoter from a mammalian imprinted gene is integrated into the genome on a different chromosome or different chromosome arm from that which naturally contains the imprinted gene. In some embodiments an RGM construct comprising an imprinted gene promoter from a mammalian imprinted gene is integrated into the genome on the same chromosome or chromosome arm as that which naturally contains the imprinted gene, but is integrated at least 20, 40, 60, 80, 100, 150, 200, 300, 400, or 500 kb away from the imprinted gene promoter or gene body of the imprinted gene. In general, an RGM construct comprising a promoter derived from a mammalian imprinted gene is used as a reporter for methylation of a region of the genome that is not the ICR that controls imprinting of the imprinted gene from which the promoter in such construct is derived. Thus, in general, the region of interest is not the ICR of an imprinted gene from which the promoter in the RGM construct was derived. For example, if the RGM construct comprises a Snrpn promoter, the construct is typically not integrated into the ICR that controls imprinting of the Snrpn gene nor used to report on methylation state of such ICR.

In some embodiments the ROI is a repetitive element such as a tandem repeat (e.g., satellite DNA), interspersed repeats such as LINEs (e.g., Alu sequences), or SINEs. In some embodiments the ROI is within up to about 10 kb, 20 kb, or 50 kb from a telomere or centromere. In some embodiments the ROI comprises a tissue-specific DMR, reprogramming-specific DMR, or disease-specific DMR. In some embodiments the ROI comprises a secondary DMR or germline-derived DMR. In some embodiments the ROI comprises an imprinting control region.

In some embodiments a ROI is any DNA region that, based on standard methylation analysis, has been found to normally be hypomethylated in the genome of cells of one or more cell types or cell states, e.g., cells of the same cell type or cell state as that of a cell into which a nucleic acid comprising an RGM construct is introduced. In some embodiments an RGM construct integrated into such a region may be used to detect that the ROI is aberrantly hypermethylated and/or to detect an increase in methylation of the region, e.g., to a hypermethylated state. In some embodiments an RGM construct integrated into such a region may be used to detect that the ROI has a normal methylation state and/or remains stably hypomethylated.

In some embodiments a ROI is any DNA region that, based on standard methylation analysis, has been found to normally be hypermethylated in the genome of cells of one or more cell types or cell states, e.g., cells of the same cell type or cell state as that of a cell into which a nucleic acid comprising an RGM construct is introduced. In some embodiments the RGM construct integrated into such a region may be used to detect that the ROI is aberrantly hypomethylated and/or to detect a decrease in methylation of the region, e.g., to a hypomethylated state. In some embodiments an RGM construct integrated into such a region may be used to detect that the ROI has a normal methylation state and/or remains stably hypermethylated.

In some embodiments the ROI is a superenhancer or enhancer that is active (i.e., able to enhance transcription of one or more genes) in ES cells and/or iPS cells but is not active in somatic cells. In some embodiments the ROI is a superenhancer or enhancer that is active in somatic cells of one or more cell types but is not active in ES cells and/or iPS cells. In some embodiments the ROI is a superenhancer or enhancer that is active in an adult stem cell, e.g., a hematopoietic stem cell, neural stem cell, intestinal stem cell, mammary stem cell, mesenchymal stem cell, olfactory stem cell, or neural crest stem cell, but is not active in at least one other type of adult stem cell. In some embodiments the ROI is a superenhancer or enhancer that is active in an adult stem cell, e.g., an adult stem cell of any of the foregoing types, but is not active in at least one type of more differentiated cell to which the adult stem cell can give rise. In some embodiments the ROI is a superenhancer or enhancer that is active in a first differentiated cell type but is not active in at least one, several, most, or essentially all other differentiated cell types. In some embodiments the ROI is a CCI or CGI shore. In some embodiments the ROI is a low CpG region. In some embodiments the low CpG region is outside of CpG shores. In some embodiments the low CpG region is a region at least 200, 500, 1000, or 2000 nt long that has no more than half the density of CpGs as does a CGI. In some embodiments the ROI is a region that is differentially bound by one or more DNA binding proteins (e.g., transcription factor, CTCF) in cells of at least two different cell types or cell states. In some embodiments the ROI is a disease-specific DMR. In some embodiments the ROI is a tissue-specific DMR.

In some embodiments the ROI is a promoter that is active (i.e., able to drive transcription of one or more genes) in ES cells and/or iPS cells but is not active in somatic cells. In some embodiments the ROI is a promoter that is active in somatic cells of one or more cell types but is not active in ES cells and/or iPS cells. In some embodiments the ROI is a promoter that is active in an adult stem cell, e.g., a hematopoietic stem cell, neural stem cell, intestinal stem cell, mammary stem cell, mesenchymal stem cell, olfactory stem cell, or neural crest stem cell, but is not active in at least one other type of adult stem cell. In some embodiments the ROI is a promoter that is active in an adult stem cell, e.g., an adult stem cell of any of the foregoing types, but is not active in at least one type of more differentiated cell to which the adult stem cell can give rise. In some embodiments the ROI is a promoter that is active in a first differentiated cell type but is not active in at least one, several, most, or essentially all other differentiated cell types.

In some embodiments the region of interest is in an autosome, and the genome of the mammalian cell comprises two copies (alleles) of the region of interest—one on each of two homologous autosomes. The ROI may be on any autosome or may be on the X or Y chromosome in various embodiments. In some embodiments the cell comprises a nucleic acid comprising an RGM construct integrated into its genome in proximity to only one of the two alleles of the region of interest. In some embodiments the nucleic acid comprising an RGM construct is integrated into the paternal allele of the ROI. In some embodiments the nucleic acid comprising an RGM construct is integrated into the maternal allele of the ROI. In some embodiments the genome of the cell comprises two nucleic acids each comprising an RGM construct, one nucleic acid integrated into each allele of the region of interest. When only one allele of a gene or region of DNA is genetically modified, this may be referred to as "monoallelic modification". When both alleles of a gene or region of DNA are genetically modified, this may be referred to as "biallelic modification". Any of the genetic modifications described herein may be monoallelic or biallelic in various embodiments. The reporter genes in the RGM constructs in the case of biallelic modification may encode the same reporter molecule or different reporter molecules. In some embodiments cells having a biallelic modification with RGM constructs that encode distinguishable reporter molecules may be used to compare the timing of methylation or demethylation of the two alleles of an ROI, e.g., as a cell undergoes a cell identity or cell state transition.

One of ordinary skill in the art can locate transcription start sites, gene bodies, exons, introns, histone modifications (methylation, acetylation), CGIs, CGI shores, promoters, enhancers, superenhancers and/or sites of DNA methylation or DMRs that have been identified using standard methods for methylation analysis in the genome of a species of interest using publicly available databases and resources such as the UCSC Genome Browser (available on the worldwide web at subdomain genome.ucsc.edu/; see, e.g., Kent, W., et al., The human genome browser at UCSC. Genome Research 2002; 12:996-1006 and/or Rosenbloom K R, et al, The UCSC Genome Browser database: 2015 update Nucleic Acids Res. 2015; 43 (Database issue): D670-81). For example human assemblies GRCh37/hg19 or GRCh38/hg38 or the mouse (*Mus musculus*) assemblies GRC37/mm9 or GRC38/mm10, or subsequent genome assemblies, may be used. One of ordinary skill in the art can design homology arms, guide RNAs, TALENs to direct integration of a nucleic acid comprising an RGM construct in proximity to a region of interest.

In some aspects described herein is a collection of mammalian cells or cell lines (a library of cells or cell lines), each comprising an RGM construct integrated at a different location in the genome of the cell. The locations may be at least 10 kb apart on average. In some embodiments the library comprises at least 500, 1000, 5000, 10000, 20000, 50000, 100000 or more cells or cell lines. The locations may be random or may be selected. In some embodiments the library comprises members in which the RGM construct is integrated within about 10 kb or about 5 kb of a TSS for each of at least 10000, 20000, or more RefSeq genes. The cells could be of any cell type in various embodiments. In some embodiments they are ES or iPS cells or fibroblasts. In some embodiments such a library could be used to develop a genome-wide profile of methylation state changes during cell state changes such as differentiation or reprogramming.

In some aspects described herein is a collection (library) of nucleic acids each comprising an RGM construct comprising homology arms homologous to sequences flanking different locations in the genome of a mammalian cell. In some embodiments the library of nucleic acids comprises at least 500, 1000, 5000, 10000, 20000, 50000, 100000 or more nucleic acids comprising different homology arms homologous to sequences flanking different locations in the genome of a mammalian cell.

In some embodiments an RGM construct may be used to detect a difference in the level of methylation of a ROI between two cells or populations of cells. In some embodiments a difference is about 5%, 10%, 15%, 20%, 25%, 30%, 40%, 50%, 60%, 70%, 80%, 90% in the level of methylation of the ROI. In some embodiments the difference is at least 20%, or at least 50%.

In some embodiments two RGM constructs may be used to detect a difference in the level of methylation of two different ROIs in the same cell or population of cells or in different cells or populations of cells. In some embodiments a difference is about 5%, 10%, 15%, 20%, 25%, 30%, 40%, 50%, 60%, 70%, 80%, 90% in the level of methylation of the two ROIs. In some embodiments an RGM construct may be used to detect a change in the level of methylation of a ROI. The change may be an increase or decrease. In some embodiments a change is an increase by about 5%, 10%, 15%, 20%, 25%, 30%, 40%, 50%, 60%, 70%, 80%, 90% from a level of about 5%, 10%, 15%, 20%, 25%, 30%, 40%, 50%, 60%, 70%, 80%, 90% methylation (up to a maximum of 100% methylation). In some embodiments a change is a decrease by about 5%, 10%, 15%, 20%, 25%, 30%, 40%, 50%, 60%, 70%, 80%, 90% from a level of about 100%, 90%, 80%, 70%, 60%, 50%, 40%, 30%, 20%, or 10% (down to a minimum of 0% methylation). In some embodiments the magnitude of the change is at least 20%, at least 30%, at least 40%, at least 50%, at least 60%, at least 70%, or at least 80%. In some embodiments a change is an increase from a level of about 5% or less methylation to a level of about 10%, 20%, 30%, 40%, 50%, 60%, 70%, 80%, 90%, or more, an increase from a level of about 5%-10% methylation to a level of about 15%, 20%, 30%, 40%, 50%, 60%, 70%, 80%, 90%, or more, an increase from a level of about 10%-20% methylation to a level of about 25%, 30%, 40%, 50%, 60%, 70%, 80%, 90%, or more, an increase from a level of about 20%-30% methylation to a level of about 35%, 40%, 50%, 60%, 70%, 80%, 90%, or more, an increase from a level of about 30%-40% methylation to a level of about 45%, 50%, 60%, 70%, 80%, 90%, or more, an increase from a level of about 40%-50% methylation to a level of about 55%, 60%, 70%, 80%, 90%, or more, an increase from a level of about 50%-60% methylation to a level of about 65%, 70%, 80%, 90%, or more, an increase from a level of about 60%-70% methylation to a level of about 75%, 80%, 90%, or more, or an increase from a level of about 70%-80% methylation to a level of about 85%, 90% or more. In some embodiments a change is a decrease from a level of about 90% or more methylation to a level of no more than 5%, 10%, 20%, 30%, 40%, 50%, 60%, 70%, 80%, or 85%, a decrease from a level of about 80%-90% methylation to a level of no more than 5%, 10%, 20%, 30%, 40%, 50%, 60%, 70%, or 75%, a decrease from a level of about 70%-80% methylation to a level of no more than 5%, 10%, 20%, 30%, 40%, 50%, 60%, or 65%, a decrease from a level of about 60%-70% methylation to a level of no more than 5%, 10%, 20%, 30%, 40%, 50%, or 55%, a decrease from a level of about 50%-60% methylation to a level of no more than 5%, 10%, 20%, 30%, 40%, or 45%, a decrease from a level of about 40%-50% methylation to a level of no more than about 5%, 10%, 20%, or 30%, or 35% methylation, a decrease from a level of about 30%-40% methylation to a level of no more than 5%, 10%, 20%, 30%, or 35% methylation, a decrease from a level of about 20%-30% methylation to a level of no more than 5%, 10%, or 15%, or a decrease from about 10% to 20% methylation to a level of no more than 5% methylation.

In some embodiments an RGM construct may be used to determine the percentage or number of cells in a population of cells that exhibit a selected level or range of levels of methylation of a ROI, e.g., the percentage or number of cells in which the ROI is hypermethylated, or the percentage or number of cells in which the ROI is hypomethylated. The selected level may be about 0% 5%, 10%, 15%, 20%, 25%, 30%, 40%, 50%, 60%, 70%, 80%, 90%, 95%, or more. In some embodiments an RGM construct may be used to determine the percentage or number of cells in a population of cells that exhibit a selected change in level methylation of a ROI, e.g., the percentage or number of cells in which the ROI changes from hypermethylated to hypomethylated, or vice versa, over a given period of time. The change may be about 10%, 15%, 20%, 25%, 30%, 40%, 50%, 60%, 70%, 80%, 90%, 95%, or more in various embodiments. In some embodiments the level of the reporter molecule and thus the level of methylation of the ROI may be measured using flow cytometry, e.g., FACS. In some embodiments flow cytometry, e.g., FACS, may be used to separate a population of cells into 2, 3, 4, 5, or more subpopulations based on the level of the reporter molecule. The populations may be further analyzed or compared using any conventional method for analyzing cells, such as gene expression profiling (e.g., using microarrays or RNA-Seq), analysis of chromatin marks (e.g., using Chip-Seq or Chip-ChIP), protein expression profiling, morphological analysis, etc. In some embodiments, cells that are isolated based on expression level of the reporter molecule (e.g., low or absent expression, or robust expression) are further maintained (e.g., in culture) for a period of time and analyzed again for the reporter molecule.

Reporter Molecules

A wide variety of reporter molecules may be used in the reporter constructs described herein. In some embodiments, the reporter molecule in an RGM construct or other reporter construct described herein is compatible with detection in individual, living mammalian cells. In some embodiments the reporter molecule is substantially non-toxic to mammalian cells when expressed at levels appropriate for its detection in a method described herein. In some embodiments, detection of the reporter molecule does not require cell lysis or permeabilization. In some embodiments the reporter molecule does not generate a detectable permanent change in the cell. In such embodiments, once the reporter molecule has been degraded or otherwise removed, the fact that the reporter molecule had been produced in the cell is no longer evident. Such reporter molecules are considered "reversible" and, in some embodiments, may be used to report on multiple cycles of methylation and demethylation of the region of interest. In some embodiments the reporter molecule creates a permanent, heritable change in the genome of the cell. In such embodiments, the fact that the reporter molecule had been produced in the cell remains evident even after the reporter molecule has been degraded or otherwise removed. Such reporter molecules are considered "irreversible". In some embodiments, an irreversible reporter molecule may be useful for lineage tracing or other settings in which it is desired to be able to permanently mark a cell and/or its progeny (descendants) based on methylation state of the region of interest.

In some embodiments, detection of the reporter molecule comprises detection of light emitted by the reporter molecule or by a chemical reaction catalyzed by the reporter molecule. For example, in some embodiments, the reporter molecule in an RGM construct or other reporter construct described herein comprises a fluorescent or bioluminescent protein or a luciferase. Such proteins are well known in the art and include both naturally occurring proteins and engineered variants designed to have one or more altered properties relative to the naturally occurring protein, such as increased photostability, increased pH stability, increased fluorescence or light output, reduced tendency to dimerize, oligomerize, aggregate or be toxic to cells, an altered absorption/emission spectrum (in the case of a fluorescent protein), altered emission spectrum (in the case of a luciferase or luminescent protein), and/or altered substrate utilization (in the case a luciferase).

Fluorescent proteins include, e.g., green fluorescent protein (GFP) from the jellyfish *Aequorea victoria*, and related proteins comprising chromophores that emit green light or light of different colors such as red, yellow, blue, and cyan. Many of these proteins are found in marine animals such as *Hydrozoa* and *Anthozoa* species, crustaceans, and comb jellies. Examples of fluorescent proteins that may be used include, e.g., GFP, EGFP, Sirius, Azurite, EBFP2, BFP, mTurquoise, ECFP, Cerulean, mTFP1, mUkG1, mAG1, AcGFP, mWasabi, EmGFP, YPF, EYFP, Topaz, SYFP2, Venus, Citrine, mKO, mKO2, mOrange, mOrange2, LSS-mOrange, PSmOrange, and PSmOrange2, mStrawberry, mRuby, mCherry, mRaspberry, tdTomato, mKate, mKate2, mPlum, mNeptune, T-Sapphire, mAmetrine, mKeima, E2-Orange, E2-Red/Green, and E2-Crimson, ZsGreen. See, e.g., See, e.g., Chalfie, M. and Kain, S R (eds.) Green fluorescent protein: properties, applications, and protocols (Methods of biochemical analysis, v. 47) Wiley-Interscience, Hoboken, N.J., 2006; Chudakov, D M, et al., Physiol Rev. 90(3):1103-63, 2010, US Pat. Pub. Nos. 20030170911, 20060194282, 20070099175, 20090203035, 20100227400; 20100184954; 20110020784; 20140237632 for further description of various reporter molecules that may be used.

As used herein, a "far red fluorescent protein" is a FP that has an emission maximum between 625 nm and 680 nm. Examples include mPlum, mNeptune, and E2-Crimson. In some embodiments a far red FP is a derivative of DsRed. As used herein, an "infrared fluorescent protein" is a FP that has an emission maximum above 680 nanometers (nm), e.g., between 680 nm and 900 nm. In some embodiments, an infrared fluorescent protein has an emission maximum above 700 nanometers (nm), e.g., between 700 nm and 750 nm, between 750 nm and 800 nm, or between 800 nm and 900 nm. Without wishing to be bound by any theory, a far red or infrared protein may prove particularly advantageous for performing imaging in intact animals (e.g., intact mice) or tissue slices due, for example, to the ability of far red and infrared light to penetrate through tissue more efficiently than light of lower wavelengths. In some embodiments, a reporter molecule for in vivo imaging has emission near or above 650 nm as signals. In some embodiments an infrared protein is a variant of a naturally occurring phytochrome. Phytochromes are photosensory receptors found in plants, fungi, bacteria and cyanobacteria that absorb light in the red and far-red part of spectrum and utilize linear tetrapyrrole bilins, such as biliverdin IXα (BV), phycocyanobilin or phytochromobilin, as chromophores. Bacterial phytochromes, also termed bacteriophytochrome photoreceptors (BphPs), use BV as a chromophore. Infrared fluorescent proteins derived by engineering BphPs (e.g., *Rhodopseudomonas palustris* BphP such as RpBphP2) include IFP1.4 (Shu, X. et al. Science 324, 804-807 (2009), IFP2.0, (Yu, D., et al., Nature Communications (2013); 5:3626|DOI: 10.1038/ncomms4626), iRFP (Filonov, G. S. et al. Nat. Biotechnol. (2011), 29, 757-761), IFPrev (Bhattacharya S, et al., J Biol Chem. 2014; 289(46):32144-52), iRFP670, iRFP682, iRFP702, iRFP713 and iRFP720 (Shcherbakova D M and Verkhusha V V; Nat Methods. 2013; 10(8):751-4); Wi-Phy (Auldridge M E, et al., J Biol Chem. 2012 Mar. 2; 287(10):7000-9). PAiRFP1 and PAiRFP2 are infrared fluorescent proteins derived from AtBphP2, from *Agrobacterium tumefaciens* (Piatkevich K D, et al., Nat Commun. 2013; 4:2153. doi: 10.1038/ncomms3153; Piatkevich, K., et al., Chem. Soc. Rev., 2013, 42, 3441).

In some embodiments a photocontrollable fluorescent protein may be used as a reporter molecule. Photocontrollable fluorescent proteins (PFPs) are FPs whose fluorescence is regulated by light irradiation of specific wavelengths. They include photoactivators and photoswitchers. Photoactivators convert from a non-fluorescent to a bright fluorescent state and can be either irreversible or reversible. Photoswitchers change their fluorescent state and emit at a different wavelength upon exposure to transient but intense light. Examples of PFPs include PAGFP, PSCFP2, KFP, Kaede, mEosFP, mEos3.1, mEos3.2, Dronpa, Dendra2, KikGR, and PamCherry1. These and other FPs are described in further detail in Nowotschin S, et al. (2009) Trends Biotechnol 27(5): 266-276 and/or Shcherbakova, D M, et al., Annu Rev Biophys. 2014; 43: 303-329. and references therein.

As used herein, "luciferase" refers to members of a class of enzymes that catalyze reactions that result in production of light. Luciferases have been identified in and cloned from a variety of organisms including fireflies, click beetles, sea pansy (*Renilla*), marine copepods, and bacteria among others. Examples of luciferases that may be used as reporter proteins include, e.g., *Renilla* (e.g., *Renilla reniformis*) luciferase, *Gaussia* (e.g., *Gaussia princeps*) luciferase), *Metridia* luciferase, firefly (e.g., *Photinus pyralis* luciferase), click beetle (e.g., *Pyrearinus termitilluminans*) luciferase, deep sea shrimp (e.g., *Oplophorus gracilirostris*) luciferase). "Luciferin" is used herein to refer to any substrate utilized by a luciferase in a light-emitting reaction. Firefly luciferin and coelenterazine are examples. Coelenterazine is the substrate for many luciferases and photoproteins including *Renilla, Gaussia,* and *Metridia* luciferases.

In some embodiments a variant of a naturally occurring luciferase that provides higher light output than the naturally occurring form and/or is capable of utilizing an analog of a naturally occurring luciferin as a substrate can be used. See, e.g., Loening, A M, et al., Protein Engineering, Design and Selection (2006) 19 (9): 391-400, for examples. NanoLuc (NL) is an engineered variant (Hall, N P, et al., ACS Chem Biol. 2012; 7(11):1848-57). Furimazine is an analog of coelenterazine optimized as a substrate for NL. The luciferase system encoded by the bacterial luciferase gene cassette (lux) has the ability to synthesize and/or scavenge all of the substrate compounds required for production of light and can therefore be used as a reporter molecule without the need to provide a luciferin. It has been codon optimized for expression in mammalian cells and successfully used to image cells in cell culture and in small animal imaging (Close D., et al., J. Biomed. Opt. 2011; 16:e12441; Close, D., et al., Sensors (Basel). 2012; 12(1):732-52).

In some embodiments, the reporter molecule in an RGM construct or other reporter construct described herein is detectable based on its effect on expression of a second reporter gene or third reporter gene in the cell. The second reporter molecule may be a directly detectable reporter molecule such as a FP or luciferase. Expression of the reporter molecule in the RGM construct will generally turn expression of the second reporter gene on or off, thereby allowing detection of the activity of the promoter in the RGM construct and thus detection of the methylation state of the region of interest in proximity to the RGM construct in the genome. For example, in some embodiments, the reporter molecule in an RGM construct comprises a site-specific recombinase, such as Cre, Flp, or other site-specific recombinase. In some embodiments, the reporter molecule in an RGM construct comprises a repressor protein, such as the Tet repressor. The use of a site-specific recombinase as a reporter molecule allows for the creation of irreversible, heritable, genome modifications upon activity of the reporter molecule. Such genome modifications can result in permanent expression of a second reporter molecule by a cell and its descendants, thereby allowing for lineage tracing.

In some aspects, use of a site-specific recombinase as a reporter molecule can convert a transient or permanent change in methylation state of a region of interest to a permanent and heritable change in the cell. However, if the RGM reporter molecule is a FP, luciferase, or other molecule that degrades or is diluted over time without creating a permanent and heritable change in the cell then the RGM construct can report on methylation changes in a reversible manner, e.g., it can report on an increase in methylation of the ROI at a first time point and then report on a decrease in methylation of the ROI at a second time point, or vice versa. In other words, in such embodiments, production of the reporter molecule encoded by the RGM construct can track the methylation state of the ROI, so that if the methylation state of the ROI changes over time, the level of the reporter molecule likewise changes.

In some embodiments in which the reporter molecule in an RGM construct comprises a site-specific recombinase, the genome of the cell into which the RGM construct is introduced typically comprises or is modified to comprise a sequence encoding a second reporter molecule that is not produced in the absence of activity of the site-specific recombinase but is produced upon a recombination event mediated by the site-specific recombinase. Thus, when the RGM promoter is active, the recombinase is produced, leading to production of the second reporter molecule. The recombination event may be removal of a sequence or may be inversion of a sequence. For purposes of description it will be assumed that the site-specific recombinase is Cre, but it should be understood that other site-specific recombinases may be used in a similar manner. In some embodiments the genome of the cell comprises a second (or third, fourth, etc.) reporter construct comprising a promoter (e.g., a constitutive promoter), a second reporter gene, and a loxP-STOP-loxP sequence (a STOP cassette). In some embodiments a nucleic acid comprising a STOP cassette and a second reporter gene is integrated into the genome of the cell downstream of an endogenous promoter. In some embodiments the nucleic acid comprising a STOP cassette and second reporter gene is integrated into the mouse Rosa26 gene locus or the human AAVS1 locus or another safe harbor locus. The STOP cassette is appropriately positioned in the second reporter construct or in the genome of the cell so that the reporter molecule encoded by the second reporter gene is not produced unless the STOP sequence is removed (i.e., the reporter gene is "off"). For example, the STOP cassette may be positioned between the promoter and the second reporter gene. Those of ordinary skill in the art are aware of suitable STOP sequences. For example, in some embodiments the STOP sequence may comprise at least a polyadenylation signal and/or stop codon to block gene transcription and/or translation in the absence of Cre. Cre-mediated excision of the STOP cassette is irreversible, thereby allowing for permanent expression of the previously transcriptionally silent reporter gene. Once activated, expression of the second reporter molecule is independent of subsequent Cre expression or activity. The stable inheritance of the active second reporter gene by the progeny of the original cell in which the RGM promoter drove transcription of Cre allows for detection of all progeny of the original cell. In some embodiments, this allows for lineage tracing. In some embodiments, the genome of the cell comprises a sequence comprising a promoter and a sequence encoding a second reporter molecule that is not operably linked to the promoter but would become so operably linked upon recombinase-mediated inversion of the sequence or upon recombinase-mediated inversion of a sequence comprising the promoter. In other words, recombinase-mediated inversion would bring the sequence encoding the second reporter molecule into operable association with the promoter, resulting in expression of the second reporter molecule. As described above, once activated, expression of the second reporter molecule is independent of subsequent Cre expression or activity. The stable inheritance of the active second reporter gene by the progeny of the original cell in which the RGM promoter drove transcription of Cre allows for detection of all progeny of the original cell.

In some embodiments, the RGM construct comprises a RGM promoter operably linked to a sequence that encodes a transcriptional repressor protein that is capable of binding to DNA in a sequence-specific manner and repressing transcription from a nearby promoter. The transcriptional repressor protein can act as a reporter molecule in the context of a cell that comprises binding sites for the repressor as follows: In such embodiments, the cell into which the RGM construct is introduced typically comprises or is modified to comprise a second reporter construct, which comprises a sequence encoding a second reporter molecule, an operably linked promoter, and a binding site for the repressor protein, wherein the binding site is positioned such that the second reporter molecule is not produced in the presence of the repressor protein because the second reporter molecule binds to the binding sites and inhibits transcription. Those of ordinary skill in the art are aware of suitable repressor proteins and the sequences in DNA to which they bind. For example, the Tet repressor (TetR), Lac repressor (LacR), or other bacterial, archael, fungal, plant, or other non-mammalian transcriptional repressor protein comprising a sequence-specific DNA binding domain (DBD) may be used. Furthermore, a DNA binding domain of a transcriptional repressor or activator (in the absence of a transcriptional activation domain) could serve as a transcriptional repressor.

The binding site(s) for the DBD may be positioned upstream from the promoter. In such embodiments, when the promoter in the RGM construct is active, the repressor protein is produced, and the second reporter molecule is not produced. When the promoter in the RGM construct is inactive, the repressor protein is not produced, and the second reporter molecule is produced. In some embodiments the second reporter molecule comprises a site-specific recombinase and the genome of the cell further comprises the genome of the cell into which the RGM construct is introduced typically comprises or is modified to comprise a sequence encoding third reporter molecule that is not produced in the absence of activity of the site-specific recombinase but is produced upon a recombination event mediated by the site-specific recombinase. For example, the genome of the cell may comprise a third reporter construct comprising a promoter, a reporter gene, and a loxP-STOP-loxP sequence (a STOP cassette), arranged such that the reporter gene is not transcribed unless the STOP cassette is removed via a recombinase-mediated recombination event. Such a system allows for generating a permanent, heritable mark when the RGM promoter is inactive. Under conditions in which the RGM promoter is inactive, the repressor protein is not produced. Consequently, the recombinase is produced and mediates recombination to excise the STOP cassette, allowing expression of the third reporter molecule. The various systems described herein make it possible to permanently mark cells based on either activity or lack of activity of the RGM promoter. Thus, in some embodiments cells are permanently marked when the ROI is methylated, e.g., hypermethylated. In some embodiments cells are permanently marked when the ROI is demethylated, e.g., hypomethylated. For example, if the RGM promoter is one that responds to methylation of the ROI by becoming less active (e.g., the Snrpn promoter) and it is desired to mark cells in which the ROI becomes demethylated (e.g., is hypomethylated), then one could use a site-specific recombinase as the reporter molecule encoded by the RGM construct. Demethylation of the ROI would result in increased activity of the RGM promoter, which drives synthesis of a transcript encoding the recombinase. The recombinase mediates recombination to activate expression of a second reporter molecule (e.g., a FP or luciferase) from a second reporter construct integrated elsewhere in the genome (or on a stable episome). The active second reporter construct remains active in the cell and is inherited by the cell's progeny, thus marking them permanently. If the RGM promoter is one that responds to methylation of the ROI by becoming less active (e.g., the Snrpn promoter) and it is desired to mark cells in which the ROI becomes methylated (e.g., is hypermethylated), then one could use an RGM construct in which the RGM promoter drives synthesis of a transcript encoding a transcriptional repressor such as TetR. In the situation in which the ROI is initially hypomethylated, the RGM promoter would drive transcription of a transcript encoding the TetR. TetR would bind to a TetO site of a second reporter construct, thereby blocking activity of the promoter in said second reporter construct. Methylation of the ROI would result in decreased activity of the RGM promoter, which would result in decreased synthesis of the TetR. The promoter in the second reporter construct would then drive synthesis of a transcript encoding a site-specific recombinase, which would then activate (via a site-specific recombination event) synthesis of a third reporter molecule such as an FP or luciferase, which could then be detected.

A large number of DBDs and the sequences to which they bind are known in the art and can be used in various embodiments. Types of DBDs include, for example, helix-turn-helix, helix-loop-helix, zinc finger, leucine zipper, winged helix, winged helix turn helix, HMG-box, immunoglobulin fold, B3 domain, and TAL effector DBD. Naturally occurring DBDs are found in prokaryotic and eukaryotic organisms, e.g., bacteria, fungi (e.g., yeast), plants, invertebrates (e.g., insects), and vertebrates. In some embodiments, a full length naturally occurring DBD-containing protein is used. In other embodiments, a DBD-containing fragment or variant is used. For example, a transcriptional activation or repression domain may be deleted. Exemplary prokaryotic transcriptional regulator families include, e.g., the LysR, AraC/XylS, TetR, LuxR, Lac/GalR, ArsR, IclR, MerR, AsnC, MarR, NtrC, OmpR, DeoR, cold shock, GntR, and Crp families. See, e.g., Swint-Kruse, L and Matthews, K (2009). Current Opinion in Microbiology, 12(2): 129-137 Wilson, C J, et al. (2007) Cellular and Molecular Life Sciences, 64(1), 3-16, Culard, F., et al., (1987) Eur. Biophys. J. 14: 169-178, and Ramos, J L, et al., (2005), Microbiol. & Mol. Biol. Rev., 69(2): 326-356, and references in the foregoing A sequence-specific DBD binds preferentially to its sequence as compared with its binding to other DNA sequences. For example, the affinity of such a DBD for a DNA segment containing a binding site for the DBD can be, e.g., at least 10-fold, 100-fold, 1000-fold or more greater than its affinity for random DNA sequences. In some embodiments, the Kd for binding of a DBD to its binding site is less than about $10^{-6}$ M, less than about $10^{-7}$ M, less than about $10^{-8}$ M, less than about $10^{-9}$, less than about $10^{-10}$ M, less than about $10^{-11}$ M, or less than about $10^{-12}$ M. One of skill in the art will readily be able to obtain sequences of numerous DBDs and the sequences to which they bind. The binding site to which the DBD binds in a sequence-specific manner may be, e.g., from about 10-15 nt to about 40-50 nt long. Multiple copies of the binding site, e.g., between 2 and 10 copies, or more, may be used. In some embodiments the bacterial Tet repressor (TetR) or Lac repressor (LacR) may be used. LacR binds to the bacterial LacO sequence. TetR binds to the 19 bp bacterial TetO sequence (5'-TCCCTATCAGTGATAGAGA-3) (SEQ ID NO: 7). In some embodiments two or more TetO sequences may be used. In some embodiments a tetracycline response element (TRE), which consists of 7 repeats of the TetO sequence separated by spacer sequences, may be used.

Those of ordinary skill in the art are aware of suitable TetO sequences and variants thereof (see, e.g., Löw, R., et al. (2010) BMC Biotechnol. 10:81).

Additional variations are within the scope of the disclosure. For example, in some embodiments an artificial transcriptional regulator may be used as a reporter molecule in an RGM construct. The term "artificial transcriptional regulator" refers to (a) a non-naturally occurring protein that comprises a sequence-specific DNA binding domain (DBD) or exhibits sequence-specific RNA-guided DNA binding and a transcriptional activation or repression domain or (b) a protein that (i) comprises a sequence-specific DNA binding domain or exhibits sequence-specific RNA-guided DNA binding and (ii) lacks a transcriptional activation or repression domain. The second type of artificial TF can reduce transcription by blocking RNA polymerase progression along the DNA template. In some embodiments the sequence-specific DNA binding domain is capable of specifically binding to a DNA sequence that does not occur naturally in the human or mouse genome. In some embodiments an artificial transcriptional regulator comprises the DBD of a TALE or ZFN but lacks the cleavage domain. In some embodiments an artificial transcriptional regulator comprises a modified Cas protein having mutations that render it catalytically inactive. An effector domain comprising a transcriptional activation domain (e.g., a multimer of the VP16 activation domain) or a transcriptional repression domain is fused to the DBD or catalytically inactive Cas protein. In some embodiments the DBD or catalytically inactive Cas (in the presence of an appropriate guide RNA) binds to binding sites in the vicinity of a promoter in DNA in a sequence-specific manner and activates or inhibits transcription from the promoter.

Other reporter molecules that may be used in certain embodiments include enzymes such as beta-galactosidase, alkaline phosphatase, or others that produce a colorimetric readout, by, e.g., catalyzing the conversion of chromogenic substrates into colored products. In one embodiment the reporter is not chloramphenicol acetyltransferase (CAT).

In certain embodiments any sequence of interest can be operably linked to an RGM promoter (e.g., a Snrpn promoter) and introduced into a cell, e.g., integrated into the genome of the cell in proximity to an ROI, in order to render expression of the sequence regulatable based on the methylation state of the ROI. For example, the sequence could encode a protein or a functional RNA. In some embodiments the sequence may encode a shRNA that may inhibit expression of another gene in the cell. Certain embodiments of the disclosure are directed to such uses of an RGM promoter and to nucleic acids comprising an RGM promoter operably linked to any sequence of interest. The nucleic acid may further comprise any of the other components that are described herein in the context of an RGM construct. The sequence of interest may encode a protein or RNA that modulates cell type, cell state, or cell phenotype and/or may encode a therapeutic protein or RNA in certain embodiments. Examples of genes of interest are mentioned above. In some embodiments the sequence may encode a gene product of any of such genes.

In some embodiments, a reporter molecule with a half-life of between about 45-60 minutes, about 60-75 minutes, or 75-90 minutes may be used. Use of a reporter molecule with fast turnover kinetics makes the time window during which the reporter molecule is detected more closely match the activity of the promoter that directs its production, which may facilitate the ability to detect reversible changes in methylation state and/or may make it possible to detect changes in methylation state more rapidly than would otherwise be the case. In some embodiments, a reporter gene encodes an mRNA that comprises a sequence that destabilizes the mRNA (an "mRNA-destabilizing sequence"). In some embodiments, the mRNA destabilizing sequence is an adenylate-uridylate-rich element (AU-rich elements; ARE). AREs are cis-acting elements found in the 3' untranslated region (UTR) of an estimated 5-8% of human mRNAs, including numerous cytokines, oncoproteins, and growth factors, and their presence generally accelerates mRNA turnover. ARE sequences are well known in the art (see, e.g., Wu, X & Brewer, G. Gene. 2012; 500(1): 10-21, and references therein). An exemplary ARE comprises 1-4 copies of the sequence UUAUUUAUU. In some embodiments a reporter gene encodes a reporter protein that comprises a sequence that destabilizes the protein ("protein destabilizing sequence") such as a PEST sequence. A protein destabilizing sequence may destabilize a protein that contains it by targeting the protein for degradation ubiquitin-mediated or ubiquitin-independent pathways.

In some embodiments a DNA methylation reporter comprises a region that encodes a polypeptide that comprises a reporter protein and one or more additional proteins (e.g., one, two, three, or more additional proteins), wherein adjacent proteins are separated by regions comprising a self-cleaving 2A peptide. Self-cleaving 2A peptides (often referred to simply as "2A peptides") mediate "ribosomal skipping" between proline and glycine residues in the peptide and inhibit peptide bond formation between these residues without affecting downstream translation. 2A peptides allow multiple proteins to be encoded by a polycistronic mRNA as a polyprotein, which dissociates into component proteins upon translation. Use of the term "self-cleaving" is not intended to imply a proteolytic cleavage reaction. Self-cleaving peptides are typically about 18-22 amino acids long and are found in members of the Picornaviridae virus family, including aphthoviruses such as foot-and-mouth disease virus (FMDV), equine rhinitis A virus (ERAV), Thosea asigna virus (TaV) and porcine teschovirus-1 (PTV-1) (Donnelly, M L, et al., J. Gen. Virol. 2001; 82, 1027-101; Ryan, M D, et al., 2001; J. Gen. Virol., 72, 2727-2732) and cardioviruses such as Theilovirus (e.g., Theiler's murine encephalomyelitis) and encephalomyocarditis viruses. Positioning a region that encodes a 2A peptide between two protein coding sequences allows the synthesis of two separate proteins by translation of a single mRNA, without requiring use of an IRES. Further description of 2A peptides and examples of their use to coexpress multiple proteins from a polycistronic mRNA are found in U.S. Patent App. Pub. No. 20120028821. The one or more additional proteins may comprise additional reporter proteins. In some embodiments open reading frames may be separated by IRES sequences to allow for production of a polycistronic transcript encoding multiple proteins from a single promoter.

In some embodiments a DNA methylation reporter comprises a region that encodes a polypeptide comprising a reporter protein linked to one or more additional proteins. The reporter protein and the one or more additional proteins are encoded by protein coding regions that are joined so as to form a single open reading frame. The polypeptide, which may be referred to as a "fusion protein" or "chimeric protein" typically has functional properties conferred by each of its component proteins.

A protein that contains two or more regions or domains (e.g., two or more regions or domains that originate from different proteins, such as a fusion protein), may comprise a linker between any two or more of the domains or regions.

A linker may serve to allow the regions or domains to fold independently and/or move flexibly in relation to each other. The linker region is typically a short polypeptide chain (e.g., 1-50 amino acids, e.g., 5-25 or 5-15 amino acids). The precise length and sequence are typically not critical. Small amino acid residues such as serine, glycine, and alanine are of use. Examples include $(Gly)_n$, $(Gly-Ser)_n$, $((Gly)_4Ser)_n$, (Gly-Ala)n, wherein n is an integer and the total number of amino acids in the linker is typically between 1 and about 30, and variants in which any of the amino acid residues is repeated with the proviso that the total number of amino acids is within one of the aforementioned ranges.

In any of the embodiments described herein that involve a DNA methylation reporter that encodes a reporter protein and one or more additional proteins, any one or more of the additional proteins may be a reporter protein. For example, a DNA methylation reporter may encode two or more reporter proteins. In some embodiments one or more of the additional proteins can be any protein, the expression of which it is of interest to control in a manner that depends on methylation of the region of interest. The protein may be a transcription factor, transcriptional co-activator, enzyme, transporter, ion channel, enzyme, etc.

In any of the embodiments described herein that involve two or more reporter molecules (e.g., two or more reporter proteins), the reporter molecules may be the same or different. For example, in embodiments in which a DNA methylation reporter encodes two or more reporter molecules, or in which a cell comprises two or more nucleic acids each encoding a reporter molecule, the reporter molecules may be the same or different. In some embodiments at least two of the reporter molecules are distinguishable from each other. Reporter molecules are distinguishable if they have distinguishable readouts or are detected using different techniques such that one can determine which molecule is being detected. In some embodiments two distinguishable reporter molecules may be: (a) first and second fluorescent proteins with distinct emission maxima; (b) a fluorescent protein and a luciferase; (c) a fluorescent protein and a site-specific recombinase, etc.

In some embodiments two or more distinct DNA methylation reporters that encode different reporter molecules are integrated into the genome of the cell. The two or more distinct reporters are typically integrated at different locations and can be used to detect the methylation state of two or more different regions of genomic DNA. In some embodiments the reporters encode reporter molecules that produce distinguishable readouts so that they can be independently detected. The two or more different reporter molecules may be of the same category (e.g., different fluorescent proteins) or different categories (e.g., a fluorescent protein and a luciferase). In some embodiments two or more fluorescent proteins with distinct emission spectra may be used. For example, a first fluorescent protein that emits green light and a second fluorescent protein that emits red light may be used. The locations at which the two or more reporters are integrated can be anywhere in the genome. They may be in the same chromosome or in different chromosomes. In some embodiments the reporters are integrated in proximity to the same region of interest in each of two homologous chromosomes (i.e., the two alleles of the region of interest present in diploid cells).

In some embodiments a reporter gene encodes a polypeptide that comprises a fragment of a reporter protein, wherein the fragment does not have the reporter activity characteristic of the full length reporter protein but is capable of physically associating with a second fragment of the reporter protein to form a functional reporter protein. The two fragments are said to "complement" each other and may be referred to as "complementation fragments" or members of a "complementation pair". Any reporter protein that can be split into two parts and reconstituted non-covalently may be used in various embodiments. In some embodiments the reporter protein is an enzyme or a chromophore. The reporter protein is detectable if the two promoters that drive expression of the members of the complementation pair are active during overlapping time periods or at least sufficiently close together in time such the proteins encoded by transcripts whose synthesis is directed by the promoters are present in the cell at the same time so that they can associate to form an active reporter molecule. Such activity may be referred to as "coincident activity".

In some embodiments, a split reporter molecule may be used to indicate whether any two promoters of interest exhibit coincident activity in a given cell. In some embodiments, two DNA methylation reporters, each comprising a RGM promoter operably linked to a sequence encoding a complementation fragment of a split reporter molecule, are integrated in proximity to regions of interest in the genome of a cell. Detection of the reporter molecule indicates that both promoters are active. If either or both promoters is inactive (as a result of methylation of the region of interest), the complementation fragment encoded by the operably linked sequence is not produced, and the reporter molecule is not detected. In some embodiments a split reporter molecule may be used to indicate both the level of methylation of a ROI in a cell and that the cell is a member of a particular cell population that characteristically expresses a certain cell type specific marker or cell state specific marker. In such embodiments, a DNA methylation reporter comprising a sequence encoding a complementation fragment of a split reporter molecule is integrated in proximity to a region of interest in the genome of a cell. A DNA sequence encoding the other complementation fragment of the split reporter molecule is placed under control of the promoter that directs expression of the marker. The DNA sequence may be inserted into the genome under control of the endogenous promoter (i.e., the promoter that is naturally present in the cell in its natural location) or the promoter and DNA sequence may be in a construct that has been introduced into the cell or an ancestor of the cell and, in some embodiments, integrated into the genome. Those of ordinary skill in the art are aware of split reporter proteins and of fragments that can serve as complementation fragments. In some embodiments, a split recombinase, e.g., split Cre, is used as a split reporter protein. For example, amino acids residues 19-59 and 60-343 of Cre can be used as complementation fragments. In some embodiments, a split luciferase is used as a split reporter protein. In some embodiments a split fluorescent protein is used.

In some embodiments, reporter molecules that generate a detectable signal based on the occurrence of fluorescence resonance energy transfer (FRET) or bioluminescence resonance energy transfer (BRET) may be used. FRET is a distance-dependent interaction between the electronic excited states of two molecules in which excitation is transferred from a donor moiety to an acceptor moiety without emission of a photon, resulting in photon emission from the FRET acceptor. In order for FRET to occur the donor and acceptor should be in very close proximity, e.g., less than approximately 10 nm, and the absorption spectrum of the acceptor must overlap the fluorescence emission spectrum of the donor. BRET is analogous to FRET but uses a bioluminescent reporter molecule such as a luciferase as an energy donor and a fluorescent moiety, e.g., a biomolecule such as GFP as the acceptor, thus eliminating the need for an excitation light source (see Pfleger, K. an Eidne, K., Nature Methods, 3(3), 165-174, 2006, for a review). In a typical BRET assay, oxidation by the donor of a suitable substrate results in transfer of energy to the acceptor, resulting in photon emission by the acceptor. A pair of reporter molecules capable of generating a detectable signal based on FRET or BRET may be referred to as a FRET or BRET pair, respectively. FRET or BRET pairs may be used to indicate whether any two promoters of interest exhibit coincident activity in a given cell. In some embodiments, a first DNA methylation reporter comprising a methylation-sensitive promoter operably linked to a first member of a FRET or BRET pair is integrated in proximity to a first region of interest in the genome of a cell. A second DNA methylation reporter comprising a methylation-sensitive promoter operably linked to the second member of the FRET or BRET pair is integrated in proximity to a second region of interest in the genome of the cell. Detection of the FRET signal (fluorescence) or BRET signal (bioluminescence), respectively, indicates that both promoters are active. If either or both regions of interest is hypermethylated, the promoter of the associated DNA methylation reporter construct is inactive, and the FRET or BRET signal is not detected. In some embodiments a FRET or BRET pair may be used to indicate both that a region of interest is hypomethylated in a cell and that the cell is a member of a particular cell population that characteristically expresses a certain marker. In such embodiments, a DNA methylation reporter comprising a sequence encoding a first member of a FRET or BRET pair is integrated in proximity to a region of interest in the genome of a cell. A DNA sequence encoding the other member of the FRET or BRET pair is placed under control of the promoter that directs expression of the marker. The DNA sequence may be inserted into the genome under control of the endogenous promoter or the promoter and DNA sequence may be in a construct that has been introduced into the cell or an ancestor of the cell and, in some embodiments, integrated into the genome. In some embodiments a FRET or BRET pair may be used to indicate whether a cell that comprises a DNA methylation reporter is a member of a particular cell population that characteristically expresses two different markers. In such embodiments a DNA sequence encoding a first member of the FRET or BRET pair is placed under control of the promoter that directs expression of the first marker, and a second DNA sequence encoding the other member of the FRET or BRET pair is placed under control of the promoter that directs expression of the second marker. In some embodiments either or both DNA sequences may be inserted into the genome under control of their respective endogenous promoters. In some embodiments one or more construct(s) that comprise the promoter operably linked to the DNA sequence may be introduced into the cell or an ancestor of the cell and, in some embodiments, integrated into the genome. Those of ordinary skill in the art are aware of reporter molecules that can be used as FRET or BRET pairs. For example, CFP/YFP variants and GFP/RFP variants can be used for FRET. RLuc/YFP variants can be used for BRET, to name a few.

In some embodiments the complementation fragments or FRET/BRET pair members are each fused to proteins or protein domains that have high affinity for each other and are prone to bind to each other when present in a cell. Such proteins or protein domains may be referred to as "interaction domains". Binding of the interaction domains with each other brings the complementation fragments close together, thereby increasing the likelihood that they will associate and reconstitute an active reporter protein. Numerous proteins are known to contain protein interaction domains. Such proteins, or the interaction domains that mediate their dimerization (dimerization domains) may be used. For example, the dimerization domains of transcription factors or receptors that function as dimers may be used. In some embodiments the dimerization domain is a coiled coil domain. In some embodiments the coiled coil domain comprises a leucine zipper. For example, a polypeptide comprising at least the leucine zipper of a transcription factor may be used. In some embodiments the transcription factor is the yeast transcription factor Gcn4.

Other types of reporter systems useful for detecting coincident activity of two or more promoters are also within the scope of the present disclosure. For example, a reporter system that comprises multiple gene products (such as those encoded by the bacterial lux operon) may be used. DNA sequences that encode different gene products can be placed under control of different promoters in order to report on coincident activity of the different promoters. It should be understood that reporter systems that can be used to report on coincident activity of two promoters can alternately or additionally be used to report on the activity of a single promoter by using a constitutive promoter as one of the two promoters so that the complementation fragment-encoding RNA whose synthesis is under control of the promoter is generally produced regardless of the cell type or other conditions. In such instances, the presence of an active, reconstituted reporter depends on the activity of the promoter that drives transcription of the other complementation fragment. It should also be understood that one or more reporter molecules useful for detecting coincident activity of two promoters may be used in combination with one or more other reporter molecules in the same cell, cell population, or organism. For example, a split reporter molecule may be used to detect coincident activity of two promoters that direct transcription of RNA encoding different markers, and a different reporter molecule may be used to detect the methylation state of a single region of interest in the same cell.

In some embodiments a protein, e.g., a reporter protein or targetable nuclease or site-specific recombinase, comprises a cellular targeting signal. The term "cellular targeting signal" refers to a peptide that when present in a protein expressed by a cell, directs the protein to a particular region in a cell (e.g., a particular type of organelle or cell structure) or directs the protein for secretion. In some embodiments the cellular targeting signal is a nuclear localization signal (NLS), which is a cellular targeting signal that directs proteins to the nucleus. A NLS often comprises one or more sequences of five basic, positively-charged amino acids. In some embodiments the cellular targeting signal is a signal peptide (also termed a secretion signal sequence), which is a cellular targeting signal that directs a protein that contains it to the secretory pathway. The protein may be secreted or may be retained at the plasma membrane as a membrane-bound (e.g., transmembrane) protein.

In some embodiments, a reporter protein is targeted to the plasma membrane as a membrane-bound protein comprising an extracellular domain. In some embodiments the extracellular domain can interact with an extracellular substance, such as an enzyme substrate, a detectable label (e.g., a small molecule fluorophore), or an affinity reagent or even another cell. Cellular targeting signals are found in numerous naturally occurring proteins, and such sequences (or variants or consensus sequences derived therefrom) may be appended to or inserted into other proteins in order to direct those proteins to a desired location. Those of ordinary skill in the art are familiar with cellular targeting sequences and their use and will be able to select and use a suitable cellular targeting sequence for purposes of targeting a protein to a desired subcellular location or for secretion or retention as a transmembrane protein. For example, in some embodiments an SV40 NLS may be used to target a protein to the nucleus. In some embodiments a cellular targeting signal that directs the protein to be retained at the plasma membrane comprises the transmembrane domain of a transmembrane protein, such as CD4.

Some naturally occurring reporter proteins may contain signal sequences capable of directing secretion of the protein in mammalian cells. For example, *Gaussia* luciferase contains such a sequence. In some embodiments such a sequence may be at least in part removed or modified to reduce or abolish its ability to direct secretion in mammalian cells.

One of ordinary skill in the art will readily be able to obtain nucleic acid sequences encoding reporter molecules described herein. It will be understood that due to the degeneracy of the genetic code, a protein sequence may be encoded by any of a wide variety of different nucleic acid sequences A nucleic acid sequence that encodes a reporter molecule or other polypeptide to be expressed in a cell which is of a different species to that in which the nucleic acid is naturally found (i.e., to which it is native) may be modified in any of a variety of ways relative to the naturally occurring sequence. Such modification may be performed, e.g., in order to increase the level of expression of the polypeptide, cause the polypeptide to be localized to a particular region or organelle of the cell, cause the polypeptide not to be localized to a particular region or organelle of the cell, cause the polypeptide to be secreted or not to be secreted, etc. Due to redundancy in the genetic code, which allows amino acids to be encoded by multiple different codons, a given polypeptide can be encoded by numerous different nucleic acid sequences. However, different organisms may use some codons encoding a particular amino acid more effectively than other codons that encode the same amino acid. The efficiency of protein translation in a non-native cell can be increased by altering the codon usage to more closely reflect preferred codon usage of the non-native cell while still encoding the same gene product, i.e., the coding sequence may be codon optimized. In some embodiments a nucleic acid sequence that has been codon optimized for expression in mammalian cells, e.g., mouse cells or human cells, may be used as a reporter gene in a reporter construct of the present disclosure or for expressing any protein in the context of the present disclosure.

Nucleic acids (e.g., vectors) comprising sequences that encode reporter molecules (such as luciferase, fluorescent proteins, targetable nucleases) are available from a variety of sources such as Addgene, Clontech, Promega, and others. For example, numerous plasmids containing sequences coding for the reporter molecules (e.g., various FPs and luciferases) described herein or others known in the art are available. In some embodiments a promoter in such a plasmid, which would ordinarily drive expression of the reporter molecule, is replaced by an RGM promoter, e.g., a Snrpn promoter. In some embodiments a sequence encoding a reporter molecule, a sequence comprising an RGM promoter, and other sequences (if desired) such as donor nucleic acid, etc., may be inserted into a cloning vector such as a TOPO cloning vector (e.g., pCR2 series), Gateway cloning vector, or the like. Nucleic acids and vectors described herein can be produced using any of the various methods known in the art for producing nucleic acid constructs. For example, they may be chemically synthesized, produced in suitable host cells, produced using PCR, etc. In some embodiments a mammalian imprinted gene promoter or portion thereof, a DMR or portion thereof, a DNA region of interest, homologous sequences useful as donor DNA (e.g., homology arms) may be amplified from genomic DNA, e.g., using PCR, and inserted into a vector upstream of a reporter gene. It will be appreciated that nucleic acids described herein can be assembled from individual components using restriction enzymes, ligation, PCR, or other standard methods known in the art.

In general, a reporter molecule may be detected using any suitable detection method and/or apparatus known in the art. One of ordinary skill in the art will be able to select a suitable method and apparatus depending on factors such as the properties of the particular reporter molecule, the conditions and goals of the assay, etc. A fluorescent molecule may be detected using a fluorimeter, flow cytometry, fluorescence microscopy. Fluorescence-activated cell sorting (FACS) may be used to analyze and/or sort cells based on fluorescence. In the luciferase reaction, light is emitted when luciferase acts on the appropriate luciferin. Photon emission can be detected by light sensitive apparatus such as a luminometer or various optical microscopes. Microplate readers, scanning spectroscopy, and microscopes coupled to charge-coupled device (CCD) cameras may be used. In some embodiments stimulated emission depletion (STED) microscopy may be used. Suitable instrumentation systems are available to automate detection of signals from intact cells, including automated fluorescence imaging and automated microscopy systems.

In some embodiments the reporter molecule may be detected in a biological sample obtained from a subject, e.g., a living subject, e.g., a living rodent. In some embodiments the biological sample comprises intact, living cells. In some embodiments the biological sample comprises an organ or tissue slice, e.g., a brain tissue slice (e.g., a hippocampal slice) or other organ or tissue slice.

In some embodiments an RGM construct is used to detect methylation in a cell-based model of an isolated organ or tissue. For example, in some embodiments cells comprising an RGM construct integrated into their genome are cultured in or on a three-dimensional scaffold. In some embodiments the scaffold comprises a hydrogel. In some embodiments the scaffold comprises a polymer. In some embodiments a polymer is a synthetic polymer, e.g., PEG. In some embodiments a polymer is a naturally occurring or synthetic polypeptide or polysaccharide. In some embodiments cells of interest comprise hepatocytes, myocytes (e.g., cardiomyocytes), or neurons. In some embodiments cells comprise fibroblasts. For example, hepatocytes and fibroblasts may be co-cultured. In some embodiments a scaffold comprises substances that may provide a supportive microenvironment for cells associated therewith. Such substances may include, e.g., growth factors, extracellular matrix (ECM) components such as ECM proteins or portions thereof (e.g., RGD-containing peptides). In some embodiments Matrigel® is used. In some embodiments an engineered in vitro model of parenchymal tissue (e.g., human liver). See, e.g., PCT/US2006/020019 (WO2006127768) or Khetani S R, Bhatia S N. Nat Biotechnol. 2008; 26:120-126, for examples.

In some embodiments cells are in an isolated organoid, embryoid body, spheroid, or other three-dimensional structure. Organoid refers to a three-dimensional cellular structure that resembles an organ or tissue of the body. In general, organoids comprise multiple differentiated cell types that are found in the relevant organ or tissue in vivo and reproduce the spatial morphology and cell-cell interactions as found in that organ or tissue. In some embodiments an organoid is an epithelial organoid. In some embodiment an organoid is a brain organoid or liver organoid. Methods for preparing organoids are known to those of ordinary skill in the art. In some embodiments an RGM construct is used to detect methylation in cells in cultured skin. In some embodiments the methylation state of a region of interest, e.g., a super-enhancer, enhancer, or promoter of a cell type specific gene or cell state specific gene, is detected or monitored as a tissue or organ develops in vivo or in an organoid, embryoid body, etc.

In some embodiments the reporter molecule may be detected in a living subject, e.g., a living mouse or other rodent. A variety of imaging methods can be used for in vitro and/or in vivo imaging, such as in vivo luminescence imaging, fluorescence imaging, magnetic resonance imaging, two-photon laser scanning microscopy (TPLSM) (Zinselmeyer, B. H. et al. Methods Enzymol 461, 349-378), photoacoustic imaging (Krumholz, A., et al. Sci Rep. 2014; 4:3939), single photon emission computed tomography (SPECT), positron emission tomography (PET). Those of ordinary skill in the art are aware of suitable systems and methods for performing in vivo imaging for detection of reporter molecules in a living subject. For example, in some embodiments the IVIS Imaging System (Xenogen, Carlsbad, Calif.) may be used. It will be understood that if luciferase expression is to be measured, an appropriate luciferin substrate is administered to the subject. If a photoactivatable reporter molecule is used, cells will be exposed to light of the appropriate wavelength.

Using the teachings of the present disclosure a suitable reporter molecule with an appropriate sensitivity and/or dynamic range for a given application (e.g., use in vitro or in vivo) can be selected. In some embodiments a baseline level of the reporter molecule that corresponds to a given level or range of levels of methylation may be determined and used as a reference level.

Targetable Nucleases and Uses Thereof

In some embodiments an RGM construct is integrated into the genome in proximity to a region of interest in the genome using a targetable nuclease. Targetable nucleases generate DNA breaks in the genome at a selected target site and can be used to produce precise genomic modifications. DNA breaks, e.g., double-stranded DNA breaks, can be repaired by various DNA repair pathways. Non-homologous end joining (NHEJ) ligates the broken ends together, sometimes with insertion or deletion of one or more nucleotides at the site of the break. Homologous recombination (HR) mediated repair (also termed homology-directed repair (HDR)) uses homologous donor DNA as a template to repair the break. If the sequence of the donor DNA differs from the genomic sequence, this process leads to the introduction of sequence changes into the genome. Precise modifications to the genome can be made by providing donor DNA comprising an appropriate sequence. Modifications that can be generated using targetable nucleases include insertions, deletions, or substitutions of one or more nucleotides, or introducing an exogenous DNA segment such as an expression cassette (a nucleic acid comprising a sequence to be expressed and appropriate expression control elements, such as a promoter, to cause the sequence to be expressed in a cell) or tag at a selected location in the genome.

There are currently four main types of targetable nuclease in use: zinc finger nucleases (ZFNs), transcription activator-like effector nucleases (TALENs), and RNA-guided nucleases (RGNs) such as the Cas proteins of the CRISPR/Cas Type II system, and engineered meganucleases. ZFNs and TALENs comprise the nuclease domain of the restriction enzyme FokI (or an engineered variant thereof) fused to a site-specific DNA binding domain (DBD) that is appropriately designed to target the protein to a selected DNA sequence. In the case of ZFNs, the DNA binding domain comprises a zinc finger DBD. In the case of TALENs, the site-specific DBD is designed based on the DNA recognition code employed by transcription activator-like effectors (TALEs), a family of site-specific DNA binding proteins found in plant-pathogenic bacteria such as *Xanthomonas* species. The Clustered Regularly Interspaced Short Palindromic Repeats (CRISPR) Type II system is a bacterial adaptive immune system that has been modified for use as an RNA-guided endonuclease technology for genome engineering. The bacterial system comprises two endogenous bacterial RNAs called crRNA and tracrRNA and a CRISPR-associated (Cas) nuclease, e.g., Cas9. The tracrRNA has partial complementarity to the crRNA and forms a complex with it. The Cas protein is guided to the target sequence by the crRNA/tracrRNA complex, which forms a RNA/DNA hybrid between the crRNA sequence and the homologous sequence in the target. For use in genome modification, the crRNA and tracrRNA components are often combined into a single chimeric guide RNA (sgRNA or gRNA) in which the targeting specificity of the crRNA and the properties of the tracrRNA are combined into a single transcript that localizes the Cas protein to the target sequence so that the Cas protein can cleave the DNA. The sgRNA often comprises an approximately 20 nucleotide guide sequence complementary to the desired target sequence followed by about 80 nt of hybrid crRNA/tracrRNA. One of ordinary skill in the art appreciates that the guide RNA need not be perfectly complementary to the target sequence. For example, in some embodiments it may have one or two mismatches. The genomic target sequence should also be immediately followed by a Protospacer Adjacent Motif (PAM) sequence. The PAM sequence is present in the DNA target sequence but not in the sgRNA sequence. The Cas protein will be directed to any DNA sequence with the correct target sequence followed by the PAM sequence. The PAM sequence varies depending on the species of bacteria from which the Cas protein was derived. In some embodiments, the targetable nuclease comprises a Cas9 protein. For example, Cas9 from *Streptococcus pyogenes* (Sp), *Neisseria meningitides, Staphylococcus aureus, Streptococcus thermophiles*, or *Treponema denticola* may be used. The PAM sequences for these Cas9 proteins are NGG, NNNNGATT, NNAGAA, NAAAAC, respectively. A number of engineered variants of the site-specific nucleases have been developed and may be used in certain embodiments. For example, engineered variants of Cas9 and Fok1 are known in the art. Furthermore, it will be understood that a biologically active fragment or variant can be used. Other variations include the use of hybrid targetable nucleases. For example, in CRISPR RNA-guided FokI nucleases (RFNs) the FokI nuclease domain is fused to the amino-terminal end of a catalytically inactive Cas9 protein (dCas9) protein. RFNs act as dimers and utilize two guide RNAs (Tsai, Q S, et al., Nat Biotechnol. 2014; 32(6): 569-576). Site-specific nucleases that produce a single-stranded DNA break are also of use for genome editing. Such nucleases, sometimes termed "nickases" can be generated by introducing a mutation (e.g., an alanine substitution) at key catalytic residues in one of the two nuclease domains of a targetable nuclease that comprises two nuclease domains (such as ZFNs, TALENs, and Cas proteins). Examples of such mutations include D10A, N863A, and H840A in SpCas9 or at homologous positions in other Cas9 proteins. A nick can stimulate HDR at low efficiency in some cell types. Two nickases, targeted to a pair of sequences that are near each other and on opposite strands can create a single-stranded break on each strand ("double nicking"), effectively generating a DSB, which can be repaired by HDR using a donor DNA template (Ran, F. A. et al. Cell 154, 1380-1389 (2013).

The term "donor nucleic acid" or "donor" refers to an exogenous nucleic acid segment that, when provided to a cell, e.g., along with a targetable nuclease, can be used as a template for DNA repair by homologous recombination and thereby cause site-specific genome modification (sometimes termed "genome editing"). The modifications can include insertions, deletions, or substitutions of one or more nucleotides, or introducing an exogenous DNA segment such as an expression cassette or tag at a selected location in the genome. A donor nucleic acid typically comprises sequences that have homology to the region of the genome at which the genomic modification is to be made. The donor may contain one or more single base changes, insertions, deletions, or other alterations with respect to the genomic sequence, so long as it has sufficient homology to allow for homology-directed repair. In some embodiments a donor nucleic acid may comprise sequences (sometimes termed "homology arms") flanking a sequence to be introduced into the genome. The homology arms are homologous to genomic sequences flanking a location in genomic DNA at which the insertion is to be made.

Donor nucleic acid can be provided, for example, in the form of DNA plasmids, PCR products, or chemically synthesized oligonucleotides, and may be double-stranded or single-stranded in various embodiments. The size of the donor nucleic can vary from as small as about 40 base pairs (bp) to about 10 kilobases (kb), or more. In some embodiments the donor nucleic is between about 1 kb and about 5 kb long. In some embodiments the homology arms are between about 100 bp-200 bp, about 200 bp-300 bp, about 300 bp-400 bp, about 400 bp-500 bp, about 500 bp-750 bp, about 750 bp-1000 bp, about 1 kb-1.5 kb, or more. The two homology arms may be about the same length (e.g., within 50-100 bp of each other) or may differ in length by more than 100 bp. Either or both homology arms could independently fall within any of the afore-mentioned ranges. One of ordinary skill in the art appreciates that the homology arms need not be perfectly homologous to the genomic DNA. In some embodiments the homologous region(s) of a donor nucleic acid have at least 50% 60%, 70%, 80%, 90%, 95%, 98%, 99%, or more sequence identity to a genomic sequence with which homologous recombination is desired. One of ordinary skill in the art also appreciates that the homology need not extend all the way to the DNA break. For example, in some embodiments the homology begins no more than 100 bp away from the break, e.g., between 1 and 100 bp away, e.g., 1-50 bp away, e.g., 1-15 bp away, from the break.

Those of ordinary skill in the art are aware of methods for performing site-specific genome modification using targetable nucleases and will be able to apply such methods to introduce a DNA methylation reporter into the genome at a location of choice or to create other genomic modifications. Those of ordinary skill in the art can, for example, design appropriate guide RNAs, TALENs, or ZFNs to generate a DNA break at a selected location in the genome, can design donor nucleic acid (e.g., comprising homology arms) to promote HDR at a DNA break generated by a targetable nuclease, and are aware of appropriate methods that can be used to introduce a targetable nuclease into cells and, where appropriate, a donor nucleic acid, and/or guide RNA. A targetable nuclease may be targeted to a unique site in the genome of a mammalian cell by appropriate design of the nuclease or guide RNA. A nuclease or guide RNA may be introduced into cells by introducing a nucleic acid that encodes it into the cell. Standard methods such as plasmid DNA transfection, viral vector delivery, transfection with synthetic mRNA (e.g., capped, polyadenylated mRNA), or microinjection can be used. If DNA encoding the nuclease or guide RNA is introduced, the coding sequences should be operably linked to appropriate regulatory elements for expression, such as a promoter and termination signal. In some embodiments a sequence encoding a guide RNA is operably linked to an RNA polymerase III promoter such as U6 or tRNA promoter. In some embodiments one or more guide RNAs and Cas protein coding sequences are transcribed from the same nucleic acid (e.g., plasmid). In some embodiments multiple guide RNAs are transcribed from the same plasmid or from different plasmids or are otherwise introduced into the cell. The multiple guide RNAs may direct Cas9 to different target sequences in the genome, allowing for multiplexed genome editing. In some embodiments a nuclease protein (e.g., Cas9) may comprise or be modified to comprise a nuclear localization signal (e.g., SV40 NLS). A nuclease protein may be introduced into cells, e.g., using protein transduction. Nuclease proteins, guide RNAs, or both, may be introduced using microinjection. Methods of using targetable nucleases, e.g., to perform genome editing, are described in numerous publications, such as Methods in Enzymology, Doudna J A, Sontheimer E J. (eds), The use of CRISPR/Cas9, ZFNs, and TALENs in generating site-specific genome alterations. Methods Enzymol. 2014, Vol. 546 (Elsevier); Carroll, D., Genome Editing with Targetable Nucleases, Annu. Rev. Biochem. 2014. 83:409-39, and references in either of these. See also U.S. Pat. Pub. Nos. 20140068797, 20140186919, 20140170753 and/or PCT/US2014/034387 (WO/2014/172470).

Accordingly in some aspects, described herein are methods of generating an engineered cell comprising introducing (a) a nucleic acid comprising an RGM construct and (b) a targetable nuclease into the cell under conditions suitable for the nucleic acid construct to serve as donor nucleic acid to integrate the RGM construct into the genome of the cell in proximity to an ROI. In some embodiments the targetable nuclease is a Cas protein and the method comprises introducing a guide RNA that direct the Cas protein to cleave the genome at a desired target location, e.g., in proximity to an ROI. In some embodiments a targetable nuclease is used to make one or more genetic modifications to the genome of a cell in addition to, or instead of, introducing an RGM construct into the genome. For example, in some embodiments a targetable nuclease is used to introduce an additional reporter construct at a site in the genome distinct from that at which the RGM construct is integrated. The additional reporter construct may be any of the additional reporter constructs described herein. In some embodiments, an additional reporter construct comprises a cell type specific regulatory element, e.g., a cell type specific promoter, operably linked to a reporter gene. In some embodiments a reporter gene is introduced into the genome such that it is placed in operable association with an endogenous regulatory element (i.e., a regulatory element that is naturally present in the cell and is in its normal position in the genome of the cell) such as an endogenous promoter. The endogenous regulatory element may be a cell-type specific or cell state specific regulatory element. The reporter molecule encoded by the additional reporter construct may be used to report on the cell identity or cell state of the cell. For example, in some embodiments expression of the reporter molecule indicates that a cell is of a certain type or is in a certain state.

In some embodiments a targetable nuclease is used to make a genetic modification at any site of interest in the genome of a cell that comprises an RGM construct or into which an RGM construct is introduced. For example, a targetable nuclease may be used to generate a mutation that is associated with a disorder, e.g., in order to create a model of the disorder. In some embodiments a targetable nuclease may be used to mutate a DNA or histone modifying enzyme, e.g., so as to reduce or abolish its activity.

In some embodiments multiple genomic modifications at different locations are generated together in a cell, e.g., by introducing multiple sgRNAs (e.g., 2, 3, 4, 5, or more), with or without one or more donor nucleic acids, into a cell. For example, two or more RGM constructs may be introduced into the genome in proximity to different regions of interest or in proximity to the two alleles of a region of interest, or an RGM construct and a cell type reporter construct may be introduced into the genome. Use of CRISPR/Cas systems to drive both non-homologous end joining (NHEJ) based gene disruption and homology directed repair (HDR) based precise gene editing to, among other things, achieve simultaneous targeting of multiple nucleic acid sequences in cells and nonhuman mammals is described in PCT/US2014/034387 (WO/2014/172470).

Cells or non-human organisms can be analyzed to identify those that have the desired modification(s) to their genome or confirm that a desired modification has occurred. Suitable methods for performing such analysis include restriction analysis, Southern blot, PCR analysis, or sequencing.

Cells

In some aspects, a cell comprising a DNA methylation reporter described herein is disclosed. In some embodiments, the cell comprises a nucleic acid construct or vector comprising a DNA methylation reporter described herein. In some embodiments a DNA methylation reporter is integrated into the genome of the cell. A DNA methylation reporter may be integrated in proximity to any region of DNA and used to evaluate the methylation state of the region.

In some embodiments the cell is a eukaryotic cell. In some embodiments, the cell is a vertebrate cell. In some embodiments, the cell is a mammalian cell. In some embodiments the mammalian cell is a eutherian mammalian cell. In some embodiments the mammalian cell is a human cell, a non-human primate cell, a rodent cell (e.g., a mouse, rat, hamster, or guinea pig cell), or rabbit cell. In some embodiments the mammalian cell is a bovine, ovine, caprine, equine, porcine, canine, or feline cell.

In some embodiments the cell is a stem cell. In some embodiments the cell is a pluripotent cell. A pluripotent cell may be an embryonic stem (ES) cell or an induced pluripotent stem (iPS) cell. In some embodiments the cell is a somatic cell. Somatic cells of interest herein are typically mammalian cells, such as, for example, human cells, primate cells, or rodent cells, e.g., mouse cells. They may be obtained by well-known methods and can be obtained from any organ or tissue containing live somatic cells, e.g., blood, bone marrow, skin, lung, pancreas, liver, stomach, intestine, heart, reproductive organs, bladder, kidney, urethra and other urinary organs, etc. Mammalian somatic cells include, but are not limited to, adipocyte (e.g., white fat cell or brown fat cell), cardiac myocyte, chondrocyte, endothelial cell, epidermal cells, epithelial cells, exocrine gland cell, fibroblast, glial cell, hematopoietic cells, hepatocyte, hair follicle cells, keratinocyte, macrophage, melanocyte, monocyte, mononuclear cell, myeloid cell, neuron, neutrophil, osteoblast, osteoclast, pancreatic islet cell (e.g., a beta cell), Sertoli cell, skeletal myocyte, smooth muscle cell, B cell, plasma cell, T cell (e.g., regulatory, cytotoxic, helper), or dendritic cell. The term "somatic cells", as used herein, also includes adult stem cells. An adult stem cell is a cell that is capable of giving rise to all cell types of a particular tissue. Exemplary adult stem cells include hematopoietic stem cells, neural stem cells, and mesenchymal stem cells. In some embodiments the cell is an adult stem cell, e.g., a hematopoietic stem cell, neural stem cell, intestinal stem cell, stem cell, or mammary stem cell.

Differentiation is the process by which a less specialized cell becomes a more specialized cell type. Differentiation often occurs in stages in which cells become more specified over a series of cell divisions until they reach full maturity, which may be referred to as "terminal differentiation". A somatic cell may be partially or completely differentiated. Cell differentiation can involve changes in the size, shape, polarity, metabolic activity, gene expression and/or responsiveness to signals of the cell. For example, hematopoietic stem cells differentiate to give rise to all the blood cell types including those of the myeloid lineage (monocytes and macrophages, neutrophils, basophils, eosinophils, erythrocytes, megakaryocytes/platelets, dendritic cells) and lymphoid lineage (T-cells, B-cells, NK-cells). During progression along the path of differentiation, the differentiation potential of a cell (the range of cells into which a cell can develop) typically becomes more restricted.

In some embodiments a cell is a progenitor cell. As used herein, a "progenitor cell" is a cell that has a more restricted differentiation potential than an adult stem cell or pluripotent cell but can both self-renew and give rise to daughter cells that are more differentiated than itself. In some embodiments the cell is a terminally differentiated cell, meaning that the cell normally lacks the capacity to give rise to cells that are more differentiated than itself.

In some embodiments a cell is a germline cell, also referred to as a germ cell. Germ line cells are any line of cells that give rise to gametes (eggs and sperm). In many animals, including mammals, the germ cells originate in the primitive streak and migrate to the developing gonads. There, they undergo cell division of two types, mitosis and meiosis, followed by differentiation into mature gametes, either eggs or sperm. Germ cells include primordial germ cells (PGCs), gametogonia, and gametocytes. In some embodiments a cell is a gamete. In some embodiments a cell is a zygote or a cell in or obtained from an embryo having no more than 2, 4, 8, 16, 32, or 64 cells.

In some embodiments the cell is a normal cell. In some embodiments the cell is an abnormal cell. An abnormal cell may have a defect in one or more biological processes and/or may exhibit one or more phenotypes that are distinct from those found in a normal matched cell. In some embodiments the cell harbors a mutation or genetic variation that is associated with a disorder. In some embodiments a mutation or genetic variation associated with a disorder is one that occurs more frequently in individuals who have the disorder than in individuals who do not have the disorder. The mutation or genetic variation may be recognized in the art as causing or contributing to the disorder. In some embodiments the cell may be genetically engineered to harbor such a mutation or genetic variation.

In some embodiments the cell is a diseased cell. A diseased cell is one that exhibits one or more manifestations of a disorder. For example, in some embodiments the cell is a cancer cell. A cancer cell may be derived from any type of cancer. "Cancer" as used herein, encompasses any type of cancer, including solid tumors (e.g., carcinomas, sarcomas), and hematologic malignancies. Solid tumors include, e.g., bladder, bone, brain (e.g., glioblastoma), breast, cervical, colon, endometrial, esophageal, gastric, liver (e.g., hepatocellular carcinoma), lung, ovarian, pancreatic, prostate, renal, skin, testicular, and thyroid cancer. Others include melanoma, retinoblastoma, and neuroblastoma. Hematological malignancies include, e.g., leukemias, lymphomas (also a solid tumor), and myeloma. In some embodiments a lymphoma is a B cell lymphoma, T cell lymphoma, Burkitt's lymphoma, Hodgkin lymphoma, mantle cell lymphoma, NK cell lymphoma, diffuse large cell lymphoma. In some embodiments a tumor is a gastrointestinal stromal tumor, e.g., a succinate dehydrogenase (SDH)-deficient gastrointestinal stromal tumor. In some embodiments a tumor is Wilm's tumor. In some embodiments a tumor is part of a multitumor syndrome, e.g., Carney triad (paragangliomas, gastric stromal tumours and pulmonary chondromas), or the dyad of paragangliomas and gastric stromal sarcomas (Carney-Stratakis syndrome). In some embodiments the disorder is a precancerous condition (i.e., a condition that can evolve into a cancer) such as myelodysplastic syndrome. In some embodiments the cancer cell is experimentally generated by expressing one or more oncogenes and/or inhibiting expression of one or more tumor suppressor genes in the cell. In some embodiments the cell is a cancer stem cell. In some embodiments a cell is obtained from a subject suffering from a disorder. A cell obtained from a subject suffering from a disorder could be the originally isolated cell or a descendant of the cell arising in cell culture after isolation of the cell. In some embodiments the disorder is cancer. In some embodiments the disorder is an autoimmune disorder. In some embodiments the disorder is a neurodegenerative disorder. In some embodiments the disorder is a psychiatric disorder.

A cell may be in a living animal, e.g., a mammal, or may be an isolated cell. Isolated cells may be primary cells, such as those recently isolated from an animal (e.g., cells that have undergone none or only a few population doublings and/or passages following isolation, e.g., up to 3-5, or up to 5-10 doublings or passages), or may be a cell of a cell line that is capable of prolonged proliferation in culture (e.g., for longer than 3 months) or indefinite proliferation in culture (immortalized cells). In some embodiments, a cell is a somatic cell. Somatic cells may be obtained from an individual, e.g., a mouse, human, or other mammal, and cultured according to standard cell culture protocols known to those of ordinary skill in the art. Cells may be obtained from any organ or tissue of interest. In some embodiments, cells are obtained from bladder, blood, blood vessel (e.g., artery or vein), breast, endocrine gland, brain, eye, exocrine gland, fat, gastrointestinal tract (e.g., stomach, small intestine, colon), heart, kidney, liver, lung, muscle, ovary, prostate gland, skin, testis, or urethra. Cells may be maintained in cell culture following their isolation. In certain embodiments, the cells are passaged or allowed to double once or more following their isolation from an individual (e.g., between 2-5, 5-10, 10-20, 20-50, 50-100 times, or more) prior to their use in a method described herein. In some embodiments, cells may be frozen and subsequently thawed prior to use. Cells may be frozen in a suitable medium (e.g., containing a cryopreservative) to help maintain viability. In some embodiments, the cells will have been passaged or permitted to double no more than 1, 2, 5, 10, 20, or 50 times following their isolation from the individual prior to their use in a method described herein. Cells may be genetically modified or not genetically modified in various embodiments. Cells may be obtained from normal or diseased tissue in various embodiments.

In some aspects, described herein are populations of cells, e.g., isolated cells, that comprise a nucleic acid comprising an RGM construct integrated into their genome. In some embodiments a population of isolated cells in any embodiment may be composed mainly or essentially entirely of cells of a particular cell type or of cells in a particular cell state. A population of isolated cells in any embodiment may additionally or alternately be composed mainly or essentially entirely of cells that have a particular genetic modification or combination thereof. In some embodiments, an isolated population of cells consists of at least 30%, 40%, 50%, 60%, 70%, 80%, 90%, 95%, 96%, 97%, 98%, 99%, 99.5%, 99.9%, or 100% cells of a particular cell type or cell state (i.e., the population is at least 30%, 40%, 50%, 60%, 70%, 80%, 90%, 95%, 96%, 97%, 98%, 99%, or 100% pure), e.g., as determined by expression of one or more markers or by any other suitable method. In some embodiments, an isolated population of cells consists of at least 30%, 40%, 50%, 60%, 70%, 80%, 90%, 95%, 96%, 97%, 98%, 99%, 99.5%, 99.9%, or 100% cells that have a particular genetic modification or combination thereof. A population of cells could be derived from a single cell or from multiple cells. In some embodiments a population of cells is derived from a single cell that has one or more particular genetic modification(s). For example, the cell may have a DNA methylation reporter integrated into its genome at a particular location. The cell may also have any one or more of the other genetic modifications described herein.

In some embodiments a population of cells in any embodiment comprises cells of multiple different cell types or of cells in multiple different cell states. For example, the population may comprise cells of at least 2, 3, 4, 5, or more different cell types, cell states, or combinations thereof. In some embodiments, an RGM construct is useful for understanding changes in DNA methylation that occur during cell state transition in heterogeneous cell populations. In some embodiments, an RGM construct is useful for understanding changes in DNA methylation that occur in particular cell types in heterogeneous cell populations. In some embodiments cells of a particular cell type or cell state of interest may be identified by their expression of cell type or cell state specific marker(s) or reporter gene(s) under control of cell type or cell state specific promoters. Since RGM constructs in certain embodiments allow measuring dynamics of DNA methylation at single-cell resolution, methylation changes occurring in particular cells of interest can be detected and distinguished from those occurring in the overall population.

In some embodiments a cell is a member of a cell line. Cell lines can be generated using methods known in the art or obtained, e.g., from depositories or cell banks such as the American Type Culture Collection (ATCC), Coriell Cell Repositories, Deutsche Sammlung von Mikroorganismen und Zellkulturen (German Collection of Microorganisms and Cell Cultures; DSMZ), European Collection of Cell Cultures (ECACC), Japanese Collection of Research Bioresources (JCRB), RIKEN, Cell Bank Australia, etc. The paper and online catalogs of the afore-mentioned depositories and cell banks are incorporated herein by reference.

Cells or cell lines may be of any cell type or tissue of origin in various embodiments. In some embodiments the cell is an adipocyte (e.g., white fat cell or brown fat cell), cardiomyocyte, chondrocyte, epithelial cell, endothelial cell, endocrine gland cell, exocrine gland cell, fibroblast, glial cell (e.g., astrocyte, oligodendrocyte, microglial cell, Schwann cell), hepatocyte, keratinocyte, melanocyte, mesenchymal cell, neuron, osteoblast, osteoclast, pancreatic islet cell (e.g., a beta cell, alpha cell), skeletal myocyte, smooth muscle cell. In some embodiments the cell is an immune cell, e.g., a B cell, plasma cell, T cell (e.g., cytotoxic, helper, regulatory, killer), dendritic cell, natural killer cell, macrophage, monocyte, neutrophil, eosinophil, basophil, or mast cell. In some embodiments a neuron is of a type that is normally found in the central nervous system (CNS), e.g., the brain. In some embodiments a neuron is of a type normally found in the peripheral nervous system (PNS). Neurons can be classified according to morphology, type(s) of neurotransmitter(s) that they produce or to which they respond, and/or region of the CNS or PNS in which they are normally found. In some embodiments a cell is a neuron that produces or responds to a particular neurotransmitter of interest. Neurotransmitters include, e.g., acetylcholine, dopamine, epinephrine, gamma-aminobutyric acid, glutamate, glycine, and serotonin. In some embodiments, an enzyme that acts in a biosynthetic pathways leading to production of a given neurotransmitter, or a receptor that binds to or takes up such neurotransmitter may be a cell type specific marker for the particular subtype of neuron that produces or responds to the neurotransmitter, respectively.

In some embodiments the cell has one or more genetic modifications in addition to the insertion of an RGM construct into its genome. In some embodiments the cell has a mutation or other genetic variation (e.g., a polymorphism) in a gene encoding a protein or RNA of interest. The mutation or genetic variation may be naturally occurring or engineered. In some embodiments the mutation or genetic variation is a disease-associated mutation, e.g., a mutation or genetic variation that causes a disorder or is associated with an increased risk of developing a disease. In some embodiments the disorder is a disorder associated with aberrant DNA methylation.

In some embodiments the cell is engineered to have increased or decreased expression or activity of a protein or RNA of interest as compared with a non-engineered control cell. The protein(s) or RNA(s) of interest can be any protein(s), or RNA(s) of interest. In some embodiments the protein is a chromatin modifying enzyme, e.g., a DNA modifying enzyme or histone modifying enzyme. For example, in some embodiments the protein is a DNA methyltransferase, a DNA demethylase, a DNA glycosylase, a histone methyltransferase, a histone demethylase, a histone acetylase, or a histone deacetylase. In some embodiments the protein is a DNA repair enzyme.

A cell may be engineered to have increased or decreased expression or activity of a protein or RNA of interest using any of a variety of methods known in the art. In some embodiments a cell may be engineered to have increased expression or activity of a protein or RNA of interest by introducing into the cell an expression construct that encodes the protein or RNA into the cell. The protein or RNA may be one that is naturally found in the cell or may be one that is not naturally found in the cell in various embodiments. In some embodiments a cell may be engineered to have increased expression or activity of an endogenous protein or RNA of interest by introducing into the cell an artificial transcriptional regulator designed to increase activity of the endogenous promoter that naturally directs transcription of such endogenous protein or RNA. In some embodiments a cell may be engineered to have decreased expression or activity of a protein or RNA of interest by introducing a mutation or deletion into the gene that encodes the RNA or protein (e.g., using a targetable nuclease), by expressing an RNAi agent such as a short hairpin RNA or artificial microRNA in the cell, or by expressing an antisense RNA in the cell. In some embodiments a cell may be engineered to have increased expression or activity of an endogenous protein or RNA of interest by introducing into the cell an artificial transcriptional regulator designed to decrease activity of the endogenous promoter that directs transcription of such endogenous protein or RNA. In some embodiments the protein is a transcription factor. Those of ordinary skill in the art are aware of the numerous mammalian transcription factors. In some embodiments the transcription factor is included in the TRANSFAC® or JASPAR database. In some embodiments the transcription factor is a master transcription factor.

In some embodiments, a RNA or protein to be expressed in a cell is under the control of a regulatable (inducible or repressible) promoter. One of ordinary skill in the art appreciates that various regulatable promoter systems are available. For example, the tetracycline-regulatable gene expression system or variants thereof (see, e.g., Gossen & Bujard, Proc. Natl. Acad. Sci. 89:5547-5551, 1992; Allen, N, et al. (2000) Mouse Genetics and Transgenics: 259-263; Urlinger, S, et al. (2000). Proc. Natl. Acad. Sci. U.S.A. 97 (14): 7963-8; Zhou, X., et al (2006). Gene Ther. 13 (19): 1382-1390; Schonig, K., et al., Methods Enzymol. 2010; 477:429-53) can be employed to provide inducible or repressible expression. One of ordinary skill appreciates that small molecules such as tetracycline, doxycycline, 4-Epidoxycycline, steroid hormones, and the like, can be used. In some embodiments a protein's activity may be regulatable using a small molecule. For example, Cre may be fused to a steroid hormone ligand binding domain so that its activity is regulated by receptor ligands. Cre-ER(T) or Cre-ER(T2) recombinases may be used, which comprise a fusion protein between a mutated ligand binding domain of the human estrogen receptor (ER) and the Cre recombinase, the activity of which can be induced by, e.g., 4-hydroxy-tamoxifen. In some embodiments, such systems may be used to control expression of any endogenous gene or exogenously introduced nucleic acid in a tissue specific, temporally defined, and/or reversible manner.

Non-Human Mammals

In some aspects, described herein are non-human mammals comprising at least one cell that comprises a nucleic acid comprising an RGM construct integrated into its genome. In some embodiments the nucleic acid is integrated in proximity to a region of interest. The region of interest may be any of the regions of interest described herein. For example, in some embodiments the region of interest is a superenhancer, enhancer, promoter, DMR, disease-specific DMR, tissue-specific DMR, CpG island, or gene body. In some embodiments the RGM construct is integrated with 10 kb, 20 kb, or 50 kb of a TSS.

In some embodiments, the non-human animal is a chimeric animal. In some embodiments between about 5% and about 95% of the animal's cells have the nucleic acid construct integrated into their genome. In some embodiments at least some germline cells of the animal harbor the nucleic acid in their genome. In some embodiments all or substantially all (e.g., at least 99%, 99.5%, 99.9%) of the cells of the non-human mammal have the nucleic acid integrated into their genome. In some embodiments cells of the non-human mammal have a single copy of the nucleic acid comprising an RGM construct integrated into their genome in proximity to a region of interest. In some embodiments the region of interest is in an autosome, and cells of the non-human mammal comprise a nucleic acid comprising an RGM construct integrated into their genome in proximity to both copies of the region of interest (i.e., in proximity to each allele of the region of interest).

The nonhuman mammals can be produced using any of a variety of methods for producing genetically modified non-human mammals known in the art. In some embodiments, a method of use to produce nonhuman mammals includes pronuclear microinjection. DNA is introduced directly into a pronucleus of a nonhuman mammal egg just after fertilization (e.g., by microinjection or piezoinjection). The egg is implanted into an appropriate foster mother, e.g., a pseudopregnant female of the same species (e.g., into the oviduct of such female). The female is then maintained under conditions that result in development of live offspring that harbor the one or more genetic modifications. Offspring are screened for the integrated DNA. Heterozygous offspring can be subsequently mated to generate homozygous animals. In the context of the present disclosure, the DNA which is introduced into the pronucleus of a non-human mammalian egg is a nucleic acid comprising an RGM construct. In some embodiments the nucleic acid comprises homology arms as described above, in order to promote homologous recombination to introduce the RGM construct into the genome in proximity to a region of interest.

In some embodiments, non-human mammals are generated from pluripotent cells, e.g., ES or iPS cells, using conventional methods. See, e.g., U.S. Patent Application Pub. No. 20110076678 for examples of generating non-human mammals from iPS cells. Such methods may be used to generate non-human mammals from ES cells. The ES or iPS cell used to derive a non-human mammal has a nucleic acid comprising an RGM construct integrated into its genome.

In some embodiments a technique useful for generating non-human mammals of the present disclosure involves introducing one or more ES and/or iPS cells comprising one or more genetic modifications into a diploid blastocyst and maintaining the blastocyst under conditions that result in development of an embryo. The embryo is then transferred into an appropriate foster mother, such as a pseudopregnant female (e.g., of the same species as the embryo). The foster mother is then maintained under conditions that result in development of live chimeric offspring that harbor the one or more genetic modifications in some of their cells. In the context of the present disclosure, the ES and/or iPS cells have an RGM construct integrated into their genome, e.g., in proximity to a region of interest. Chimeric animals in which the ES and/or iPS cells have contributed to the germline (i.e., the germ line of the chimeric animal contains cells derived from the introduced cell ES or iPS cells) can be bred to generate animals that have the genetic modification in all or substantially all of their cells.

In some embodiments a method of producing a non-human mammal comprises injecting non-human mammalian ES cells or iPSCs that are genetically modified to harbor an RGM construct integrated into their genome into a non-human tetraploid blastocyst, transferring the blastocyst into an appropriate foster mother, e.g., a pseudopregnant female of the same species, and allowing the blastocyst to develop. The resulting non-human mammal is derived from the ES cells or iPSCs cells and thus harbors the RGM construct in its cells. In some embodiments, said non-human mammalian ES cells or iPSCs cells are mouse cells and said non-human mammalian embryo is a mouse. In some embodiments, said mouse cells are injected into said non-human tetraploid blastocysts by microinjection. In some embodiments laser-assisted micromanipulation or piezoinjection is used.

In some embodiments a non-human mammal comprising cells that comprise a nucleic acid comprising an RGM construct in their genome is generated from a zygote (a one cell embryo) comprising a targetable nuclease and an RGM construct, wherein the targetable nuclease cleaves genomic DNA at a target site in the region of interest, promoting integration of the nucleic acid by homology directed repair. For example, in some embodiments the nonhuman animal is generated from a zygote comprising a guide RNA, Cas9 protein, and a nucleic acid comprising an RGM construct, wherein the guide RNA guides the Cas9 protein to cleave the genomic DNA of the zygote at a target site in the region of interest. The guide RNA, Cas9 protein, and nucleic acid may be introduced into the zygote using a variety of methods. In some embodiments Cas9 mRNA, sgRNA, and nucleic acid comprising an RGM construct are introduced into the zygote, e.g., by injection. In some embodiments Cas9 protein, sgRNA, and nucleic acid comprising an RGM construct are introduced into the zygote, e.g., by injection. The zygote may be cultured in vitro, e.g., to the blastocyst stage, and transferred into a foster nonhuman mammalian mother. The foster nonhuman mammalian mother is maintained under conditions suitable for production of one or more offspring harboring the nucleic acid comprising an RGM construct in their genome, thereby producing a nonhuman mammal comprising an RGM construct in its genome.

In some embodiments a nucleic acid comprising an RGM construct may be introduced into an embryo, fetus, postnatal, juvenile, or adult non-human mammal. In some embodiments the nucleic acid may be injected into an organ or tissue such as the heart, brain, liver, etc. The nucleic acid may be taken up by some of the animal's cells and integrate into the genome.

In some embodiments the non-human mammal is of any mouse strain known in the art. Examples include C57BL/6J, 129S1/SvImJ, A/J, AKR/J, BALB/cByJ, BTBR T+tf/J, C3H/HeJ, CAST/EiJ, DBA/2J, FVB/NJ, MOLF/EiJ, KK/HIJ, NOD/ShiLtJ, NZW/LacJ, PWD/PhJ, and WSB/EiJ, CD-1, CBA, ICR, or Balb/C. In some aspects, various mouse strains and mouse models of human disease are used in conjunction with the methods of producing a nonhuman mammal comprising an RGM construct integrated into its genome described herein. One of ordinary skill in the art appreciates the thousands of commercially and non-commercially available strains of laboratory mice that have specific genetic modifications (e.g., transgenes, knockouts, tissue or cell type specific Cre recombinase lines, Tet transactivator lines, Tet responder lines), which may be constitutive or conditional (e.g., inducible). One of ordinary skill in the art also appreciates the thousands of commercially and non-commercially available strains of laboratory mice for modeling human disease. For example, numerous mouse strains harboring particular genetic modifications and/or useful as models for human disease are available from Jackson Laboratories (Bar Harbor, Me.) (JAX® mice), RIKEN, EMMA, Taconic Biosciences (Hudson, N.Y.), and other sources. Mice models exist for diseases such as cancer, cardiovascular disease, autoimmune diseases and disorders, inflammatory diseases, diabetes, neurological diseases (including neurodegenerative disease and neurodevelopmental diseases), psychiatric diseases, endocrine deficiency, hearing loss), hematological disease, inflammation, musculoskeletal disorders, metabolic disease, vision loss), cardiovascular disease, and other diseases. In some aspects, a method of producing a nonhuman mammal comprising an RGM construct in its genome further comprises mating one or more commercially and/or non-commercially available nonhuman mammal with the nonhuman mammal comprising an RGM construct in its genome produced by the methods described herein. In some aspects, nonhuman mammals produced by the methods described herein are provided.

In some embodiments, methylation state of a region of interest may be detected or monitored in vivo in a non-human mammal (e.g., a mouse) comprising an RGM construct integrated into its genome in proximity to the region of interest. Suitable methods for performing in vivo imaging are known in the art.

In some aspects, the present disclosure provides isolated cells obtained from any of the non-human mammals described herein, wherein the cells comprise a nucleic acid comprising an RGM construct integrated into their genome. The cells may be obtained from any organ or tissue of the animal and may be of any cell type (see discussion of various tissues, organs, and cell types above). It should be understood that cells "obtained" from a subject such as a non-human animal include the cells originally removed from the animal as well as progeny of those cells. In some embodiments DNA methylation of a region of interest may be detected or monitored in the cells using the RGM construct, as described herein.

In some aspects, the present disclosure provides tissue or organ samples obtained from any of the non-human mammals described herein, wherein cells in the tissue or organ sample comprise a nucleic acid comprising an RGM construct integrated into their genome. The tissue or organ sample may be obtained from any organ or tissue of the animal. In some embodiments DNA methylation of a region of interest may be detected or monitored in cells in the sample using the RGM construct, as described herein.

In some embodiments two or more biological samples comprising cells may be obtained from a non-human mammal. The methylation state of a region of interest at a first time point is compared with the methylation state of the same region of interest at one or more subsequent time points. The samples may be obtained from the same tissue or organ (e.g., blood cells, skin cells).

In some embodiments animals generated according to methods described herein may be useful in the identification of candidate agents for treatment of disease and/or for testing agents for potential toxicity or side effects, such as those potentially arising from aberrant methylation of a region of interest. In some embodiments any method described herein may comprise contacting an animal generated according to methods described herein with a test agent (e.g., a small molecule, nucleic acid, polypeptide, lipid, etc.).

Kits

The disclosure further provides packaged products and kits, including a construct or composition described herein, packaged into suitable packaging material. The term "packaging material" refers to a physical structure housing the product or components of the kit. The packaging material can maintain the components sterilely, and can be made of material commonly used for such purposes (e.g., paper, corrugated fiber, glass, plastic, foil, ampules, etc.).

In certain embodiments, a packaged product or kit includes a container, such as a sealed pouch or shipping container, or an article of manufacture, for example, to carry out an assay described herein, such as a tissue culture dish, tube, flask, roller bottle or plate (e.g., a single multi-well plate or dish such as an 8, 16, 32, 64, 96, 384 and 1536 multi-well plate or dish).

A label or packaging insert can be included, listing contents or appropriate written instructions, for example, practicing a method of the disclosure. Instructions may be on "printed matter," e.g., on paper or cardboard within the kit, on a label affixed to the package, kit or packaging material, or attached to a tissue culture dish, tube, flask, roller bottle, plate (e.g., a single multi-well plate or dish such as an 8, 16, 32, 64, 96, 384 and 1536 multi-well plate or dish) or vial containing a component of the kit. Instructions may comprise voice or video tape and additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Disclosed kits can optionally include additional components, such as buffering agent, a preservative, or a reagent. Each component of the kit can be enclosed within an individual container or in a mixture and all of the various containers can be within single or multiple packages.

In some aspects, the present disclosure provides kits containing any one or more of the RGM constructs, nucleic acids, and/or vectors described herein. A kit may comprise 2, 3, 4, or more RGM constructs, nucleic acids, and/or vectors, at least some of which may comprise different reporter genes. In some embodiments a kit may comprise a transfection reagent, DNA modifying enzyme, a buffer solution, a cell. In some embodiments a kit may comprise instructions for use of the kit to detect or monitor DNA methylation in cells.

Applications

DNA methylation reporter constructs described herein have a number of different uses and may be used in a wide variety of methods. This section describes certain non-limiting applications and methods of use. In general, any of the RGM constructs described herein and/or any of the mammalian cells described herein may be used in various embodiments, unless otherwise indicated or unless the context clearly dictates otherwise. Without limiting the foregoing, in some embodiments mouse cells or human cells are used; in some embodiments an RGM construct encoding a fluorescent protein or a luciferase as a reporter molecule may be used.

In some embodiments, a DNA methylation reporter is used to detect methylation state (or change in methylation state) of a genomic region of interest during a cell identity transition. A "cell identity transition" is a change from one cell type to another cell type. In some embodiments, a DNA methylation reporter described herein is used to detect methylation state of a genomic region of interest during a cell state transition. In some embodiments a cell state transition is a transition from one state of differentiation to a second state of differentiation within a particular cell lineage. In some embodiments a cell state transition is a change from a pluripotent state to a non-pluripotent state. In some embodiments a cell state transition is a change from a non-pluripotent state (e.g., a unipotent or multipotent state) to a pluripotent state. In some embodiments a cell state transition is a change from a pluripotent state to a multipotent state. In some embodiments a cell state transition is a change from a multipotent state to a unipotent state. In some embodiments a cell state transition is a change from a terminally differentiated state to a multipotent or pluripotent state. In some embodiments a cell state transition is a change from a post-mitotic state to an actively dividing state. In some embodiments, a DNA methylation reporter described herein is used to detect methylation state of a genomic region of interest one or more times prior to the beginning of a cell identity transition or cell state transition and one or more times after a cell identity transition or cell state transition has started and/or one or more times after a cell identity transition or cell state transition has occurred. A methylation reporter may thus be used to detect a change in methylation state that occurs during or temporally correlated with a cell identity transition or cell state transition. DNA methylation during or correlated with any type of cell identity transition or cell state transition can be detected in various embodiments. In some embodiments the cell identity transition or cell state transition occurs in an isolated cell, e.g., a cell in cell culture. In some embodiments the cell identity transition or cell state transition occurs in vivo, i.e., within a living animal.

In some aspects, cell state reflects the fact that cells of a particular type can exhibit variability with regard to one or more features and/or can exist in a variety of different conditions, while retaining the features of their particular cell type and not gaining features that would cause them to be classified as a different cell type. The different states or conditions in which a cell can exist may be characteristic of a particular cell type (e.g., they may involve properties or characteristics exhibited only by that cell type and/or involve functions performed only or primarily by that cell type) or may occur in multiple different cell types. Sometimes a cell state reflects the capability of a cell to respond to a particular stimulus or environmental condition (e.g., whether or not the cell will respond, or the type of response that will be elicited) or is a condition of the cell brought about by a stimulus or environmental condition. Cells in different cell states may be distinguished from one another in a variety of ways. For example, they may express, produce, or secrete one or more different genes, RNAs, proteins, or other molecules, exhibit differences in protein modifications such as phosphorylation, acetylation, etc., or may exhibit differences in appearance. Thus a cell state may be a condition of the cell in which the cell expresses, produces, or secretes one or more markers, exhibits particular protein modification(s), has a particular appearance, and/or will or will not exhibit one or more biological response(s) to a stimulus or environmental condition. Markers can be assessed using methods well known in the art, e.g., gene expression can be assessed at the mRNA level using Northern blots, cDNA or oligonucleotide microarrays, or sequencing (e.g., RNA-Seq), or at the level of protein expression using protein microarrays, Western blots, flow cytometry, immunohistochemistry, etc. Modifications can be assessed, e.g., using antibodies that are specific for a particular modified form of a protein, e.g., phospho-specific antibodies, or mass spectrometry.

Another example of cell state is "activated" state as compared with "resting" or "non-activated" state. Many cell types in the body have the capacity to respond to a stimulus by modifying their state to an activated state. The particular alterations in state may differ depending on the cell type and/or the particular stimulus. A stimulus could be any biological, chemical, or physical agent to which a cell may be exposed. A stimulus could originate outside an organism (e.g., a pathogen such as virus, bacteria, or fungi (or a component or product thereof such as a protein, carbohydrate, or nucleic acid, cell wall constituent such as bacterial lipopolysaccharide, etc.) or may be internally generated (e.g., a cytokine, chemokine, growth factor, or hormone produced by other cells in the body or by the cell itself). For example, stimuli can include interleukins, interferons, or TNF alpha. Immune system cells, for example, can become activated upon encountering foreign (or in some instances host cell) molecules. Cells of the adaptive immune system can become activated upon encountering a cognate antigen (e.g., containing an epitope specifically recognized by the cell's T cell or B cell receptor) and, optionally, appropriate co-stimulating signals. Activation can result in changes in gene expression, production and/or secretion of molecules (e.g., cytokines, inflammatory mediators), and a variety of other changes that, for example, aid in defense against pathogens but can, e.g., if excessive, prolonged, or directed against host cells or host cell molecules, contribute to diseases.

Fibroblasts are another cell type that can become activated in response to a variety of stimuli (e.g., injury (e.g., trauma, surgery), exposure to certain compounds including a variety of pharmacological agents, radiation, etc.) leading them, for example, to secrete extracellular matrix components. In the case of response to injury, such ECM components can contribute to wound healing. However, fibroblast activation, e.g., if prolonged, inappropriate, or excessive, can lead to a range of fibrotic conditions affecting diverse tissues and organs (e.g., heart, kidney, liver, intestine, blood vessels, skin) and/or contribute to cancer.

Another example of cell state reflects the condition of a cell as either responsive (sensitive) or non-responsive (resistant) to a particular stimulus (e.g., a particular substance with which the cell is contacted, such as a hormone, growth factor, chemokine, therapeutic agent). For example, insulin-resistant skeletal muscle cells exhibit markedly reduced insulin-stimulated glucose uptake and a variety of other metabolic abnormalities that distinguish these cells from cells with normal insulin sensitivity. In some aspects, an RGM construct may be used to detect or monitor methylation changes that accompany any change in cell state.

In some embodiments a cell comprising a nucleic acid comprising an RGM construct integrated into its genome is exposed to an agent or condition that induces the cell to undergo a cell state transition or cell identity transition. For example, the cell may be subjected to a reprogramming protocol. A "reprogramming protocol" refers to any treatment or combination of treatments that causes at least some cells subjected to it to become reprogrammed. In some embodiments a "reprogramming protocol" refers to a set of manipulations (e.g., introduction of nucleic acid(s), e.g., vector(s), carrying particular genes) and/or culture conditions (e.g., culture in medium containing particular compounds) in vitro that generates pluripotent cells from somatic cells, or that generates a first differentiated cell type from a first differentiated cell type without going through a pluripotent intermediate state. The transcription factors, small molecules, or other agents that mediate reprogramming may be referred to as reprogramming agents. In some embodiments, a DNA methylation reporter is used to detect methylation state (or change in methylation state) of a genomic region of interest during natural or experimentally induced differentiation. Cells may be exposed to agents or conditions that can promote differentiation, such as retinoids (e.g., retinoic acid), various growth factors, and/or may be subjected to withdrawal of one or more agents that promote maintenance of a particular state and thereby blocked differentiation.

In some embodiments, a DNA methylation reporter described herein is used to detect the effect of an agent or condition or combination thereof on the methylation state of a genomic region of interest. The agent may or may not affect the identity or state of the cell in various embodiments. In some embodiment a method of evaluating the effect of an agent on the methylation state of a DNA region of interest in a cell comprises steps of: contacting one or more cells comprising (i) a mammalian imprinted gene promoter; and (ii) a sequence that encodes a reporter molecule with a test agent; measuring expression of the reporter molecule; and comparing the level of expression of the reporter molecule with a control value, wherein a difference between the measured value and the control value indicates that the test agent modulates the methylation state of the region of interest. In general, any of a wide variety of agents can be evaluated. In some embodiments, the agent is a small molecule, polypeptide, nucleic acid, lipid, or sugar. In some embodiments a library of compounds may be tested, e.g., a small molecule library, natural product library, peptide library. In some embodiments the agent is a nucleic acid that is introduced into the cell. For example, the nucleic acid may comprise a siRNA. In some embodiments the agent is expressed in the cell. In some embodiments a high throughput screen is performed, in which at least about 20,000 agents (e.g., small molecule compounds or nucleic acids) are tested. Cells may be placed in individual wells of a microtiter plate with different compounds. Agents that increase or inhibit methylation or demethylation of one or more ROIs may be identified.

In some aspects of any screening and/or characterization methods, agents may be contacted with cells comprising an RGM construct, sometimes referred to as "test cells" (and optionally control cells) at one or more predetermined concentrations. In some embodiment the concentration is about up to 1 nM. In some embodiments the concentration is between about 1 nM and about 100 nM. In some embodiments the concentration is between about 100 nM and about 10 µM. In some embodiments the concentration is at or above 10 µM, e.g., between 10 µM and 100 µM. Following incubation for an appropriate time, optionally a predetermined time, the effect of agents or composition on the level of the reporter molecule in the test cells is determined. Cells can be contacted for various periods of time. In certain embodiments cells are contacted for between 12 hours and 20 days, e.g., for between 1 and 10 days, for between 2 and 5 days, or any intervening range or particular value. Cells can be contacted transiently or continuously. If desired, the agent can be removed prior to assessing the effect on the cells.

Conditions that may be tested or used in various embodiments may include electrical or mechanical stimulation, exposure to other cells or cell products such as extracellular matrix components, growth on or in particular substrates or matrices, etc. In some embodiments the methylation state of a region of interest, e.g., a superenhancer, enhancer, or promoter of a cell type specific gene or cell state specific gene, is detected or monitored as a cell undergoes a cell identity or cell state transition such as reprogramming or differentiation or is exposed to agent(s) or condition(s) that might or might not promote reprogramming or differentiation (e.g., agents being tested for use in such processes). In some embodiments, particular methylation changes that accompany or are required for reprogramming or differentiation may be identified. In some embodiments differences in methylation state of a ROI between cells that are in different states or have different identities may be determined. In some embodiments an agent or condition that inhibits or increases a methylation change that would normally occur during cell differentiation or that would typically occur during reprogramming is identified.

In some embodiments, the agent is a DNA methylation inhibitor. A variety of DNA methylation inhibitors are known in the art. See, e.g., Lyko, F. and Brown, R., Journal of the National Cancer Institute, 97(20):1498-1506, 2005. Inhibitors of DNA methylation include nucleoside DNA methyltransferase inhibitors such as 5-azacytidine, 5-azadeoxycytidine, and zebularine, non-nucleoside inhibitors such as the polyphenol (−)-epigallocatechin-3-gallate (EGCG) and the small molecule RG108 (2-(1,3-dioxo-1,3-dihydro-2H-isoindol-2-yl)-3-(1H-indol-3-yl)propanoic acid), compounds described in WO2005085196 and phthalamides, succinimides and related compounds as described in WO2007007054. Additional classes of compounds are: (1) 4-aminobenzoic acid derivatives, such as the antiarrhythmic drug procainamide and the local anesthetic procaine; (2) the psammaplins, which also inhibits histone deacetylase (Pina, I. C., J Org Chem., 68(10):3866-73, 2003); (3) 4-aminoquinoline-based inhibitors, such as SGI-1027 and its analogs (Rilova, E., et al., ChemMedChem. 2014 March; 9(3):590-601); and (4) oligonucleotides, including siRNAs, shRNAs, and specific antisense oligonucleotides, such as MG98. DNA methylation inhibitors may act by a variety of different mechanisms. The nucleoside inhibitors are metabolized by cellular pathways before being incorporated into DNA. After incorporation, they function as suicide substrates for DNMT enzymes. The nonnucleoside inhibitors procaine, epigallocatechin-3-gallate (EGCG), and RG108 have been proposed to inhibit DNA methyltransferases by masking DNMT target sequences (i.e., procaine) or by blocking the active site of the enzyme (i.e., EGCG and RG108). In some embodiments the agent is an inhibitor of MEK or GSK3. In some embodiments the agent is leukemia inhibitory factor (LIF).

In some embodiments, a DNA methylation reporter may be used to analyze the functional and/or temporal relationship between DNA methylation and transcription initiation or transcriptional silencing of a gene. For example, a DNA methylation reporter located in proximity to a regulatory region of a gene, such as a promoter region, could be used to determine whether methylation of the regulatory region precedes silencing of transcription of the gene, or whether silencing of transcription precedes methylation.

In some aspects, a DNA methylation reporter may be used in cell lineage tracing. Lineage tracing refers to identifying the descendants of a single cell. In lineage tracing, an individual cell is marked in such a way that the mark is transmitted to the cell's descendants, resulting in a set of marked cells that arose from the same founder cell. Lineage tracing is useful, e.g., in understanding normal tissue development, cell and tissue turnover, and disease. Among other things, it can provide information regarding the number of descendants of the founder cell, their location, and their differentiation status. In some embodiments, a marked cell whose lineage is to be traced can be introduced into a subject, e.g., a non-human mammal. The mark allows the cell and its descendants to be distinguished from the cells and tissues of the subject. A variety of marks can be used. In general, any of the reporter genes described herein can serve as a genetic label that marks a cell, e.g., for purposes of lineage tracing. Genetic labels that are particularly suitable for lineage tracing include those that encode fluorescent proteins, luciferases, and enzymes that act on a substrate to produce a colored substance. If stably integrated into the genome, a genetic label is inherited by the cell's descendants, thus marking them permanently. In some embodiments, cells are marked as a result of recombination mediated by a site-specific recombinase that is encoded by a reporter gene transcribed under control of an RGM promoter integrated into the genome in proximity to a region of interest as described above. Cells in which the ROI has a particular methylation state or has undergone a change in methylation state, and their progeny, can thus be detected regardless of subsequent changes in the methylation state of the ROI.

In some embodiments an RGM construct is used together with a site-specific recombinase that is expressed in a cell- or tissue-specific manner. The site-specific recombinase activates the expression of a reporter gene as described above (e.g., through excision of a STOP cassette), resulting in permanent genetic labeling of all descendants of the marked cells. The genetic label can then be used to identify the cells in which the tissue- or cell-specific promoter was active, and the RGM reporter molecule can be used to determine the level of methylation of the region of interest.

In some aspects, DNA methylation reporter constructs described herein could be used in combination with any of a variety of methods and tools known in the art that are useful for marking, tracking, and/or manipulating cells in vitro or in vivo, such as multicolor labelling by electroporation of plasmids (e.g., methods known as StarTrack, MAGIC, and CLoNe), DNA barcoding, LeGO vectors, Brainbow technology, RGB marking, optogenetics). RGB marking refers to the tagging of individual cells with unique hues resulting from simultaneous expression of the three basic colors red, green and blue, provides a convenient toolbox for the study of the CNS anatomy at the single-cell level. Using γ-retroviral and lentiviral vector sets. RGB (Gomez-Nicola, D., et al., Sci Rep. 2014; 4: 7520.) In some embodiments, such methods may be used to detect or track single cells or clones of cells harboring a DNA methylation reporter in vitro or in vivo. The DNA methylation reporter is used to detect or monitor methylation of a region of interest. In particular embodiments, cells harboring a DNA methylation reporter construct may be detected or tracked in the central nervous system, in the hematopoietic system, in an organ or organism undergoing development or regeneration or wound healing, during an immune response, in a tumor.

In some aspects, a DNA methylation reporter may be used to evaluate the effect of an agent on methylation of a DNA region of interest, identify agents that modulate methylation of a region of interest, or identify candidate therapeutic agents for treating a disease characterized by aberrant methylation of a region of interest (e.g., in which aberrant methylation of a region of interest causes, wholly or partly, or contributes to the disease or to one or more symptoms of the disease). As used herein, "treating" a disease is understood to include, for example, ameliorating the disease in whole or in part, reducing the severity of the disease, eliminating, alleviating or reducing one or more symptoms of the disease, etc.

In some aspects, described herein is a method of evaluating the effect of an agent on the methylation state of a DNA region of interest in a cell comprising steps of: contacting one or more cells comprising an RGM construct integrated in proximity to a region of interest in the genome with a test agent; measuring expression of the reporter molecule; and comparing the level of expression of the reporter molecule with a control value, wherein a difference between the measured value for the level of expression and the control value indicates that the test agent modulates the methylation state of the region of interest. An agent that modulates the methylation state of a region of interest may be referred to as a methylation modulator. In some embodiments cells are subjected to conditions that would normally cause an alteration in the methylation state of an ROI. In some embodiments an agent that inhibits such alteration, e.g., prevents it from occurring, may be identified.

In some embodiments, a DNA methylation reporter may be used to identify a candidate therapeutic agent for treating a disorder associated with aberrant DNA methylation. Aberrant DNA methylation plays a role in a number of different disorders. In some aspects, inhibiting development of aberrant methylation or restoring a more normal DNA methylation pattern in cells of a subject suffering from such a disorder is useful for treating such diseases. In some embodiments, a DNA methylation reporter construct is inserted in proximity to a region of genomic DNA that is aberrantly methylated in a disorder. Cells harboring the DNA methylation reporter construct in proximity to the region may be used to identify agents that affect the methylation state of the region, e.g., agents that decrease or increase methylation of the region. In some embodiments, aberrant DNA methylation of one or more regions of genomic DNA occurs in cancer cells of a subject with cancer. In some embodiments, aberrant DNA methylation of one or more regions of genomic DNA occurs in one or more types of subtypes of immune cells of a subject suffering from an autoimmune disease. In some embodiments, aberrant DNA methylation of one or more regions of genomic DNA occurs in neurons or glial cells of a subject suffering from a neurological disorder.

Non-limiting information regarding certain disorders associated with aberrant DNA methylation may be found in Longo, D., et al. (eds.), Harrison's Principles of Internal Medicine, 18th Edition; McGraw-Hill Professional, 2011 and/or in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), available on the worldwide web at subdomain ncbi.nlm.nih.gov/omim/ and/or in Online Mendelian Inheritance in Animals (OMIA), a database of genes, inherited disorders and traits in animal species (other than human and mouse), available on the worldwide web at subdomain omia.angis.org.au/contact-.shtml.

In some embodiments the disorder associated with aberrant DNA methylation is fragile X syndrome, a heritable neurodevelopmental disorder caused by a CGG repeat mutation on chromosome that expands the 5'-non-coding region of the fragile X mental retardation 1 (FMR1) gene (Gene ID No: 2332 (human), Gene ID No: 14265 (mouse)). FMR1 encodes the fragile X mental retardation protein (FMRP), which regulates protein expression by interacting with mRNA. The so-called full mutation (>200 CGG repeats) leads to hypermethylation of the FMR1 promoter, which transcriptionally silences FMR1 and reduces FMRP levels, resulting in the disease phenotype. In some embodiments, a DNA methylation reporter construct is inserted in proximity to the FMR1 promoter in a normal cell or in a cell harboring a CGG repeat mutation associated with fragile X syndrome.

The DNA methylation reporter may be used to identify agents that affect the methylation status of the FMR1 promoter (e.g., agents that inhibit or enhance methylation of the FMR1 promoter).

Autism spectrum disorders (ASD) are increasingly common neurodevelopmental disorders characterized by characterized by impaired social interactions, impairment in communication, as well as restrictive or repetitive behaviors and interests. Aberrant DNA methylation has been implicated as playing a role in ASD. A number of genomic regions that are aberrantly methylated in cells of subjects with autism have been identified. In some embodiments the ROI is in the SHANK3 gene. SHANK3 is strongly suspected as being involved in the pathogenesis and neuropathology of ASD. Five CpG islands have been identified in the SHANK3 gene, and tissue-specific expression of SHANK3 is regulated by DNA methylation in an epigenetic manner. Increased DNA methylation has been identified in three intragenic CGIs (CGI-2, CGI-3 and CGI-4) in ASD brain tissues, associated with altered expression and alternative splicing of SHANK3 isoforms (Zhu, L., et al., Hum Mol Genet. 2014 Mar. 15; 23(6):1563-78).

In some embodiments the disorder associated with aberrant DNA methylation is cancer. Aberrant DNA methylation is a prominent finding in all cancers in which it has been studied. The transcriptional start sites of many genes that encode tumor suppressors, such as retinoblastoma-associated protein 1 (RB 1), MLH1, p16, and BRCA1, among others, lie within or contain CGIs. The promoters of these genes have been found to be extensively methylated in various tumors. Promoter methylation may contribute to silencing or maintenance of silencing of tumor suppressor genes. ARHI and PEG3 are tumor suppressor genes that are themselves imprinted genes. Methylation of the promoter region of the allele of these genes that is normally expressed, leading to silencing of expression, is implicated as a cause of ovarian cancer, and re-expression of these genes can inhibit ovarian cancer growth (Feng, W., et al., Cancer. 2008; 112(7):1489-502).

In some embodiments the ROI is the promoter region of the succinate dehydrogenase C (SDHC) gene. Loss of SDH function is a driver mechanism in several cancers. SDH-deficient gastrointestinal stromal tumors (dSDH GISTs) often harbor deleterious mutations in SDH subunit genes (SDHA, SDHB, SDHC, and SDHD, termed SDHx), but some are SDHx wild type (WT). Genome-wide DNA methylation and expression profiling recently identified SDHC promoter-specific CpG island hypermethylation and gene silencing in SDHx-WT dSDH GISTs (15 of 16 cases), six in the setting of the multitumor syndrome Carney triad (Killian, J K, et al., Sci Transl Med. 2014; 6(268):268ra177), providing an explanation for the pathogenesis of dSDH GIST, whereby loss of SDH function results from either SDHx mutation or SDHC promoter hypermethylation. An agent that could at least in part reverse SDHC promoter hypermethylation is a candidate agent for treatment of cancers associated with SDHC promoter hypermethylation, including SDHx-WT dSDH GISTs.

Myelodysplastic syndrome (MDS) is a group of neoplastic disorders of hematopoietic stem cells (HSCs) that is characterized by, among other things, inefficient hematopoiesis and susceptibility to acute myeloid leukemia (AML). AML is characterized by accumulation of immature myeloid cells in the bone marrow and peripheral blood. Promoter DNA hypermethylation and associated silencing of the tumor suppressor gene CDKN2b, encoding p15INK4b, has been reported to occur in up to 80% of AML patients. The DNA methylation inhibitors 5-azacitidine (AzaC) and 5-aza-2'-deoxycytidine (decitabine) are used in the treatment of a subset of patients with these diseases and may act at least in part by reactivating expression of tumor suppressors such as CDKN2b. Methylation within gene bodies has also been observed in cancer cells and has been reported to lead to increased transcription, which could increase transcription of genes that contribute to abnormally increased cell proliferation in cancer or other proliferative disorders.

Aberrant DNA methylation is also associated with resistance of cancers to various chemotherapeutic agents, which can lead to treatment failure. In some instances, aberrant methylation can also or alternatively confer sensitivity to various agents. For example, epigenetic inactivation of argininosuccinate synthetase (ASS1), due to aberrant methylation in the ASS1 promoter correlates with transcriptional silencing and contributes to treatment failure and clinical relapse in ovarian cancer but confers arginine auxotrophy and sensitivity to arginine deprivation (Nicholson, U, et al., Int J Cancer. 2009; 125(6): 1454-63). Downregulation of polo-like kinase 2 due to methylation of the CpG island in the Plk2 gene promoter can confer resistance to platinum-based therapy and taxane-based therapy (e.g., paclitaxel) (Syed, N., et al., Cancer Res. 2011 May 1; 71(9):3317-27). Promoter methylation in p57(Kip2) causes carboplatin resistance but also results in collateral sensitivity to the CDK inhibitor seliciclib (Coley, H M, et al., Br J Cancer. 2012; 106(3):482-9). In some embodiments an ROI is a promoter region of a gene characterized in that aberrant methylation of the ROI, affects the resistance or sensitivity of a cell to a particular agent, e.g., a chemotherapeutic agent or other drug. In some embodiments an agent that inhibits or decreases methylation of a region that, when methylated, confers resistance to a therapeutic agent, could be used to prevent or reduce the likelihood of emergence of resistance to the therapeutic agent. A subject in need of treatment may be treated with both the therapeutic agent and the methylation modulator (combination therapy). In some embodiments an agent that increases methylation of a region that, when methylated, confers sensitivity to a therapeutic agent, could be used to enhance the efficacy of the therapeutic agent. A subject in need of treatment may be treated with both the therapeutic agent and the methylation modulator. It should be understood that agents administered in a combination therapy approach need not be administered in the same composition (although they may be), nor at the same time (although they may be). The agents may be administered in any appropriate temporal relationship to each other to achieve the desired effect.

In some embodiments a DNA methylation reporter may be used to evaluate or monitor the methylation state of a region of interest in cancer cells isolated from a subject with cancer on in cancer cells in vivo in a non-human subject. The cancer may have been experimentally induced by introducing cancer cells into the subject or may have arisen in a cancer-prone non-human animal. The non-human animal may be one that harbors a genetic modification that increases its risk of developing cancer, such as a knockout of a tumor suppressor gene, a transgene that encodes an oncogene, or a combination thereof. The cells may harbor an RGM construct integrated into their genome in proximity to a region of interest, e.g., a promoter or enhancer or gene body of an oncogene or tumor suppressor gene.

Aberrant DNA methylation has been linked to a wide variety of other diseases, including autoimmune diseases such as rheumatoid arthritis (Nakano K., et al., (2013) DNA methylome signature in rheumatoid arthritis, Ann Rheum Dis., 72(1):110-7) and lupus (Coit, P., et al., Genome-wide DNA methylation study suggests epigenetic accessibility and transcriptional poising of interferon-regulated genes in naïve CD4+ T cells from lupus patients. J Autoimmun. 2013 June; 43:78-84), neurodegenerative diseases such as Alzheimer's disease (De Jager, P. L. et al. Alzheimer's disease pathology is associated with early alterations in brain DNA methylation at ANK1, BIN1 and other loci. Nat. Neurosci. Nat Neurosci. 2014 September; 17(9):1156-63), psychiatric disorders such as schizophrenia, depressive disorders, and bipolar disorder, to name a few.

Aberrant DNA methylation of DNA regions that regulate expression of genes involved in autoimmunity or inflammation may cause or contribute to autoimmune and inflammatory diseases. In some embodiments a gene involved in autoimmunity or inflammation encodes a cytokine-regulating protein, cytokine-regulating microRNA (miRNA). In some embodiment a gene involved in autoimmunity is a cytokine gene, cytokine receptor gene, or cytokine-responsive gene. "Cytokine gene" refers to a gene that encodes a cytokine or cytokine subunit (chain). "Cytokine receptor gene" refers to a gene that encodes a cytokine receptor or cytokine receptor subunit (chain). Cytokines include, for example, chemokines, interferons, interleukins, lymphokines, and tumor necrosis factor alpha. In some embodiments a cytokine is an interleukin (IL) e.g., any of IL-1 to IL-38. In particular embodiments a cytokine is IL-2, IL-3, IL-4, IL-5, IL-6, IL-7, IL-10, IL-12, IL-15, IL-17, IL-21, IL-23, IL-27, or IL-35. In some embodiments a cytokine is an interferon, e.g., an IFN-alpha, IFN-beta, IFN-gamma. One of ordinary skill in the art appreciates the various genes that encode chemokines, interferons, interleukins, lymphokines, tumor necrosis factor alpha, and receptors for any one or more of these. In some embodiments the cytokine is one that stimulates development, survival, activation, proliferation, and/or differentiation of one or more types or subtypes of immune system cells, e.g., T cells (e.g., CD4+ helper T cells, CD8+ cytotoxic T cells, Tregs, Th17 cells), NK cells, B cells, dendritic cells, monocytes, macrophages, or precursors of any of the foregoing. Cytokine-regulating proteins include, e.g., a transcription factors that increases or decreases expression of one or more cytokines or cytokine receptors. Cytokine-regulating miRNAs include miRNAs that inhibit expression of one or more cytokines or cytokine receptors. "Cytokine-responsive gene" refers to genes whose expression is regulated by one or more cytokines.

In some aspects, aberrant methylation of regulatory regions (e.g., promoters, enhancers, superenhancers) of cytokine genes, cytokine receptor genes, or cytokine-regulatory genes may result in aberrant expression of such genes (e.g., aberrantly increased expression of pro-inflammatory cytokines or their receptors or aberrantly reduced expression of anti-inflammatory cytokines or their receptors) which may cause or contribute to autoimmune and inflammatory diseases. For example, in some embodiments aberrantly reduced methylation of regulatory regions (e.g., promoters) of cytokine genes, cytokine receptor genes, or cytokine-regulatory genes may result in aberrantly increased expression of pro-inflammatory cytokines or their receptors, thereby causing or contributing to autoimmune disease or inflammation; in some embodiments aberrantly increased methylation of regulatory regions (e.g., promoters) of cytokine genes, cytokine receptor genes, or cytokine-regulatory genes may result in aberrantly decreased expression of anti-inflammatory cytokines or their receptors, thereby causing or contributing to autoimmune disease or inflammation. In some embodiments aberrantly reduced methylation of regulatory regions (e.g., promoters) of pro-inflammatory cytokine-responsive genes may result in aberrantly increased expression of such genes, thereby causing or contributing to autoimmune disease or inflammation. In some embodiments aberrantly increased methylation of regulatory regions (e.g., promoters) of anti-inflammatory cytokine-responsive genes may result in aberrantly decreased expression of such genes, thereby causing or contributing to autoimmune disease or inflammation.

In some embodiments, aberrant DNA methylation of a regulatory region (e.g., a promoter, enhancer, or superenhancer) of a gene that regulates the development, survival, activation, activity, proliferation, and/or differentiation of immune cells may cause or contribute to autoimmune or inflammatory disease. For example, in some embodiments, aberrant DNA methylation of a regulatory region (e.g., a promoter, enhancer, or superenhancer) of a gene that regulates development, survival, activation, activity, proliferation, and/or differentiation of immune cells promotes the development, survival, activation, proliferation, and/or differentiation of one or more types or subtypes of immune system cells that causes or contributes to an autoimmune or inflammatory disease or inhibits the development, survival, activation, activity, proliferation, and/or differentiation of one or more types or subtypes of immune system cells that would normally contribute to proper regulation of the immune system so as to inhibit autoimmunity or inflammation. In some embodiments the gene encodes a transcription factor that contributes to the establishment or maintenance of cell identity of such immune cells.

Autoimmune diseases include, for example, acute disseminated encephalomyelitis, alopecia areata, antiphospholipid syndrome, autoimmune hepatitis, autoimmune myocarditis, autoimmune pancreatitis, autoimmune polyendocrine syndromes, autoimmune uveitis, inflammatory bowel disease (Crohn's disease, ulcerative colitis), type I diabetes mellitus (e.g., juvenile onset diabetes), multiple sclerosis, scleroderma, ankylosing spondylitis, sarcoid, pemphigus vulgaris, pemphigoid, psoriasis, myasthenia gravis, systemic lupus erythemotasus, rheumatoid arthritis, juvenile arthritis, psoriatic arthritis, Behcet's syndrome, Reiter's disease, Berger's disease, dermatomyositis, polymyositis, antineutrophil cytoplasmic antibody-associated vasculitides (e.g., granulomatosis with polyangiitis (also known as Wegener's granulomatosis), microscopic polyangiitis, and Churg-Strauss syndrome), scleroderma, Sjögren's syndrome, anti-glomerular basement membrane disease (including Goodpasture's syndrome), dilated cardiomyopathy, primary biliary cirrhosis, thyroiditis (e.g., Hashimoto's thyroiditis, Graves' disease), transverse myelitis, and Guillaine-Barre syndrome. Inflammatory diseases include autoimmune diseases and other diseases in which there is excessive or inappropriate inflammation. In some embodiments aberrant DNA methylation may cause or contribute to one or more such disorders.

In some embodiments a DNA region of interest is a regulatory region (e.g., a promoter, enhancer, or superenhancer) or gene body of a cytokine gene, cytokine receptor gene, cytokine regulatory gene, or cytokine-responsive gene. In some embodiments a DNA region of interest is a regulatory region (e.g., a promoter, enhancer, or superenhancer) or gene body of a gene involved in the development, survival, activation, proliferation, and/or differentiation of one or more types of subtypes of immune cells, such as a gene that encodes a transcription factor that contributes to the establishment or maintenance of cell identity of such cells. In some embodiments an RGM construct is integrated into a regulatory region (e.g., a promoter, enhancer, or superenhancer) or gene body of a cytokine gene, cytokine receptor gene, cytokine regulatory gene, cytokine-responsive gene, or gene involved in the development, survival, activation, proliferation, and/or differentiation of one or more types of subtypes of immune cells.

In some embodiments, a DNA methylation reporter may be used to identify an agent that selectively increases or decreases the methylation of a region that is aberrantly methylated in cells from a subject with a disorder associated with aberrant DNA methylation. For example, it would be of interest to identify agents that can selectively cause an increase or decrease in methylation of a region of DNA that is aberrantly hypermethylated in such a disorder or that can selectively cause an increase or decrease in methylation of a region of DNA that is aberrantly hypomethylated in such a disorder. Selectively causing an increase or decrease in methylation of a region of DNA refers to causing an increase or decrease in methylation of the region without significantly affecting the methylation state of most other regions in the genome. In some embodiments a selective agent increases methylation of the region of interest by at least 50% or to a level of at least 80%, 90%, or more, but has no more than a 1%, or in some embodiments no more than a 5%, or in some embodiments no more than a 10% effect on the overall level of methylation in the genome. In some embodiments a selective agent decreases methylation of the region of interest by at least 50% or to a level of no more than 20%, or no more than 10%, but has no more than a 1%, or in some embodiments no more than a 5%, or in some embodiments no more than a 10% effect on the overall level of methylation in the genome. In some embodiments a selective agent decreases methylation of an aberrantly hypermethylated region to an approximately normal level for that region, but has no more than a 1%, or in some embodiments no more than a 5%, or in some embodiments no more than a 10% effect on the overall level of methylation in the genome. In some embodiments a selective agent increases methylation of an aberrantly hypomethylated region to an approximately normal level for that region, but has no more than a 1%, or in some embodiments no more than a 5%, or in some embodiments no more than a 10% effect on the overall level of methylation in the genome. In some embodiments, agents that can selectively cause an increase in methylation of a region of DNA that is aberrantly hypermethylated in cells from a subject with a disorder associated with aberrant DNA methylation can be used to generate a cell-based model or an animal model of the disorder. In some embodiments, agents that can selectively cause a decrease in methylation of a region of DNA that is aberrantly hypomethylated in cells from a subject with a disorder associated with aberrant DNA methylation can be used to generate a cell-based model or an animal model of the disorder. The cell-based or animal model may be used to screen for agents that could be used to treat the disorder.

Agents that can cause a selective decrease in methylation of a region of DNA that is hypermethylated in a disorder or that can cause a selective increase in methylation of a region of DNA that is hypomethylated in a disorder can serve as candidate therapeutic agents for treating the disorder. Thus in some embodiments, a DNA methylation reporter may be used to identify a candidate therapeutic agent for a disorder associated with aberrant DNA methylation. Such a candidate therapeutic agent may, for example, cause reactivation of an aberrantly silenced gene such as a tumor suppressor gene (which may have an aberrantly hypermethylated promoter region) or may inhibit expression of an aberrantly expressed gene that causes or contributes to a disorder (e.g., an oncogene, in the case of cancer). The term "oncogene" encompasses nucleic acids that, when expressed, can increase the likelihood of or contribute to cancer initiation or progression. Normal cellular sequences ("proto-oncogenes") can be activated to become oncogenes (sometimes termed "activated oncogenes") by mutation and/or aberrant expression. In various embodiments an oncogene can comprise a complete coding sequence for a gene product or a portion that maintains at least in part the oncogenic potential of the complete sequence or a sequence that encodes a fusion protein. Oncogenic mutations can result, e.g., in altered (e.g., increased) protein activity, loss of proper regulation, or an alteration (e.g., an increase) in RNA or protein level. Aberrant expression may occur, e.g., due to chromosomal rearrangement resulting in juxtaposition to regulatory elements such as enhancers, epigenetic mechanisms, or due to amplification, and may result in an increased amount of proto-oncogene product or production in an inappropriate cell type. Proto-oncogenes often encode proteins that control or participate in cell proliferation, differentiation, and/or apoptosis. These proteins include, e.g., various transcription factors, chromatin remodelers, growth factors, growth factor receptors, signal transducers, and apoptosis regulators. A tumor suppressor gene (TSG) may be any gene wherein a loss or reduction in function of an expression product of the gene can increase the likelihood of or contribute to cancer initiation or progression. Loss or reduction in function can occur, e.g., due to mutation or epigenetic mechanisms. Many TSGs encode proteins that normally function to restrain or negatively regulate cell proliferation and/or to promote apoptosis. Exemplary oncogenes include, e.g., MYC, SRC, FOS, JUN, MYB, RAS, RAF, ABL, ALK, AKT, TRK, BCL2, WNT, HER2/NEU, EGFR, MAPK, ERK, MDM2, CDK4, GLI1, GLI2, IGF2, etc. Exemplary TSGs include, e.g., RB, TP53, APC, NF1, BRCA1, BRCA2, PTEN, CDK inhibitory proteins (e.g., p16, p21), PTCH, WT1, Polo-like kinases, SFRP1, APC, HHIP, SOCS1, CASP8, and RASSF1A etc. It will be understood that a number of these oncogene and TSG names encompass multiple family members and that many other oncogenes and TSGs are known. In some embodiments a ROI is a promoter region of a TSG, e.g., a TSG characterized in that hypermethylation of its promoter region is found in cancer.

In some embodiments the disorder associated with aberrant DNA methylation is an imprinting disorder. Imprinting disorders can sometimes result from loss of function of the allele of an imprinted gene that is normally expressed. Loss of function of the allele that is normally expressed may occur due to deletion, mutation, hypermethylation, or other causes. The other allele (the imprinted allele) may be normal, but is silenced by imprinting. In some embodiments, a candidate therapeutic agent may be one that could cause demethylation of a DMR (e.g., a DMR that acts as an ICR) that causes the silencing of the imprinted allele. In some embodiments, such an agent may be identified by integrating a DNA methylation reporter in proximity to the DMR in the chromosome in which the DMR normally acts to silence the imprinted allele. Test agents are screened to identify one or more agents that cause expression of the reporter molecule. In some embodiments such an agent may then be tested to determine its effect on expression of the imprinted allele by, e.g., directly measuring a gene product of the imprinted allele.

In some embodiments the imprinting disorder is Beckwith-Wiedemann syndrome (BWS; Online Mendelian Inheritance in Man (OMIM) #130650), a condition that is characterized by macrosomia, macroglossia, abdominal wall defects, and variable minor features. The relevant imprinted chromosomal region in BWS is 11p15.5, which consists of two imprinted domains, IGF2/H19 and CDKN1C/KCNQ1OT1, H19DMR and KvDMR1 being the respective imprinting control regions. Loss of methylation (LOM) at KvDMR1 and gain of methylation (GOM) at H19DMR are causes of BWS. In some embodiments an RGM construct may be integrated into 11p15.5 and used to detect or monitor methylation of H19DMR and/or KvDMR1 and/or to identify an agent that modulates the methylation state.

A candidate therapeutic agent identified according to any of the methods may be tested in isolated cells, e.g., cells obtained from a subject suffering from the disorder of interest or cells that are genetically engineered to harbor one or more mutations that causes or contributes to the disorder. For example, the effect of a candidate therapeutic agent for cancer may be tested to determine its effect on the proliferation of cancer cells in vitro. Numerous cancer cell lines are known in the art. An agent that inhibits the proliferation of cancer cells is a candidate therapeutic agent for treating cancer.

A candidate therapeutic agent identified according to any of the methods may be tested in human subjects with the disease or in non-human animals (e.g., animals that serve as a model for a disease) by determining whether the agent alleviates symptoms or signs of the disease or otherwise shows evidence of efficacy. One of ordinary skill in the art is aware of suitable animal models for disorders associated with aberrant DNA methylation and imprinting disorders. For example, a candidate therapeutic agent for treating cancer can be administered to non-human mammal that serves as an animal model for cancer (e.g., an animal with a spontaneously arising cancer or a cancer that is experimentally produced by, e.g., injecting or otherwise introducing cancer cells into the animal). The effect on one or more properties of the cancer (e.g., cancer development, size, growth rate, rate of metastasis, etc.) is determined.

A subject, e.g., a human subject suffering from a disorder associated with aberrant DNA methylation, may be tested to determine or confirm that the subject suffers from aberrant DNA methylation. In some embodiments, a subject may be tested to determine or confirm that a particular aberrant DNA methylation pattern (e.g., aberrant methylation of a particular genomic region) exists in at least some of the subject's cells prior to administration of an agent that is intended to affect the DNA methylation pattern in that region. In some embodiments, a cancer may be tested to determine or confirm that a particular aberrant DNA methylation pattern (e.g., aberrant methylation of a particular genomic region) exists in at least some of the cancer cells prior to administration of an agent that is intended to affect the DNA methylation pattern in that region. The subject may be tested by obtaining a sample comprising cells from the subject and utilizing standard methods for methylation analysis such as bisulfite sequencing.

In some embodiments contacting comprises administration of an agent to a subject, which may be by any route (e.g., oral, intravenous, intraperitoneal, gavage, topical, transdermal, intramuscular, enteral, subcutaneous), may be systemic or local, may include any dose (e.g., from about 0.01 mg/kg to about 500 mg/kg), may involve a single dose or multiple doses. An agent may be combined with a physiologically acceptable carrier (e.g., water, saline, 5% dextrose), excipients, or other substances conventionally combined with active agents for administration to a subject.

In some embodiments a genome-wide screen may be performed using cells that have an RGM construct integrated into their genome, e.g., in proximity to an ROI. The genome-wide screen may be performed using a library of test cells that overexpress or substantially lack expression of most (e.g., at least 80%, 85%, 90%, 95%, 96%, 97%, 97%, 99%, or 100%) of the genes in a given mammalian genome, i.e., a set of cells, cell populations, or cell lines wherein each cell, cell population, or cell line has one gene that is knocked out (e.g., by a mutation introduced by genome editing, such as through use of CRISPR technology), inhibited by RNAi, or overexpressed. In some embodiments the library of cells is generated by introducing a cDNA expression library, or an shRNA library, or a variomics library into cells or cell line of interest. In some embodiments at least 10,000 genes, at least 15,000 genes, or more, are tested. In some embodiments the screen is a pooled screen wherein members of the library are cultured together. In some embodiments, cells that have a phenotype of interest are identified and, optionally, separated from the other cells. In some embodiments the particular gene that is altered (e.g., knocked out) or overexpressed in such cells is identified. The different members of the library may bear DNA barcodes to allow them to be readily distinguished. In some embodiments the screen involves different members of the library being cultured in separate vessels, e.g., wells of a microwell plate. The genome-wide screen may, for example, identify genes that regulate or otherwise affect the methylation state of the ROI. In some embodiments the library of cells is subjected to conditions that would normally cause an alteration in the methylation state of the ROI. Cells in which such alteration fails to occur may be identified. In some embodiments the screen may identify one or more genes that is essential for methylation of a ROI. In some embodiments, e.g., where aberrant methylation of the ROI occurs in a disorder, such genes may be targets for drug discovery, e.g., discovery of agents that modulate expression or activity of the genes and thus modulate methylation of the ROI.

In some embodiments, DNA methylation, detected using an RGM, can be used as a readout to distinguish and/or isolate different cell types. In some embodiments, cell types that are relevant for purposes such as regenerative medicine and/or cell transplantation (e.g. beta cells, neurons, or other cell types mentioned herein) may be identified or isolated. For example, cells may have an RGM construct integrated into their genome in a ROI whose methylation state (e.g., hypermethylated or hypomethylated) is characteristic of a given cell type of interest. Cells in which the ROI has a methylation state characteristic of the cell type of interest may be isolated from the population. In some embodiments cells can be subjected to reprogramming, transdifferentiation, or differentiation and then analyzed to determine the methylation level of the ROI. Cell types of interest may then be isolated from the population. In some embodiments, the RGM construct may be integrated into the genome flanked by sites for a site-specific recombinase. If desired the RGM construct may be excised by expressing or delivering the recombinase to the cells.

All patents, patent applications, and publications (e.g., scientific articles, books, websites, and databases) mentioned herein are incorporated by reference in their entirety. It is also noted that the references cited in the various references cited herein are also considered to be incorporated herein. In case of a conflict between the specification and any of the incorporated references, the specification (including any amendments thereof, which may be based on an incorporated reference), shall control. Complete citations for certain references cited in the application are collected in the Reference List.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a", "an", and "the" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. Embodiments are disclosed in which exactly one member of the group is present in, employed in, or otherwise relevant to a given product or process. Embodiments in which more than one, or all of the group members are present in, employed in, or otherwise relevant to a given product or process are also disclosed. Furthermore, it is to be understood that disclosed herein are all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects described herein where appropriate. It is also contemplated that any of the embodiments or aspects can be freely combined with one or more other such embodiments or aspects whenever appropriate. Section headings are for convenience only and not intended to limit the disclosure in any way. Where elements are presented as lists, e.g., in Markush group or similar format, it is to be understood that each subgroup of the elements is also disclosed, and any element(s) can be removed from the group. It should be understood that, in general, where an aspect or embodiment is/are referred to as comprising particular elements, features, etc., certain aspects and embodiments could consist, or consist essentially of, such elements, features, etc. For purposes of simplicity those aspects and embodiments may not in every case have been specifically set forth in so many words herein. It should also be understood that any embodiment or aspect can be explicitly excluded from the claims, regardless of whether the specific exclusion is recited in the specification. For example, any one or more reporter molecules, reporter genes, regions of interest, nucleic acids, polypeptides, cells, species or types of organism, agents, disorders, subjects, or combinations thereof, can be excluded.

Where the claims or description relate to a composition of matter, e.g., a nucleic acid, polypeptide, cell, or non-human animal, it is to be understood that methods of making, obtaining, or using the composition of matter according to any of the methods disclosed herein, and methods of using the composition of matter for any of the purposes disclosed herein are disclosed, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are disclosed, unless otherwise indicated or unless it would be evident to one of ordinary skill in the art that a contradiction or inconsistency would arise. Unless clearly indicated to the contrary, in any methods described or claimed herein that include more than one act, the order of the acts of the method is not necessarily limited to the order in which the acts of the method are recited, but the disclosure includes embodiments in which the order is so limited. Where the disclosure refers to a method it should be understood that any components needed or useful for performing the method can be provided and that the method can be performed under appropriate conditions and for an appropriate time to achieve a desired result or outcome. Unless otherwise indicated or evident from the context, any product or composition described herein may be considered "isolated" or "purified".

Where ranges are given herein, embodiments are disclosed in which the endpoints are included, embodiments are disclosed in which both endpoints are excluded, and embodiments are disclosed in which one endpoint is included and the other is excluded. It should be assumed that both endpoints are included unless indicated otherwise. Furthermore, unless otherwise indicated or otherwise evident from the context and understanding of one of ordinary skill in the art, values that are expressed as ranges can assume any specific value or subrange within the stated ranges in different embodiments, to the tenth of the unit of the lower limit of the range, unless the context clearly dictates otherwise.

Where a series of numerical values (e.g., a percentage) is stated herein, the disclosure discloses embodiments that relate to any intervening value or range defined by any two values in the series. The lowest value may be taken as a minimum and the greatest value may be taken as a maximum. Where a set of ranges is set forth, the disclosure discloses embodiments that relate to any range that encompasses any two or more of the ranges, using either endpoint of the lowest range as the lower endpoint and either endpoint of the highest range as the higher endpoint. For example, where the ranges 1-10, 10-100, 100-500, 500-1000, 1000-2000 is recited, ranges such as 1-100, 1-500, 10-500, 100-1000, 500-2000, 1-2000, etc., are disclosed. Furthermore, where a set of lower endpoints and a set of higher endpoints for a range are set forth, the disclosure encompasses embodiments that relate to all possible ranges that have a member of the set of lower endpoints as a lower endpoint and a member of the set of upper endpoints as an upper endpoint, i.e., all combinations of lower endpoints and higher endpoints are disclosed. For example, if a nucleic acid sequence is said to extend from −300, −200, or −100 to +1, +100, or +200, the disclosure provides embodiments that extend from −300 to +1, −300 to +100, −300 to +200, −200 to +1, −200 to +100, −200 to +200, −100 to +1, −100 to +100, and −100 to +200.

EXAMPLES

Example 1: A Methylation Sensitive Reporter System Based on a Minimal Promoter

We set out to generate a DNA methylation reporter system that is capable of visualizing genomic methylation states at single cell resolution. The design of the reporter was based on two premises: (i) previous observations suggesting that CpG sites can serve as cis-acting signals, affecting the methylation state of adjacent CpGs (Brandeis et al., 1994; Mummaneni et al., 1995; Turker, 2002); (ii) a methylation sensitive promoter, when introduced in proximity to a CpG region of choice, may be utilized to report on methylation changes of the adjacent sequences. Thus, an important issue in establishing a DNA methylation reporter was identifying a methylation sensitive promoter that can be affected by exogenous methylation changes without being independently regulated by the DNA methylation machinery. Constitutively active genes usually contain hypomethylated high density CpG islands (CGIs) in their promoter regions and are not regulated by DNA methylation (Deaton and Bird, 2011) whereas gene promoters associated with low density CGI are activated and repressed in a tissue-specific manner. Because methylation of both classes of promoters is either not affected by DNA methylation or is regulated by the DNA methylation machinery in a tissue-dependent manner, these promoters are typically not well suited for use as DNA methylation reporters. In contrast, imprinted gene promoters exhibit inherent sensitivity to DNA methylation of adjacent genomic regions, resulting in transcriptional activation or silencing. This mechanism has been established for a sub-group of germline-derived differentially methylated regions (DMRs), sometimes termed "imprinting control regions" (ICR) that affect in cis the methylation state of secondary regulatory promoter elements, which in turn control imprinted gene activity. Importantly, the methylation state of such regions is subsequently maintained throughout normal development, and is therefore not regulated by the DNA methylation machinery in a tissue-specific manner (Ferguson-Smith, 2011). We hypothesized that these intrinsic characteristics of imprinted gene promoters make them attractive as putative methylation sensors. An example of the phenomenon of imprinting is the Prader-Willi Angelman region, in which a DMR at the Snrpn gene promoter region controls its parent-of-origin monoallelic expression (Buiting et al., 1995; Kantor et al., 2004). Thus, we identified the Snrpn promoter as an attractive candidate to generate a DNA methylation reporter.

Figure 6A:
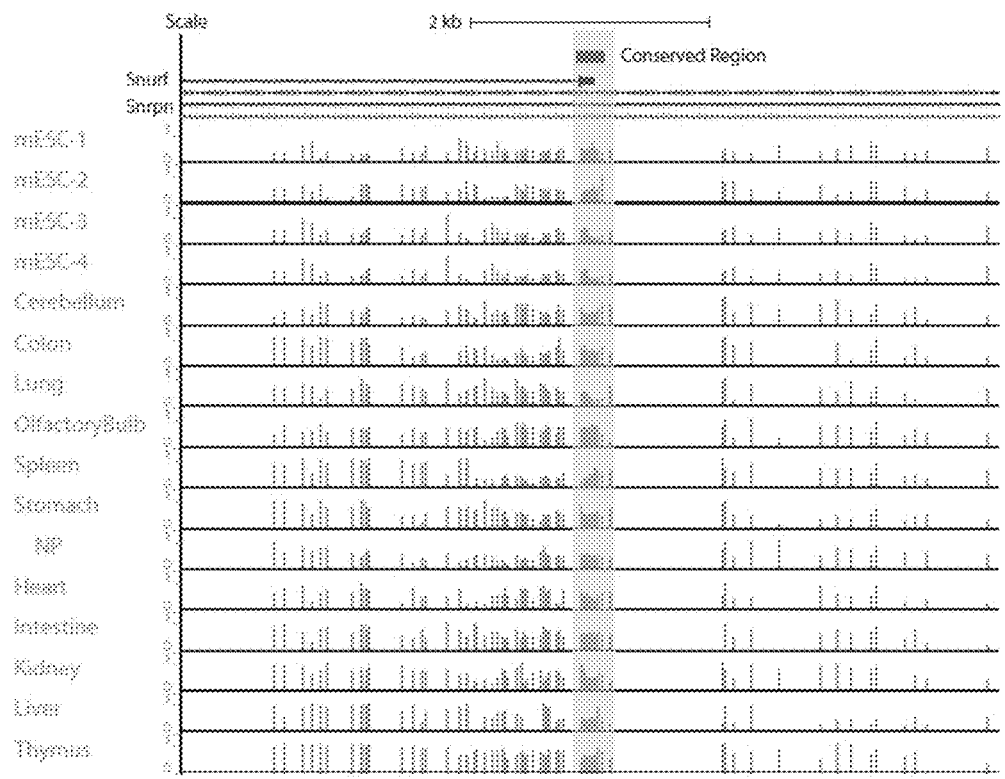
FIGS. 6A-6B illustrate that a minimal Snrpn promoter can be utilized to report on real time changes in DNA methylation (FIG. 6A) Shown are average methylation levels in different mouse cell types, in respect to the Snrpn promoter region. DNA methylation varies from 1—hypermethylated to 0—hypomethylated; the imprinted DMR is marked by light blue. Note the intermediate methylation levels, representing a typical monoallelic methylation at imprinted DMR regions.

To establish a DNA methylation reporter, we generated a synthetic minimal Snrpn promoter that includes the conserved elements between human and mouse and contains the endogenous imprinted DMR region (FIG. 6A). The minimal promoter region driving GFP was cloned into a sleeping beauty transposon vector (Ivics et al., 1997) to facilitate stable single copy integration into the genome.

The sequence of the Snrpn minimal promoter is underlined in the following ~1.5 kb of mouse genomic sequence, in which the "G" residue in bold, italic font is the transcription start site (TSS) for a transcript that encodes the Snrpn protein and the protein known as SNRPN upstream reading frame (Snurf), and the "ATG" in bold, italic font corresponds to the start codon of the transcript:

```
                                          (SEQ ID NO: 3)
GTAGATTAAGAACCAGCCTCAGAAAAGCAACAACAAAATACACACCCT

GCAGCGCTGAGCTACACTCCACCATTCCTAGCCCTAGTCTATTGTCTT

TTCATTTTTCCATAAGTAGTCTGTCCTTGTGATTTTCATTTGCATTTC

CATGGTGACTGACAATAGTATCTAATTGTTTAGTTCTATGTAAATAGA

TTTCTTCAGCTGTTTTCGAAAGTTCAGGTTTTGGTTACATTTAGAACT
```

-continued
```
GAATGTATCTTCATTGAAGTTGAATTTAGGATGTTTGCGAACTGGATG

CTAGCTCAGTGCGGGGGAAGGGAAGTAGAGAACTTCCAACTTTGTTA

GAATACCTCATTAACAGTTCTTGCAGGCCCTCATTAAGCTATGCTAAA

CCCATGTAAATTTAGCTTCCTTAGTTTTCTCCTTGCCATTTTGTTTTC

CTAATCTTCAAATAATTGCATATTGAAGTTACTACCACAATAATACTT

TTACTAGGCAGACAGGAAATTAATAGGTCAAAAGTAACTGAAATAAAT

TCTTATATATGTATCCACAATCTACAAAATGTTTTTGTTTTTGTTTTT

AGATATTGTTACAAATTGAACCTGGCCTTGAGTATGCAAAAATACTGC

TTTCTTAGAATAAGTTTCCTAAGAGCTGGAATTACTGGATGGCATTTC

TATGAGGTCATATATTTGTTAGTAAATAGTGTCTACTTTTCACCCCCC

AGGCATAACAACATTTAGGAAGCCCTGTCTCTAAAACCAACAACAACA

AAAGAAGCAGATACATAAGTTTCATAACTGAATGTTCTTCCTATTAAA

ATTTAATCACACCATGATCTGGAGGAAATAGTTTTCTCCCAGTCATAT

GTTCTAACACAGAGAAAGAAAATACAAGTAATACTACATTAATGTAGA

ATGTAGAATTAGGAATCAGGATAACTTTTTTTTCTGTACAGAATTTTA

AGTATCTGACAATTTGGCTGGGCTTCATGTTTGATTGTGTGTGTGTGT

GTGTGTGTGTGTGTGTGTGATACACTATGTAACATGATATAGCCTA

GAAACCAGTCTTCCTCATATTGGAGATCAAACCTTTTTCCTCTCCCA

CATAATAAAAATCTGTGTGATGCTTGCAATCACTTGGGAGCAATTTTT

TTAAAAAATTAAATGTATTTAGTAATAGGCAATTATATCCATTATTCC

AGATTGACAGTGATTTTTTTTTTTTAATACACGCTCAAATTTCCGCA

GTAGGAATGCTCAAGCATTCCTTTTGGTAGCTGCCTTTTGGCAGGACA

TTCCGGTCAGAGGGACAGAGACCCCTGCATTGCGGCAAAAATGTGCGC

ATGTGCAGCCATTGCCTGGGACGCATGCGTAGGGAGCCGCGCGACAAA

CCTGAGCCATTGCGGCAAGACTAGCGCAGAGAGGAGAGGGAGCCGGAG

ATGCCAGACGCTTGGTTCTGAGGAGTGATTTGCAACGCAATGGAGCGA

GGAAGGTCAGCTGGGCTTGTGGATTCT.
```

Figure 6B:
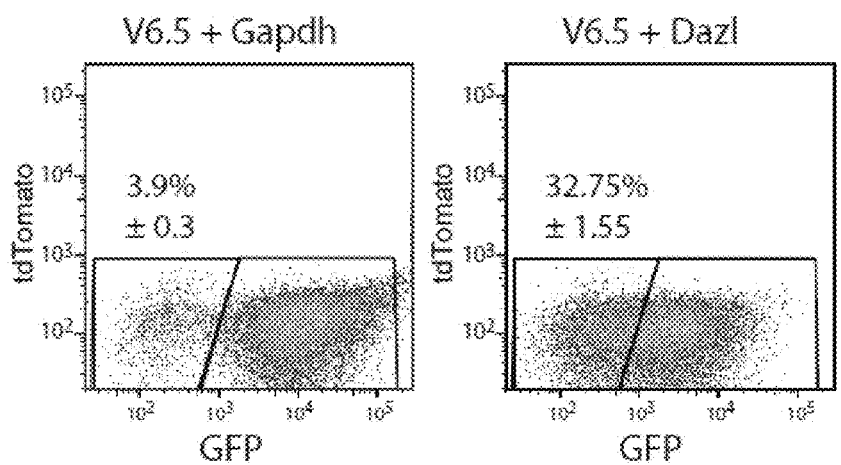

Recent studies have demonstrated that different CGI vectors, when stably inserted into mouse embryonic stem cells (mESCs), adopt a methylation pattern that corresponds to the in vivo methylation pattern of the respective endogenous sequence (Sabag et al., 2014). To test whether DNA methylation can propagate into the Snrpn promoter region in vivo, we designed an experimental system in which the CGI regions of the Gapdh and Dazl genes were cloned upstream of our reporter (FIG. 1A). The promoter of Gapdh encompasses a hypomethylated CGI consistent with constitutive expression in all tissues. In contrast, the Dazl promoter-associated CGI is hypermethylated in all tissues excluding the germ cells (Hackett et al., 2013). Given the different expression and methylation patterns of both genes, we hypothesized that upon stable integration of the two reporter vectors into the genome of mESCs the Gapdh CGI would maintain its hypomethylated state, while the Dazl CGI would be subjected to de novo methylation (Sabag et al., 2014). FIG. 6B shows that more than 95% of cells carrying the Gapdh reporter expressed GFP. In contrast, more than 30% of cells carrying the Dazl reporter were GFP negative, corresponding to reporter silencing. The effect of the Dazl reporter becomes more robust upon continued passage, with more than 80% of the cells faithfully silencing their reporter within 4 weeks (FIG. 1B).

Figure 1F:
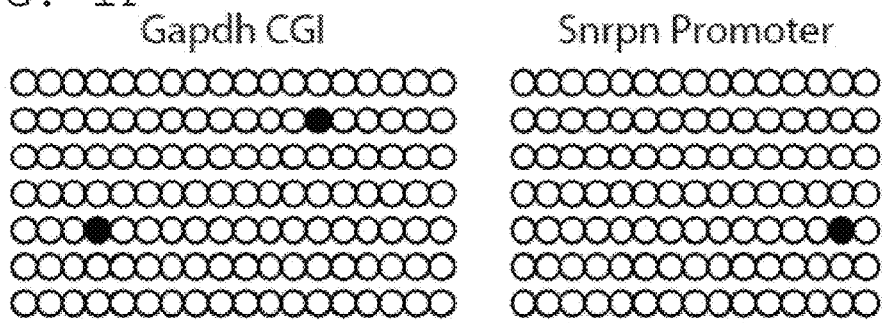
Figure 1G:
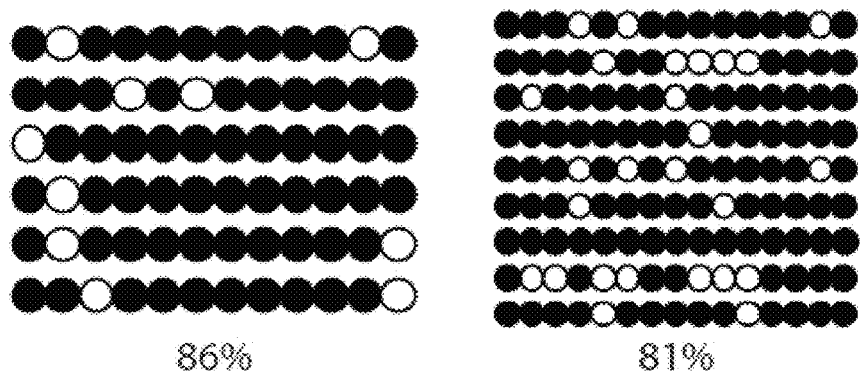

To assess the DNA methylation levels of the Gapdh and Dazl reporters following introduction into mESCs, we sorted Gapdh GFP positive and Dazl GFP negative cell populations (FIGS. 1C-1D). The GFP expression state was stable upon continuous culture and passaging of the two sorted cell populations for over 7 weeks (FIG. 1E). DNA was extracted from both Gapdh GFP positive and Dazl GFP negative cells and subjected to bisulfite conversion and PCR sequencing. FIG. 1F shows that Gapdh GFP positive cells maintained the hypomethylated state at both Gapdh CGI and the Snrpn promoter regions, whereas Dazl GFP negative cells became highly de novo methylated at the Dazl CGI region and its corresponding downstream Snrpn promoter (FIG. 1G). These results are consistent with the hypothesis that DNA methylation can be propagated from the CGI into the Snrpn promoter region resulting in repression of transcriptional activity.

Example 2: DNA Methylation Reporter is a Reporter for In Vivo Demethylation

The experiments described in Example 1 showed that the DNA methylation reporter (also referred to as a "reporter of genomic methylation" (RGM)) faithfully reports on de novo methylation imposed in vivo on the unmethylated Dazl CGI donor test sequence. Conversely, we were interested to assess whether a methylated and silent donor Snrpn promoter can be reactivated by means of demethylation acquired in vivo. For this we used the CpG methyltransferase M.SssI to in vitro methylate both Gapdh and Dazl reporter constructs. Treatment of the plasmids with M.SssI enzyme followed by bisulfite conversion, PCR amplification and sequencing, confirmed the complete hypermethylation of both the CGI and Snrpn promoter regions (FIGS. 2A and 2B).

Figure 2D:
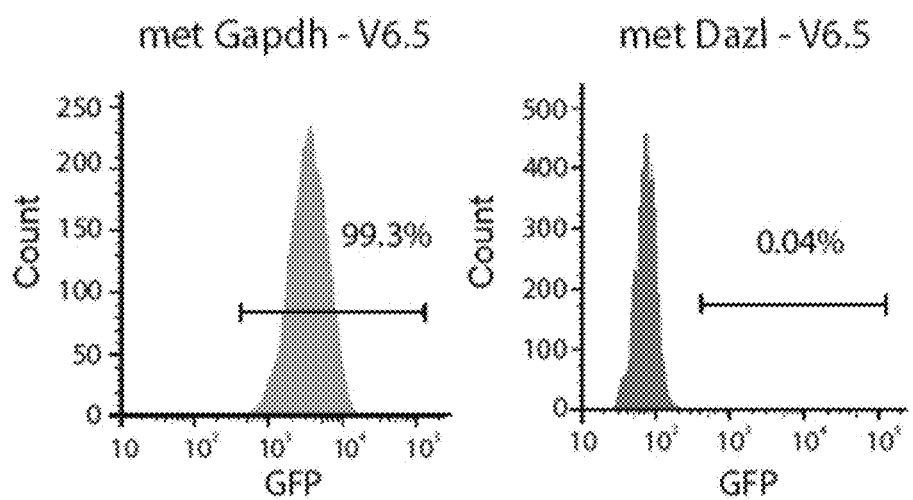
Figure 2E:
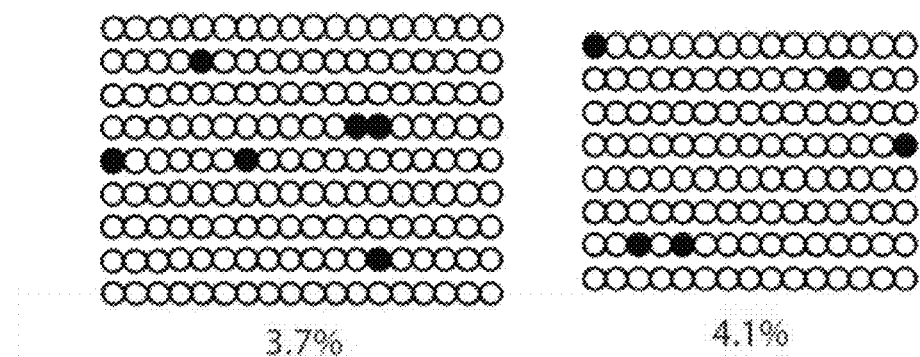
Figure 2F:
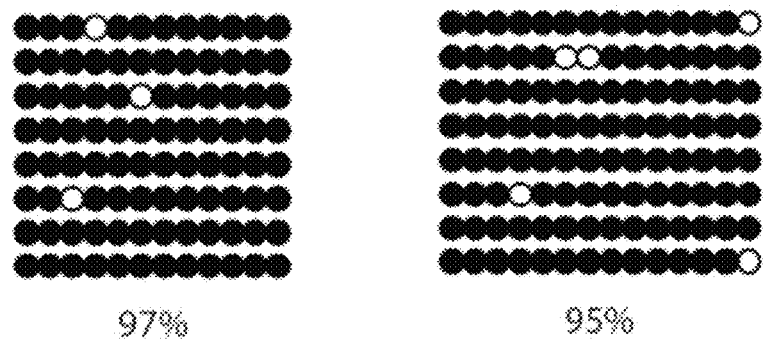

ESCs were transfected with either Gapdh or Dazl reporter and selected for cells carrying stably integrated vectors. Following two weeks of culture we identified robust activation of GFP in virtually all cells carrying the integrated Gapdh reporter. In contrast, cells carrying the Dazl reporter remained GFP negative (FIGS. 2C and 2D). To assess the DNA methylation state of the Gapdh and Dazl CGI and the respective downstream Snrpn promoter regions, DNA was extracted from the two cell lines, subjected to bisulfite conversion, PCR amplification and sequencing. FIG. 2E demonstrates that, consistent with high GFP expression, the Gapdh CGI and its downstream Snrpn promoter had become fully demethylated. In contrast, the Dazl CGI and its downstream Snrpn promoter sequences maintained the hypermethylated state in agreement with complete repression of the GFP signal (FIG. 2F). Thus, our data support the hypothesis that a Snrpn promoter can faithfully report on in vivo demethylation of the CGI in its proximity. These experiments indicate that the Snrpn promoter is a faithful reporter of the methylation state of adjacent sequences.

Example 3: Dnmt1, 3a and 3b Mediate Methylation and Reporter Activity

We used ESCs deficient for the DNA methyltransferases Dnmt1, Dnmt3a and Dnmt3b to gain mechanistic insights into demethylation and de novo methylation imposed on the Snrpn promoter in transfected ESCs. FIG. 2G shows that introduction of an in vitro methylated Dazl Snrpn vector into Dnmt1 mutant cells resulted in about 50% GFP positive cells in contrast to no GFP positive cells when inserted into wild type (wt) cells. Because Dnmt1 is the maintenance DNA methyltransferase (Li et al., 1992), this result indicates that reactivation of the methylated Dazl reporter in Dnmt1 deficient cells occurred by passive demethylation. To clarify the mechanism of de novo methylation, we introduced an unmethylated version of both vectors into mESCs deficient for both de novo DNA methyltransferases Dnmt3a and Dnmt3b (Pawlak and Jaenisch, 2011). FIG. 2H shows that the vast majority of cells carrying the Dazl or the Gapdh reporters were positive for GFP unlike reporter expression in control V6.5 cells (FIG. 1B and FIG. 6B), which is consistent with Dnmt3a/b mediating de novo methylation and reporter silencing.

Recent studies have shown that culturing mESCs in 2i medium (inhibitors of MEK and GSK3), and leukemia inhibitory factor (LIF) results in downregulation of Dnmt3a and Dnmt3b, consequently leading to global hypomethylation (Lee et al., 2014). To assess whether these culture conditions affect reporter activity, we transfected the unmethylated Gapdh and Dazl reporters into wt mESCs cultured in 2i and LIF. FIG. 2I shows that the great majority of the stably transfected cells were GFP positive, consistent with 2i-mediated downregulation of the Dnmt3a and 3b.

Figures 3A, 3B:
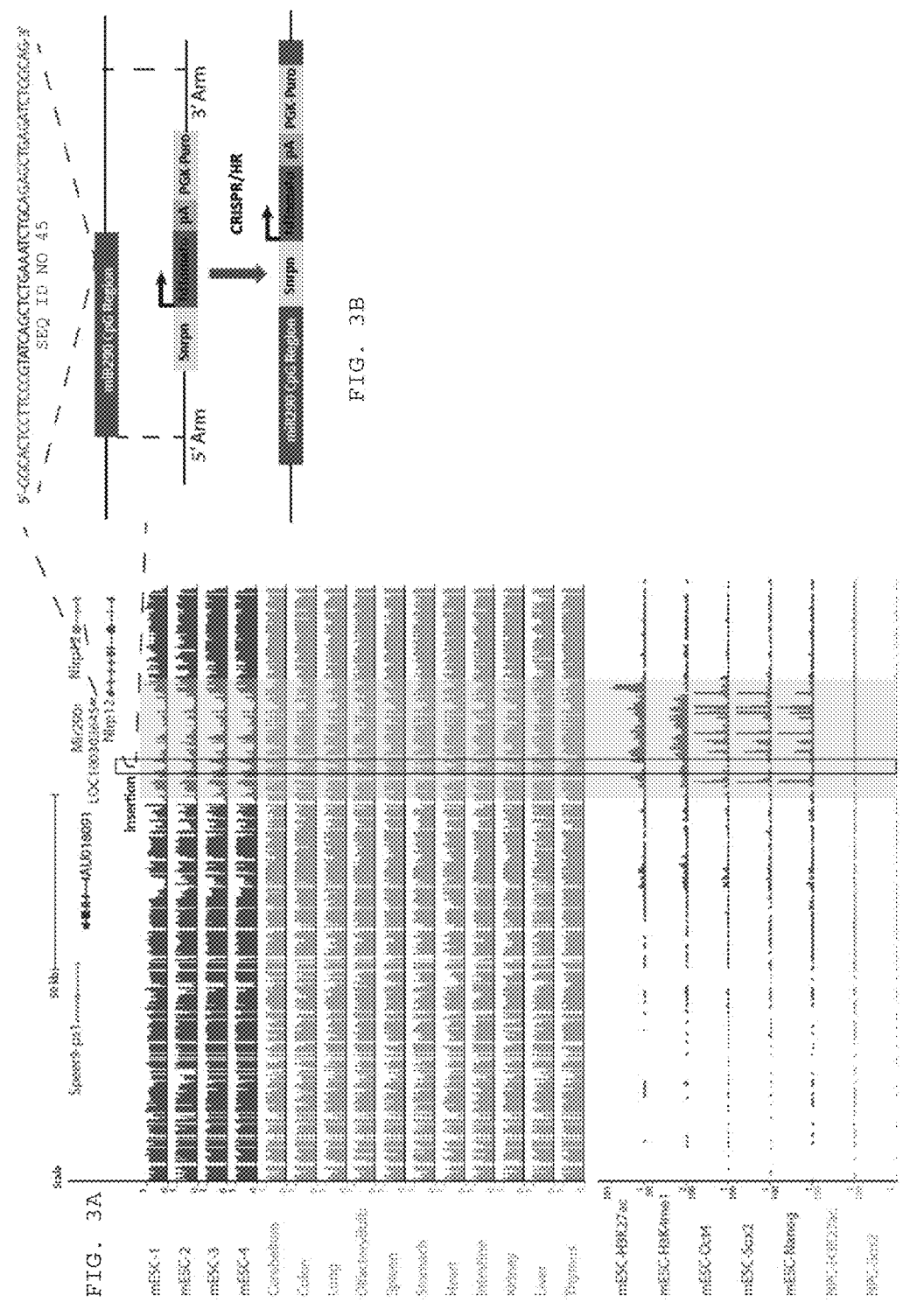

Example 4: RGM can Report on Methylation of Pluripotency Specific Superenhancers Pluripotency master transcription factors, together with Mediator, have been shown to form superenhancers (SE) at key pluripotency genes (Dowen et al., 2014; Whyte et al., 2013). Comparing ChIP-seq and DNA methylation data demonstrates that the enhancer marks of the pluripotent-specific SE miR290 and Sox2 are active and non-methylated in mESCs but methylated and not active in somatic cells (FIG. 3A and FIG. 7A). We assessed whether RGM could be used for monitoring tissue-specific DNA methylation changes of miR290 and Sox2 SE regions. For this, we inserted, utilizing CRISP/Cas mediated gene editing, a Snrpn tdTomato reporter into the endogenous miR290 and Sox2 superenhancers (FIG. 3B and FIG. 7B, respectively) using as recipient cells the previously established Oct4, Sox2, Klf4 and c-Myc (OSKM) polycistronic dox-inducible secondary reprogrammable mESCs (Carey et al., 2011; USSN), which also carried a GFP reporter knocked into the endogenous Nanog locus. Correct integration of the vector was validated by PCR and Southern analysis (FIG. 7C). FIG. 3C shows that both targeted ESC lines (miR290 #21 and Sox2 #2) expressed tdTomato as well as Nanog-GFP. To assess whether the tdTomato expression correlated with hypomethylation of the inserted RGM, DNA extracted from the bulk mESCs population was bisulfite converted, amplified by PCR and sequenced, with the PCR amplification including both the SE CpG region and the downstream Snrpn promoter. As predicted from the methylation maps (FIG. 3A and FIG. 7A), both endogenous miR290 and Sox2 CpG regions were mostly hypomethylated (FIG. 3D). Importantly, the Snrpn promoter was also hypomethylated (FIG. 3D) consistent with reporter expression. Of note, a few highly methylated alleles were detected (FIG. 3D), possibly reflecting an inherent variation in the bulk population due to the presence of cells that carry an inactive reporter. We conclude that RGM can report on the methylation state of distal genomic regulatory regions.

Example 5: Dynamic De Novo DNA Methylation During Differentiation

Figure 4A:
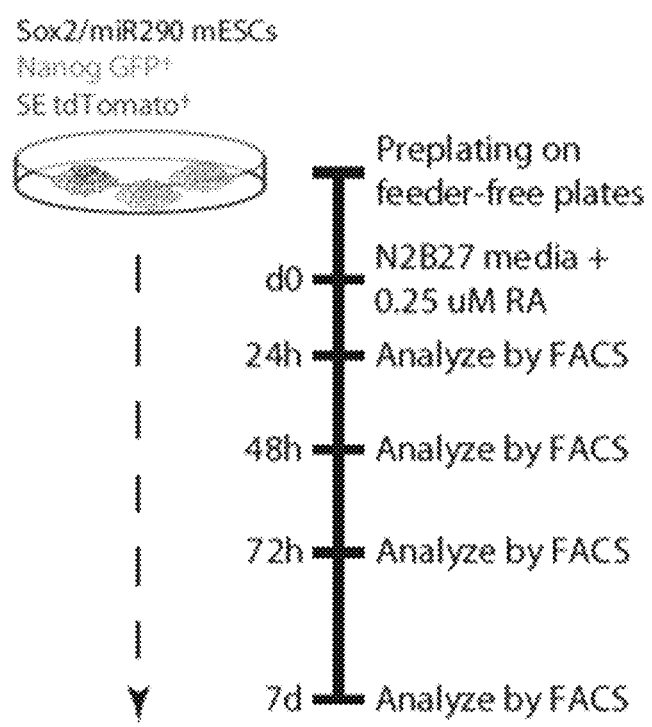
Figure 4B:
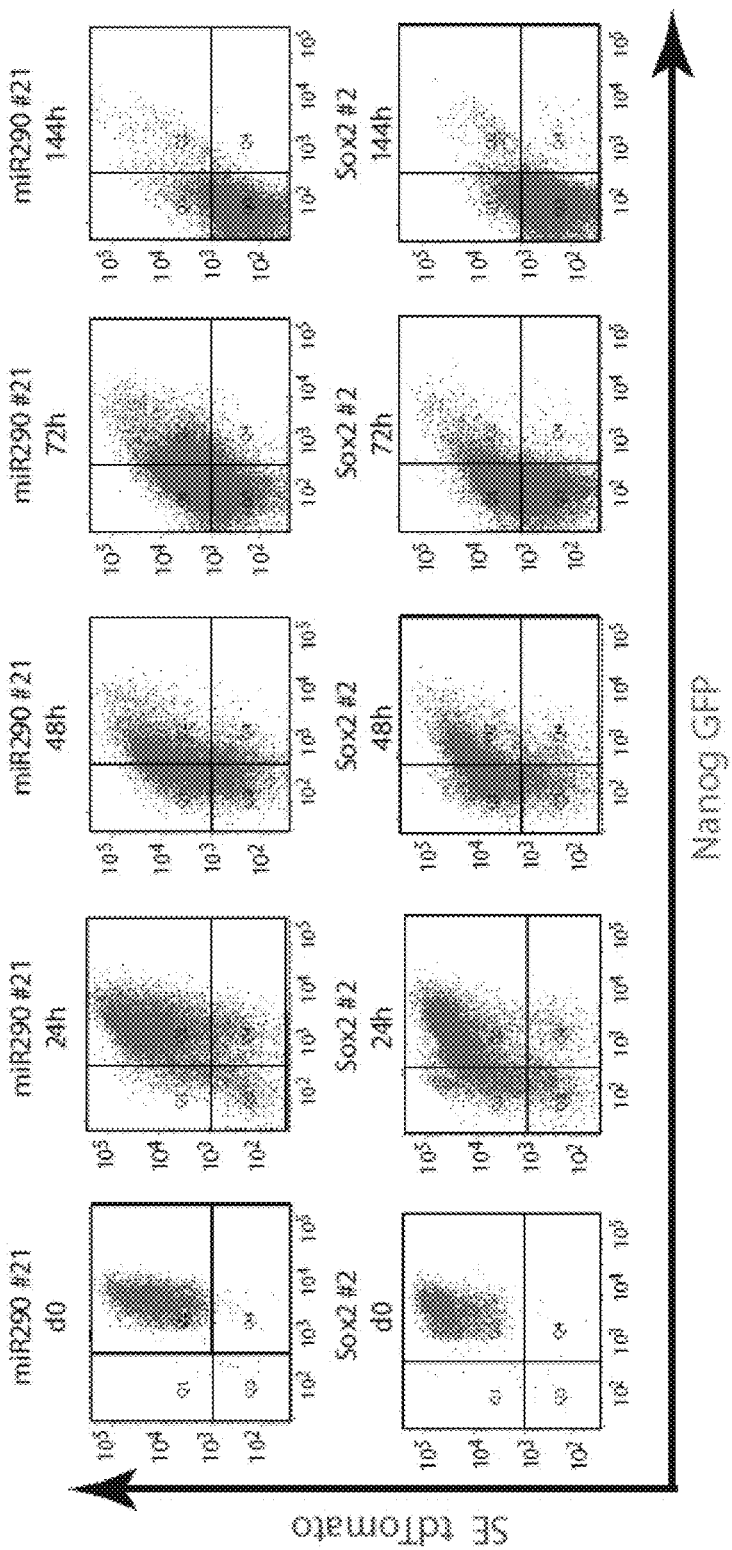
Figure 4C:
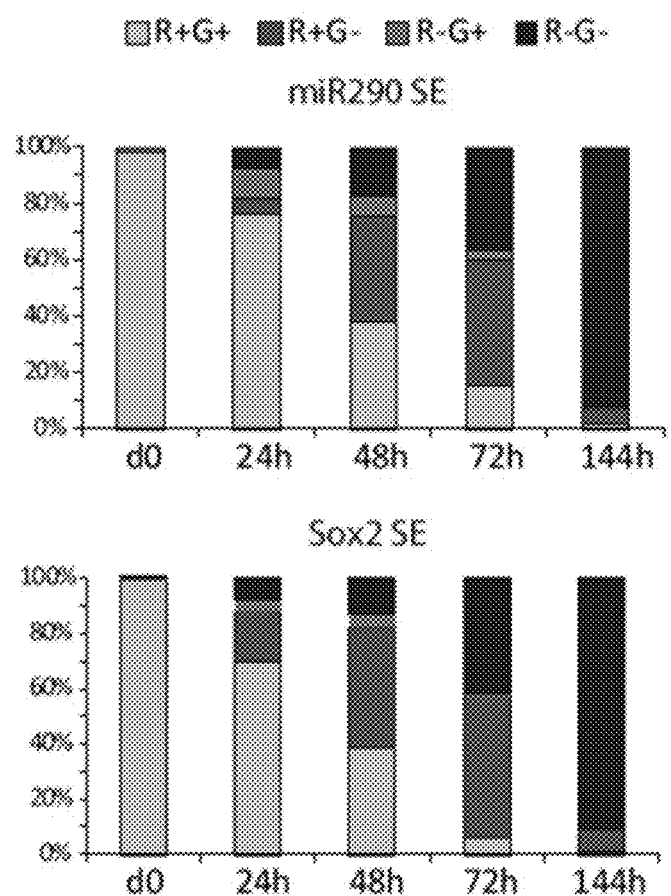

We investigated whether RGM also allows tracing of real-time changes in genomic DNA methylation during in vitro differentiation. ESCs carrying the tdTomato reporters reflecting DNA methylation levels at the SE regions, were exposed to Retinoic Acid (RA), which induces a rapid exit from pluripotency, and cellular differentiation (Rhinn and Dolle, 2012). The presence of the Nanog-GFP reporter allowed monitoring exit from pluripotency by loss of GFP expression. Sorted double positive (tdTomato$^+$/GFP$^+$) miR290 and Sox2 cells were plated on feeder-free gelatin coated plates, treated with 0.25 uM RA the following day (FIG. 4A) and analyzed at different times after addition of RA (FIGS. 4A and 4B). As expected, undifferentiated cells were double positive (tdTomato$^+$/GFP$^+$). Upon induction of differentiation a gradual reduction in the fraction of double positive cells was observed with most disappearing over the time course of 7 days, resulting in a largely double negative cell population (FIGS. 4B and 4C). However, tdTomato and Nanog-GFP positive cells disappeared with different kinetics: while singly tdTomato positive cells (tdTomato$^+$/GFP$^-$) appeared after 2 days, a few if any single Nanog-GFP positive cells (tdTomato$^-$/GFP$^+$) were detected during differentiation (FIGS. 4B and 4C). This suggested that Nanog was silenced prior to methylation and silencing of the miR290 and Sox2 SEs.

To confirm that loss of the tdTomato signal correlated with accumulation of de novo methylation in both SE regions, we sorted the three main populations following 48 hours of RA differentiation (FIG. 4C). DNA was extracted from the three cell populations (tdTomato$^+$/GFP$^+$, tdTomato$^+$/GFP$^-$ and tdTomato$^-$/GFP$^-$) and subjected to bisulfite sequencing. FIGS. 4D and 4E show the methylation state of both the endogenous miR290 and Sox2 SE and their respective Snrpn promoter regions. In contrast to the bulk population of mESCs (FIG. 3D), the sorted double positive cells did not harbor completely methylated alleles, consistent with the notion that methylated alleles in the bulk population represent intrinsic variation. The methylation of both miR290 (FIG. 4D) and Sox2 (FIG. 4E) in single positive cells (tdTomato$^+$/GFP$^-$) was low, consistent with tdTomato expression. The overall increased de novo methylation in the single positive cells, compared with the double positive cells, may suggest that this intermediate cell population is both transient and unstable. Finally, in agreement with the silencing of tdTomato expression, the double negative cells (tdTomato$^-$/GFP$^-$) exhibited robust hypermethylation on both endogenous SE regions and their respective Snrpn promoters (FIGS. 4D and 4E). Our data suggest that RGM can report on in vivo acquired methylation of genomic sequences upon exiting from pluripotency, and that the differentiation of ESCs induces silencing of Nanog prior to de novo methylation of the two miR290 and Sox2 SEs.

Figure 5A:
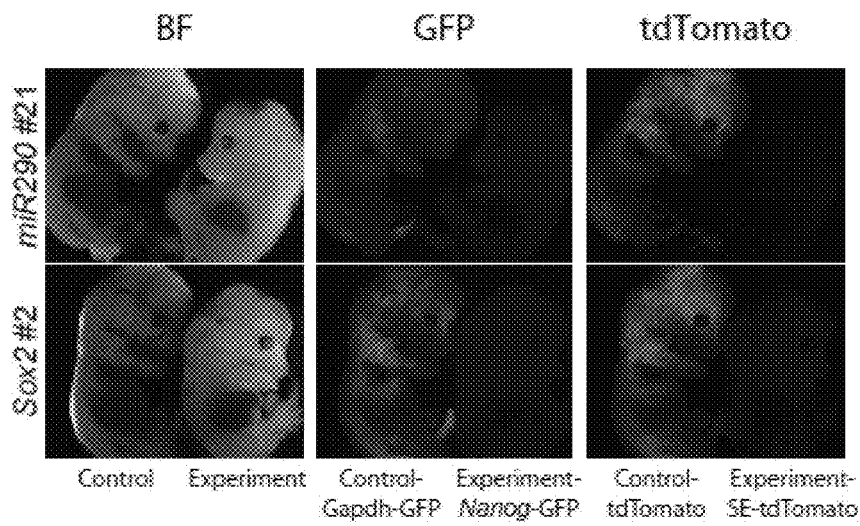
FIGS. 5A-5G show the dynamics of DNA demethylation of miR290 and Sox2 SE regions during cellular reprogramming.
Figure 5B:
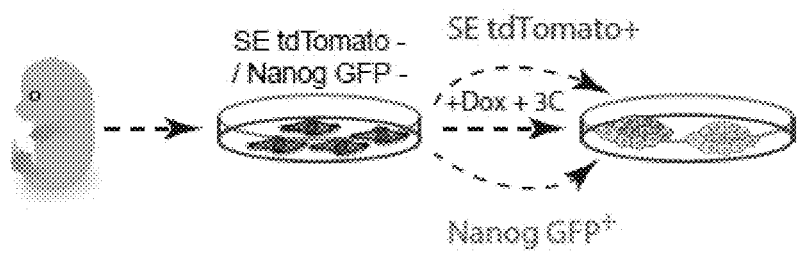

To test whether in vivo differentiation resulted in silencing of the tdTomato reporter in both miR290 and Sox2 SE regions, we analyzed 13.5 dpi chimeric embryos. As control, we injected ESCs harboring the Gapdh CGI reporter driving a GFP sequence (FIG. 1A), which had also been infected with lentiviruses resulting in constitutive expression of tdTomato. The robust expression of GFP in the Gapdh control embryos, demonstrated the widespread expression signature of the Snrpn promoter throughout mouse tissues (FIG. 5A). Unlike the Gapdh control, both miR290 and Sox2 embryos were completely negative for both GFP and tdTomato, demonstrating robust repression of Nanog and the Snrpn promoter (respectively) during in vivo differentiation (FIG. 5A).

Example 6: DNA Demethylation During Cellular Reprogramming

Figure 5C:
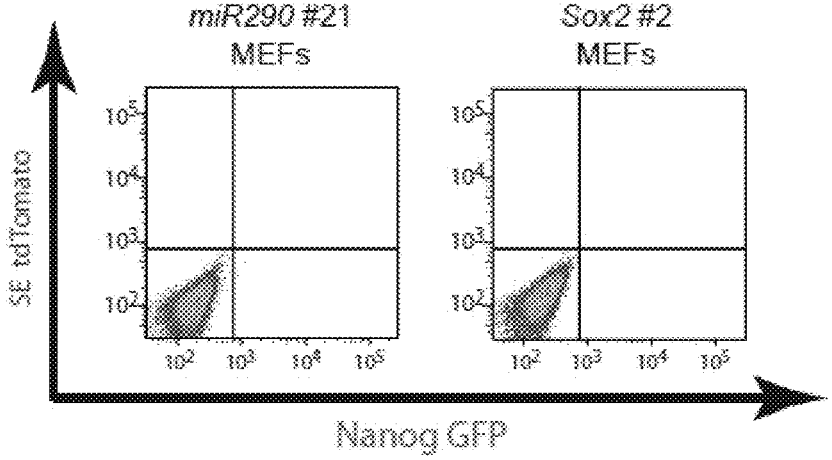
Figure 5D:
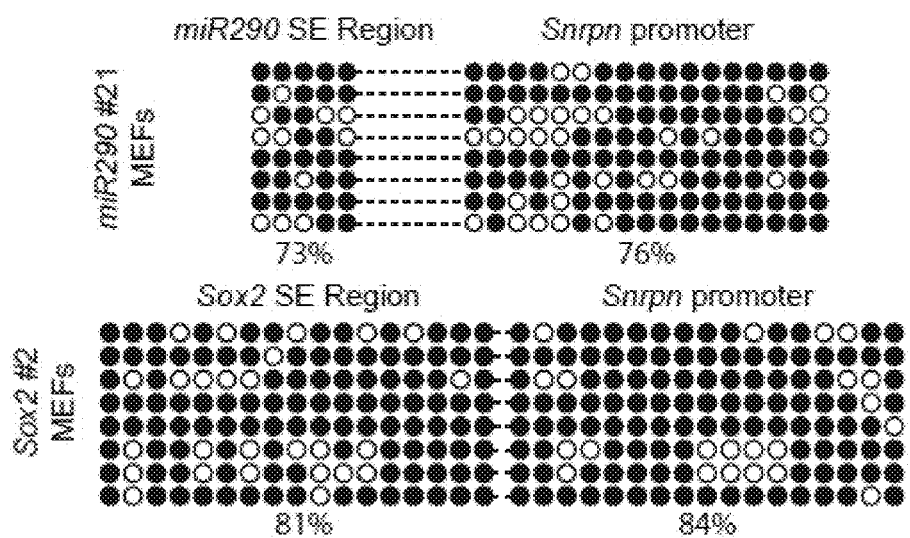
Figure 8A:
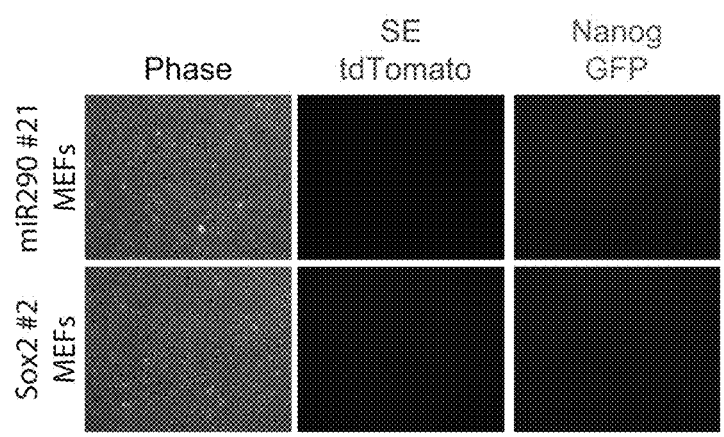
FIGS. 8A-8B illustrate reprogramming of MEFs isolated from miR290 and Sox2 reporter cell lines.

Reprogramming of somatic cells to iPS cells involves demethylation and activation of the pluripotency SEs Sox2 and miR290 (compare FIGS. 3A and 7A). We investigated whether RGM could be used to capture demethylation events that are gradually acquired during cellular reprogramming. For this we used secondary Dox-inducible reprogrammable MEFs isolated from 13.5 dpi chimeric embryos that had been injected at the blastocyst stage with the OSKM DOX inducible ESCs (Carey et al., 2011) carrying Nanog-GFP and the tdTomato reporter reflecting DNA methylation levels at the Sox2 or miR290 SE alleles (see FIG. 5A). Culture of these MEFs in DOX induces the reprogramming factors while Nanog-GFP activation allows monitoring the course of reprogramming in the bulk somatic cell population (Buganim et al., 2012). As expected, MEFs isolated from 13.5 dpi embryos were negative for both GFP and tdTomato expression, as measured by FACS analysis (FIG. 5C and FIG. 8A). Importantly, consistent with tdTomato repression, both endogenous miR290 and Sox2 SE regions as well as their corresponding downstream Snrpn promoter regions were hypermethylated (FIG. 5D).

Figure 5E:
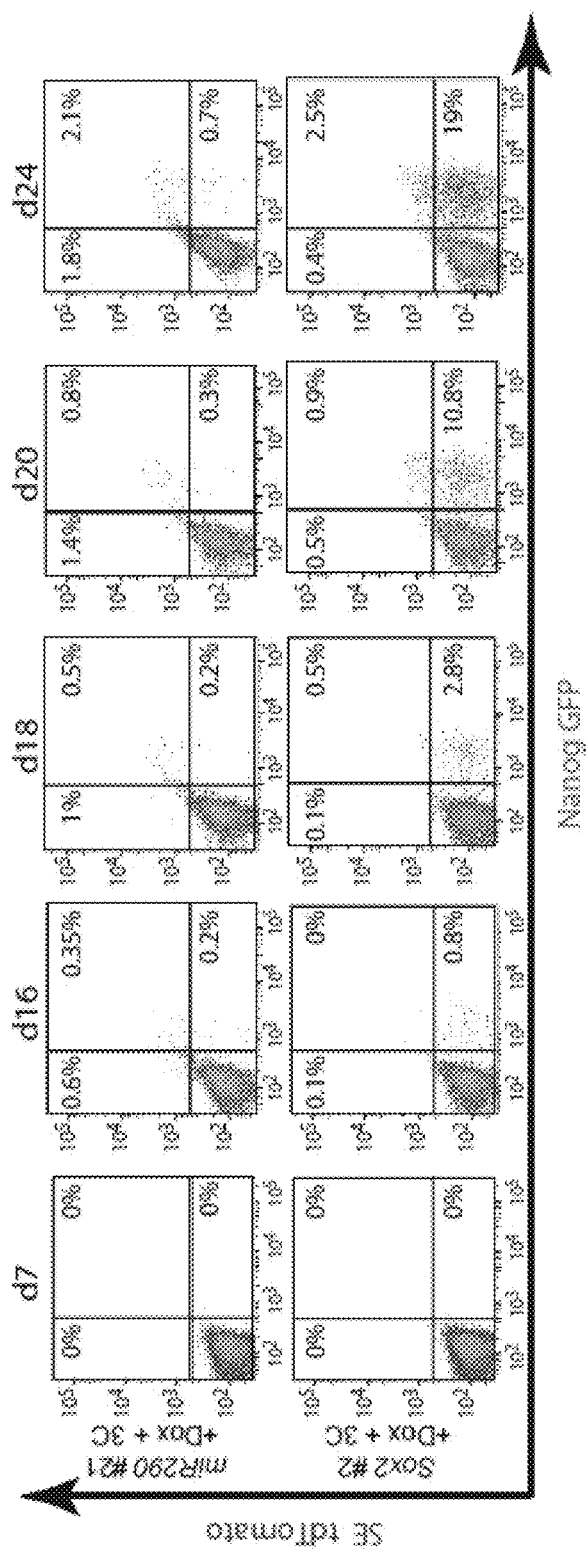
Figure 8B:
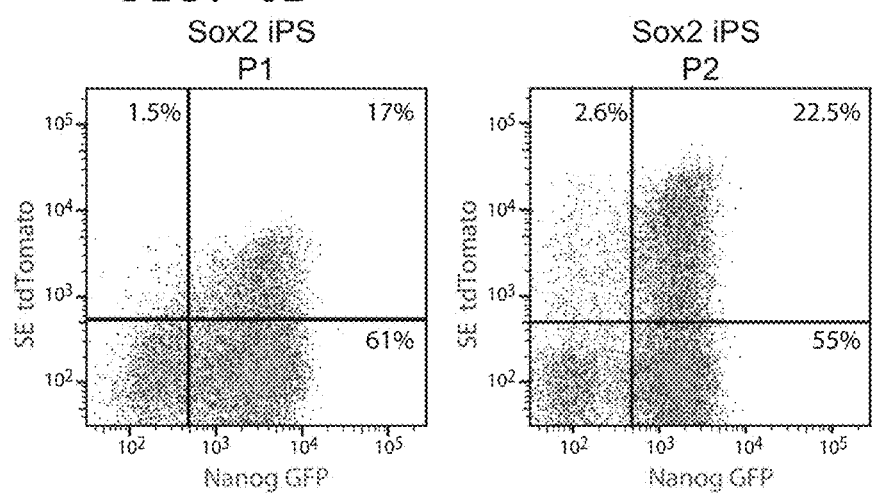

To test whether reprogramming-induced demethylation can be visualized by RGM, we treated the secondary MEFs with serum and LIF medium supplemented with 2 ug/ml doxycycline (Dox). While both miR290 and Sox2 MEFs were successfully reprogrammed, resulting in double positive cells (tdTomato$^+$/GFP$^+$, data not shown), the overall course of reprogramming was protracted and highly inefficient making it difficult to assess the reporter dynamics. It was recently shown that a combination of three chemicals, TGF-β antagonist ALK5 inhibitor II; GSK3b antagonist CHIR99021 and Ascorbic Acid, an enzymatic cofactor (from here on referred to as 3C), results in more efficient and synchronous reprogramming (Vidal et al., 2014). We reprogrammed both miR290 and Sox2 MEFs using 3C culture conditions and monitored the dynamics of reporter activation by flow cytometry. While the first expression of tdTomato$^+$ and GFP$^+$ cells emerged at day 16 (FIG. 5E), reporter activation of both miR290 and Sox2 occurred with different kinetics. FIG. 5E shows accumulation of miR290 reporter cells that activated both GFP and tdTomato (tdTomato$^+$/GFP$^+$) over time. A small population of single positive GFP cells appeared in late stages of reprogramming consistent with a stochastic sequence of events in the reprogramming of the miR290 SE region. Compared with miR290 reporter cells (i.e., cells bearing RGM in the miR290 SE), Sox2 cells (i.e., cells bearing RGM in the Sox2 SE) showed a more robust and defined dynamics of activation of both reporters (GFP and tdTomato). By day 16 a population of single positive GFP cells (tdTomato$^-$/GFP$^+$) had accumulated, which gradually shifted to become double positive (tdTomato$^+$/GFP$^+$) over time (FIG. 5E and FIG. 8B).

Figure 5F:
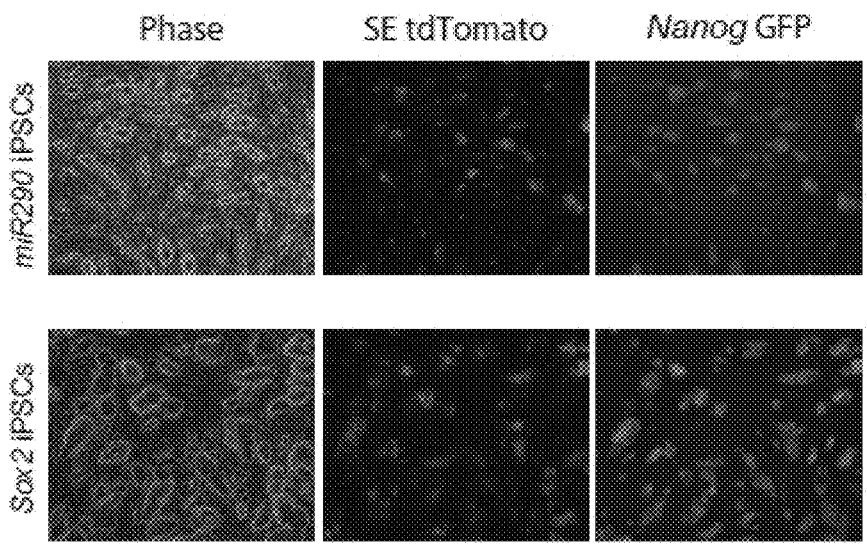
Figure 5G:
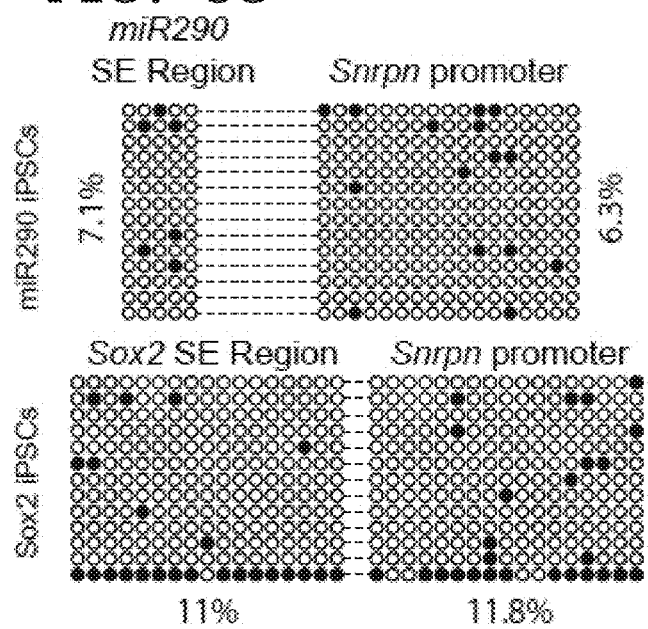

Our results suggest that reprogramming of both miR290 and Sox2 SE regions are late events, with the Sox2 SE region being reprogrammed subsequently to the activation of endogenous Nanog. miR290 and Sox2 double positive (tdTomato$^+$/GFP$^+$) cells invariably proceed to a Dox independent iPS cell state (FIG. 5F). To assess the methylation state of the Sox2 and miR290 SEs, we performed bisulfite sequencing on DNA extracted from sorted double positive (tdTomato⁺/GFP⁺) iPS cells. As shown in FIG. 5G, both miR290 and Sox2 SE regions, and their corresponding downstream Snrpn promoters were demethylated. These results suggest that RGM can faithfully visualize demethylation of regulatory genomic regions during reprogramming at single cell resolution.

DISCUSSION

We have generated a DNA methylation reporter (RGM) that allows real time imaging of DNA methylation with single cell resolution. The design of the reporter system took advantage of the intrinsic characteristics of imprinted gene promoters, for which the transcriptional activity reflects the DNA methylation state of adjacent sequences. Importantly, imprinted promoters are neutral to developmental or tissue specific DNA methylation changes, with their activity strictly dependent on the methylation state of the adjacent regulatory elements. This is in contrast to CGI sequences such as Gapdh or tissue-specific elements such as the Dazl promoter associated sequences, which become demethylated or de novo methylated, respectively, when inserted into the genome of ESCs (Brandeis et al., 1994; Sabag et al., 2014). This indicates that methylation of these elements as opposed to imprinted promoters is sequence—dependent and subject to trans-acting signals and cell state-dependent regulation.

The RGM reporter system described here is based on the Snrpn minimal promoter that does not induce methylation changes by itself but drives GFP expression solely dependent on the methylation state of surrounding sequences. Consistent with this premise, ES cells appeared GFP positive when stably transfected with the methylated or unmethylated Gapdh/Snrpn-GFP vector, but were GFP negative when transfected with the methylated or unmethylated Dazl/Snrpn-GFP reporter. This indicates that the Snrpn promoter region can be used as a faithful sensor for regional methylation changes of adjacent sequences.

To investigate whether RGM can report on the methylation state of endogenous loci we chose two pluripotent-specific SEs that are upstream of the miR290 and Sox2 genes, and that are known to be active and unmethylated in ESCs but become methylated and inactive upon cellular differentiation. CRISPR/Cas mediated insertion of the Snrpn-tdTomato reporter into ESCs resulted in tdTomato positive clones but tdTomato expression was silenced in mid-gestation chimeric embryos, which reflects the demethylation state of the SEs in pluripotent cells and their de novo methylation upon induction of differentiation. Conversely, MEFs isolated from chimeric embryos were tdTomato negative with both elements highly methylated. Upon conversion of the MEFs into iPSCs, however, the cells became tdTomato positive reflecting demethylation of the SEs during reprogramming to pluripotency. Our results establish that RGM reporter activity faithfully mirrors the changes of DNA methylation imposed on endogenous genomic elements during development, upon cellular differentiation and during reprogramming.

Changes in DNA methylation during development, lineage commitment and disease are dynamic and studies of epigenetic changes have been hampered by two experimental constraints that limit mechanistic studies of methylation and gene regulation. (i) One limitation of current methodology (standard methods for methylation analysis used in the art prior to the present disclosure) is that it provides only a static "snapshot" view of the methylation state during cell state transitions and (ii) another restriction is that current methylation analyses require the examination of multiple cells precluding assessment of epigenetic changes in single cells. Given the overwhelming evidence of cell-cell heterogeneity in embryos, cultured cells or disease states such as cancer (Junker and van Oudenaarden, 2014), this is a serious limitation for a mechanistic understanding of the epigenetic state and gene expression during these complex processes. The RGM reporter system overcomes some of the limitations of conventional methylation analyses by providing real time visualization of DNA methylation at single cell resolution.

Reprogramming of somatic cells into iPSCs involves extensive resetting of the epigenome (Buganim et al., 2013; Hanna et al., 2010), and coinciding with this notion, recent studies identified key role for epigenetic modifiers during this process (Mansour et al., 2012; Rais et al., 2013; Soufi et al., 2012). However, the exact kinetics of these epigenetic changes during the reprogramming process are difficult to define because of cell heterogeneity and the stochastic nature of the reprogramming process. Here we followed the methylation changes of two SEs associated with Sox2 and mir290, both of which are methylated and inactive in somatic cells but are unmethylated and activated in iPS and ES cells. Utilizing RGM we show that demethylation of both miR290 and Sox2 SEs are late events in the reprogramming process. Simultaneous activation of endogenous Nanog and miR290 SE demethylation, is consistent with Nanog directly regulating the expression of miR290 cluster during reprogramming to iPS cells (Gingold et al., 2014). The gradual activation of the Sox2 tdTomato reporter followed expression of endogenous Nanog, consistent with demethylation of Sox2 SE being a late event in the process (Buganim et al., 2012).

As RGM allows measuring dynamics of DNA methylation at single-cell resolution, it provides a framework for understanding epigenetic changes during cell state transition in heterogeneous cell populations. For example, replacing the fluorescent protein in the reporter system with Cre-Lox will enable the generation of epigenetic lineage tracing maps. Furthermore, utilizing RGM together with conventional gene expression reporters may offer detailed insights into the interplay between epigenetic cues and the execution of tissue-specific gene expression programs. The use of fluorescent reporters (or other reporters) as readout for locus-specific methylation changes may also provide an effective screening platform for the isolation of small molecule compounds that affect the methylation state of specific genomic regions.

Materials and Methods mESCs Cell Culture

V6.5 mouse embryonic stem cells (mESCs) were cultured on irradiated mouse embryonic fibroblasts (MEFs) with standard ESCs medium: (500 ml) DMEM supplemented with 10% FBS (Hyclone), 10 ug recombinant leukemia inhibitory factor (LIF), 0.1 mM beta-mercaptoethanol (Sigma-Aldrich), penicillin/streptomycin, 1 mM L-glutamine and 1% nonessential amino acids (all from Invitrogen). For experiments in 2i culture conditions, mESCs were cultured on gelatin-coated plates with N2B27+2i+LIF medium containing: (500 ml), 240 ml DMEM/F12 (Invitrogen; 11320), 240 ml Neurobasal media (Invitrogen; 21103), 5 ml N2 supplement (Invitrogen; Ser. No. 17/502, 048), 10 ml B27 supplement (Invitrogen; Ser. No. 17/504, 044), 10 ug recombinant LIF, 0.1 mM beta-mercaptoethanol (Sigma Aldrich), penicillin/streptomycin, 1 mM L-glutamine and 1% nonessential amino acids (all from Invitrogen), 50 ug/ml BSA (Sigma), PD0325901 (Stemgent, 1 uM), CHIR99021 (Stemgent, 3 uM).

Plasmid Cloning

To clone the PiggyBac-Insulator-GapdhCGI-Snrpn-GFP-polyA-PGK-PURO-sv40PolyA-Insulator construct, the minimal Snrpn promoter was PCR amplified using primers A1 and A2 (see complete primer list below). Snrpn PCR fragment was subsequently digested using Mfe1 and Nhe1 restriction enzymes. GapdhCGI sequence was PCR amplified using primers A3 and A4, following digestion using Sbf1 and Mfe1. A pCR2.1-TOPO-TA cloning vector (Life technologies) vector containing a GFP-PolyA-PGK-Puro cassette was digested using Sbf1 and Nhe1. Subsequently, these 3 DNA fragments were cloned using three-way ligation. The resulting GapdhCGI-Snrpn-GFP-PolyA-PGK-Puro cassette was then cloned into a PiggyBac transposon using the restriction enzymes Sbf1 and SacII to generate the PiggyBac-Insulator-GapdhCGI-Snrpn-GFP-polyA-PGK-PURO-sv40PolyA-Insulator vector. For the PiggyBac-Insulator-DazlCGI-Snrpn-GFP-polyA-PGK-PURO-sv40PolyA-Insulator construct, the same method was used, except that DazlCGI DNA fragment was PCR amplified using primers A5 and A6.

To clone the mi290 super enhancer (SE) targeting vector, the 5' homology arm was PCR amplified using the primers B1 and B2, this DNA fragment was then digested using Sbf1 and Mfe1 restriction enzymes. The 3' homology arm was PCR amplified using the Primers B3 and B4, following digestion with Asc1 and Fse1 restriction enzymes. Both homology arms were subsequently ligated with Snrpn-tdTomato-PolyA-PGK-Puro fragment that had been digested with Nhe1 and Asc1 restriction enzymes, and a pCR2.1-TOPO-TA cloning vector (Life Technologies) backbone that had been digested with Sbf1 and Fse1. To clone the Sox2 SE targeting vector, the same method was used except that 5' homology arm was amplified using primers C1 and C2, and the 3' homology arm was amplified using primers C3 and C4.

CRISPR oligonucleotides were ligated into px330 vector using BbsI restriction site as previously described (Wang et al., 2013). For the mi290 SE region oligonucleotides D3 and D4 were used and for the Sox2 SE region, the oligonucleotides D1 and D2 were used (see complete primer list below).

Reporter Cell Lines

To generate stably integrated Gapdh and Dazl reporter cell lines, either Gapdh- or Dazl-modified PiggyBac transposon (see above), and a helper plasmid expressing transposase, were transfected into mESCs cells using Xfect mESC Transfection Reagent (Clontech), according to the provider's protocol. Stably integrated reporter cells were selected with puromycin (2 mg/ml) for four days.

To generate miR290 and Sox2 SE reporter cell lines, targeting vectors and CRISPR/Cas9 were transfected into mESCs using Xfect mESC Transfection Reagent (Clontech), according to the provider's protocol. 48 hours following transfection, cells were FACS sorted for tdTomato expression, and plated on MEF feeder plates. Single colonies were further analyzed for proper integration by southern blot and PCR analysis.

Flow Cytometry

To assess the proportion of GFP and tdTomato in the established reporter cell lines, a single cell suspension was filtered, and assessed on the LSR II SORP, LSRFortessa SORP or FACSCanto II.

Retinoic Acid-Induced Differentiation mESCs carrying the reporter for both miR290 and Sox2 SE region, were sorted for double positive GFP and tdTomato expression, and plated on gelatin coated plates in ES cell medium (+LIF). The next day, cells were washed with PBS and resuspended in basal N2B27 medium (2i medium without LIF, Insulin and the two inhibitors), supplemented with 0.25 uM retinoic acid (RA). Medium was replaced every other day.

Blastocyst Injections for the Generation of Chimeras and Secondary MEFs

Blastocyst injections were performed using (C57B1/6× DBA) B6D2F2 host embryos. In brief, B6D2F1 females were hormone primed by an i.p. injection of PMS (Pregnant Mare Serum Gonadotropin, EMD Millipore) followed 46 h later by an injection of hCG (human Chorionic Gonadrotropin, VWR). Embryos were harvested at the morula stage and cultured in a $CO_2$ incubator overnight. On the day of the injection, groups of embryos were placed in drops of M2 medium and using a 16 um diameter injection pipet (Origio, Inc.) approximately 10 cells were injected into the blastocoel cavity of each embryo using a Piezo micromanipulator (Prime Tech, Ltd). About 20 blastocysts were subsequently transferred to each recipient female; the day of injection was considered as 2.5 dpc. Fetuses were collected at 13.5 dpc for the extraction of embryonic fibroblasts as described before (Buganim et al., 2012).

Southern Blots 10-15 ug of genomic DNA was digested with appropriate restriction enzymes overnight. Subsequently, genomic DNA was separated on a 0.7% agarose gel, transferred to a nylon membrane (Amersham) and hybridized with $^{32}P$ random primer (Stratagene) labeled probes.

Reprogramming to iPSCs

MEFs isolated from miR290 and Sox2 fetuses, were plated at density of 50,000 cells per 6-well in gelatin coated plates with standard MEF medium (mESCs media without LIF). The following day MEF medium was replaced with mESCs medium containing 2 mg/ml doxycycline (Sigma). Alternatively, cells were grown in mESCs medium containing 2 mg/ml doxycycline and a combination of 3 compounds: TGF-3 antagonist ALK5 inhibitor II; GSK3b antagonist CHIR99021 and Ascorbic Acid, as described before (Vidal et al., 2014). Medium was replaced every other day during the course of reprogramming.

Bisulfite Conversion, PCR and Sequencing

Bisulfite conversion of DNA was established using the EpiTect Bisulfite Kit (Qiagen) following the manufacturer's instructions. The resulting modified DNA was amplified by first round of nested PCR, following a second round using loci specific PCR primers (see complete list of primers below). The first round of nested PCR was done as follows: 94° C. for 4 min; 55° C. for 2 min; 72° C. for 2 min; Repeat steps 1-3 1×; 94° C. for 1 min; 55° C. for 2 min; 72° C. for 2 min; Repeat steps 5-7 35×; 72° C. for 5 min; Hold 12° C. The second round of PCR was as followed: 95° C. for 4 min; 94° C. for 1 min; 55° C. for 2 min; 72° C. for 2 min; Repeat steps 2-4 35×; 72° C. for 5 min; Hold 12° C. The resulting amplified products were gel-purified, subcloned into A pCR2.1-TOPO-TA cloning vector (Life Technologies), and sequenced.

Primer List—Cloning

| | | |
|---|---|---|
| A1 | snrpnF-mfe | aattaacaattgACGCTCAAATTTCCGC AGTAGG (SEQ ID NO: 8) |
| A2 | snrpnR-nhe | aattaaGCTAGCAGAATCCACAAGCCCA GCTG (SEQ ID NO: 9) |
| A3 | gapdhF-sbf | AATTAACCTGCAGGAGCCGAGAGGAATG AGGTTAGTC (SEQ ID NO: 10) |
| A4 | gapdhR-mfe | AATTAACAATTGGAGAGAGGCCCAGCTA CTCG (SEQ ID NO: 11) |
| A5 | dazlF-sbf | AATTAACCTGCAGGTTATGCCCTCTCCC CACTTCTC (SEQ ID NO: 12) |
| A6 | dazlR-mfe | AATTAACAATTGCCAAGCACCCTACAGC TCG (SEQ ID NO: 13) |
| B1 | miR290-5F | AATTAACCTGCAGGGATACTGTGTCTTG GGGAGAAAGC (SEQ ID NO: 14) |
| B2 | miR290-5R | AATTAACAATTGATACGGGAAGGAGTGC CGGG (SEQ ID NO: 15) |
| B3 | miR290-3F | AATTAAGGCGCGCCCAGCTCTGAAATCT GCAGAGCTG (SEQ ID NO: 16) |
| B4 | miR790-3R | AATTAAGGCCGGCCGGCATTTGCCACTA TGCCTGC (SEQ ID NO: 17) |
| C1 | Sox2-5F | AATTAACCTGCAGGCCGGGGTTTCCTGA TCTCTTGC (SEQ ID NO: 18) |
| C2 | Sox2-5R | AATTAACAATTGTCTGGCTCGGAAAGCT GGG (SEQ ID NO: 19) |
| C3 | Sox2-3F | AATTAAGGCGCGCCGGAGGGGCTGCAT TCTCAG (SEQ ID NO: 20) |
| C4 | Sox2-3R | AATTAAGGCCGGCCGCTACGAAACAGGT TCGAGACC (SEQ ID NO: 21) |
| D1 | SOX2-SE CR42 | CACCGCCAGCTTTCCGAGCCAGATG (SEQ ID NO: 22) |
| D2 | SOX2-SE CR42 | AAACCATCTGGCTCGGAAAGCTGGC (SEQ ID NO: 23) |
| D3 | miR290-EN2 CR43 | CACCGCAGATTTCAGAGCTGATAC (SEQ ID NO: 24) |
| D4 | miR290-EN2 CR43 | AAACGTATCAGCTCTGAAATCTGC (SEQ ID NO: 25) |

Primer List—Bisulfite

| | |
|---|---|
| GFP Nested R | CTCGACCAAAATAAACACCACC CC (SEQ ID NO: 26) |
| Dazl Nested F | CGATTAGAGAGTAGGTTTTGTT TGG (SEQ ID NO: 27) |
| Dazl F | TTGAGTTCGGGTGTATGTGGAA GG (SEQ ID NO: 28) |
| Dazl R | CGTCAATTACCAAACACCCTAC AAC (SEQ ID NO: 29) |
| Dazl-Snrpn F | CGAGTTGTAGGGTGTTTGGTAA TTG (SEQ ID NO: 30) |
| Dazl-Snrpn R | ACGTTACAAATCACTCCTCAAA ACC (SEQ ID NO: 31) |
| Gapdh Nested F | GGTTGTAGGAGAAGAAAATGAG ATTAG (SEQ ID NO: 32) |
| Gapdh F | GGTTGTAGGAGAAGAAAATGAG ATTAG (SEQ ID NO: 33) |
| Gapdh R | ACGTCAATTAAAAAAAAACCCA ACTAC (SEQ ID NO: 34) |
| Gapdh-Snrpn F | TAGTTTAAGGGCGTAGAGGTTT GAG (SEQ ID NO: 35) |
| Gapdh-Snrpn R | ACGTTACAAATCACTCCTCAAA ACC (SEQ ID NO: 36) |
| miR290 Nested F | GAGGGGATTTTTTGGGGTAGAG (SEQ ID NO: 37) |
| miR290 Nested R | CCCTTACTCACCATACTAACAA AATCC (SEQ ID NO: 38) |
| miR290-Snrpn F | GATTTTTTGGGGTAGAGGTAGG TGTG (SEQ ID NO: 39) |
| miR290-Snrpn R | CCACAAACCCAACTAACCTTCC TC (SEQ ID NO: 40) |
| Sox2 Nested F | GTGGTTGTTGTGTTTAGTATGT GGG (SEQ ID NO: 41) |
| Sox2 Nested R | CCCTTACTCACCATACTAACAA AATCC (SEQ ID NO: 42) |
| Sox2-Snrpn F | GGTTGTTGTGTTTAGTATGTGG GTT (SEQ ID NO: 43) |
| Sox2-Snrpn R | CCACAAACCCAACTAACCTTCC (SEQ ID NO: 44) |

REFERENCE LIST

Bird, A. (2002). DNA methylation patterns and epigenetic memory. Genes & development 16, 6-21.

Brandeis, M., Frank, D., Keshet, I., Siegfried, Z., Mendelsohn, M., Nemes, A., Temper, V., Razin, A., and Cedar, H. (1994). Sp1 elements protect a CpG island from de novo methylation. Nature 371, 435-438.

Buganim, Y., Faddah, D. A., Cheng, A. W., Itskovich, E., Markoulaki, S., Ganz, K., Klemm, S. L., van Oudenaarden, A., and Jaenisch, R. (2012). Single-cell expression analyses during cellular reprogramming reveal an early stochastic and a late hierarchic phase. Cell 150, 1209-1222.

Buganim, Y., Faddah, D. A., and Jaenisch, R. (2013). Mechanisms and models of somatic cell reprogramming. Nature reviews Genetics 14, 427-439.

Buiting, K., Saitoh, S., Gross, S., Dittrich, B., Schwartz, S., Nicholls, R. D., and Horsthemke, B. (1995). Inherited microdeletions in the Angelman and Prader-Willi syndromes define an imprinting centre on human chromosome 15. Nature genetics 9, 395-400.

Carey, B. W., Markoulaki, S., Hanna, J. H., Faddah, D. A., Buganim, Y., Kim, J., Ganz, K., Steine, E. J., Cassady, J. P., Creyghton, M. P., et al. (2011). Reprogramming factor stoichiometry influences the epigenetic state and biological properties of induced pluripotent stem cells. Cell stem cell 9, 588-598.

Cedar, H., and Bergman, Y. (2012). Programming of DNA methylation patterns. Annual review of biochemistry 81, 97-117.

Deaton, A. M., and Bird, A. (2011). CpG islands and the regulation of transcription. Genes & development 25, 1010-1022.

Dowen, J. M., Fan, Z. P., Hnisz, D., Ren, G., Abraham, B. J., Zhang, L. N., Weintraub, A. S., Schuijers, J., Lee, T. I., Zhao, K., et al. (2014). Control of cell identity genes occurs in insulated neighborhoods in Mammalian chromosomes. Cell 159, 374-387.

Ferguson-Smith, A. C. (2011). Genomic imprinting: the emergence of an epigenetic paradigm. Nature reviews Genetics 12, 565-575.

Gingold, J. A., Fidalgo, M., Guallar, D., Lau, Z., Sun, Z., Zhou, H., Faiola, F., Huang, X., Lee, D. F., Waghray, A., et al. (2014). A genome-wide RNAi screen identifies opposing functions of Snai1 and Snai2 on the Nanog dependency in reprogramming. Molecular cell 56, 140-152.

Hackett, J. A., Sengupta, R., Zylicz, J. J., Murakami, K., Lee, C., Down, T. A., and Surani, M. A. (2013). Germline DNA demethylation dynamics and imprint erasure through 5-hydroxymethylcytosine. Science 339, 448-452.

Hanna, J. H., Saha, K., and Jaenisch, R. (2010). Pluripotency and cellular reprogramming: facts, hypotheses, unresolved issues. Cell 143, 508-525.

Hnisz, D., Abraham, B. J., Lee, T. I., Lau, A., Saint-Andre, V., Sigova, A. A., Hoke, H. A., and Young, R. A. (2013). Super-enhancers in the control of cell identity and disease. Cell 155, 934-947.

Hon, G. C., Rajagopal, N., Shen, Y., McCleary, D. F., Yue, F., Dang, M. D., and Ren, B. (2013). Epigenetic memory at embryonic enhancers identified in DNA methylation maps from adult mouse tissues. Nature genetics 45, 1198-1206.

Irizarry, R. A., Ladd-Acosta, C., Wen, B., Wu, Z., Montano, C., Onyango, P., Cui, H., Gabo, K., Rongione, M., Webster, M., et al. (2009). The human colon cancer methylome shows similar hypo- and hypermethylation at conserved tissue-specific CpG island shores. Nature genetics 41, 178-186.

Ivics, Z., Hackett, P. B., Plasterk, R. H., and Izsvak, Z. (1997). Molecular reconstruction of Sleeping Beauty, a Tc1-like transposon from fish, and its transposition in human cells. Cell 91, 501-510.

Jaenisch, R., and Bird, A. (2003). Epigenetic regulation of gene expression: how the genome integrates intrinsic and environmental signals. Nature genetics 33 Suppl, 245-254.

Jones, P. A. (2012). Functions of DNA methylation: islands, start sites, gene bodies and beyond. Nature reviews Genetics 13, 484-492.

Junker, J. P., and van Oudenaarden, A. (2014). Every cell is special: genome-wide studies add a new dimension to single-cell biology. Cell 157, 8-11.

Kantor, B., Kaufman, Y., Makedonski, K., Razin, A., and Shemer, R. (2004). Establishing the epigenetic status of the Prader-Willi/Angelman imprinting center in the gametes and embryo. Human molecular genetics 13, 2767-2779.

Lee, H. J., Hore, T. A., and Reik, W. (2014). Reprogramming the methylome: erasing memory and creating diversity. Cell stem cell 14, 710-719.

Li, E., Bestor, T. H., and Jaenisch, R. (1992). Targeted mutation of the DNA methyltransferase gene results in embryonic lethality. Cell 69, 915-926.

Mansour, A. A., Gafni, O., Weinberger, L., Zviran, A., Ayyash, M., Rais, Y., Krupalnik, V., Zerbib, M., Amann-Zalcenstein, D., Maza, I., et al. (2012). The H3K27 demethylase Utx regulates somatic and germ cell epigenetic reprogramming. Nature 488, 409-413.

Mummaneni, P., Walker, K. A., Bishop, P. L., and Turker, M. S. (1995). Epigenetic gene inactivation induced by a cis-acting methylation center. The Journal of biological chemistry 270, 788-792.

Pawlak, M., and Jaenisch, R. (2011). De novo DNA methylation by Dnmt3a and Dnmt3b is dispensable for nuclear reprogramming of somatic cells to a pluripotent state. Genes & development 25, 1035-1040.

Rais, Y., Zviran, A., Geula, S., Gafni, O., Chomsky, E., Viukov, S., Mansour, A. A., Caspi, I., Krupalnik, V., Zerbib, M., et al. (2013). Deterministic direct reprogramming of somatic cells to pluripotency. Nature 502, 65-70.

Reik, W., Dean, W., and Walter, J. (2001). Epigenetic reprogramming in mammalian development. Science 293, 1089-1093.

Rhinn, M., and Dolle, P. (2012). Retinoic acid signalling during development. Development 139, 843-858.

Rivera, C. M., and Ren, B. (2013). Mapping human epigenomes. Cell 155, 39-55.

Sabag, O., Zamir, A., Keshet, I., Hecht, M., Ludwig, G., Tabib, A., Moss, J., and Cedar, H. (2014). Establishment of methylation patterns in ES cells. Nature structural & molecular biology 21, 110-112.

Smith, Z. D., Chan, M. M., Humm, K. C., Karnik, R., Mekhoubad, S., Regev, A., Eggan, K., and Meissner, A. (2014). DNA methylation dynamics of the human preimplantation embryo. Nature 511, 611-615.

Smith, Z. D., and Meissner, A. (2013). DNA methylation: roles in mammalian development. Nature reviews Genetics 14, 204-220.

Soufi, A., Donahue, G., and Zaret, K. S. (2012). Facilitators and impediments of the pluripotency reprogramming factors' initial engagement with the genome. Cell 151, 994-1004.

Stadler, M. B., Murr, R., Burger, L., Ivanek, R., Lienert, F., Scholer, A., van Nimwegen, E., Wirbelauer, C., Oakeley, E. J., Gaidatzis, D., et al. (2011). DNA-binding factors shape the mouse methylome at distal regulatory regions. Nature 480, 490-495.

Turker, M. S. (2002). Gene silencing in mammalian cells and the spread of DNA methylation. Oncogene 21, 5388-5393.

Vidal, S. E., Amlani, B., Chen, T., Tsirigos, A., and Stadtfeld, M. (2014). Combinatorial Modulation of Signaling Pathways Reveals Cell-Type-Specific Requirements for Highly Efficient and Synchronous iPSC Reprogramming. Stem cell reports 3, 574-584.

Wang, H., Yang, H., Shivalila, C. S., Dawlaty, M. M., Cheng, A. W., Zhang, F., and Jaenisch, R. (2013). One-step generation of mice carrying mutations in multiple genes by CRISPR/Cas-mediated genome engineering. Cell 153, 910-918.

Whyte, W. A., Orlando, D. A., Hnisz, D., Abraham, B. J., Lin, C. Y., Kagey, M. H., Rahl, P. B., Lee, T. I., and Young, R. A. (2013). Master transcription factors and mediator establish super-enhancers at key cell identity genes. Cell 153, 307-319.

Xie, W., Schultz, M. D., Lister, R., Hou, Z., Rajagopal, N., Ray, P., Whitaker, J. W., Tian, S., Hawkins, R. D., Leung, D., et al. (2013). Epigenomic analysis of multilineage differentiation of human embryonic stem cells. Cell 153, 1134-1148.

Ziller, M. J., Gu, H., Muller, F., Donaghey, J., Tsai, L. T., Kohlbacher, O., De Jager, P. L., Rosen, E. D., Bennett, D. A., Bernstein, B. E., et al. (2013). Charting a dynamic DNA methylation landscape of the human genome. Nature 500, 477-481.

What is claimed is:

1. A method of detecting the methylation state of a DNA region of interest in the genome of a cell comprising:
   (a) providing a mammalian cell comprising a nucleic acid comprising (i) a Snrpn promoter; and (ii) a sequence that encodes a reporter molecule, wherein the promoter is operably linked to the sequence that encodes the reporter molecule, and wherein the nucleic acid is integrated into the genome of the cell at a location no more than 1 kilobase downstream of a region of interest in the genome of the cell that is at least 100 base pairs long and comprises at least 10 CpGs; and
   (b) measuring expression of the reporter molecule by the cell wherein expression of the reporter molecule is indicative of hypomethylation of the DNA region of interest and lack of expression of the reporter molecule is indicative of hypermethylation of the DNA region of interest, thereby detecting the methylation state of the region of interest.

2. The method of claim 1, wherein the sequence of the promoter comprises SEQ ID NO: 1 or SEQ ID NO: 2.

3. The method of claim 1, wherein the reporter molecule comprises a fluorescent protein or a luciferase.

4. The method of claim 1, wherein measuring expression of the reporter molecule comprises measuring fluorescence or bioluminescence by performing fluorescence or bioluminescence imaging.

5. The method of claim 1, wherein the nucleic acid is integrated into the genome at a location no more than 10 kB away from a transcriptional start site.

6. The method of claim 1, wherein the cell is a human cell or mouse cell.

7. The method of claim 1, wherein the reporter molecule comprises a site-specific recombinase, and the genome of the cell further comprises recombination sites for the recombinase flanking a DNA segment whose excision or inversion results in a detectable change in the cell so that expression of the reporter molecule causes excision or inversion of the DNA segment, thereby permitting detection of expression of the reporter molecule.

8. The method of claim 7, wherein the genome of the cell comprises a sequence encoding a second reporter molecule, and wherein excision or inversion of the DNA segment results in turning expression of the second reporter molecule on or off.

9. The method of claim 7, wherein the second reporter molecule comprises a fluorescent protein or a luciferase.

10. The method of claim 1, wherein the genome of the cell further comprises a cell type or cell state specific promoter operably linked to a nucleic acid sequence that encodes an additional reporter molecule.

11. The method of claim 1, wherein the region of interest is not the promoter region or gene body of the Snrpn gene.

12. The method of claim 1, wherein the nucleic acid is integrated at a location no more than 250 nucleotides downstream of the region of interest.

13. The method of claim 1, wherein the nucleic acid is integrated at a location no more than 100 nucleotides downstream of the region of interest.

14. A method of monitoring the methylation state of a region of interest in a cell over a period of time comprising steps of:
   (a) providing a mammalian cell comprising a nucleic acid comprising (i) a Snrpn promoter; and (ii) a sequence that encodes a reporter molecule, wherein the promoter is operably linked to the sequence that encodes the reporter molecule, and wherein the nucleic acid is integrated into the genome of the cell at a location no more than 1 kilobase downstream of a region of interest in the genome of the cell that is at least 100 base pairs long and comprises at least 10 CpGs; and (b) measuring expression of the reporter molecule by the cell at two or more time points, wherein an increase in expression of the reporter molecule between first and second time points is indicative of a decrease in the level of methylation of the region of interest, and a decrease in expression of the reporter molecule between first and second time points is indicative of an increase in the level of methylation of the region of interest, thereby monitoring the methylation state of the region of interest over a period of time.

15. The method of claim 14, wherein the method further comprises: exposing the cell to an agent or condition of interest; and comparing the level of expression of the reporter molecule between two or more of the time points at which expression of the reporter molecule is measured in step (b), wherein a difference in the level of the reporter molecule between at least two of the time points at which expression of the reporter molecule is measured in step (b) indicates that the agent or condition affects methylation of the region of interest.

16. The method of claim 14, wherein at least two of the time points are at least 12 hours apart.

17. A method of evaluating the effect of an agent on the methylation state of a DNA region of interest in a cell comprising steps of: contacting a mammalian cell with a test agent, wherein the cell comprises a nucleic acid comprising (i) a Snrpn promoter; and (ii) a sequence that encodes a reporter molecule, wherein the promoter is operably linked to the sequence that encodes the reporter molecule, and wherein the nucleic acid is integrated into the genome of the cell at a location no more than 1 kilobase downstream of a region of interest in the genome of the cell that is at least 100 base pairs long and comprises at least 10 CpGs; measuring expression of the reporter molecule; and comparing the level of expression of the reporter molecule with a control value, wherein a difference between the measured value and the control value indicates that the test agent modulates the methylation state of the region of interest.

18. The method of claim 17, wherein the method comprises detecting an increase in the level of expression of the reporter molecule as compared to the control value, thereby determining that the agent decreases methylation of the region of interest.

19. The method of claim 17, wherein the method comprises detecting a decrease in the level of expression of the reporter molecule as compared to the control value, thereby determining that the agent increases DNA methylation of the region of interest.

20. The method of claim 17, wherein the test agent is a small molecule.

* * * * *

SEQUENCE LISTING

<160> NUMBER OF SEQ ID NOS: 46

<210> SEQ ID NO 1
<211> LENGTH: 284
<212> TYPE: DNA
<213> ORGANISM: Unknown
<220> FEATURE:
<223> OTHER INFORMATION: Snrpn minimal promoter

<400> SEQUENCE: 1

```
acgctcaaat ttccgcagta ggaatgctca agcattcctt ttggtagctg ccttttggca      60
ggacattccg gtcagaggga cagagacccc tgcattgcgg caaaaatgtg cgcatgtgca     120
gccattgcct gggacgcatg cgtagggagc cgcgcgacaa acctgagcca ttgcggcaag     180
actagcgcag agaggagagg gagccggaga tgccagacgc ttggttctga ggagtgattt     240
gcaacgcaat ggagcgagga aggtcagctg gcttgtgga ttct                       284
```

<210> SEQ ID NO 2
<211> LENGTH: 206
<212> TYPE: DNA
<213> ORGANISM: Unknown
<220> FEATURE:
<223> OTHER INFORMATION: Snrpn minimal promoter

<400> SEQUENCE: 2

```
caggacattc cggtcagagg gacagagacc cctgcattgc ggcaaaaatg tgcgcatgtg      60
cagccattgc ctgggacgca tgcgtaggga gccgcgcgac aaacctgagc cattgcggca     120
agactagcgc agagaggaga gggagccgga gatgccagac gcttggttct gaggagtgat     180
ttgcaacgca atggagcgag gaaggt                                          206
```

<210> SEQ ID NO 3
<211> LENGTH: 1515
<212> TYPE: DNA
<213> ORGANISM: Unknown
<220> FEATURE:
<223> OTHER INFORMATION: Snrpn promoter region

<400> SEQUENCE: 3

```
gtagattaag aaccagcctc agaaaagcaa caacaaaata cacaccctgc agcgctgagc      60
tacactccac cattcctagc cctagtctat tgtcttttca ttttttccata agtagtctgt    120
ccttgtgatt ttcatttgca tttccatggt gactgacaat agtatctaat tgtttagttc    180
tatgtaaata gatttcttca gctgttttcg aaagttcagg ttttggttac atttagaact    240
gaatgtatct tcattgaagt tgaatttagg atgtttgcga actggatgct agctcagtgc    300
gggggggaagg gaagtagaga acttccaact ttgttagaat acctcattaa cagttcttgc    360
aggccctcat taagctatgc taaacccatg taaatttagc ttccttagtt ttctccttgc    420
cattttgttt tcctaatctt caaataattg catattgaag ttactaccac aataatactt    480
ttactaggca gacaggaaat taataggtca aaagtaactg aaataaattc ttatatatgt    540
atccacaatc tacaaaatgt ttttgttttt gttttagat attgttacaa attgaacctg    600
gccttgagta tgcaaaaata ctgctttctt agaataagtt tcctaagagc tggaattact    660
ggatggcatt tctatgaggt catatatttg ttagtaaata gtgtctactt ttcaccccc    720
aggcataaca acatttagga agccctgtct ctaaaaccaa caacaacaaa agaagcagat    780
acataagttt cataactgaa tgttcttcct attaaaattt aatcacacca tgatctggag    840
gaaatagttt tctcccagtc atatgttcta acacagagaa agaaaataca agtaatacta    900
```

```
cattaatgta gaatgtagaa ttaggaatca ggataacttt ttttctgta cagaatttta    960 agtatctgac aatttggctg ggcttcatgt ttgattgtgt gtgtgtgtgt gtgtgtgtgt   1020
gtgtgtgtga tacactatgt aacatgatat agcctagaaa ccagtcttcc tcatattgga   1080
gatcaaacct tttttcctct cccacataat aaaaatctgt gtgatgcttg caatcacttg   1140
ggagcaattt ttttaaaaaa ttaaatgtat ttagtaatag gcaattatat ccattattcc   1200
agattgacag tgattttttt tttttttaata cacgctcaaa tttccgcagt aggaatgctc   1260
aagcattcct tttggtagct gccttttggc aggacattcc ggtcagaggg acagagaccc   1320
ctgcattgcg gcaaaaatgt gcgcatgtgc agccattgcc tgggacgcat gcgtagggag   1380
ccgcgcgaca aacctgagcc attgcggcaa gactagcgca gagaggagag ggagccggag   1440
atgccagacg cttggttctg aggagtgatt tgcaacgcaa tggagcgagg aaggtcagct   1500
gggcttgtgg attct                                                   1515

<210> SEQ ID NO 4
<211> LENGTH: 1442
<212> TYPE: DNA
<213> ORGANISM: Unknown
<220> FEATURE:
<223> OTHER INFORMATION: IGF2R promoter-associated differentially
      methylated region

<400> SEQUENCE: 4
gcagaagact ccactagaat aatctactct ggagacaatg acatcatgtg agcaaccaca     60
caggaagcta actgagagac gtgaagggta aagtcttgaa agcctacaga gatgaccacc    120
tctcaaccct tgtcaaaaga agaaaaagct tcaaccactg acaaatggct actttaaata    180
aggaaaactg agagttgcca cagaagggt caatctgcag ttgaaaccac cactacccaa    240
ctccaagagc atcgcgtggg ttcgcactcc ctggagactg cacactagag gggacgcctc    300
cgaagcccca cggctggaac ttcaatggaa acgtgcagcg gacaaaagc ccagccttag    360 ctctgccccc tgcaacttcc gacggacaca ccgggccccg ggagtcgcac aaagccgccc    420
gacttatgac agccacaagt ggccgggcac gggggctcc gggggccagt gccacggcgg    480
cgcgtcctcc tgcgccgccg cggccaccac gcgggcaact ttcccgcggg ggcggggcgg   540
ggcggaggtc tgcgtgtcct cggggctccg cgcccgccac gcaagacacc cacctgcaca   600
gggcgtccaa gtcgacggcc tgggcctgcg cggagcccgc ggccgccagg agcagcagca   660
gcaggagcgg cggcaggagc gcgacgcgcg gcccggaggg caccggtccc agctgaacgg   720
cccgcatcgc gtgtggcgtg gggctcacgg cggctggccg tttggagccg cgcctgggac   780
acggtcgcgc caccacagcg gagtcgaagc tgcaacggga gctggaggga gaaagaggag   840
agagaactgg agccagggg gagtgcgacg aggaggcgct ccgtggccgt ccccggagcg   900
tcacgtgacc tgagtcggcc cgccccgcc ccgcctcctg ctcacgtgac gtcctcgttc   960
aggtgctctc cgcccagtcc cgggtcacat gagcatcgca cgcgcgcggg acaggaagtg   1020
ttgcgggccg ggcacgagcg ccaggtacct actcgaggcc tgacaacccc agggttgctc   1080
acgcgcggag aggggtgacg cctcagagcc agacctcagt ttccccgtcc agcacccagg   1140
ttgcgtctgc gcttgagcgc ttcctaactc tctcttcttc aaccgagacc agtacggtgg   1200
ccgagatgga gttaggtgga aaagcccagg ttgatgttta gtgttgcaag tggatgcagg   1260
gttaagaggt cagtctttct agaatcccgc gtggagtttt ccgactcatg ccccggagag   1320
cctcacagca gctctgtgga aatgtgactt cccaagcagg gctttctaca gcaagttagg   1380
```

```
tgactggtgg actaatatgc agtgtgcaga gaaaccaaaa tgtaacaagc aaatgacaaa    1440
ca                                                                   1442

<210> SEQ ID NO 5
<211> LENGTH: 6753
<212> TYPE: DNA
<213> ORGANISM: Unknown
<220> FEATURE:
<223> OTHER INFORMATION: GNAS promoter-associated differentially
      methylated region

<400> SEQUENCE: 5
gcccttcctt tgttcccttt atcggaacca ccctccatgt tggttctgtc ctttctaaaa      60
gcttgattca aatcctgatc tgagaaggag ggagaaacac acacctttca ccatctaccc     120
catttcctcc tctccacttc ctgcccaaag agcccggatg ctgcatggac gcctcagaaa     180
gcacatccat tttctccctt ctttcccact gctcctacag gagcaaaggt gtccgtccga     240
tcatttatgt aaccagaccc cacacttcct tacattggac cctttgttcc agataggtga     300
aggtgtgccc gctctgcccc gccccttcta ttcagtcaag acatcttgct atggagaccc     360
attccaggcg ccattttctc catctggtct ttgcaacccc tcctattgga ggccttctct     420
ttccattttc atgccgttct gctctttcac aaggagactg gcatgctctg gaggtttctc     480
cctgtcagag aagcacgata taagaaagaa tgtggaacaa aggattctca cagatcataa     540
gaatgtctga acaaagagaa cctgaaacca ttttttttc cttttggatg aatggtgctt     600
tagggatggg tgtgagaggc ctggagagcc acaagaccc gcgtggcggt ctccttgggt      660
cgccaacctc agcgtctact gacctttcac cttgtgcagg gttcagcatc tctgggaaat     720 gaaatcgtc catcttgtac tgctcgtctg catcggagca gtaagctctc tttctccata     780
ggcctggccc accacctcca ggccctggaa aagcctctct ccgcggtgcc tcggcgatag     840
ccctctctgt gtagtgagtt agcctaccgc catcatgagc ccaagggatg gtccatgggg     900
gtccctgacc ttcccacctt gccttggcga tttagggcat caaaaagctt ggcccccaag     960
gcactcacgg cgaccgtggc cttctaggcc tggccgccat acgcccgccc gccaaccgct    1020
tccaaccaac ccagcaagca caacctcttt gggcgttcca acgcggcgcc ccctattgga    1080
cctcccaccc atatccggtt tccggtccga agcccctgc tcattcgcca ggcatccttg     1140
attggcgtga ccccagccca atagctgacc tgtcgctggg gtcggagggg agtgggctag    1200
tggttgagac ccagttggcc tattcggtgt atgttcaaac cgtttcgcca ttttgagtgt    1260
gtgtgtgtgt atatgtgggg gagggtagtt ggccaaactt tggaccaaag ttcaaagtgt    1320
ccggcatgca gtgtgttcag ccgtagagtt gaggtgacac gccttcggca ggtcgcaggc    1380
attctctggg ggttcacttt gtctgctttc ttctactcag ggtgaccacg tggacgctgt    1440
aggcaagggg ctgtagtgtg ccgagcctgt agtgagaaga gggacatgtt agacttcaga    1500
gaattaaatc tgccgcggca cacagcatgc atcttgcaat atacccatct gcatggtgca    1560
taattgccgc agcctgcttt atgtaccact tcatactctc ttttctcagg gtcctgcagg    1620
ccagacctgc ccactgccta gctgtattgc aacaaaagac aatgcctcgc gccatcgcca    1680
ttacctactg gcaaaatgtc cgcggtgtgc gcgtgccgcg ggcgcgcggc aaaacaaaaa    1740
aaaacagaac cccaaaggca aacaattaac aaaaaaaccc tgcccaggaa taatctgcag    1800
atcccagacc taaagcattt tatgattatt cgctgagccc accgggcaat gtgactgtat    1860
aaactcctgc agctctgagc ccaccccggc accgcaaggg gcgcgcagcc gcaggctttg    1920
```

```
tgaccgcgct taatttcgcc tgggtggact gttgcagttc aacgtatagc aaatgctcta    1980
tggtgctcac aacagaagga ggaggggata aaaggggget ggagaagggc ttgagagagg    2040
aaatgaacac ggaatccgca gctggcgctg gtggctggaa gatgcgagtc tcggcagctg    2100
ttgccaccat ggcacggttg gtcggtgggt taagtgcatt tcaggttttc tagtctgcga    2160
gaccacccta aatgggccat caactacacc ccaaatctcc ttttgccttt acccagaaga    2220
cagaagtaca agacctgagc taggtggggg gtcttccggt aagccttaag ccccctcccc    2280
tatttgcacg aaagcggcaa acatgaataa ctcctaaggg ggctttgctt gattttctgc    2340
agtgcactgc tgagaccttt atttctactg catcaccgtc catataaaca gagcaagccc    2400
tgactacaac acactatacc actgttgaga gctccgaggt gtaatgggga tggggacat    2460 tgaagggatt tgctggagcc atccccaaca aacagcaaac ataaacatta aaaaagaaa    2520 aaaaaggaa aaaaagaaa taagaaaag taccctagag catttacgaa acaaattgcg    2580
tgtttacatt cggcacttcc tcaccctgtc tctaccettc cggtgggctc acgaccacct    2640
gtcgcatttg tgtgtgtgtg tgcctctacc cctttccttg tatcctaaag cctccatttc    2700
ctgacttgga gatgagtatg ggtaattgcc tgagtgtggg gtccttagat aaggaattta    2760
ccgcatactg gggtaatctg gggtgataaa gccctcctgc agtccctcct ccctcgaga    2820 agaatcagat ggggagggag cttcagcg tctgtactct aacagaccaa tgcccacgtc    2880
ttgcgtcacg tgtcccagca acgcaagaga gctcgctcgc tctctggcca gggaaaaagc    2940
gagctagaga gactcggaat cagtccggga gaggagagga cggagccgaa cgtccctaca    3000
aggcctccgc tcatcagccc ccttacccaa agtcgggagc agccggcacc gggagccagc    3060
tcccggagcc ggctcagcac tgagacctgc gtcctctggc ggcagagaaa gagttctatt    3120
tacgattttc gagacgaatc ggcacgctct taaatgccaa gaaggcggag ctaaagtaca    3180
gcaaagtacg aagagagaac agaaaagttc ctaaagttgt tggccgacca cagcccgaag    3240
gggtaagtgt aactaggaag gtgacagact tcaccagcaa gagatgactc acttcagcca    3300
tggtcctggg ttctagcccc tgattatcta tccttacaaa gttttggaaac tgaggctgga    3360 gaacttttcca acaaaaattt gaatttttta aaaaaaaatt ttttttcacc ctagtttggc    3420
tgggtgctcc gtcttacggg gccccaaatt tattttgaaa agtcgccacc gtgttatggg    3480
catgttcaac tgcctccacg gcaataatat gtcaggacaa cacgtatatcc ccctgaagt    3540 cggggagcag cccgagcaag aacctttgga agccccaggg gcagctgccc ccggtgctgg    3600
ggctggccca gccgaagaaa tggcgaccga accggactcc gaaccgtcta acaatgagcc    3660
cgtccccgac gagactggca gtgagatcag tggacccca gaagactcca aatctgacat    3720
ccaaagcccc tgccaggcct tcgaggaagt ccgagtgggt ggagactaca gcccacctcc    3780
ggaggaagcc atgccattcg agacacaaca gcccagcctg ggagatttct ggcccaccct    3840
ggagcagcca ggaccatctg ggaccccatc aggcctccaa gccttcaacc cagcgatttt    3900
ggagcccggg accccactg cgcgcagccc aggcctggga gcctatacccc ccccaccaga    3960 agaagctatg ccatttgagt tcaacgagcc tgcccaggga gaccatagcc agcctccctt    4020
gcaagtccca gaccttgcgc caggaggtcc ggaagcattg gtcccagag ctcttccgc    4080 ggagcccggg aacatcagat ttgaaaacgc tggcttccga gaagactaca gccctccccc    4140
tgaagaatct gtgccatttc aggtcggtgg agaagaattc gggggcgata gcccaccccc    4200
aggactcccg cgagtcatcc cacaaaatcgg cattggcggc gagttcccga cagtcgcggt    4260
```

```
cccgagtgcg ctctgcctcg ctcccgccga gaacgcgcct ccccctctggg tccgaggcgc    4320 cattgacaga ccattccgcg aggctgtcag atctcctcct aacttcgcat gcgacagccc    4380
cccgatggag atcaccagac ccctgcttga gattggcaga gcctccattg gggtcgacga    4440
cgacaccgct gtcaatatgg acagcccccc aatcgcaagt gatggcccgc ccatcgaagt    4500
ctcgggagcc ccagataaga gcgagtgcgc agagagaccc ccagttgagc gagaagcagc    4560
cgagatggaa ggaagcccta ccaccgccac tgcggtggaa ggaaaagtcc cctctccgga    4620 gagagggac ggatcttcca cccagcctga agcaatggat gccaagccag cccctgctgc    4680
ccaagccgtc tctaccggat ctgatgctgg agctcctacg gattccgcga tgctcacaga    4740
tagccagagc gatgccggag aagacgggac agccccagga acgccttcag atctccagtc    4800
ggatcctgaa gaactcgaag aagcccccagc tgtccgcgcc gatcctgacg gaggggcagc    4860
cccagtcgcc ccagccactc ctgccgagtc cgagtctgaa ggcagcagag atccagccgc    4920
cgagccagcc tccgaggcag tccctgccac cacggccgag tctgcctccg gggcagcccc    4980
tgtcacccag gtggagcccg cagccgcggc agtctctgcc accctggcgg agcctgccgc    5040
ccgggcagcc cctatcaccc caaggagcc cactacccgg gcagtcccct ctgctagagc    5100
ccatccggcc gctggagcag tccctggcgc cccagcaatg tcagcctctg ctagggcagc    5160
tgccgctagg gcagcctatg caggtccact ggtctgggga ccaggtcac tctcagctac    5220 tcccgccgct cgggcatccc ttcctgcccg cgcagcagct gccgcccggg cagcctctgc    5280
tgcccgcgca gtcgctgctg ccggtcagc ctctgccgcc cccagcaggg cccatcttag    5340
accccccagc cccgagatcc aggttgctga cccgcctact ccgcggcctc ctccgcggcc    5400
gactgcctgg cctgacaagt acgagcgggg ccgaagctgc tgcaggtacg aggcatcgtc    5460
tggcatctgc gagatcgagt cctccagtga tgagtcggaa gaaggggcca ccggctgctt    5520
ccagtggctt ctgcggcgaa accgccgccc tggcctgccc cggagccaca cggtcgggag    5580
caacccagtc cgcaacttct tcacccgagc cttcggaagc tgcttcggtc tatccgagtg    5640
tacccgatca cgatccctca gccccgggaa ggccaaggat cctatggagg agaggcgcaa    5700
acagatgcgc aaagaagcca ttgagatgcg agagcagaag cgcgcagata agaaacgcag    5760
caagctcatc gacaagcaac tggaggagga gaagatggac tacatgtgta cacaccgcct    5820
gctgcttcta ggtaatgcgg cagcttctgc ccctgggcag tagggccgcc cgggccgccc    5880
ggggaggggg tggcagggcc ttccggtggg gcttgggcct tgcccgcggg aggaggggt    5940 ccggaaaccc tgttagaagt tccagggagg gaccccaac tctgccctgg ggtgggagag    6000
gggccttttg gagagttcgg gtggccgaac tatatgccct ccagggagaa aagtggtgcc    6060
gagcgacact gagggtcgtt accgccgga ggccagcgcc agcgccagcg atcgtaggct    6120
ggacaggcgg gggcgtgagg tgagcccaga actgctgggg tgggcccttc ggggctcccc    6180
cggctcgatt gttcgtgacc gcggtgggct agggccatcc gggtgcgcgc cccgcctcg    6240 cctggcacgg ctgcttcgac tcagacagct tgttgttggt gtgtgttggt gtccattttc    6300
tgtgttcgcc tgtgcatgac atgctcagtg tgtcccagta ccatcccag gcactttcaa    6360 cgtacccgcc gatttatat ttgtactcta aaataggtta ccttgtgatt tgcgccatgg    6420
cgcggccaaa actttccgtg ctggtacact ctgtaataac ctgtgtgcag actctctgca    6480
gcgagcagag ggaaaacgcg caggcaacgg tggcgtggca tcctgggtaa tctgctgggc    6540
cgatgactgg ggggagtggg gcctgccgcc gcgggcctcc ataaccttt cccggtatgt    6600 ctctctctct cttttcccct ttgcgctaag catatcctca cttctcaata cgtatgtcaa    6660
```

| | |
|---|---|
| acccteeege cttaacggtt gaaaaaccag acactcaggg cttttgggtt gttcaaaaca | 6720 |
| tgtgtattt gtattctgtg cacatgcaca cac | 6753 |

<210> SEQ ID NO 6
<211> LENGTH: 2784
<212> TYPE: DNA
<213> ORGANISM: Unknown
<220> FEATURE:
<223> OTHER INFORMATION: MEG3 promoter-associated differentially methylated region

<400> SEQUENCE: 6

| | |
|---|---|
| cttgtcaggg gccttctttt ggggggctct ttgcaaaaat ggggtgtttt ctttctctcc | 60 |
| cagtatctga cacattcaga aagctctttt tgatgccccc aaagccctaa accttcattt | 120 |
| tcaccctccg aagtgcatcg gttcctacct taacaacgcc cccacccctg aaaaggcctg | 180 |
| agtcacctcg ccggcaagct gctgatcggt aaccctgggc tcagcggtgg cttttctcag | 240 |
| tgcctctcag ccccaggacc cgagtcacag tggcatccta ggcttgctgg ccataggggg | 300 |
| cttacgcgaa agcagctgca gaggcgtaaa taaggcggcg gcggggggt gggggtgggg | 360 |
| ggctcttcca gcttcatgtc ctccacaggg cctctgactt tccttttagg gtctcaatca | 420 |
| ttctcgctcc ttttctgtca ccagacgctt cttctttgga ctcacagttg ccacccacct | 480 |
| gtcaccccaa gatagatcct tcgtcccttt caacagcatt ctgacctttt cgagaggaca | 540 |
| tttgatggac atgttgcccc ctttgccact tagggtaggc agagcagccg gaggtaccac | 600 |
| ctgttaagga ttagctctcc tgtgccaagt ctcagagcgt ccgcagccag cagctacgca | 660 |
| ccatagcaac atgtgtctgc ttgggctgcg gagagggggg ggcgcccttc aaagtgtggg | 720 |
| gaatcagccc gatttggggg tgtactctaa gcattaccac agggaccca ttttcactaa | 780 |
| ttaagtactt ttcttagggg gcacagttgc gcctatattc acagtacact ccgggttgct | 840 |
| gggtacccct gtaacgggca gaaatgggtc cttgggaaag ggcggaatag cgcaaggttt | 900 |
| ttggtgcaca ggttgtatct tctgtaaagc ctgggactca aaatcaaggt ccttttgcct | 960 |
| caacaatgcc aaattccccg tatcaagata gtccgtcaga atcggggtac cctatgtggg | 1020 |
| ggtgacagcc tccaggctaa catttgggaa tcaattattt tatctgggat ttttattaaa | 1080 |
| aatttccagt gcaattagga aaaaacaacg ctctcctttc ctaagccgga gcccctgact | 1140 |
| gatgttctga gaaacccagg caagccatct gccgatcccc ggtaccccac ctttatcctt | 1200 |
| ggtcgcctga gaacaatcac cagttggggt tatttccccc cagtttctgt ctacaaatcg | 1260 |
| cccttccatc cacaactagg gctcatgtag ggaaaaatca ccagcgacca cagggtgttg | 1320 |
| gtcatggcgg ccaggggcac tgcggcagat tttttttcc ttcgttcttt gctgcagtct | 1380 |
| gggtgcggct acagcaattt gtcatagaat ctgggggct catttttccg gccaatcact | 1440 |
| tttagagaaa tgagcgcatt gcagcagaat gcgctgacgt caaagaccac cccttctgcg | 1500 |
| cctttatata aacccaccc agccagcccc tagcacagaa gacgaagagc tggaatagag | 1560 |
| ctcgcctcgg ctctgctggc cttggctgca gctcttccag aaacccgggg cgcccacaga | 1620 |
| agaatctctt acctggtgag tggttagcca tcctttgcct gaaaggatgt gcaaaaatga | 1680 |
| agacgacatc actatctggc ttcggctccg tcctcctgga catgccgaaa ggccagtgct | 1740 |
| ggggaccttc tcccaaagcc agcccttag cctggtcccc agcatccaac acgaaattct | 1800 |
| gcaaggaaaa gaatcctcag gcacattttt ctcgcgggtg tggggggtc cggtccacta | 1860 |
| gggcttttttt tctcactagt gtgggcagcg cggtagagac cctgattaag aaaagcagca | 1920 |

```
ataatgagat attccgcccc caaatccagt gtattttgt ttctggggtc taaaaacctg    1980
gttttggtgg ctgaaagccc cccttagaat cgcattaatg gtgagagaca tggcggcgat    2040
gcatcatccc gcaagcccca taaaatgggg gggggtacc tgaaaagggg ggtctcgagc    2100
catctttttc tcctagccag gttctcggcg aacgtgggc gtaagattta gaggttcatg    2160
ttgaccagca attctgaatc cagatactcg ggtttagtat agacctaacc tcgggcaaaa    2220
tatagtggga aaaaaatgt aaccattact agccgtttcc tgacgcagct actttaacag    2280
cggaaagaga gggcgtcaaa ggcaaatcta gccggagacc cccagatcac agagaaggct    2340
gcggaaccgg ggggcaaagg cagaatagat gtgggggtg ggctagggta gaaaaaaccc    2400
cacgtccttg cgtctcatag gaaggaaaag ataaaatgca gaaaggggg tgtgtggagg    2460 tgtgggggt gatctgagtg ctggaaattt ggaggcaggg ttcttttgg cattgcgcat    2520 gatggctgcg gctagattct gacgtgttga aggcttttga cttttggtaa atcaccttt    2580 gccgtttcct ttgtccccgt gaagccccc ctggccgccc cctcctcatt ctgggctggc    2640
tggctgaggg ggggggcagc ctgagggctg cgacgtggca ggtttctaga atgttctatt    2700
gatggccgca agagggcgct ggtggcactg cggaattttg ggggcgggg tggggaggga    2760 agaggaggtg gcctttgttc tcct                                          2784

<210> SEQ ID NO 7
<211> LENGTH: 19
<212> TYPE: DNA
<213> ORGANISM: Unknown
<220> FEATURE:
<223> OTHER INFORMATION: bacterial TetO

<400> SEQUENCE: 7
tccctatcag tgatagaga                                                 19

<210> SEQ ID NO 8
<211> LENGTH: 34
<212> TYPE: DNA
<213> ORGANISM: Unknown
<220> FEATURE:
<223> OTHER INFORMATION: primer

<400> SEQUENCE: 8
aattaacaat tgacgctcaa atttccgcag tagg                                34

<210> SEQ ID NO 9
<211> LENGTH: 32
<212> TYPE: DNA
<213> ORGANISM: Unknown
<220> FEATURE:
<223> OTHER INFORMATION: primer

<400> SEQUENCE: 9
aattaagcta gcagaatcca caagcccagc tg                                  32

<210> SEQ ID NO 10
<211> LENGTH: 37
<212> TYPE: DNA
<213> ORGANISM: Unknown
<220> FEATURE:
<223> OTHER INFORMATION: primer

<400> SEQUENCE: 10
aattaacctg caggagccga gaggaatgag gttagtc                             37
```

<210> SEQ ID NO 11
<211> LENGTH: 32
<212> TYPE: DNA
<213> ORGANISM: Unknown
<220> FEATURE:
<223> OTHER INFORMATION: primer

<400> SEQUENCE: 11
aattaacaat tggagagagg cccagctact cg                              32

<210> SEQ ID NO 12
<211> LENGTH: 36
<212> TYPE: DNA
<213> ORGANISM: Unknown
<220> FEATURE:
<223> OTHER INFORMATION: primer

<400> SEQUENCE: 12
aattaacctg caggttatgc cctctcccca cttctc                          36

<210> SEQ ID NO 13
<211> LENGTH: 31
<212> TYPE: DNA
<213> ORGANISM: Unknown
<220> FEATURE:
<223> OTHER INFORMATION: primer

<400> SEQUENCE: 13
aattaacaat tgccaagcac cctacagctc g                               31

<210> SEQ ID NO 14
<211> LENGTH: 38
<212> TYPE: DNA
<213> ORGANISM: Unknown
<220> FEATURE:
<223> OTHER INFORMATION: primer

<400> SEQUENCE: 14
aattaacctg cagggatact gtgtcttggg gagaaagc                        38

<210> SEQ ID NO 15
<211> LENGTH: 32
<212> TYPE: DNA
<213> ORGANISM: Unknown
<220> FEATURE:
<223> OTHER INFORMATION: primer

<400> SEQUENCE: 15
aattaacaat tgatacggga aggagtgccg gg                              32

<210> SEQ ID NO 16
<211> LENGTH: 37
<212> TYPE: DNA
<213> ORGANISM: Unknown
<220> FEATURE:
<223> OTHER INFORMATION: primer

<400> SEQUENCE: 16
aattaaggcg cgcccagctc tgaaatctgc agagctg                         37

<210> SEQ ID NO 17
<211> LENGTH: 35
<212> TYPE: DNA
<213> ORGANISM: Unknown
<220> FEATURE:
<223> OTHER INFORMATION: primer

<400> SEQUENCE: 17
aattaaggcc ggccggcatt tgccactatg cctgc                             35

<210> SEQ ID NO 18
<211> LENGTH: 36
<212> TYPE: DNA
<213> ORGANISM: Unknown
<220> FEATURE:
<223> OTHER INFORMATION: primer

<400> SEQUENCE: 18
aattaacctg caggccgggg tttcctgatc tcttgc                            36

<210> SEQ ID NO 19
<211> LENGTH: 31
<212> TYPE: DNA
<213> ORGANISM: Unknown
<220> FEATURE:
<223> OTHER INFORMATION: primer

<400> SEQUENCE: 19
aattaacaat tgtctggctc ggaaagctgg g                                 31

<210> SEQ ID NO 20
<211> LENGTH: 34
<212> TYPE: DNA
<213> ORGANISM: Unknown
<220> FEATURE:
<223> OTHER INFORMATION: primer

<400> SEQUENCE: 20
aattaaggcg cgccggaggg ggctgcattc tcag                              34

<210> SEQ ID NO 21
<211> LENGTH: 36
<212> TYPE: DNA
<213> ORGANISM: Unknown
<220> FEATURE:
<223> OTHER INFORMATION: primer

<400> SEQUENCE: 21
aattaaggcc ggccgctacg aaacaggttc gagacc                            36

<210> SEQ ID NO 22
<211> LENGTH: 25
<212> TYPE: DNA
<213> ORGANISM: Unknown
<220> FEATURE:
<223> OTHER INFORMATION: primer

<400> SEQUENCE: 22
caccgccagc tttccgagcc agatg                                        25

<210> SEQ ID NO 23
<211> LENGTH: 25
<212> TYPE: DNA
<213> ORGANISM: Unknown
<220> FEATURE:
<223> OTHER INFORMATION: primer

<400> SEQUENCE: 23
aaaccatctg gctcggaaag ctggc                                        25

<210> SEQ ID NO 24

```
<211> LENGTH: 24
<212> TYPE: DNA
<213> ORGANISM: Unknown
<220> FEATURE:
<223> OTHER INFORMATION: primer

<400> SEQUENCE: 24
caccgcagat tcagagctg atac                                      24

<210> SEQ ID NO 25
<211> LENGTH: 24
<212> TYPE: DNA
<213> ORGANISM: Unknown
<220> FEATURE:
<223> OTHER INFORMATION: primer

<400> SEQUENCE: 25
aaacgtatca gctctgaaat ctgc                                     24

<210> SEQ ID NO 26
<211> LENGTH: 24
<212> TYPE: DNA
<213> ORGANISM: Unknown
<220> FEATURE:
<223> OTHER INFORMATION: primer

<400> SEQUENCE: 26
ctcgaccaaa ataaacacca cccc                                     24

<210> SEQ ID NO 27
<211> LENGTH: 25
<212> TYPE: DNA
<213> ORGANISM: Unknown
<220> FEATURE:
<223> OTHER INFORMATION: primer

<400> SEQUENCE: 27
cgattagaga gtaggttttg tttgg                                    25

<210> SEQ ID NO 28
<211> LENGTH: 24
<212> TYPE: DNA
<213> ORGANISM: Unknown
<220> FEATURE:
<223> OTHER INFORMATION: primer

<400> SEQUENCE: 28
ttgagttcgg gtgtatgtgg aagg                                     24

<210> SEQ ID NO 29
<211> LENGTH: 25
<212> TYPE: DNA
<213> ORGANISM: Unknown
<220> FEATURE:
<223> OTHER INFORMATION: primer

<400> SEQUENCE: 29
cgtcaattac caaacaccct acaac                                    25

<210> SEQ ID NO 30
<211> LENGTH: 25
<212> TYPE: DNA
<213> ORGANISM: Unknown
<220> FEATURE:
<223> OTHER INFORMATION: primer

<400> SEQUENCE: 30
```
cgagttgtag ggtgtttggt aattg                                       25

<210> SEQ ID NO 31
<211> LENGTH: 25
<212> TYPE: DNA
<213> ORGANISM: Unknown
<220> FEATURE:
<223> OTHER INFORMATION: primer

<400> SEQUENCE: 31
acgttacaaa tcactcctca aaacc                                       25

<210> SEQ ID NO 32
<211> LENGTH: 27
<212> TYPE: DNA
<213> ORGANISM: Unknown
<220> FEATURE:
<223> OTHER INFORMATION: primer

<400> SEQUENCE: 32
ggttgtagga gaagaaaatg agattag                                     27

<210> SEQ ID NO 33
<211> LENGTH: 27
<212> TYPE: DNA
<213> ORGANISM: Unknown
<220> FEATURE:
<223> OTHER INFORMATION: primer

<400> SEQUENCE: 33
ggttgtagga gaagaaaatg agattag                                     27

<210> SEQ ID NO 34
<211> LENGTH: 27
<212> TYPE: DNA
<213> ORGANISM: Unknown
<220> FEATURE:
<223> OTHER INFORMATION: primer

<400> SEQUENCE: 34
acgtcaatta aaaaaaaacc caactac                                     27

<210> SEQ ID NO 35
<211> LENGTH: 25
<212> TYPE: DNA
<213> ORGANISM: Unknown
<220> FEATURE:
<223> OTHER INFORMATION: primer

<400> SEQUENCE: 35
tagtttaagg gcgtagaggt ttgag                                       25

<210> SEQ ID NO 36
<211> LENGTH: 25
<212> TYPE: DNA
<213> ORGANISM: Unknown
<220> FEATURE:
<223> OTHER INFORMATION: primer

<400> SEQUENCE: 36
acgttacaaa tcactcctca aaacc                                       25

<210> SEQ ID NO 37
<211> LENGTH: 22
<212> TYPE: DNA

```
<213> ORGANISM: Unknown
<220> FEATURE:
<223> OTHER INFORMATION: primer

<400> SEQUENCE: 37 gagggattt tttggggtag ag                                              22

<210> SEQ ID NO 38
<211> LENGTH: 27
<212> TYPE: DNA
<213> ORGANISM: Unknown
<220> FEATURE:
<223> OTHER INFORMATION: primer

<400> SEQUENCE: 38
cccttactca ccatactaac aaaatcc                                        27

<210> SEQ ID NO 39
<211> LENGTH: 26
<212> TYPE: DNA
<213> ORGANISM: Unknown
<220> FEATURE:
<223> OTHER INFORMATION: primer

<400> SEQUENCE: 39
gattttttgg ggtagaggta ggtgtg                                         26

<210> SEQ ID NO 40
<211> LENGTH: 24
<212> TYPE: DNA
<213> ORGANISM: Unknown
<220> FEATURE:
<223> OTHER INFORMATION: primer

<400> SEQUENCE: 40
ccacaaaccc aactaacctt cctc                                           24

<210> SEQ ID NO 41
<211> LENGTH: 25
<212> TYPE: DNA
<213> ORGANISM: Unknown
<220> FEATURE:
<223> OTHER INFORMATION: primer

<400> SEQUENCE: 41
gtggttgttg tgtttagtat gtggg                                          25

<210> SEQ ID NO 42
<211> LENGTH: 27
<212> TYPE: DNA
<213> ORGANISM: Unknown
<220> FEATURE:
<223> OTHER INFORMATION: primer

<400> SEQUENCE: 42
cccttactca ccatactaac aaaatcc                                        27

<210> SEQ ID NO 43
<211> LENGTH: 25
<212> TYPE: DNA
<213> ORGANISM: Unknown
<220> FEATURE:
<223> OTHER INFORMATION: primer

<400> SEQUENCE: 43
ggttgttgtg tttagtatgt gggtt                                          25
```

```
<210> SEQ ID NO 44
<211> LENGTH: 22
<212> TYPE: DNA
<213> ORGANISM: Unknown
<220> FEATURE:
<223> OTHER INFORMATION: primer

<400> SEQUENCE: 44
ccacaaaccc aactaaccttt cc                                              22

<210> SEQ ID NO 45
<211> LENGTH: 51
<212> TYPE: DNA
<213> ORGANISM: Unknown
<220> FEATURE:
<223> OTHER INFORMATION: DNA methylation reporter

<400> SEQUENCE: 45
ggcactcctt cccgtatcag ctctgaaatc tgcagagctg agatctggca g              51

<210> SEQ ID NO 46
<211> LENGTH: 49
<212> TYPE: DNA
<213> ORGANISM: Unknown
<220> FEATURE:
<223> OTHER INFORMATION: DNA methylation reporter

<400> SEQUENCE: 46
ccacacccag ctttccgagc cagatgagga gggggctgca ttctcagac                 49
```